(12) United States Patent
Hochrein et al.

(10) Patent No.: US 12,385,040 B2
(45) Date of Patent: Aug. 12, 2025

(54) ALLOSTERIC CONDITIONAL GUIDE RNAS FOR CELL-SELECTIVE REGULATION OF CRISPR/CAS

(71) Applicant: California Institute of Technology, Pasadena, CA (US)

(72) Inventors: Lisa Hochrein, Pasadena, CA (US); Mikhail H. Hanewich-Hollatz, Pasadena, CA (US); Zhewei Chen, Pasadena, CA (US); Heyun Li, Pasadena, CA (US); Shashank Gandhi, Pasadena, CA (US); Marianne Bronner, Pasadena, CA (US); Niles A. Pierce, Pasadena, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 18/537,662

(22) Filed: Dec. 12, 2023

(65) Prior Publication Data

US 2024/0132882 A1    Apr. 25, 2024

Related U.S. Application Data

(62) Division of application No. 17/584,237, filed on Jan. 25, 2022, now Pat. No. 11,873,485.

(60) Provisional application No. 63/181,808, filed on Apr. 29, 2021, provisional application No. 63/141,865, filed on Jan. 26, 2021.

(51) Int. Cl.
*C12N 15/11* (2006.01)
*C12N 9/22* (2006.01)

(52) U.S. Cl.
CPC ............... *C12N 15/11* (2013.01); *C12N 9/22* (2013.01); *C12N 2310/15* (2013.01); *C12N 2310/20* (2017.05); *C12N 2310/344* (2013.01); *C12N 2310/531* (2013.01); *C12N 2310/532* (2013.01); *C12N 2800/80* (2013.01)

(58) Field of Classification Search
None
See application file for complete search history.

(56) References Cited

U.S. PATENT DOCUMENTS

| | | |
|---|---|---|
| 4,714,680 A | 12/1987 | Civin |
| 4,868,105 A | 9/1989 | Urdea et al. |
| 4,897,355 A | 1/1990 | Eppstein et al. |
| 4,965,204 A | 10/1990 | Civin |
| 5,057,410 A | 10/1991 | Kawasaki et al. |
| 5,061,620 A | 10/1991 | Tsukamoto et al. |
| 5,118,801 A | 6/1992 | Lizardi et al. |
| 5,124,246 A | 6/1992 | Urdea et al. |
| 5,270,163 A | 12/1993 | Gold et al. |
| 5,312,728 A | 5/1994 | Lizardi et al. |
| 5,424,413 A | 6/1995 | Hogan et al. |
| 5,459,127 A | 10/1995 | Felgner et al. |
| 5,563,256 A | 10/1996 | Chakraborty et al. |
| 5,571,670 A | 11/1996 | Urdea et al. |
| 5,579,793 A | 12/1996 | Gajewski et al. |
| 5,624,802 A | 4/1997 | Urdea et al. |
| 5,635,352 A | 6/1997 | Urdea et al. |
| 5,643,741 A | 7/1997 | Tsukamoto et al. |
| 5,656,731 A | 8/1997 | Urdea |
| 5,677,136 A | 10/1997 | Simmons et al. |
| 5,681,697 A | 10/1997 | Urdea et al. |

(Continued)

FOREIGN PATENT DOCUMENTS

| | | |
|---|---|---|
| AU | 2003226729 A1 | 10/2003 |
| CA | 2994958 A1 | 2/2017 |

(Continued)

OTHER PUBLICATIONS

Briner et al., Guide RNA Functional Modules Direct Cas9 Activity and Orthogonality. Molecular Cell (2014), 56: 333-339 (Year: 2014).*

Zetsche et al., Cpf1 Is a Single RNA-Guided Endonuclease of a Class 2 CRISPR-Cas System. Cell (2015), 163: 759-771 (Year: 2015).*

(Continued)

*Primary Examiner* — Abigail Vanhorn
*Assistant Examiner* — Catherine Konopka
(74) *Attorney, Agent, or Firm* — Knobbe Martens Olson & Bear LLP

(57) ABSTRACT

Programmable guide RNAs (gRNAs) play a central role in the CRISPR revolution sweeping biology and medicine by directing the function of a Cas protein effector to a target gene of choice. To achieve programmable control over regulatory scope, the activity of a conditional guide RNA (cgRNA) depends on the presence or absence of an RNA trigger, allowing for cell-selective regulation of CRISPR/Cas function. Unlike a standard gRNA, a cgRNA is programmable at multiple levels, with the target-binding sequence controlling the target of Cas activity (edit, silence, induce, or bind a gene of choice) and the trigger-binding sequence controlling the scope of Cas activity. cgRNA mechanisms that are allosteric allow for independent design of the target and trigger sequences, providing the flexibility to select the regulatory target and scope independently. Disclosed herein are allosteric cgRNA mechanisms for both ON→OFF logic (conditional inactivation by an RNA trigger) and OFF→ON logic (conditional activation by an RNA trigger). Allosteric cgRNAs enable restriction of CRISPR/Cas function to a desired cell type, tissue, organ, or disease state. Allosteric cgRNAs provide a versatile platform for cell-selective and tissue-selective research tools, biotechnologies, diagnostics, and therapeutics.

22 Claims, 81 Drawing Sheets

Specification includes a Sequence Listing.

(56) References Cited

U.S. PATENT DOCUMENTS

| | | |
|---|---|---|
| 5,681,702 A | 10/1997 | Collins et al. |
| 5,691,145 A | 11/1997 | Pitner et al. |
| 5,710,264 A | 1/1998 | Urdea et al. |
| 5,716,827 A | 2/1998 | Tsukamoto et al. |
| 5,750,397 A | 5/1998 | Tsukamoto et al. |
| 5,780,610 A | 7/1998 | Collins et al. |
| 5,784,487 A | 7/1998 | Cooperman |
| 5,849,481 A | 12/1998 | Urdea et al. |
| 5,876,924 A | 3/1999 | Zhang et al. |
| 5,902,724 A | 5/1999 | Lane et al. |
| 5,928,913 A | 7/1999 | Efstathiou et al. |
| 5,989,823 A | 11/1999 | Jayasena et al. |
| 6,007,994 A | 12/1999 | Ward et al. |
| 6,128,587 A | 10/2000 | Sjolander |
| 6,130,047 A | 10/2000 | Nadeau et al. |
| 6,232,462 B1 | 5/2001 | Collins et al. |
| 6,242,246 B1 | 6/2001 | Gold et al. |
| 6,255,469 B1 | 7/2001 | Seeman et al. |
| 6,261,783 B1 | 7/2001 | Jayasena et al. |
| 6,264,825 B1 | 7/2001 | Blackburn et al. |
| 6,361,944 B1 | 3/2002 | Mirkin et al. |
| 6,361,945 B1 | 3/2002 | Becker et al. |
| 6,485,965 B1 | 11/2002 | Klatzmann et al. |
| 6,506,559 B1 | 1/2003 | Fire et al. |
| 6,555,367 B1 | 4/2003 | Spence et al. |
| 6,696,285 B1 | 2/2004 | Mills et al. |
| 6,899,871 B2 | 5/2005 | Kasahara et al. |
| 7,033,834 B2 | 4/2006 | Valerio et al. |
| 7,632,641 B2 | 12/2009 | Dirks et al. |
| 7,709,198 B2 | 5/2010 | Luo et al. |
| 7,727,721 B2 | 6/2010 | Pierce et al. |
| 7,960,357 B2 | 6/2011 | Dirks et al. |
| 8,105,778 B2 | 1/2012 | Dirks et al. |
| 8,124,751 B2 | 2/2012 | Pierce et al. |
| 8,241,854 B2 | 8/2012 | Yin et al. |
| 8,318,921 B2 | 11/2012 | Pierce et al. |
| 8,478,543 B2 | 7/2013 | Pierce et al. |
| 8,497,364 B2 | 7/2013 | Pierce et al. |
| 8,507,204 B2 | 8/2013 | Pierce et al. |
| 8,604,182 B2 | 12/2013 | Luo et al. |
| 8,658,361 B2 | 2/2014 | Wu et al. |
| 8,658,780 B2 | 2/2014 | Pierce et al. |
| 8,877,438 B2 | 11/2014 | Yin |
| 8,951,726 B2 | 2/2015 | Luo et al. |
| 8,962,241 B2 | 2/2015 | Yin et al. |
| 8,962,582 B2 | 2/2015 | Dirks et al. |
| 9,217,151 B2 | 12/2015 | Yin et al. |
| 9,315,862 B2 | 4/2016 | Smolke et al. |
| 9,353,404 B2 | 5/2016 | Fletcher |
| 9,834,439 B2 | 12/2017 | Yin et al. |
| 9,856,472 B2 | 1/2018 | Pierce et al. |
| 10,283,767 B2 | 5/2019 | Moc et al. |
| 10,450,599 B2 | 10/2019 | Pierce et al. |
| 10,815,519 B2 | 10/2020 | Husain et al. |
| 11,214,825 B2 | 1/2022 | Pierce et al. |
| 11,873,485 B2 | 1/2024 | Hochrein et al. |
| 2001/0014445 A1 | 8/2001 | Urnovitz |
| 2001/0026918 A1 | 10/2001 | Collins et al. |
| 2002/0051769 A1 | 5/2002 | Zhang |
| 2002/0102584 A1 | 8/2002 | Hester et al. |
| 2002/0137035 A1 | 9/2002 | Stender et al. |
| 2002/0172950 A1 | 11/2002 | Kenny et al. |
| 2003/0056177 A1 | 3/2003 | Nara et al. |
| 2003/0092162 A1 | 5/2003 | Shankara et al. |
| 2003/0129611 A1 | 7/2003 | Bao et al. |
| 2003/0207295 A1 | 11/2003 | Gunderson et al. |
| 2003/0215821 A1 | 11/2003 | Gunderson et al. |
| 2004/0005552 A1 | 1/2004 | Lane et al. |
| 2004/0009510 A1 | 1/2004 | Seiwert et al. |
| 2004/0018491 A1 | 1/2004 | Gunderson et al. |
| 2004/0043386 A1 | 3/2004 | Pray et al. |
| 2004/0115686 A1 | 6/2004 | Dolginow et al. |
| 2004/0126773 A1 | 7/2004 | Beske et al. |
| 2004/0223953 A1 | 11/2004 | Kung et al. |
| 2004/0265934 A1 | 12/2004 | Stender et al. |
| 2005/0089864 A1 | 4/2005 | Li et al. |
| 2005/0100893 A1 | 5/2005 | Gunderson et al. |
| 2005/0112614 A1 | 5/2005 | Cook et al. |
| 2005/0233332 A1 | 10/2005 | Collis |
| 2005/0239061 A1 | 10/2005 | Marshall et al. |
| 2005/0260635 A1 | 11/2005 | Dirks et al. |
| 2006/0035375 A1 | 2/2006 | Head et al. |
| 2006/0088864 A1 | 4/2006 | Smolke et al. |
| 2006/0156226 A1 | 7/2006 | Dejean et al. |
| 2006/0228733 A1 | 10/2006 | Pierce et al. |
| 2006/0234261 A1 | 10/2006 | Pierce et al. |
| 2007/0007221 A1 | 1/2007 | Mann |
| 2007/0072215 A1 | 3/2007 | Seelig et al. |
| 2007/0087334 A1 | 4/2007 | Dirks et al. |
| 2007/0117109 A1 | 5/2007 | Rothemund |
| 2008/0038725 A1 | 2/2008 | Luo et al. |
| 2008/0183958 A1 | 7/2008 | Cheriton |
| 2008/0214488 A1 | 9/2008 | Pierce et al. |
| 2009/0011956 A1 | 1/2009 | Yin et al. |
| 2009/0123914 A1 | 5/2009 | Erikson et al. |
| 2009/0197271 A1 | 8/2009 | Kotlikoff et al. |
| 2009/0227774 A1 | 9/2009 | Turberfield et al. |
| 2009/0247615 A1 | 10/2009 | Pierce et al. |
| 2009/0311799 A1 | 12/2009 | Sotzing et al. |
| 2010/0021901 A1 | 1/2010 | Yin et al. |
| 2010/0021904 A1 | 1/2010 | Pierce et al. |
| 2010/0035233 A1 | 2/2010 | Yin et al. |
| 2010/0047926 A1 | 2/2010 | Dirks et al. |
| 2011/0059064 A1 | 3/2011 | Possani-Postay et al. |
| 2011/0104676 A1 | 5/2011 | Pierce et al. |
| 2011/0287557 A1 | 11/2011 | Zhang et al. |
| 2011/0288148 A1 | 11/2011 | Pierce et al. |
| 2011/0288832 A1 | 11/2011 | Pierce et al. |
| 2011/0313030 A1 | 12/2011 | Dirks et al. |
| 2012/0021410 A1 | 1/2012 | Yin et al. |
| 2012/0022243 A1 | 1/2012 | Yin et al. |
| 2012/0022244 A1 | 1/2012 | Yin |
| 2012/0190835 A1 | 7/2012 | Pierce et al. |
| 2012/0251583 A1 | 10/2012 | Rothemund |
| 2012/0324341 A1 | 12/2012 | Herve |
| 2013/0171621 A1 | 7/2013 | Luo et al. |
| 2014/0032558 A1 | 1/2014 | Renders et al. |
| 2014/0068797 A1 | 3/2014 | Doudna et al. |
| 2014/0107983 A1 | 4/2014 | Wolfe et al. |
| 2014/0270545 A1 | 9/2014 | Ghessassi |
| 2014/0280167 A1 | 9/2014 | Ghessassi |
| 2014/0301644 A1 | 10/2014 | Koh et al. |
| 2015/0004615 A1 | 1/2015 | Pierce et al. |
| 2015/0154347 A1 | 6/2015 | Wolfe et al. |
| 2017/0009278 A1 | 1/2017 | Sderberg et al. |
| 2017/0022499 A1 | 1/2017 | Lu et al. |
| 2017/0037432 A1 | 2/2017 | Donohoue et al. |
| 2017/0067096 A1 | 3/2017 | Wassie et al. |
| 2017/0124217 A1 | 5/2017 | Hassanzadeh et al. |
| 2017/0166952 A1 | 6/2017 | Wang et al. |
| 2017/0327888 A1 | 11/2017 | Ong et al. |
| 2018/0010166 A1 | 1/2018 | Pierce et al. |
| 2018/0066303 A1 | 3/2018 | Husain et al. |
| 2018/0362944 A1 | 12/2018 | Hanewich-Hollatz et al. |
| 2019/0073345 A1 | 3/2019 | Jain et al. |
| 2019/0141203 A1 | 5/2019 | Morita |
| 2019/0163750 A1 | 5/2019 | Sage et al. |
| 2019/0233806 A1 | 8/2019 | Garreau De Loubresse et al. |
| 2019/0382758 A1 | 12/2019 | Aoki et al. |
| 2020/0140920 A1 | 5/2020 | Pierce et al. |
| 2020/0239879 A1 | 7/2020 | Choudhary et al. |
| 2022/0090163 A1 | 3/2022 | Pierce et al. |
| 2022/0282300 A1 | 9/2022 | Pierce et al. |
| 2022/0348909 A1 | 11/2022 | Hochrein et al. |
| 2023/0193362 A1 | 6/2023 | Pierce et al. |

FOREIGN PATENT DOCUMENTS

| | | |
|---|---|---|
| EP | 0070685 A2 | 1/1983 |
| EP | 0273085 A1 | 7/1988 |
| EP | 0731848 A1 | 9/1996 |
| EP | 1071023 A2 | 1/2001 |
| EP | 1479766 A1 | 11/2004 |
| EP | 1634890 A1 | 3/2006 |

(56) References Cited

FOREIGN PATENT DOCUMENTS

| | | |
|---|---|---|
| EP | 1730161 A2 | 12/2006 |
| EP | 1931806 A2 | 6/2008 |
| EP | 2055781 A2 | 5/2009 |
| EP | 2155770 A1 | 2/2010 |
| EP | 2460893 A1 | 6/2012 |
| EP | 2500439 A1 | 9/2012 |
| EP | 2630260 A1 | 8/2013 |
| EP | 1910572 B1 | 12/2015 |
| EP | 2529030 B1 | 3/2019 |
| EP | 3481843 A2 | 5/2019 |
| EP | 3507296 A1 | 7/2019 |
| EP | 3638789 A2 | 4/2020 |
| EP | 3943613 A1 | 1/2022 |
| HK | 40062706 | 6/2022 |
| HK | 40008988 | 7/2022 |
| IL | 264831 A | 3/2019 |
| IL | 264152 A | 5/2019 |
| IL | 290679 A | 4/2022 |
| WO | 92/03464 A1 | 3/1992 |
| WO | 93/15102 A1 | 8/1993 |
| WO | 94/01550 A1 | 1/1994 |
| WO | 95/16055 A1 | 6/1995 |
| WO | 99/31276 A1 | 6/1999 |
| WO | 01/40516 A2 | 6/2001 |
| WO | 01/94632 A2 | 12/2001 |
| WO | 03/83131 A1 | 10/2003 |
| WO | 2005/098049 A2 | 10/2005 |
| WO | 2006/002167 A2 | 1/2006 |
| WO | 2006/048025 A1 | 5/2006 |
| WO | 2007/002006 A2 | 1/2007 |
| WO | 2007/008276 A2 | 1/2007 |
| WO | 2007/044727 A2 | 4/2007 |
| WO | 2007/141809 A1 | 12/2007 |
| WO | 2007/148337 A2 | 12/2007 |
| WO | 2008/106658 A2 | 9/2008 |
| WO | 2008/144562 A1 | 11/2008 |
| WO | 2011/126996 A2 | 10/2011 |
| WO | 2012/054795 A1 | 4/2012 |
| WO | 2014/074648 A2 | 5/2014 |
| WO | 2015/035139 A2 | 3/2015 |
| WO | 2015/118029 A1 | 8/2015 |
| WO | 2015/168404 A1 | 11/2015 |
| WO | 2015/180929 A1 | 12/2015 |
| WO | 2016/011089 A1 | 1/2016 |
| WO | 2016/022866 A1 | 2/2016 |
| WO | 2016/094867 A1 | 6/2016 |
| WO | 2017/004261 A1 | 1/2017 |
| WO | 2017/189525 A1 | 11/2017 |
| WO | 2017/223449 A1 | 12/2017 |
| WO | 2018/000946 A1 | 1/2018 |
| WO | 2018/009463 A2 | 1/2018 |
| WO | 2018/044939 A1 | 3/2018 |
| WO | 2018/217905 A1 | 11/2018 |
| WO | 2018/231730 A2 | 12/2018 |
| WO | 2021/022178 A1 | 2/2021 |
| WO | 2021/221789 A2 | 11/2021 |
| WO | 2022/016479 A1 | 1/2022 |
| WO | 2022/164796 A1 | 8/2022 |

OTHER PUBLICATIONS

Jin et al., Programmable CRISPR-Cas Repression, Activation, and Computation with Sequence-Independent Targets and Triggers. ACS Synth. Bio. (2019), 8: 1583-1589 (Year: 2019).*

Mali et al., Cas9 as a versatile tool for engineering biology. Nature Methods (2013), 10: 957-963 (Year: 2013).*

Ma et al., Get ready for the CRISPR/Cas system: A beginner's guide to the engineering and design of guide RNAs. J Gene Med. (2021), 23:e3377 (Year: 2021).*

Hanewich-Hollatz et al., Conditional Guide RNAs: Programmable Conditional Regulation of CRISPR/Cas Function in Bacterial and Mammalian Cells via Dynamic RNA Nanotechnology. ACS Cent Sci (2019), 5: 1241-1249 (Year: 2019).*

Lima W.F. et al., "Binding and cleavage specificities of human Argonaute2," J Biol Chem, vol. 284, p. 26017-26028, 2009.

Lin et al., "DNA Tile Based Self-Assembly: Building Complex Nanoarchitectures", ChemPhysChem, vol. 7, pp. 1641-1647, 2006.

Lin, et al. 2018. "A Hybridization-Chain-Reaction-Based Method for Amplifying Immunosignals." Nature Methods 15 (4): 275-78. https://doi.org/10.1038/nmeth.4611.

Lin, F. et al., Standardization of Diagnostic Immunohistochemistry Literature Review and Geisinger Experience, Archives of Pathology & Laboratory Medicine, vol. 138, No. 12, pp. 1564-1577, (2014).

Linuma et al., "Polyhedra Self-Assembled from DNA Tripods and Characterized with 3D DNA-PAINT," Science, vol. 344, No. 6179, pp. 65-69, 2014.

Liu et al., "Approaching The Limit: Can One DNA Oligonucleotide Assemble into Large Nanostructures?", Anqew. Chem. Int. Ed., vol. 45, paqes 1942-1945, 2006.

Liu et al., "DNA nanotubes self-assembled from triple-crossover tiles as templates for conductive nanowires", PNAS, vol. 101, No. 3, pp. 717-722, Jan. 20, 2004.

Liu et al., "A colorimetric lead biosensor using DNAzyme-directed assembly of gold nanoparticles," J. Am. Chem. Soc., vol. 125, No. 22, pp. 6642-6643, 2003.

Liu et al., Rescue of Fragile X Syndrome Neurons by DNA Methylation Editing of the FMR1 Gene. Cell 2018, 172 (5), 979-992.e6. httos://doi.ora/10.1016/i.cell.2018.01.012.

Liu, Y.; Zou, R. S.; He, S.; Nihongaki, Y.; Li, X.; Razavi, S.; Wu, B.; Ha, T. Very Fast CRISPR on Demand. Science 2020, 368 (6496), 1265-1269.

Ma et al., Multiplexed Labeling of Genomic Loci with DCas9 and Engineered SgRNAs Using CRISPRainbow. Nat. Biotechnol. 2016, 34 (5), 528-530. https://doi.org/10.1038/nbt.3526.

Macechko et al., "Comparison of Immunologic Amplification vs Enzymatic Deposition of Fluorochrome-conjugated Tyramide as Detection Systems for FISH," J Histochem Cytochem, 45(3), 00, 359-363, 1997.

MacFadden et al., Mechanism and Structural Diversity of Exoribonuclease-Resistant RNA Structures in Flaviviral RNAs. Nat. Commun. 2018, 9 (1), 119. https://doi.org/10.1038/s41467-017-02604-y.

Mahato et al., "Modulation of gene expression by antisense and antigene oligodeoxynucleotides and small interfering RNA", Expert Opin. Drug Deliv., vol. 2, No. 1, pp. 3-28.2005.

Mali et al., CAS9 Transcriptional Activators for Target Specificity Screening and Paired Nickases for Cooperative Genome Engineering. Nat. Biotechnol. 2013, 31, 833-838.

Mali, P et al . . . 'RNA-Guided Human Genome Engineering via Cas9', Science, 339: 823-26., (2013).

Manche et al., "Interactions between Double-Stranded RNA Regulators and the Protein Kinase DAI", Molecular and Cellular Biology, vol. 12, No. 11, pp. 5238-5248, Nov. 1992.

Manoharan et al., "RNA Interference and Chemically Modified Small Interfering RNAs." Current O12inion in Chemical Biology 8 (2004): 570-579.

Markowitz et al., "The Effect of Commencing Combination Antiretroviral Therapy Soon after Human Immunodeficiency Virus Type 1 Infection on Viral Replication and Antiviral Immune Responses", The Journal of Infectious Diseases, vol. 179, pp. 525-537, 1999.

Martinot-Peignoux et al., "Assessment of Viral Loads in Patients with Chronic Hepatitis C with AMPLICOR HCV MONITOR Version 1.0, COBAS HCV Monitor Version 2.0, and QUANTIPLEX HCV RNA Version 2.0 Assays", Journal of Clinical Microbiology, vol. 38, No. 7, pp. 2722-2725, Jul. 2000.

Masu, H et al., "An activatable siRNA probe: trigger-RNA-dependent activation of RNAi function," Chem., Int. Ed., vol. 48, pp. 9481-9483, 2009.

Mathews, David H. et al., "22 predicting rna secondary structure," Cold Spring Harbor Monograph Archive, vol. 43, pp. 631-657, 2006.

Mathieu et al., "Six-Helix Bundles Designed from DNA", Nano Lett., vol. 5, No. 4, pp. 661-665, 2005.

Matsui, T. et al., "Expression of Unphosphorylated Form of Human Double-Stranded RNA-Activated Protein Kinase in *Escherichia coli*", Biochemical and Biophysical Research Communications, vol. 284, No. 3, pp. 798-807,2001.

(56) References Cited

OTHER PUBLICATIONS

McIntyre, G. J et al., "The effects of stem length and core placement on shRNA activity" BMC Mol. Biol., vol. 12, pp. 34, 2011.

McLennan, R. et al., Neural crest migration is driven by a few trailblazer cells with a unique molecular signature narrowly confined to the invasive front, Development, vol. 142, No. 11, pp. 2014-2025, (2015).

Meinhardt et al., "Wavelength-dependent Penetration Depths of Ultraviolet Radiation in Human Skin." Journal of Biomedical Optics, vol. 13.4, pp. 044030-1-044030-5, Jul./Aug. 2008.

Meyer et al., Improving Fold Activation of Small Transcription Activating RNAs (STARs) with Rational RNA Engineering Strategies: Improving Small Transcription Activating RNAs. Biotechnol. Bioeng, 113 (1), 216-225. https://doi.org/10.1002/bit.25693, 2016.

Misteli, T.; Spector, D. L. Applications of the Green Fluorescent Protein in Cell Biology and Biotechnology. Nat Biotech 1997, 15 (10), 961-964.

Mitchell et al., "Self-Assembly of Chiral DNA Nanotubes", J. Am. Chem. Soc., vol. 126, pp. 16342-16343, 2004.

Mittelstadt, et al., "Interaction of human tRNA-dihydrouridine synthase-2 with interferon-induced protein kinase PKR," Nucleic Acids Research, vol. 36, No. 3, pp. 998-1008, (2008).

Mockl et al., Filamentation and Restoration of Normal Growth in *Escherichia coli* Using a Combined CRISPRi SgRNA/Antisense RNA Approach. PLoS One 2018, 13 (9), e0198058.

Mohr et al., "Catalytic Enantioselective Decarboxylative Protonation." Journal of American Chemical Society, vol. 128.35, pp. 11348-11349, 2006.

Mohr et al., "Natural Products as Inspiration for the Development of Asymmetric Catalysis." Nature, vol. 455, pp. 323-332, Sep. 18, 2008.

Moon et al., Improving CRISPR Genome Editing by Engineering Guide RNAs. Trends Biotechnol. 2019, 37 (8), 870-881., https://doi.org/10.1016/j.tibtech.2019.01.009.

Morgan et al., Manipulation of Nuclear Architecture through CRISPR-Mediated Chromosomal Looping. Nat. Commun. 2017, 8 (1), 15993. https://doi.org/10.1038/ncomms15993.

Moroz-Omori et al., Photoswitchable GRNAs for Spatiotemporally Controlled CRISPR-Cas-Based Genomic Regulation. ACS Cent. Sci. 2020, 6 (5), 695-703. https://doi.org/10.1021/acscentsci.9b01093.

Myers et al., Discovery of Proteins Associated with a Predefined Genomic Locus via DCas9-APEX-Mediated Proximity Labeling. Nat. Methods 2018, 15 (6), 437-439. https://doi.org/10.1038/s41592-018-0007-1.

Nakano et al., "Selection for thermodynamically stable DNA tetraloops using temperature gradient gel electrophoresis reveals four motifs: d(cGNNAg), d(cGNABg), d(cCNNGg), and d(gCNNGc)," Biochemistry, vol. 41, pp. 14281-14292, American Chemical Society, 2002.

Naked Scientists (The): Science Radio & Science Podcasts, "RNA-away cancer cells", Sep. 12, 2010, http://www.thenakedscientists.com/HTML/content/news/2051/.

Nargessi et al., "Quantitation of progesterone receptor mRNA in breast carcinoma by branched DNA assay", Breast Cancer Research and Treatment, vol. 50, pp. 57-62, 1998.

National Science Foundation, "These Cells Will Self-Destruct in Five . . . Four . . . ", Press Release 10-160, p. 1-3, 2010.

Nieto, M. et al., "In situ hybridization analysis of chick embryos in whole mount and tissue sections," Methods in Cell Biology, vol. 51, pp. 219-235, 1996.

Nihongaki, Y.; Otabe, T.; Sato, M. Emerging Approaches for Spatiotemporal Control of Targeted Genome with Inducible CRISPR-Cas9. Anal Chem 2018, 90 (1), 429-439.

Nikolakakis, K et al., Use of Hybridization Chain Reaction-Fluorescent In Situ Hybridization to Track Gene Expression by Both Partners during Initiation of Symbiosis, Applied and Environmental Microbiology, vol. 81, No. 14, pp. 4728-4735, (2015).

Nissim et al., Programmable Regulation of Gene Networks with an Integrated RNA and CRISPR/Cas Toolkit in Human Cells. Mol Cell 2019, 54 (4), 698-710.

Noll et al., "Formation and Repair of Interstrand Cross-Links in DNA." Chemical Reviews, vol. 106.2, pp. 277-301, 2006.

Noll et al., "Preparation of Interstrand Cross-Linked DNA Oligonucleotide Duplexes." Frontiers in Bioscience, vol. 9, pp. 421-437, Jan. 1, 2004.

Nolte et al., Clinical Comparison of an Enhanced-Sensitivity Branched-DNA Assay and Reverse Transcription-PCR for Quantitation of Human Immunodeficiency Virus Type 1 RNA in Plasma, Journal of Clinical Microbiology, vol. 36, No. 3, pp. 716-720, 1998.

Nolte, et al., Branched DNA Signal Amplification for Direct Quantitation of Nucleic Acid Sequences in Clinical Specimens, Advances in Clinical Chemistry, vol. 33, pp. 201-235, 1998.

Duckworth et al., "A Universal Method for the Preparation of Covalent Protein-DNA Conjugates for Use in Creating Protein Nanostructures", Agnew. Chem. Int. Ed., vol. 46, pp. 8819-8822, 2007.

Dunn JJ, et al., "Complete nucleotide-sequence of bacteriophage-T7 DNA and the locations of T7 genetic elements." J Mol Biol, vol. 166, pp. 477-535, 1983.

Eckstein, F., "Phosphorthioate oligodeooxynucleotides: what is their origin and what is unique about them?" Antisense Nucleic Acid Drug Dev., vol. 10, pp. 117-121, 2000.

Eddy, S.R., "Non-coding RNA genes and the modern RNA world." Nature Reviews, vol. 2, pp. 919-929, 2001.

Elbashir et al., "Functional anatomy of siRNAs for mediating efficient RNAi in Drosophila melanogaster embryo lysate", The EMBO Journal, vol. 20, No. 23, pp. 6877-6888, 2001.

Elbeik et al., Quantitative and Cost Comparison of Ultrasensitive Human Immunodeficiency Virus Type 1 RNA Viral Load Assays: Bayer bDNA Quantiplex Versions 3.0 and 2.0 and Roche PCR Amplicor Monitor Version 1.5, Journal of Clinical Microbiology, vol. 38, No. 3, pp. 1113-1120, Mar. 2000.

Elghanian et al., "Selective colorimetric detection of polynucleotides based on the distance-dependent optical properties of gold nanoparticles," Science, vol. 277, No. 5329, pp. 1078-1081, 1997.

Ellington, A. et al., "In vitro selection of RNA molecules that bind specific ligands," Nature, vol. 346, pp. 818-822, Aug. 30, 1990.

Elmen et al., "Locked Nucleic Acid (LNA) Mediated Improvements in siRNA Stability and Functionality." Nucleic Acids Research, vol. 33.1, pp. 439-447, 2005.

Engel et al., "Detection of circulating tumour cells in patients with breast or ovarian cancer by molecular cytogenetics", British Journal of Cancer, vol. 81, No. 7, pp. 1165-1173, 1999.

Enquist et al., "The Total Synthesis of (−)-Cyanthiwigin F by Means of Double Catalytic Enantioselective Alkylation." Nature 453.7199 (Jun. 26, 2008) 1228-1231.

Evanko, "Hybridization chain reaction", Nature Methods, vol. 1, No. 3, pp. 186-187, Dec. 2004.

Feldkamp et al., "Rational Design of DNA Nanoarchitectures", Angew. Chem. Int. Ed., vol. 45, pp. 1856-1876, 2006.

Felgner et al., "Nomenclature for Synthetic Gene Delivery Systems", Human Gene Therapy, vol. 8, pp. 511-512, Mar. 20, 1997.

Femino, A et al., "Visualization of Single Molecules of mRNA in Situ." Methods of Enzymology, vol. 361, pp. 245-304, 2003.

Femino, A. et al., "Visualization of single RNA transcripts in situ," Science, vol. 280, Issue 5363, pp. 585-590, Apr. 24, 1998.

Ferkol et al., "Gene Transfer into the Airway Epithelium of Animals by Targeting the Polymeric Immunoglobulin Receptor", J. Clin. Invest., vol. 95, pp. 493-502, Feb. 1995.

Ferkol et al., "Regulation of the phosphoenolpyruvate carboxykinase/human factor IX gene introduced into the lives of adult rats by receptor-mediated gene transfer", The FASEB Journal, vol. 7, DD. 1081-1091, Aug. 1993.

Ferre, F., "Gene Quantification", © Birkhauser Boston 1998, Foreword by Edwin Southern (Advanced biomedical technologies), 379 pages.

Ferreira et al., "The Palladium-Catalyzed Oxidative Kinetic Resolution of Secondary Alcohols with Molecular Oxygen." Journal of American Chemical Society, vol. 123.31, pp. 7725-7726, 2001.

(56) References Cited

OTHER PUBLICATIONS

Ferry et al., Rational Design of Inducible CRISPR Guide RNAs for de Novo Assembly of Transcriptional Programs. Nat Commun 2017, 8, 2109.
File History for U.S. Appl. No. 12/790,379, filed May 28, 2010; entitled "Hybridization Chain Reaction Amplification for In Situ Imaging".
File History for U.S. Appl. No. 13/186,315, filed Jul. 19, 2011; entitled Triggered Molecular Geometry Based Bioimaging Probes.
File History of U.S. Appl. No. 16/005,445.
File History of U.S. Appl. No. 15/639,100.
File History of U.S. Appl. No. 15/689,786.
File History of U.S. Appl. No. 14/033,081.
Fire et al., "Potent and specific genetic interference by double-stranded RNA in Caenorhabditis elegans", Nature, vol. 391, pp. 806-811, Feb. 19, 1998.
Flamm et al., "RNA folding at elementary step resolution," RNA, 2000, pp. 325-338, vol. 6, Cambridge University Press.
Fox et al., "Antiviral treatment normalizes neurophysiological but not movement abnormalities in simian immunodeficiency virus-infected monkeys", J Clin Invest., vol. 106, No. 1, pp. 37-45, 2000.
Friedrich et al., A Cellular Screening Assay to Test the Ability of PKR to Induce Cell Death in Mammalian Cells, Molecular Therapy, vol. 12, No. 5, pp. 969-975, Nov. 2005.
Friedrich et al., "RNA molecules as anti-cancer agents", Seminars in Cancer Biology, vol. 14, DD. 223-230, 2004.
Fu et al., "DNA Double-Crossover Molecules", Biochemistry, vol. 32, pp. 3211-3220, 1993.
Gall, J. et al., "Formation and detection of RNA-DNA hybrid molecules in cytological preparations," Proc Natl Acad Sci USA, vol. 63, No. 2, DD. 378-383, Jun. 1, 1969.
Gao et al., Delineation of the Exact Transcription Termination Signal for Type 3 Polymerase III. Mol. Ther. Nucleic Acids 2018, 10, 36-44.
Garcia et al., "Impact of Protein Kinase PKR in Cell Biology: from Antiviral to Antiproliferative Action." Microbiology and Molecular Biology Reviews, vol. 70, No. 4, pp. 1032-1060, Dec. 2006.
Garg et al., "A Ligand-free Solid-supported System for Sonogashira Couplings: Applications in Nucleoside Chemistry." Chem. Commun. (2005) 4551-4553.
Garg et al., "Development of an Enantiodivergent Strategy for the Total Synthesis of(+)- and (−)-Dragmacidin F from a Single Enantiomer of Quinic Acid." Journal of American Chemical Society 127 (2005) 5970-5978.
Gasparro et al., Site-specific targeting of psoralen photadducts with a triple helix-forming oligonuicleotide: characterization of psoralen monoadduct and crosslink formation. Nucleic Acids Research 22 (1994), DD. 2845-2852.
Gaudelli et al., Programmable Base Editing of A•T to G•C in Genomic DNA without DNA Cleavage. Nature 2017, 551 (7681), 464-471. https://doi.org/10.1038/nature24644.
Geary et al., A Single-Stranded Architecture for Cotranscriptional Folding of RNA Nanostructures. Science 2014, 345 (6198), 799-804.
Gilbert, L et al. 'CRISPR-Mediated Modular RNA-Guided Regulation of Transcription in Eukaryotes', Cell, 154: 442-51, (2013).
Gilman et al., "The Biological Actions and Therapeutic Applications of the B-Chloroethyl Amines and Sulfides." Science 103.2675 (Apr. 5, 1946): 409-415.
Glick et al., Metabolic Load and Heterologous Gene Expression. Biotechnol. Adv. 1995, 13 (2), 247-261. https://doi.org/10.1016/0734-9750(95)00004-A.
Goodman, R.P.; Schaap, I.A.T.; Tardin, C.F.; Erben, C.M.; Berry, R.M.; Schmidt, C.F.; and Turberfield, A.K. "Rapid chiral assembly of rigid DNA blocks for molecular nanofabrication." Science, 310, 2005.
Green et al., "DNA Hairpins: Fuel for Autonomous DNA Devices", Biophysical Journal, vol. 91, pp. 2966-2975, Oct. 2006.
Green et al., Toehold Switches: De-Novo-Designed Regulators of Gene Expression. Cell 2014, 159 (4), 925-939.

Gross-Thebing et al., "Simultaneous high-resolution detection of multiple transcripts combined with localization of proteins in whole-mount embryos", BMC Biology, vol. 12, No. 55, 2014.
Ha et al., Regulation of microRNA biogenesis, Nature Reviews Molecular Cell Biology, vol. 15, pp. 509-524. Jul. 16, 2014.
Hanewich-Hollatz et al. "Conditional Guide RNAs: Programmable Conditional Regulation of CRISPR/Cas Function in Bacterial and Mammalian Cells via Dynamic RNA Nanotechnology" ACS Cent Sci., Jul. 24, 2019, vol. 5, No. 7, DD 1241-1249.
Nowak et al., Guide RNA engineering for versatile Cas9 functionality. Nucleic Acids Research (2016), 44(20): 9555-9564 (Year: 2016).
Nutiu et al., "Structure-switching signaling aptamers," J. Am. Chem. Soc., vol. 125, pp. 4771-4778, American Chemical Society, 2003.
Oesinghaus, L.; Simmel, F. C. Switching the Activity of Cas12a Using Guide RNA Strand Displacement Circuits. Nat. Commun. 2019, 10 (1), 1-11. https://doi.org/10.1038/s41467-019-09953-w.
Opalinska et al., "Nucleic-Acid Therapeutics: Basic Principles and Recent Applications", Nature Reviews Drug Discovery, vol. 1, pp. 503-514, 2002.
Ouporov, Igor V., and Leontis, Necocles B., "Refinement of the Solution Structure of a Branched DNA Three-Way Junction," Biophysical Journal, vol. 68, pp. 266-274. Jan. 1995.
Pachl et al., "Rapid and Precise Quantification of HIV-1 RNA in Plasma Using a Branched DNA Signal Amplification Assay", Journal of Acquired Immune Deficiency Syndromes and Human Retrovirology, vol. 8, pp. 446-454, 1995.
Pardee et al., Paper-Based Synthetic Gene Networks. Cell 2014, 159 (4), 940-954. https://doi.org/10.1016/j.cell.2014.10.004.
Pardee et al., Rapid, Low-Cost Detection of Zika Virus Using Programmable Biomolecular Components. Cell 2016, 165 (5), 1255-1266, https://doi.org/10.1016/j.cell.2016.04.059.
Pardi et al., MRNA Vaccines—a New Era in Vaccinology. Nat. Rev. Drug Discov. 2018, 17 (4), 261-279. https://doi.org/10.1038/nrd.2017.243.
Park et al., "Programmable DNA Self-Assemblies for Nanoscale Organization of Ligands and Proteins." Nano Letters, vol. 5, pp. 729-733, 2005.
Park et al., "Rapid Identification of Candida dubliniensis Using a Species-Specific Molecular Beacon", Journal of Clinical Microbiology, vol. 38, No. 8, pp. 2829-2836, 2000.
Park et al., "Three-Helix Bundle DNA Tiles Self-Assemble into 2D Lattice or 1D Templates for Silver Nanowires", Nano Lett., vol. 5, No. 4, pp. 693-696, 2005.
Patel et al., Cancer Biology & Therapy, vol. 14, No. 8, pp. 693-696; Aug. 2013.
Paterson et al., Efficient Translation of Prokaryotic MRNAs in a Eukaryotic Cell-Free System Requires Addition of a Cap Structure. Nature 1979, 279 (5715), 692-696., https://doi.ora/10.1038/279692a0.
Patterson, B., Techniques in Quantification and Localization of Gene Expression, Springer Science+Business Media, LLC, © 2000 Springer Science+Business Media New York, Originally published by Birkhauser Boston in 2000, 157 pages.
Paul et al., "A self-replicating ligase ribozyme", PNAS, vol. 99, No. 20, pp. 12733-12740, Oct. 1, 2002.
Pawlotsky et al., "Quantification of hepatitis C virus RNA in serum by branched DNA-based signal amplification assays", Journal of Virological Methods, vol. 79, pp. 227-235, 1999.
Peng et al., Facile SNP detection using bifunctional, cross-linking oligonucleotide probes, Nucleic Acids Research vol. 36 No. 5e31 (2008), pp. 1-7.
Perales et al., "Gene Transfer in vivo: Sustained Expression and Regulation of Genes Introduced into the Liver by Receptor-Targeted Uptake", Proceedings of the National Academy of Sciences of the United States of America, vol. 91, pp. 4086-4090, Apr. 1994.
Pernthaler, A. et al., "Fluorescence in situ hybridization and catalyzed reporter deposition for the identification of marine bacteria," Applied and Environmental Microbiology, vol. 68, No. 6, pp. 3094-3101, Jun. 2002.
Pieles, U. and Englisch, U., "Psoralen covalently linked to oligodeoxyribonucleotides: synthesis, sequence specific recognition

(56) References Cited

OTHER PUBLICATIONS of DNA and photo-cross-linking to purimidine residues of DNA," Nucleic Acids Research, vol. 17, pp. 285-299, 1989.
Piette, D. et al., "An optimized procedure for whole-mount in situ hybridization on mouse embryos and embryoid bodies," Nature Protocols, vol. 3, No. 7, pp. 1194-1201, 2008.
Pijlman et al., A Highly Structured, Nuclease-Resistant, Noncoding RNA Produced by Flaviviruses Is Required for Pathogenicity. Cell Host Microbe 2008, 4 (6), 579-591.
Pinheiro et al., Challenges and Opportunities for Structural DNA Nanotechnol. Nat. Nanotechnol. 2011, 6 (12), 763-772., https://doi.org/Doi 10.1038/Nnano.2011.187.
Piston et al., "Fluorescent protein FRET: the good, the bad and the ugly", Trends Biochem Sci., Sep. 2007, vol. 32, No. 9, pp. 407-414.
Piyush K. Jain et al: "Development of Light-Activated CRISPR Using Guide RNAs with Photocleavable Protectors", Angewandte Chemie International Edition, vol. 55, No. 40, Aug. 24, 2016 (Aug. 24, 2016), pp. 12440-12444, XP055736874.
Player, "An Enhanced-Sensitivity Branched-DNA Assay for Quantification of Human Immunodeficiency Virus Type 1 RNA in Plasma", 2001.
Player, A. et al., "Single-copy gene detection using branched DNA (bDNA) in situ hybridization," The Journal of Histochemistry and Cytochemistry, vol. 49, No. 5, pp. 603-611, 2001.
Pouton et al., "Key issues in non-viral gene delivery", Advanced Drug Delivery Reviews, vol. 46, pp. 187-203, 2001.
Product: VERSANT HIV-1 RNA 3.0 Assay (bDNA), PMA No. BP000028/0, Approval Date: Sep. 11, 2002.
Provost, P. et al., "Ribonuclease activity and RNA binding of recombinant human Dicer," EMBO J., vol. 21, pp. 5864-5874, 2002.
Qi et al., "Surface Transfer Doping of Diamond (100) by Tetrafluorotetracyanoquinodimethane", J. Am. Chem. Soc., vol. 129, pp. 8084-8085, 2007.
Qi, L. S.; Larson, M. H.; Gilbert, L.A.; Doudna, J. A.; Weissman, J. S.; Arkin, A. P.; Lim, W. A. Repurposing CRISPR as an RNA-Guided Platform for Sequence-Specific Control of Gene Expression. Cell 2013, 152 (5), 1173-1183. https://doi.org/10.1016/j.cell.2013.02.022.
Qian et al., "Recent Developments in Signal Amplification Methods for In Situ Hybridization," Diagnostic Molecular Pathology, vol. 12, No. 1, pp. 1-13, 2003.
Qian et al., Scaling Up Digital Circuit Computation with DNA Strand Displacement Cascades. Science 2011, 332 (6034), 1196-1201. https://doi.org/Doi10.1126/Science.1200520.
Qian, X., L. Jin, and R.V. Lloyd, In situ hybridization: basic approaches and recent development. The Journal of Histotechnology, 2004. 27(1): p. 53-67.
Rachofsky et al., "Probing structure and dynamics of DNA with 2-aminopurine: Effects of local environment on fluorescence," Biochemistry, vol. 40, DD. 946-956, 2001.
Raj et al., "Imaging Individual mRNA Molecules Using Multiple Singly Labeled Probes." Nature Methods 5.1O (Oct. 2008): 877-879.
Rana et al., Chemical Communications 52 :3524-3527 (Year: 2016).
Ravan, H., Isothermal RNA detection through the formation of DNA concatemers containing HRP-mimicking DNAzymes on the surface of gold nanoparticles, Biosensors and Bioelectronics, vol. 80, pp. 67-73, 2016.
Read et al., "Barriers to Gene Delivery Using Synthetic Vectors", Advances in Genetics, vol. 53, pp. 19-46, 2005.
Regulation of CRISPR/Cas Function in Bacterial and Mammalian Cells via Dynamic RNA Nanotechnology. ACS Cent. Sci. 2019, 5 (7), 1241-1249. (27) Liu, Y.; Zhan, Y.; Chen, Z.; He, A.; Li, J.; Wu, H.; Liu, L.; Zhuang, C.; Lin, J.; Guo, X.; Zhang, Q.; Huang, W.; Cai, Z. Directing Cellular Information Flow via CRISPR Signal Conductors. Nat Methods 2016, 13, 938-944.
Reif et al., "Compact Error-Resilient Computational DNA tiling Assemblies." In Proc. 10.sup.th International Meeting on DNA Computing; 2004.
Reif et al., "Complexity of Graph Self-Assembly in Accretive Systems and Self-Destructible Systems." In Proc. 11.sup. th International Meeting on DNA Computing; 2005.
Reynolds et al., "Rational siRNA Design for RNA Interference." Nature Biotechnology, vol. 22.3, pp. 326-330, Mar. 2004.
Rosen et al., Whole-Mount Insitu Hybridization in the Mouse Embryo: Gene-Expression in three Dimensions, Trends Genet., vol. 9, No. 5, 1993, pp. 162-166.
Rosenthal, A. et al., "Localizing transcripts to single cells suggests an important role of uncultured deltaproteobacteria in the termite gut hydrogen economy," PNAS, vol. 110, No. 40, DD. 16163-16168, Oct. 1, 2013.
Ross et al., Quantitation of hepatitis C virus RNA by third generation branched DNA-based signal amplification assay, Journal of Virological Methods, vol. 101, No. 1-2, pp. 159-168, 2002.
Roth et al., Selective for the Queuosine Precursor PreQ1 Contains an Unusually Small Aptamer Domain. Nat. Struct. Mol. Biol. 2007, 14 (4), 308-317, https://doi.orQ/10.1038/nsmb1224.
Rothemund et al., "Design and Characterization of Programmable DNA Nanotubes", J. Am. Chem. Soc., vol. 126, pp. 16344-16352, 2004.
Rothemund et al., "The Program-size complexity of self-assembled squares (extended abstract)." In Proceedings of the thirty-second annual ACM symposium on Theory of computing; ACM Press: 2000.
Rothemund et al., "Algorithmic Self-Assembly of DNA Sierpinski Triangles." PLoS Biology, vol. 2, pp. 2041-2053, 2004.
Rothemund, P.W.K., "Folding DNA to creat nanoscale shapes and patterns", Nature, vol. 440, pp. 297-302, 2006.
Sahin et al., MRNA-Based Therapeutics—Developing a New Class of Drugs. Nat. Rev. Drug Discov. 2014, 13 (10), 759-780, https://doi.org/10.1038/nrd4278.
Sahu et al., "A self-Assembly Model of Time-Dependent Glue Strength." In Proc. 11th International Meeting on DNA Computing; 2005.
Sambrook et al. (Molecular Cloning: A Laboratory Manual. Cold Spring Harbor Laboratory Press, N.Y. (1989).
Sander, J et al., 'CRISPR-Cas systems for editing, regulating and targeting genomes', Nat Biotech, 32: 347-55., (2014).
Santalucia J. "A unified view of polymer, dumbbell, and oligonucleotide DNA nearest-neighbor thermodynamics" Proc Natl Acad Sci 95:1460-1465 (1998).
Saunders et al., "Introduction of DNA into Bacteria." Methods in Microbiology 29 (1999): 3-49.
Scharer et al., "DNA Interstrand Crosslinks: Natural and Drug-Induced DNA Adducts that Induce Unique Cellular Responses." ChemBioChem 6 (2005): 27-32.
Scherer et al., "Approaches for the sequence-specific knockdown of mRNA", Nature Biotechnoloav, vol. 21, No. 12, pp. 1457-1465, 2003.
Schipani, Vanessa, "A targeted cancer therapy?" The Scientist, Sep. 7, 2010 blog post, http://www.the-scientist.com/blog/display/57674/.
Schulman et al., "Synthesis of crystals with a programmable kinetic barrier to nucleation", PNAS, vol. 104, No. 39, pp. 15236-15241, Sep. 25, 2007.
Schulte-Merker et al., "no tail (ntl) is the zebrafish homologue of the mouse T (Brachyury) gene." Development 120 (1994): 1009-1015.
Schwartz et al., "Cloning and Functional Analysis of Multiply Spliced mRNA Species of Human Immunodeficiency Virus Type 1", Journal of Virology, vol. 64, No. 6, pp. 2519-2529, Jun. 1990.
Schwarzkopf et al., Multiplexed MiRNA Northern Blots via Hybridization Chain Reaction. Nucleic Acids Res. 2016, 44 (15), e129, https://doi.org/10.1093/nar/gkw503.
Schweitzer et al., "Combining nucleic acid amplification and detection," Curr Opin Biotechnol, 12, pp. 21-27, 2001.
Seelig et al., "Catalyzed Relaxation of a Metastable DNA Fuel", Journal American Chemical Society, vol. 128, No. 37, pp. 12211-12220, 2006.
Seelig et al., Enzyme-Free Nucleic Acid Logic Circuits. Science 2006, 314 (5805), 1585-1588.

(56) References Cited

OTHER PUBLICATIONS

Seeman et al., Nucleic Acid Nanostructures: Bottom Up Control of Geometry on the Nanoscale, Reports on Progress in Physics, vol. 68, pp. 237, 2005.
Seeman, "De Novo Design of Sequences for Nucleic Acid Structural Engineering", Journal of Biomolecular Structure & Dynamics, pp. 573-581, vol. 8, No. 3, 1990.
Seeman, "DNA in a material world", Department of Chemistry, New York University, NATURE, vol. 421, pp. 427-431 (Jan. 23, 2003).
Seeman, "Nucleic acid junctions and lattices," J. Theor. Biol., vol. 99, pp. 237-247, Academic Press Inc. (London) Ltd., 1982.
Seeman, "Nucleic acid nanostructures and topology", Angew. Chem. Int. Ed. vol. 37, pp. 3220-3238 (1998).
Segondy et al., "Comparison of the Quantiplex HIV-1 RNA 2.0 Assay with the Amplicor HIV-1 Monitor 1.0 Assay for Quantitation of Levels of Human Immunodeficiency Virus Type 1 RNA in Plasma of Patients Receiving Stavudine-Didanosine Combination Therapy", Journal of Clinical Microbiology, vol. 36, No. 11, pp. 3392-3395, Nov. 1998.
Sekulic et al., "A Direct Linkage between the Phosphoinositide 3-Kinase-AKT Signaling Pathway and the Mammalian Target of Rapamycin in Mitogen-stimulated and Transformed Cells," Cancer Research, vol. 60, pp. 3504-3513, 2000.
Serra M.J., Turner D.H., "Predicting thermodynamic properties of RNA" Methods Enzymol 259: 242-261 (1995).
Shagin et al., GFP-like Proteins as Ubiquitous Metazoan Superfamily: Evolution of Functional Features and Structural Complexity. Mol. Biol. Evol. 2004, 21 (5), 841-850. https://doi.org/10.1093/molbev/msh079.
Shah et al., "The Fries Isomerization of Acetyl and Benzoyl Esters of Umbelliferones." J. Org. Chem. 19 (1954): 1681-1685,.
Shah, S. et al., "Single-molecule RNA detection at depth via hybridization chain reaction and tissue hydrogel embedding and clearing," Development, 41 pages, Jun. 2016.
Shaner et al., "A guide to choosing fluorescent proteins", Nature Methods, vol. 2, No. 12, pp. 905-909, Dec. 2005.
Sharma et al., "DNA-Tile-Directed Self-Assembly of Quantum Dots into Two-Dimensional Nanopatterns", Angew. Chem. Int. Ed., vol. 47, pp. 5157-5159, 2008.
Sharma et al., "Control of Self-Assembly of DNA Tubules through Integration of Gold Nanoparticles" Science, pp. 112-116, 2009.
Shen et al., Conditional Knockouts Generated by Engineered CRISPR-Cas9 Endonuclease Reveal the Roles of Coronin in C. Elegans Neural Development. Dev. Cell 2014, 30 (5), 625-636.
Sherman et al., "Quantitative Evaluation of Hepatitis C Virus RNA in Patients with Concurrent Human Immunodeficiency Virus Infections", Journal of Clinical Microbiology, vol. 31, No. 10, pp. 2679-2682, Oct. 1993.
Shih et al., "A 1.7-kilobase single-stranded DNA that folds into a nanoscale octahedron", Nature, vol. 427, pp. 618-621, Feb. 12, 2004.
Shir et al., "Inhibition of glioma growth by tumor-specific activation of double-stranded RNA-dependent protein kinase PKR", Nature Biotechnology, vol. 20, pp. 895-900, Sep. 2002.
Shlyakhtenko et al., "Structure and Dynamics of Three-Way DNA Junctions: Atomic Force Microscopy Studies." Nucleic Acids Research. 2000. 28(19): 3472-3477.
Shlyakhtenko et al., "Structure of Three-Way DNA Junctions 1. Non-Planar DNA Geometry" Journal of Biomolecular Structure and Dynamics, vol. 11: pp. 1175-1189, Nov. 6, 1994.
Silverman et al., "Oligonucleotide Probes for RNA-Targeted Fluorescence In Situ Hybridization." Advances in Clinical Chemistry 43 (2007): 79-115.
Silverman et al., "Quenched Autoligation Probes Allow Discrimination of Live Bacterial Species by Single Nucleotide Differences in rRNA." Nucleic Acids Research 33.15 (2005): 4978-4986.
Singleton, P. et al., "Dictionary of Microbiology and Molecular Biology," 2nd Edition, J. Wiley & Sons, 1994.
Siolas et al., "Synthetic shRNAs as Potent RNAi Triggers." Nature Biotechnology 23.2 (Feb. 2005): 227-231.
Situma et al., "Immobilized molecular beacons: A new strategy using UV-activated poly(methyl methacrylate) surfaces to provide large fluorescence sensitivities for reporting on molecular association events." Analytical Biochemistry 363 (2007) 35-45.
Siu, K.-H.; Chen, W. Riboregulated Toehold-Gated GRNA for Programmable CRISPR-Cas9 Function. Nat. Chem. Biol. 2019, 15 (3), 217-220. https://doi.org/10.1038/s41589-018-0186-1.
Smith et al., Determination of Cryptosporidium parvum oocyst viability by fluorescence in situ hybridization using a ribosomal RNA-directed probe. J Appl Microbiol 96(2):409-417, 2004.
Sokol et al., "Real time detection of DNA.circle-solid.RNA hybridization in living cells", Proc. Natl. Acad. Sci. USA, vol. 95, pp. 11538-11543, Sep. 1998.
Stack, E., et al. Multiplexed immunohistochemistry, imaging, and quantitation: A review, with an assessment of Tyramide signal amplification, multispectral imaging and multiplex analysis, . Methods, vol. 70, No. 1, (2014).
Steckelberg et al., A Folded Viral Noncoding RNA Blocks Host Cell Exoribonucleases through a Conformationally Dynamic RNA Structure. Proc. Natl. Acad. Sci. 2018, 115 (25), 6404-6409. https://doi.ora/10.1073/pnas.1802429115.
Steckelberg et al., Exoribonuclease-Resistant RNAs Exist within Both Coding and Noncoding Subgenomic RNAs. mBio 2018, 9 (6), e02461-18, /mbio/9/6/mBio.02461-18.atom. https://doi.ora/10.1128/mBio.02461-18.
Aagaard et al., "RNAi Therapeutics: Principles, Prospects and Challenges." Advanced Drug Delivery Reviews, vol. 59, pp. 75-86, 2007.
Ablain et al., A CRISPR/Cas9 Vector System for Tissue-Specific Gene Disruption in Zebrafish. Dev. Cell 2015, 32 (6), 756-764. https://doi.org/10.1016/j.devcel.2015.01.032.
Abudayyeh,.O et al. C2c2 is a single-component programmable RNA-guided RNA-targeting CRISPR effector, Science, (2016).
Acharya, A, Multiplexed Analysis of Diverse RNA Classes via Hybridization Chain Reaction. PhD Thesis, California Institute ofTechnology, 2016.
Acloque, H. et al., "In situ hybridization analysis of chick embryos in whole-mount and tissue sections," Methods in Cell Biology, vol. 87, pp. 169-185, 2008.
Allan et al., "A Concise Total Synthesis of (-)-Quinocarcin via Aryne Annulation," Journal of American Chemical Society, vol. 130, pp. 17270-17271, 2008.
Amarzguioui et al., "Rational design and in vitro and in vitro delivery of Dicer substrate siRNA," Nature Protocols, vol. 1, No. 2, pp. 508-617, 2006.
An, C. I. et al., "Artificial control of gene expression in mammalian cells by modulating RNA interference through aptamer-small molecule interaction," RNA, vol. 12, 710-716, 2006.
Andronescu et al., "A New Algorithm for RNA Secondary Structure Design", J. Mol. Biol., vol. 336, pp. 607-624, 2004.
Antao et al., In Situ Hybridization Using the bDNA Technology. In: Patterson B.K. (eds) Techniques in Quantification and Localization of Gene Expression. Birkhauser, Boston, MA. (Year: 2000).
Anzalone et al., Search-and-Replace Genome Editing without Double-Strand Breaks or Donor DNA. Nature 2019, 576 (7785), 149-157. https://doi.org/10.1038/s41586-019-1711-4.
Appendix Feb. 12, 2020, Prepared by the Examiner on Feb. 12, 2020.
Asbury, C.L., "Kinesin: world's tihiest biped", Current Opinion in Cell Biology, vol. 17, pp. 89-97, 2005.
Aubrey et al., An Inducible Lentiviral Guide RNA Platform Enables the Identification of Tumor-Essential Genes and Tumor-Promoting Mutations in Vivo. Cell Rep. 2015, 10 (8), 1422-1432.
Barish et al., "An Information-Bearing seed for nucleating algorithmic self assembly." Proceedings of the National Academy of Sciences, vol. 106, pp. 6054, 2009.
Barrangou, R, et al., 2007. 'CRISPR Provides Acquired Resistance Against Viruses in Prokaryotes', Science, 315, pp. 1709-1712, (2007).
Barroso-Chinea, P. et al., "Detection of two different mRNAs in a single section by dual in situ hybridization: A comparison between

(56) References Cited

OTHER PUBLICATIONS colorimetric and fluorescent detection," Journal of Neuroscience Methods, vol. 162, Issues 1-2, pp. 119-128, May 15, 2007.
Bates et al., "Multicolor super-resolution imaging with photoswitchable fluorescent probes." Science, vol. 317, pp. 1749-1759, 2007.
Bath et al., "DNA nanomachines", Nature Nanotechnology, vol. 2, pp. 275-284, May 2007.
Bayer Versant (TM) HCV RNA 3.0 Assay (bDNA), Premarket Approval (PMA) Notice, 2004.
Bayer Versant® HCV RNA 3.0 Assay (bDNA) product manual (date 2003).
Bayer Versant® HIV-1 RNA 3.0 Assay (bDNA) FDA Summary of Safety and Effectiveness (approval date 2002).
Behenna et al., "The Enantioselective Tsuji Allylation," Journal of American Chemical Society, vol. 126.46 pp. 15044-15045, 2004.
Beisel, C. L. et al., "Design of small molecule-responsive microRNAs based on structural requirements for Drosha processing," Nucleic Acids Res., vol. 39, pp. 2981-2994, 2011.
Beisel, C. L et al., "Model-guided design of ligand-regulated RNAi for programmable control of gene expression," Mol. Syst. Biol., vol. 4, pp. 224, 2008.
Berry et al., "HIV-1 and HIV-2 Molecular Diagnosis", HIV and the New Viruses Second Edition, pp. 207-222, Copyright © 1999 Academic Press.
Bertero et al., Optimized Inducible ShRNA and CRISPR/Cas9 Platforms for in Vitro Studies of Human Development Using HPSCs. Development 2016, 143 (23), 4405.
Bhatia et al., Icosahedral DNA Nanocapsules by Modular Assembly, Angew. Chem. Int. Ed., vol. 48, pp. 4134-4137, 2009.
Bloomfeld et al., "Nucleic Acids: Structures, Properties, and Functions," University Science Books, Table of Contents Only, 2000.
Boehm et al., Interrogating the Degradation Pathways of Unstable MRNAs with XRN1-Resistant Sequences. Nat. Commun. 2016, 7 (1), 13691. https://doi.org/10.1038/ncomms13691.
Bois et al., "Topological constraints in nucleic acid hybridization kinetics", Nucleic Acids Research, vol. 33, No. 13, pp. 4090-4095, 2005.
Bois J.S., "Analysis of interacting nucleic acids in dilute solutions" Ph.D. Thesis. California Institute of Technology. (2007).
Bolt et al., "Differential Reactivities of the mono- and di-epoxide of 1,3-butadiene," Toxicology, vol. 113, pp. 294-296, 1996.
Bonnet et al. Thermodynamic basis of the enhanced specificity of structured DNA probes, Proc. Natl. Acad. Sci. USA vol. 96 (May 1999), pp. 6171-6176.
Bouchard, H, et al., Antibody-drug conjugates: A new wave of cancer drugs. Bioorganic & Medicinal Chemistry Letters, vol. 24, No. 23, pp. 5357-5367, (2014).
Briner et al., Guide RNA Functional Modules Direct Cas9 Activity and Orthogonality. Mol Cell 2014, 56 (2), 333-339. https://doi.org/10.1016/j.molcel.2014.09.019.
Brummelkamp, T. R. et al., "A system for stable expression of short interfering RNAs in mammalian cells" Science, vol. 296, pp. 550-553, 2002.
Bumcrot et al., "RNAi Therapeutics: A Potential New Class of Pharmaceutical Drugs." Nature Chemical Biology 2.12 (Dec. 2006): 711-719.
Bushnell et al., "ProbeDesigner: for the design of probesets for branched DNA (bDNA) signal amplification assays," Bioinformatics, vol. 15, No. 5, pp. 348-355, 1999.
Butterfoss et al., Computer-Based Design of Novel Protein Structures, Annu. Rev. Biophys. Biomol. Struct., vol. 35, paqes 49-65, 2006.
Caltech News Release, "Caltech Scientists Create New Process to Program", Sep. 6, 2010.
Caplen, "RNAi as a gene therapy approach", Expert Opin. Biol. Ther., vol. 3, No. 4, pp. 575-586, 2003.
Capodieci, P. et al., "Gene expression profiling in single cells within tissue," Nat Methods, vol. 2, No. 9, DD. 663-665, Sep. 2005.
Carbonell-Ballestero et al., Dealing with the Genetic Load in Bacterial Synthetic Biology Circuits: Convergences with the Ohm's Law. Nucleic Acids Res. 2016, 44 (1), 496-507. https://doi.org/10.1093/nar/qkv1280.
Castanotto et al., "The Promises and Pitfalls of RNA-Interface-Based Therapeutics." Nature, vol. 457, pp. 426-433, Jan. 22, 2009.
Cerutti et al., "On the Origin and Functions of RNA-Mediated Silencing: From Protists to Man." Current Genetics, vol. 50, pp. 81-99, 2006.
Chan, PM et al., "Method for multiplex cellular detection of mRNAs using quantum dot fluorescent in situ hybridization," Nucleic Acids Research, vol. 33, Issue 18, pp. e161, Jan. 1, 2005.
Chapell, et al., Renaissance in RNA Synthetic Biology: New Mechanisms, Applications and Tools for the Future. Curr Opin Chem Biol 28, 47-56, 2015.
Chapman et al., The Structural Basis of Pathogenic Subgenomic Flavivirus RNA (SfRNA) Production. Science 2014, 344 (6181), 307-310. https://doi.org/10.1126/science.1250897.
Chappell et al., Creating Small Transcription Activating RNAs. Nat. Chem. Biol., 11 (3), 214-220. https://doi.orq/10.1038/nchembio.1737, 2015.
Ke et al. "Scaffolded DNA Origami of a DNA Tetrahedron Molecular Container," Nanoletters, 2009. 9(6): 2445-2447.
Kenny et al., Detection of Viral Infection and Gene Expression in Clinical Tissue Specimens Using Branched DNA (BDNA) In Situ Hybridization, vol. 50, No. 9, pp. 1219-1227, 2002.
Kern et al., An Enhanced-Sensitivity Branched-DNA Assay for Quantification of Human Immunodeficiency Virus Type 1 RNA in Plasma, Journal of Clinical Microbiology, vol. 34, No. 12, pp. 3196-3202, 1996.
Kerstens, H.M. et al., "A novel in situ hybridization signal amplification method based on the deposition of biotinylated tyramine," The Journal of Histochemistry and Cytochemistry, vol. 43, No. 4, pp. 347-352, 1995.
Kieft et al., New Hypotheses Derived from the Structure of a Flaviviral Xrn1-Resistant RNA: Conservation, Folding, and Host Adaptation. RNA Biol 2015, 12 (11), 1169-1177. httDs://doi.ora/10.1080/15476286.2015.1094599.
Killops, K.L., Campos, L.M., Hawker, C.J, Robust, Efficient, and Orthogonal Synthesis of Dendrimers via Thiol-ene "Click" Chemistry. Journal of the American Chemical Society, 2008. 130: p. 5062-5064.
Kim et al., "Strategies for Silencing Human Disease Using RNA Interference." Nature Review Genetics 8 (Mar. 2007) 173-184.
Kim et al., "Synthetic dsRNA Dicer substrates enhance RNAi potency and efficacy", Nature BiotechnoloaY, vol. 23, No. 2, pp. 222-226, Feb. 2005.
Kim et al., CRISPR/Cas-Based Devices for Mammalian Synthetic Biology. Curr. Opin. Chem. Biol. 2019, 52, 23-30. https://doi.org/10.1016/j.cbpa.2019.04.015.
Kim et al., RNA Therapy: Current Status and Future Potential. Chonnam Med. J. 2020, 56 (2), 87. https://doi.org/10.4068/cmj.2020.56.2.87.
Kim J. et al., "Construction of an in vitro bistable circuit from synthetic transcriptional switches." Mal Syst Biol, vol. 2, pp. 68, 2006.
Kislauskis et al. "Isoform-specific 3'-untranslated Sequences Sort a-cardiac and 13-cytoplasmic Actin Mesenger RNAs to Different ytoplasmic Compartments," The Journal of Cell Biology, 123(1), DD. 165-172, 1993.
Knight, S. C.; Tjian, R.; Doudna, J. A. Genomes in Focus: Development and Applications of CRISPR-Cas9 Imaging Technologies. Angew Chem Int Ed 2018, 57 (16), 4329-4337.
Knorre et al., "Photoaffinity Labeling as an Approach to Study Supramolecular Nucleoprotein Complexes," FEBS Letters 433 (1998): 9-14.
Knott et al., CRISPR-Cas Guides the Future of Genetic Engineering. Science 2018, 361 (6405), 866-869.
Kobertz et al., "An Efficient Synthesis of a Furan-Side Furocoumarin Thymidine Monoadduct." J. Org. Chem. 62.8 (1997) 2630-2632.
Kobertz et al., "Solid-Phase Synthesis of Oligonucleotides Containing a Site-Specific Psoralen Derivative." Journal of American Chemical Society 119 (1997): 5960-5961.

(56) References Cited

OTHER PUBLICATIONS

Kobertz et al., "Total Synthesis of a Cis-Syn 2-Carbomethoxypsoralen Furan-Side Thymidine Monoadduct." Journal of American Chemical Society, vol. 118, pp. 7101-7107, 1996.
Kolberg et al., "Branched DNA (bDNA) Technology for Direct Quantification of Nucleic Acids: Research and Clinical Applications", pp. 327-338, 1998.
Koos, et al. 2015. "Proximity-Dependent Initiation of Hybridization Chain Reaction." Nature Communications 6: 7294. https://doi.org/ARTN 7294 10.1038/ncomms8294.
Kosman, D. et al., "Multiplex detection of RNA expression in Drosophila embryos," Science, vol. 305, Issue 5685, pp. 846, Aug. 6, 2004.
Kumar D, Kim SH, Yokobayashi Y (2011) Combinatorially inducible RNA interference triaaered by chemically modified oligonucleotides. J Am Chem Soc 133:2783-2788.
Kumar, D. et al., "Conditional RNA interference mediated by allosteric ribozyme," J Am Chem Soc, vol. 131, pp. 13906-13907, 2009.
Kundert et al., Controlling CRISPR-Cas9 with Ligand-Activated and Ligand-Deactivated SgRNAs. Nat Commun 2019, 10 (1), 2127. https://doi.org/10.1038/s41467-019-09985-2.
Kurreck, J. Angew. "RNA interference: from basic research to therapeutic applications" Chem., Int. Ed., vol. 48, pp. 1378-1398, 2009.
Kuzuya et al., "Six-Helix and Eight-Helix DNA Nanotubes Assembled from Half-Tubes", Nano Lett., vol. 7, No. 6, pp. 1757-1763, 2007.
Lacenere et al., "Effects of a Modified Dye-Labeled Nucleotide Spacer Arm on Incorporation by Thermophilic DNA Polymerases." Nucleosides, Nucleotides, and Nucleic Acids, vol. 25, pp. 9-15, 2006.
Ladiges et al., "Tissue specific expression of PKR protein kinase in aging B6D2F1 mice," Mechanisms of Ageing and Development, vol. 114, pp. 123-132, 2000.
Lan et al., A simple, reliable, and sensitive method for nonradioactive in situ hybridization: use of microwave heating to improve hybridization efficiency and preserve tissue morphology. J Histochem Cvtochem 44(3):281-287. 1996.
Larson et al., CRISPR Interference (CRISPRi) for Sequence-Specific Control of Gene Expression. Nat Protoc 2013, 8, 2180-2196.
Larsson, C. et al., "In situ detection and genotyping of individual mRNA molecules," Nature Methods, vol. 7, pp. 395-397, May 1, 2010.
Larsson, C. et al., "In situ genotyping individual DNA molecules by target-primed rolling-circle amplification of padlock probes," Nature Methods, vol. 1, No. 3, pp. 227-232, Dec. 2004.
Lawley et al., "DNA Adducts from Chemotherapeutic Agents." Mutation Research—Fundamental and Molecular mechanisms of Mutagenesis 355 (1996): 13-40.
Lawrence et al., "Highly Localized Tracks of Specific Transcripts within Interphase Nuclei Visualized by In Situ Hybridication," Cell, 57, pp. 493-502, 1989.
Layzer et al., "In Vivo Activity of Nuclease-Resistant siRNAs," RNA, vol. 10, pp. 766-771, 2004.
Le et al., "DNA-Templated Self-Assembly of Metallic Nanocomponent Arrays on a Surface", Nano Lett., vol. 4, No. 12, pp. 2343-2347, 2004.
Lee et al., "A self-replicating peptide", Nature, vol. 382, pp. 525-528, Aug. 8, 1996.
Lee et al., "Aptamer database" Nucleic Acids Research, 32: D95-100, 2004.
Lee et al., Programmable Control of Bacterial Gene Expression with the Combined CRISPR and Antisense RNA System. Nucleic Acids Res. 2016, 44 (5), 2462-2473.
Lee, S. K. et al., "Conditional RNAi: towards a silent gene therapy," Adv. Drug Delivery Rev, vol. 61, pp. 650-664, 2009.
Lehmann, R. et al., "In situ hybridization to RNA," Methods in Cell Biology, vol. 44, pp. 575-598, 1994.
Leino, et al., 2019. "Optimization of Proximity-Dependent Initiation of Hybridization Chain Reaction for Improved Performance." Molecular Systems Design & Engineering 4 (5): 1058-65. https://doi.org/10.1039/C9ME00079H.
Leisinger, B. Viral Load Testing for HIV Beyond the CD4 Count, Laboratory Medicine, vol. 30, No. 2, DD, 102-109, 1999.
Letter accompanying subsequently filed items dated Oct. 28, 2013 in European Aoolication No. 12 161 252.7.
Letter accompanying subsequently filed items dated Mar. 17, 2014 in European Application No. 12 161 252.7.
Levsky, J et al., "Single-cell gene expression profiling," Science, vol. 297, Issue 5582, pp. 836-840, Aug. 2, 2002.
Levy et al., "Exponential growth by cross-catalytic cleavage of deoxyribozymogens", PNAS, vol. 100, No. 11, pp. 6416-6421, May 27, 2003.
Li et al., "Single-chain antibodies against DNA aptamers for use as adapter molecules on DNA tile arrays in nanoscale materials organization." Organic and Biomolecular Chemistry 2006, pp. 3420-3426. 2006.
Li et al., "The structure of FtsZ filaments in vivo suggests a force-generating role in cell division." EMBO J., vol. 26, pp. 4694-4708. 2007.
Li et al., A new class of homogenous nucleic acid probes based on specific displacement hybridization, Nucleic Acids Research, vol. 30, No. 2e5 (2002), DD. 1-9.
Chappell et al., The Centrality of RNA for Engineering Gene Expression. Biotechnol. J.m 8 (12), 1379-1395. httos://doi.ora/Doi 10.1002/Biot.201300018, 2013.
Chavez et al., Highly Efficient Cas9-Mediated Transcriptional Programming. Nat. Methods 2015, 12 (4), 326-328. https://doi.org/10.1038/nmeth.3312.
Check, "RNA to the rescue?", Nature, vol. 425, pp. 10-12, Sep. 4, 2003.
Chen et al., "DNA-Directed Assembly of Single-Wall Carbon Nanotubes." J.Am. Chem. Soc., vol. 129, 2007.
Chen et al., "Invadable self-assembly: Combining robustness with efficiency." In Proceedings of the 15.sup.th annual ACM-SIAM Symposium on Discrete Algorithms (SODA); 2004.
Chen et al., Chemically Controlled Epigenome Editing through an Inducible DCas9 System. J. Am. Chem. Soc. 2017, 139 (33), 11337-11340. https://doi.org/10.1021/jacs.7b06555.
Chen, Bet al. 'Dynamic Imaging of Genomic Loci in Living Human Cells by an Optimized CRISPR/Cas System', Cell, 155: 1479-91, (2013).
Chen, et al. 2016. "Nanoscale Imaging of RNA with Expansion Microscopy." Nature Methods 13 (8): 679-84.
Chen, Yet al. Profiling of Multiple Glycans on Whole Living Cell Surfaces, Analytical Chemistry, vol. 85, No. 22, pp. 11153-11158, (2013).
Chernoff et al., "Quantification of Cytomegalovirus DNA in Peripheral Blood Leukocytes by a Branched-DNA Signal Amplification Assay", Journal of Clinical Microbiology, vol. 35, No. 11, p. 2740-2744, Nov. 1997.
Choi and Love et al., Immuno-Hybridization Chain Reaction for Enhancing Detection of Individual Cytokine-Secreting Human Peripheral Mononuclear Cells, Analytical Chemistry 83 :6890-6895 , 2011.
Choi et al., "Programmable in situ amplification for multiplexed imaging of mRNA expression," Nature Biotechnology, vol. 28, No. 11, pp. 1208-1214, 2010.
Choi, H. et al., Next-generation in situ hybridization chain reaction: higher gain, lower cost, greater durability, vol. 8, No. 5, DD. 4284-4294 (2014).
Clay, H. et al., "Multiplex fluorescent in situ hybridization in zebrafish embryos using tyramide signal amplification," Zebrafish, vol. 2, No. 2, pp. 105-111, Aug. 2005.
Cleve et al., "Direct quantitation of HIV by flow cytometry using branched DNA signal amplification", Molecular and Cellular Probes, vol. 12, pp. 243-247, 1998.
Coburn et al., "siRNAs: a new wave of RNA-based therapeutics", Journal of Antimicrobial Chemotherapy, vol. 51, pp. 753-756, 2003.

(56) References Cited

OTHER PUBLICATIONS

Coleman et al., "Template-Directed Corss-Linking of Oligonucleotides: Site-Specific Covalent Modification of dG-N7 Within Duplex DNA." J. Org. Chem. 60 (1995): 6252-6253.
Coleman, R.S, and Pires, R.M., Covalent cross-linking of duplex DNA using 4-thio-2'-deoxyuridine as a readily modifiable platform for introduction of reactive functionality into oligonucleotides. Nucleic Acids Research, vol. 25: p. 4771-4777, 1997.
Collingwood et al., Chemical Modification Patterns Compatible with High Potency Dicer-Substrate Small Interfering RNAs. Oliaonucleotides 2008, 18 (2), 187-199.
Collins et al., "A branched DNA signal amplification assay for quantification of nucleic acid targets below 100 molecules/ml," Nucleic Acids Res, 25(15), pp. 2979-2984, 1997.
Collins et al., "Branched DNA (bDNA) Technology for Direct Quantification of Nucleic Acids: Design and Performance", pp. 205-223, 1998.
Cong, L.; Ran, F. A.; Cox, D.; Lin, S.; Barretto, R.; Habib, N.; Hsu, P. D.; Wu, X.; Jiang, W.; Marraffini, L.A.; Zhang, F. Multiplex Genome Engineering Using CRISPR/Cas Systems. Science 2013, 339 (6121), 819-823. https://doi.org/10.1126/science.1231143.
Coppelli et al., "Oligonucleotides as Anticancer Agents: From the Benchside to the Clinic and Beyond", Current Pharmaceutical Design, vol. 11, pp. 2825-2840, 2005.
Cox, K.H. et al., "Detection of mRNAs in sea urchin embryos by in situ hybridization using asymmetric RNA probes," Developmental Biology, vol. 101, Issue 2, pp. 485-502, Feb. 1984.
Cullen et al., "Genome-wide Screening for Gene Function Using RNAi in Mammalian Cells." Immunology and Cell Biology 83 (2005) 217-223.
Czauderna et al., "Structural Variations and Stabilising Modifications of Synthetic siRNAs in Mammalian Cells," Nucleic Acids Research, vol. 31.11, pp. 2705-2716, 2003.
Dabby et al., Synthetic Molecular Machines for Active Self-Assembly: Prototype Algorithms, Desiqns, and Experimental Study. thesis, 2013.
Dabby Nl, Chen HL, Schaeffer JM, Winfree E. "The kinetics of toehold-mediated four-way branch migration." California Institute of Technology Thesis, Chapter 5 (2013), pp. 75-105.
Dailey et al., "Quantification of HCV RNA in Liver Tissue by bDNA Assay", Methods in molecular medicine, vol. 19, No. 1543-1894, pp. 119-129, 1998.
Darnell, D.K. et al., "GEISHA: an in situ hybridization gene expression resource for the chicken embryo," Cytogenetic and Genome Research, vol. 117, No. 1-4, pp. 30-35, Jul. 2007.
De Matos, et al., Heparanase expression in lung carcinoid tumors by immunohistochemistry. Ejc Supplements , vol. 3, No. 2, pp. 342 (2005).
Decroly et al., Conventional and Unconventional Mechanisms for Capping Viral MRNA. Nat. Rev. Microbial. 2012, 10 (1), 51-65. https://doi.org/10.1038/nrmicro2675.
Definition for "substantial" from Merriam-Webster Online Dictionary. Downloaded from merriam-webster.com; downloaded on Mar. 5, 2008.
Delebecque et al., Designing and Using RNA Scaffolds to Assemble Proteins in Vivo. Nat. Protoc. 2012, 7 (10), 1797-1807. https://doi.org/Doi10.1038/Nprot.2012.102.
Delebecque et al., Organization of Intracellular Reactions with Rationally Designed RNA Assemblies. Science 2011, 333(6041), 470-474. https://doi.org/10.1126/science.1206938.
Denkers, N et al., "FISHing for chick genes: Triple-label whole-mount fluorescence in situ hybridization detects simultaneous and overlapping gene expression in avian embryos," Developmental Dynamics, vol. 229, Issue 3, pp. 651-657, Mar. 2004.
Detmer et al., "Accurate Quantification of Hepatitis C Virus (HCV) RNA from All HCV Genotypes by Using Branched-DNA Technology", Journal of Clinical Microbiology, vol. 34, No. 4, pp. 901-907, Apr. 1996.

Dias et al., "Antisense Oligonucleotides: Basic Concepts and Mechanisms." Molecular Cancer Therapeutics, vol. 1, pp. 347-355, Mar. 2002.
Dicarlo, J et al.. 'RNA-guided gene drives can efficiently bias inheritance in wild yeast', bioRxiv, (2015).
Dietz et al., "Folding DNA into Twisted and Curved Nanoscale Shapesm," Science, vol. 325, pp. 725-730, 2009.
Dirks et al., "A Partition Function Algorithm for Nucleic Acid Secondary Structure Including Pseudoknots." Journal of Comgutational Chemistry 24.13 (2003) 1664-1677.
Dirks et al., "An Algorithm for Computing Nucleic Acid Base-Pairing Probabilities Including Pseudoknots." Journal of Comgufational Chemistry 25:1O (2004): 1295-1304.
Dirks et al., "Paradigms for computational nucleic acid design," Nucleic Acids Research, vol. 32, No. 4, pp. 1392-1403, Oxford University Press, 2004.
Dirks et al., "Thermodynamic Analysis of Interacting Nucleic Acid Strands." SIAM Review 49.1 (2007): 65-88.
Dirks et al., "Triggered amplification by hybridization chain reaction," PNAS, vol. 101, No. 43, DD. 15275-15278, Oct. 26, 2004.
Dirks et al., Retraction for "Selective cell death mediated by small conditional RNAs" (which appeared in issue 39, Sep. 28, 2010 of Proc Natl Acad Sci USA), Proc Natl Acad Sci USA, Jan. 2, 2013 vol. 110, No. 1, p. 384.
Dohjima, T. et al., "Small Interfering RNAs Expressed from a Pol III Promoter Suppress the EWS/Fli-1 Transcript in an Ewing Sarcoma Cell Line", Molecular Therapy, vol. 7, No. 6, pp. 811-816, Jun. 2003.
Douglas et al., "DNA-nanotube-induced alignment of membrane proteins for NMR structure determination", PNAS, vol. 104, No. 16, pp. 6644-6648, Apr. 17, 2007.
Douglas et al., "Self-assembly of DNA into nanoscale three-dimensional shapes", Nature, vol. 459, pp. 414-418, May 21, 2009.
Du, Qa et al., "A systematic analysis of the silencing effects of an active siRNA at all single-nucleotide mismatched target sites." Nucleic Acids Res, vol. 33, pp. 1671-1677, 2005.
Stemmer, et al., Single Step Assembly of a Gene and Entire Plasmid from Large Nos. of Oligodeoxyribonnucleotides. Gene, vol. 164, pp. 49-53 (1995).
Storhoff et al., "One-pot colorimetric differentiation of polynucleotides with single base imperfections using gold nanoparticles," J. Am. Chem. Soc., 120, pp. 19 9-1964, 1998.
Strader et al., "Diagnosis, Management, and Treatment of Hepatitis C", Hepatology, vol. 39, No. 4, pp. 1147-1171, 2004.
Stratagene Catalog. gene characterization kits. Stratagene Catalog, p. 39, 1988.
Stuheimer et al. "Global Structure of Three-Way DNA Junctions with and without Additional Unpaired Bases: A Fluorescence Resonance Energy Transfer Analysis". Biochemistry, vol. 35, pp. 13530-13538, 1997.
Sun et al., "Side Chain Chemistry Mediates Backbone Fragmentation in Hydrogen Deficient Peptide Radicals." Journal of Proteome Research 8 (2009) 958-966.
Szucs et al., A New Subclass of Exoribonuclease-Resistant RNA Found in Multiple Genera of Flaviviridae. 2020, 11 (5), 15.
Takei et al., "A Small Interfering RNA Targeting Vascular Endothelial Growth Factor as Cancer Therapeutics." Cancer Research 64. (May 15, 2004): 3365-3370.
Tang et al., Aptazyme-Embedded Guide RNAs Enable Ligand-Responsive Genome Editing and Transcriptional Activation. Nat Commun 2017, 8, 15939.
Tani et al., "Synthesis and Structural Analysis of 2-Quinuclidonium Tetrafluoroborate." Nature 441 (Jun. 8, 2006) 731-734.
Tautz, D. et al., "A non-radioactive in situ hybridization method for the localization of specific RNAs in Drosophila embryos reveals translational control of the segmentation gene hunchback," Chromosoma, vol. 98, Issue 2, pp. 81-85, Aug. 1989.
Tedeschi et al., "Quantification of Hepatitis C Virus (HCV) in Liver Specimens and Sera from Patients with Human Immunodeficiency Virus Coinfection by Using the Versant HCV RNA 3.0 (Branched DNA-Based) DNA Assay", Journal of Clinical Microbiology, vol. 41, No. 7, pp. 3046-3050, Jul. 2003.

(56) References Cited

OTHER PUBLICATIONS

Thisse, B., "Spatial and temporal expression of the zebrafish genome by large-scale in situ hybridization screening," Methods in Cell Biology, vol. 77, pp. 505-519, 2004.
Thisse, C. et al., "High-resolution in situ hybridization to whole-mount zebrafish embryos," Nature Protocols, vol. 3, No. 1, DD. 59-69, Jan. 2008.
Thomas et al., "Photoaffinity Cross-Linking and RNA Structure Analysis." Methods in Enzymology 318 (2000) 136-147.
Thompson, N.L.; Lieto, AM., and Allen, N.W. "Recent advances in fluorescence correlation spectroscopy." Curr. Opin. Struct. Biol., 12, 2002.
Tijsterman et al., "Dicers at RISC: The Mechanism of RNAi", Cell, vol. 117, pp. 1-3, 2004.
Trail, P., Antibody drug conjugates as cancer therapeutics, Antibodies, vol. 2, No. 1 pp. 113-129, (2013).
Trimoulet et al., Evaluation of the VERSANT HCV RNA 3.0 Assay for Quantification of Hepatitis C Virus RNA in Serum, Journal of Clinical Microbiology, vol. 40, No. 6, pp. 2031-2036, 2002.
Tsien, R. Y. The Green Fluorescent Protein. Annu Rev Biochem 1998, 67 (1), 509-544. https://doi.org/10.1146/annurev.biochem.67.1.509.
Tsongalis et al., Branched DNA Technology in Molecular Diagnostics, American Journal of Clinical Pathology, vol. 126, No. 3, 448-453, 2006.
Tuerk, C et al., "Systematic evolution of ligands by exponential enrichment: RNA ligands to bacteriophage T4 DNA polymerase," Science, vol. 249, No. 4968, pp. 505-510, Aug. 3, 1990.
Tuleuova, N. et al., "Modulating endogenous gene expression of mammalian cells via RNA-small molecule interaction," Biochem. Biophys. Res. Commun., vol. 376, pp. 169-173, 2008.
Turberfield, et al., "DNA fuel for free-running nanomachines,"Physical Review Letters, vol. 90, No. 11, pp. 118102-1-118102-4, Mar. 21, 2003.
Turk, Greg and Levoy, Marc. "Zippered polygon meshes from range images." In SIGGRAPH, pp. 311-318, 1994.
Tyagi et al., "Molecular Beacons: Probes that Fluoresce upon Hybridization," Nature Biotechnology 14, pp. 303-308, 1996.
Tyagi et al., "Multicolor Molecular Beacons for Allele Discrimination," Nature Biotechnology, vol. 16, pp. 49-53, Jan. 1998.
U.S. File history of U.S. Appl. No. 11/471,278, filed Jun. 19, 2006.
U.S. File History of U.S. Appl. No. 14/320,479.
U.S. File History of U.S. Appl. No. 14/497,070.
U.S. File history of U.S. Appl. No. 16/294,864, filed Mar. 6, 2019.
U.S. File History printed Jun. 16, 2009 for U.S. Appl. No. 11/087,937, filed Mar. 22, 2005, entitled "Hybridization Chain Reaction."
U.S. File History printed Jun. 16, 2009 for U.S. Appl. No. 11/371,346, filed Mar. 7, 2006, entitled "Hybridization Chain Reaction Amplification for In Situ Imaging."
U.S. File History printed Jun. 16, 2009 for U.S. Appl. No. 11/371,347, filed Mar. 7, 2006, entitled "Colorimetric Readout of Hybridization Chain Reaction."
U.S. File History printed Jun. 16, 2009 for U.S. Appl. No. 11/544,306, filed Oct. 6, 2006, entitled "PKR Activation via Hybridization Chain Reaction."
U.S. File History printed Jun. 16, 2009 for U.S. Appl. No. 12/040,735, filed Feb. 29, 2008, entitled "Triaaered RNAi."
U.S. File History printed Jun. 4, 2010 for U.S. Appl. No. 12/454,743, filed May 22, 2009, entitled "Triaaered RNAi."
U.S. File History printed Jun. 4, 2010 for U.S. Appl. No. 12/454,799, filed May 22, 2009, entitled "Compositions and Methods for Detecting Analytes."
U.S. File History printed Jun. 4, 2010 for U.S. Appl. No. 12/467,755, filed May 18, 2009, entitled "Shielded Cross-Linking Probes."
U.S. File History printed Jun. 4, 2010 for U.S. Appl. No. 12/611,875, filed Nov. 3, 2009, entitled "Hybridization Chain Reaction."
U.S. File History printed Jun. 16, 2009 for U.S. Appl. No. 12/152,893, filed May 16, 2008, entitled "A Versatile Nucleic Acid Hairpin Motif for Programming Biomolecular Self-Assembly Pathways,".
U.S. File History printed Jun. 4, 2010 for U.S. Appl. No. 12/395,489, filed Feb. 27, 2009, entitled "TRIGGERED RNAi,".
Urdea et al., "Branched DNA (bONA) Technology", Chapter 33, Bayer Diagnostics, pp. 388-395, 2000.
Urdea, M.S., "Branched DNA Signal Amplification—Does bDNA represent post-PCR amplification technology?", Biotechnology, vol. 12, pp. 926-928, Sep. 1994.
Van De Corput et al., "Sensitive mRNA Detection by Fluorescence In Situ Hybridization Using Horseradish Peroxidase-labeled Oligodeoxynucleotides and Tyramide Signal Amplification," J. Histochem Cvtochem, 46(11), DD. 1249-1259, 1998.
Venkataraman et al. "Selective Cell Death Mediated by Small Conditional RNAs", Proc Natl Acad Sci USA, early edition, aDoroved Jul. 21, 2010, p. 1-6.
Venkataraman et al., "An Autonomous Polymerization Motor Powered by DNA Hybridization." Nature Nanotechnology 2 (Aug. 2007): 490-494.
Vermeulen et al., "The contributions of dsRNA structure to Dicer specificity and efficiency", RNA, vol. 11, pp. 674-682, 2005.
Versant Bayer, HCV RNA 3.0 Assay (bDNA), Summary of Safety and Effectiveness, Indications for Use; No date provided on item, but it purports to relate to Versant, which may be in line with the other Versant items in the present IDS.
Vieregg et al., "Selective Nucleic Acid Capture with Shielded Covalent Probes", J. Am. Chem. Soc., 2013, vol. 135, 9691-9699.
Hansma et al., "DNA Binding to Mica Correlates with Cationic Radius: Assay by Atomic Force Microscopy", Biophysical Journal, vol. 70, pp. 1933-1939, Apr. 1996.
Hao et al. "Programmable Live-Cell CRISPR Imaging with Toehold-Switch-Mediated Strand- Displacement" Angew Chem Int Ed, Nov. 9, 2020, vol. 59, No. 46, pp. 20612-20618.
Harland, R.M., "In situ hybridization : an improved whole-mount method for Xenopus embryos," Methods Cell Biol., vol. 36, DD. 685-695, 1991.
Hartley et al., "Detection of Chemical-Induced Differential Expression of Rat Hepatic Cytochrome P450 MRNA Transcripts Using Branched DNA Signal Amplification Technology", Druq Metabolism and Disposition, vol. 28, No. 5, 2000, paQes 608-616.
Hashimoto et al., "Recent Progress in Diazirine-Based Photoaffinity Labeling." Eur. J. Org. Chem. (2008): 2513-2523.
Haugland RP. The Handbook: A Guide to Fluorescent Probes and Labeling Technologies. 10th Ed. Molecular Probes/Invitrogen; 2005.
Hawkins et al., "Comparison of Plasma Virus Loads among Individuals Infected with Hepatitis C Virus (HCV) Genotypes 1, 2, and 3 by Quantiplex HCV RNA Assay Versions 1 and 2, Roche Monitor Assay, and an In-House Limiting Dilution Method", Journal of Clinical Microbiology, vol. 35, No. 1, pp. 187-192, Jan. 1997.
Hayat, Comparison of Immunohistochemistry, in situ Hybridization, Fluorescence in situ Hybridization, and chromogenic in situ Hybridization, Handbook of Immunohistochemistry and in Situ Hybridization of Human Carcinomas, 1st Edition, Molecular Genetics; Lung and Breast Carcinomas, 2004.
He et al., "Hierarchical self-assembly of DNA into symmetric supramolecular polyhedral," Nature, vol. 452, pp. 198-202, 2008.
Hearst et al., "Psoralen Photochemistry." Ann. Rev. Bio12hts. Bioeng. 10 (1981): 69-86.
Heidel, J.D., "Targeted, systematic non-viral delivery of small interfering RNA in vivo", Doctoral thesis, California Institute of Technology, pp. 1-128, 2005.
Hell, S.W., "Far-field optical nanoscopy.", Science, vol. 316, pp. 1153-1158, 2007.
Hendricks et al., "Quantitation of HBV DNA in Human Serum Using a Branched DNA (bDNA) Signal Amplification Assay", American journal of clinical pathology, vol. 104, No. 5, pp. 537-546, 1995.
Herath et al., "Synthesis of Acrimarins from 1,3,5-Trioxygenated-9-acridone Derivatives." Journal of Heteroctclic Chem. 41 (2004): 23-28.
Higuchi et al. Selective regulation of mutant K-ras mRNA expression by photo-cross-linking antisense oligonucleotide. Nucleic Acids Symposium Series (2007) vol. 51 (1) pp. 443-444.

(56) References Cited

OTHER PUBLICATIONS

Hilton et al., Epigenome Editing by a CRISPR-Cas9-Based Acetyltransferase Activates Genes from Promoters and Enhancers. Nat Biotechnol 2015, 33, 510.

Hirosawa et al., Cell-Type-Specific Genome Editing with a MicroRNA-Responsive CRISPR-Cas9 Switch. Nucleic Acids Res 2017, 45 (13), e118.

Hochrein et al., "Conditional Dicer Substrate Formation via Shape and Sequence Transduction with Small Conditional RNAs," J. Am. Chem. Soc., vol. 135, pp. 17322-17330, 2013.

Hochrein et al., High-Performance Allosteric Conditional Guide RNAs for Mammalian Cell-Selective Regulation of CRISPR/Cas. ACS Synth. Biol. 2021, 10 (5), 964-971. https://doi.org/10.1021/acssynbio.1c00037.

Hochrein et al., Signal Transduction in Human Cell Lysate via Dynamic RNA Nanotechnology. ACS Synth. Biol. 2018, 7 (12), 2796-2802.

Hodinka et al. ,The clinical utility of viral quantitation using molecular methods, Clinical and Diagnostic Virology, vol. 10, No. 1, pp. 25-47, 1998.

Hofacker et al., "Fast folding and comparison of RNA secondary structures," Monatshefte flir Chemie, vol. 125, pp. 167-188, 1994.

Hokaiwado et al., "RNAi-based drug discovery and its application to therapeutics", IDrugs, vol. 11, No. 4, pp. 274-278, 2008.

Horvath, P et al.. 'CRISPR/Cas, the Immune System of Bacteria and Archaea', Science, 327: 167-70, (2010).

Hu-Lieskovan et al., "Sequence-Specific Knockdown of EWS-FLI1 by Targeted, Nonviral Delivery of Small Interfering RNA Inhibits Tumor Growth in a Murine Model of Metastatic Ewing's Sarcoma." Cancer Research 65.19 (Oct. 1, 2005): 8984-8992.

Hughes et al., "Double Labeling wit Fluorescence In Situ Hybridization in Drosophila Whole-Mount Embryos," BioTechniques, vol. 24, No. 4, pp. 530-532, 1998.

Huizenga et al., "A DNA Aptamer That Binds Adenosine and ATP." Biochemistry 34, pp. 656-665, 1995.

Husain, N. 2016. "Mapping MRNA and Protein Expression with High Signal-to-Background in Diverse Organisms." PhD Thesis, California Institute of Technology.

Huss, D. et al., "Combinatorial analysis of mRNA expression patterns in mouse embryos using hybridization chain reaction." Cold Spring Harbor Protocols, pp. 259-269 (2015).

Idrovo et al., "Hepatitis C virus RNA quantification in right and left lobes of the liver in patients with chronic hepatitis C", Journal of Viral Hepatitis, vol. 3, pp. 239-246, 1996.

Iqbal et al., "A review of molecular recognition technologies for detection of biological threat agents", Biosensors & Bioelectronics, vol. 15, pp. 549-578, 2000.

Iqbal, J et al., "The hybridization chain reaction in the development of ultrasensitive nucleic acid assays," TrAC Trends in Analytical Chemistry, vol. 64, pp. 86-99, Jan. 2015.

Isaacs et al., RNA Synthetic Biology. Nat. Biotechnol. 2006, 24 (5), 545-554. httos://doi.ora/10.1038/nbt1208.

Jacob et al., "Comparison of Quantitative HCV RNA Assays in Chronic Hepatitis C", Microbiology and Infectious Disease, American journal of clinical pathology, vol. 107, No. 3, pp. 362-367, Mar. 1997.

Jagus et al., "PKR, apoptosis and cancer", The International Journal of Biochemistry & Cell Biology, vol. 31, pp. 123-138, 1999.

Jain. K, et al: "Development of light-activated CRISPR using guide RNAs with photocleavable protectors." Angewandte Chemie International Edition vol. 55 No. 40 (Aug. 24, 2016), pp. 12440-12444.

Jayasena, "Aptamers: An Emerging Class of Molecules That Rival Antiodies in Diagnostics", Clinical Chemistry, vol. 45, No. 9, pp. 1628-1650, 1999.

Jhaveri et al., "In vitro selection of signaling aptamers", Nature Biotechnology, vol. 18, pp. 1293-1297, Dec. 2000.

Jin et al., Programmable CRISPR-Cas Repression, Activation, and Computation with Sequence-Independent Targets and Triggers. ACS Synth. Biol. (2019), 8: 1583-1589 (Year: 2019).

Jinek et al., A Programmable Dual-RNA-Guided DNA Endonuclease in Adaptive Bacterial Immunity. Science (2012), 337: 816-821 (Year: 2012).

Jinek M et al., "A three-dimensional view of the molecular machinery of RNA interference," Nature, vol. 457, pp. 405-412, 2009.

Johnston et al., "Psoralen-DNA Photoreaction: Controlled Production of Mono- and Diadducts with Nanosecond Ultraviolet Laser Pulses," Science, New Series, vol. 197, No. 4306, pp. 906-908, Aug. 26, 1977.

Jones et al., The 5'→3' Exoribonuclease XRN1/Pacman and Its Functions in Cellular Processes and Development: The 5'→3' Exoribonuclease XRN1/Pacman and Its Functions. Wiley Interdiscip. Rev. RNA 2012, 3(4), 455-468. httos://doi.ora/10.1002/wrna.1109.

Jonoska et al., "DNA cages with icosahedral symmetry bionanotechnology," Algorithmic Bioprocesses, 2008.

Judge et al., "Design of Noninflammatory Synthetic siRNA Mediating Potent Gene Silencing in Vivo." Molecular Therapy, vol. 13.3, pp. 494-505., Mar. 2006.

Judge et al., "Overcoming the Innate Immune Response to Small Interfering RNA", Human Gene Therapy, vol. 19, pp. 111-124, Feb. 2008.

Julian et al., "Biomimetic Approaches to Gas Phase Peptide Chemistry: Combining Selective Binding Motifs with Reactive Carbene Precursors to Form Molecular Mousetraps." International Journal of Mass Spectrometry, vol. 228, pp. 851-864, 2003.

Julian et al., "Molecular Mousetraps: Gas-Phase Studies of the Covalent Coupling of Noncovalent Complexes Initiated by Reactive Carbenes Formed by Controlled Activation of Diazo Precursors." Agnew. Chem.Int. Ed., vol. 42.9, pp. 1012-1015, 2003.

Jung, C et al., Diagnostic applications of nucleic acid circuits, Accounts of Chemical Research, vol. 47, No. 6, DD. 1825-183, (2014).

Kadnikov et al., "Synthesis of Coumarins via Palladium-Catalyzed Carbonylative Annulation of Internal Alkynes by o-Iodophenols." Organic Letters 2.23 (2000): 3643-3646.

Vodovozova et al., "Photoaffinity Labeling and Its Application in Structural Biology." Biochemistry (Moscow) 72.1 (2007): 1-20.

Voigt et al., Detection and Quantification of RNA Decay Intermediates Using XRN1-Resistant Reporter Transcripts. Nat. Protoc. 2019, 14 (5), 1603-1633. httos://doi.ora/10.1038/s41596-019-0152-8.

Volker et al., "Conformational energetics of stable and metastable states formed by DNA triple repeat oligonucleotides: implications for triplet expansion diseases," PNAS, vol. 99, No. 23, pp. 14700-14705, Nov. 12, 2002.

Von Kiedrowski, "A Self-Replicating Hexadeoxynucleotide", Agnew. Chem. Int. Ed. Engl., vol. 25, No. 10, pp. 932-935, 1986.

Voorhoeve et al., "Knockdown Stands Up .:" Trends in Biotechnology 21.1 (Jan. 2003) 2-4.

Wagner et al., "Transferrin-Polycation Conjugates as Carriers for DNA Uptake into Cells", Proceedings of the National Academy of Sciences of the United States of America, vol. 87, DD. 3410-3414, May 1990.

Wallner, G, et al., "Optimizing fluorescent in situ hybridization with rRNA-targeted oligonucleotide probes for flow cytometric identification of microorganisms," Cytometry, vol. 14, Issue 2, pp. 136-143. 1993.

Wang et al., A MicroRNA-Inducible CRISPR-Cas9 Platform Serves as a MicroRNA Sensor and Cell-Type-Specific Genome Regulation Tool. Nat. Cell Biol. 2019, 21 (4), 522-530. https://doi.org/10.1038/s41556-019-0292-7.

Wang et al., Optimized CRISPR Guide RNA Design for Two High-Fidelity Cas9 Variants by Deep Learning. Nat Commun 2019, 10 (1), 4284. https://doi.org/10.1038/s41467-019-12281-8.

Wang et al., Signal Amplification Techniques: BONA, Hybrid Capture, Advanced Techniques in Diagnostic Microbiology, DD. 228-242, 2006.

Wang, et al., 2018. "Multiplexed Imaging Using Same Species Primary Antibodies with Signal Amplification." BioRxiv, January, 274456. https://doi.org/10.1101/274456.

Wang, F. et al. From Cascaded Catalytic Nucleic Acids to Enzyme-DNA Nanostructures: Controlling Reactivity, Sensing, Logic Opera-

(56) References Cited

OTHER PUBLICATIONS tions, and Assembly of Complex Structures. Chemical Reviews, vol. 114 No. 5, 00. 2881-2941, 2014 (uploaded in three parts).
Wang, F. et al. From Cascaded Catalytic Nucleic Acids to Enzyme-DNA Nanostructures: Controlling Reactivity, Sensing, Logic Operations, and Assembly of Complex Structures. Chemical Reviews, vol. 114 No. 5, pp. 2881-2941, (2014).
Wang, F. et al., "RNAscope: A novel in situ RNA analysis platform for formalin-fixed, paraffin-embedded tissues," The Journal of Molecular Diagnostics, vol. 14, No. 1, pp. 22-29, Jan. 2012.
Wassarman et al., "Psoralen Crosslinking of Small RNAs in vitro." Molecular Biology Reports 17 (1993): 143-151.
Weikersheimer, P.B., "Viral Load Testing for HIV Beyond the CD4 Count", Laboratory Medicine, vol. 30, No. 2, Feb. 1999.
Weiszmann, R. et al., "Determination of gene expression patterns using high-throughput RNA in situ hybridization to whole-mount Drosophila embryos," Nature Protoc., vol. 4, No. 5, DD. 605-618, 2009.
White et al., "The Catalytic Asymmetric Total Synthesis of Elatol." Journal of American Chemical Society 130.3 (2008): 810-811.
Wiedorn, K.H. et al., "Comparison of in-situ hybridization, direct and indirect in-situ PCR as well as 484 tyramide signal amplification for the detection of HPV," Histochemistry and Cell Biology, vol. 111, Issue 2, DD. 89-95, Jan. 1999.
Wijen et al., "The in vivo Genetic Activity Profile of the Monofunctional Nitrogen Mustard 2-Chloroethylamine Differs Drastically from its Bifunctional Counterpart Mechlorethamine." Carcinoaenesis 21.10 (2000) 1859-1867.
Wilber et al., "Quantification of HCV RNA in Clinical Specimens by Branched DNA (bDNA) Technology", Methods in Molecular Medicine, vol. 19, No. 1543-1894, pp. 71-78, 1998.
Wilber, J.C., Branched DNA for Quantification of Viral LOAD, Immunological Investigations, vol. 26, Nos. 1-2, pp. 9-13, 1997.
Wilkie et al., "Transcribed genes are localized according to chromosomal position within polarized Drosophila embryonic nuclei," Current Biology, vol. 9, pp. 1263-1266, 1999.
Williams, B.R.G., "PKR; a sentinel kinase for cellular stress", Oncogene, vol. 18, pp. 6112-6120, 1999.
Willis, M.C., et al., "Photocross-linking of 5-lodouracil-Substituted RNA and DNA to Proteins," Science, vol. 262, pp. 1255-1257, 1993.
Winfree et al., "Design and self-assembly of two-dimensional DNA crystals", Nature, vol. 394, pp. 539-544, Aug. 6, 1998.
Winfree, E. "On the computational power of DNA annealing and ligation." Computation and Neural Systems, California Institute of Technology, May 25, 1995.
Winfree, E., "Algorithmic Self-Assembly of DNA, Ph.D. thesis", Thesis, California Institute of Technology, 1998.
Wiznerowicz, M. et al., "Tuning silence: conditional systems for RNA interference," Nat. Methods, vol. 3, pp. 682-688, 2006.
Wolfe et al., Constrained Multistate Sequence Design for Nucleic Acid Reaction Pathway Engineering. J. Am. Chem. Soc. 2017, 139 (8), 3134-3144.
Wolfe et al., Sequence Design for a Test Tube of Interacting Nucleic Acid Strands. ACS Synth. Biol. 2015, 4 (10), 1086-1100.
Wu et al., "Receptor-mediated in Vitro Gene Transformation by a Soluble DNA Carrier System", The Journal of Biological Chemistry, vol. 262, No. 10, pp. 4429-4432, 1987.
Wu et al., "A Model for the Double-stranded RNA (dsRNA)-dependent Dimerization and Activation of the dsRNA-activated Protein Kinase PKR", The Journal of Biological Chemistry, vol. 272, No. 2, pp. 1291-1296, 1997.
Wu et al., Metabolic Burden: Cornerstones in Synthetic Biology and Metabolic Engineering Applications. Trends Biotechnol. 2016, 34 (8), 652-664, https://doi.org/10.1016/j.tibtech.2016.02.010.
Xie, Z et al., "Logic integration of mRNA signals by an RNAi-based molecular computer" Nucleic Acids Res., vol. 38, pp. 2692-2701, 2010.
Yamaguchi, T. et al., "In situ DNA-hybridization chain reaction (HCR): a facilitated in situ HCR system for the detection of environmental microorganisms," Environmental Microbiology, vol. 17, Issue 7, pp. 2532-2541, Jul. 2015.
Yan et al., "DNA-Templated Self-Assembly of Protein Arrays and Highly Conductive Nanowires", Science, vol. 301, pp. 1882-1884, Sep. 26, 2003.
Yin et al., "Programming biomolecular self-assembly pathways", Nature, vol. 451, pp. 318-323, Jan. 17, 2008.
Yin et al., "A Unidirectional DNA Walker that Moves Autonomously along a Track." Angewandte Chemie International Edition, vol. 43, pp. 4906-4911, 2004.
Yin, P.; Hariadi, R.; Sahu, S.; Choi, H.M.T.; Park, S.H.; :LaBean, T.H.; J.H. Reif, "Programming DNA Tube Circumferences." Science 2008, 321, 824-826.
Yin, P .; Hartemink, "Theoretical and practical advances in genome halving." A.K. Bioinformatics 2005, 21, 869-879.
Yin, P .; Turberfield, A.J .; Reif, J.H. "Designs of Autonomous Unidirectional Walking DNA Devices." In Proc. 10th International Meeting on DNA computing; 2004.
Ying et al., Activatable CRISPR Transcriptional Circuits Generate Functional RNA for MRNA Sensing and Silencing. Angew. Chem. Int. Ed. 2020, 59, 18599-18604.
Yoshimura et al., "Interstrand Photocrosslinking of DNA via p. carbamoylvinyl Phenol Nucleoside." Bioorganic & Medicinal Chemistry Letters, vol. 15, pp. 1299-1301, 2005.
Yu et al., "Clinical Evaluation of the Automated Cobas Amplicor HCV Monitor Test Version 2.0 for Quantifying Serum Hepatitis C Virus RNA and Comparison to the Quantiplex HCV Version 2.0 Test", Journal of Clinical Microbiology, vol. 38, No. 8, pp. 2933-2939, Auq.2000.
Yu et al., "Clinical application of the Quantiplex HCV RNA 2.0 and Amplicor HCV Monitor assays for quantifying serum hepatitis C virus Rna", J Clin Pathol, vol. 52, pp. 807-811, 1999.
Yu et al., RNA Drugs and RNA Targets for Small Molecules: Principles, Progress, and Challenges. Pharmacol. Rev. 2020, 72 (4), 862-898. https://doi.org/10.1124/pr.120.019554.
Yurke, et al., "A DNA-fuelled molecular machine made of DNA" Nature, vol. 406, Aug. 10, 2000, pp. 605-608.
Zadeh et al., "Software News and Updates NUPACK: Analysis and Design of Nucleic Acid Systems", Journal of Computational Chemistry, vol. 32, No. 1, pp. 170-173, 2011.
Zadeh et al., "Nucleic acid sequence design via efficient ensemble defect optimization," J. Comput. Chem., vol. 32, pp. 439-452, 2011.
Zadeh, "Algorithms for nucleic acid sequence design," Doctoral Thesis [online] orally defended Dec. 8, 2009 (Dec. 8, 2009), published May 25, 2010 (May 25, 2010), [Retrieved on Jun. 7, 2011], pp. 1-85, Retrieved from the Internet: <URL: http://resolver.caltech.edu/CaltechTHESIS:05112010-205335518>.
Zalatan et al., Engineering Complex Synthetic Transcriptional Programs with Crispr Rna Scaffolds. Cell 2015, 160 (1-2), 339-350. https://doi.org/10.1016/j.cell.2014.11.052.
Zetsche et al., Multiplex Gene Editing by CRISPR-Cpf1 Using a Single CrRNA Array. Nat Biotechnol 2016, 35, 31-34.
Zhang et al., Conformational flexibility facilitates self-assembly of complex DNA nanostructures, PNAS, vol. 105, No. 31, pp. 10665-10669, 2008.
Zhang et al., Cooperative Hybridization of Oligonucleotides. J Am Chem Soc 2011, 133 (4), 1077-1086. https://doi.org/Doi 10.1021/Ja109089q.
Zhang et al., Engineering Entropy-Driven Reactions and Networks Catalyzed by DNA. Science 2007, 318 (5853), 1121-1125., https://doi.org/papers://865820FC-FC44-4379A720006E449021CA/Paper/p1718.
Zhang et al., Targeted Gene Silencing by Small Interfering RNA-Based Knock-Down Technology, Current Pharmaceutical Biotechnology, vol. 5, pp. 1-7, 2004.
Zhang et al., Winfree, E. Control of DNA Strand Displacement Kinetics Using Toehold Exchanae. J. Am. Chem. Soc. 2009, 131, 17303-17314.
Zhang, D. Y. et al., "Dynamic DNA nanotechnology using strand-displacement reactions," Nat. Chem., vol. 3, pp. 103-113, 2011.
Zhang, H. et al., DNA-Mediated Homogeneous Binding Assays for Nucleic Acids and Proteins, Chemical Reviews vol. 113, No. 4, DD. 2812-2841, (2013).

(56) References Cited

OTHER PUBLICATIONS

Zhang, L., Zhou, W., Velculescu, V.E.; Kern, S.E., Hruban, R.H., Hamilton, S.R.; Vogelstein, B.; and Kinzler, K.W. "Gene expression profiles in normal and cancer cells." Science, 276:1268-1272, 1997.
Zheng et al., "Activation of the protein kinase PKR by short double-stranded RNAs with single- stranded tails", RNA, vol. 10, pp. 1934-1945, 2004.
Zhong et al., "High hepatitis B virus (HBV) DNA viral load is an important risk factor for HBV reactivation in breast cancer patients undergoing cytotoxic chemotherapy", Journal of Viral Hepatitis, vol. 11, pp. 55-59, 2004.
Zhou et al., "RNA Interference and Potential Applications", Current Topics in Medicinal Chemistry, vol. 6, pp. 901-911, 2006.
Zhou, H. et al., "Two-color, rolling-circle amplification on antibody microarrays for sensitive, multiplexed serum-protein measurements," Genome Biology, vol. 5, Issue 4, Article R28, pp. R28.1-R28.12, 2004.
Zimmer, M. Green Fluorescent Protein (GFP): Applications, Structure, and Related Photophysical Behavior. Chem Rev 2002, 102 (3), 759-782. https://doi.org/10.1021/cr010142r.
Zuker et al., "Optimal computer folding of large RNA sequence using thermodynamics and auxiliary information," Nucleic Acids Research, vol. 9, No. 1, pp. 133-147, 1981.
Jones et al., Different Tertiary Interactions Create the Same Important 3D Features in a Distinct Flavivirus XrRNA. 13.
Kim et al., De nova-designed translation-repressing riboregulators for multi-input cellular logic. Nature Chemical Biology, vol. 15, pp. 1173-1182, 2019.
Liu et al., Directing Cellular Information Flow via CRISPR Signal Conductors. Nat Methods 2016, 13, 938-944.
U.S. File History for U.S. Appl. No. 13/186,228, filed Jul. 19, 2011, entitled "Biomolecular Self-Assembly".
U.S. File History for U.S. Appl. No. 13/186,331, filed Jul. 19, 2011, entitled "Self-Assembled Polynucleotide Structure".

* cited by examiner

Standard guide RNA (gRNA) logic and function gRNA structure and interactions

Conditional guide RNA (cgRNA) ON→OFF logic and function

Conditional guide RNA (cgRNA) OFF→ON logic and function

Cell-selective spatiotemporal control of gene silencing

Cell-selective spatiotemporal regulatory control

Independent diagnosis and treatment

"If X then regulate Y"
treat diseased cells leaving healthy cells untouched
(cancer, autoimmune, microbiome, infectious disease,...)

Allosteric ON→OFF terminator switch cgRNA (Mechanism 1A)

---

Mechanism 1A: Schematic

Mechanism 1A: Annotated Schematic

Allosteric OFF→ON terminator switch cgRNA (Mechanism 1B)

Mechanism 1B: Annotated Schematic

Allosteric ON→OFF splinted switch cgRNA (Mechanism 2A)

Mechanism 2A: Schematic

Mechanism 2A: Annotated Schematic

ON State

OFF State

Allosteric OFF→ON splinted switch cgRNA (Mechanism 2B)

---

Mechanism 2B: Schematic

Mechanism 2B: Annotated Schematic

OFF State

ON State

Allosteric OFF→ON split-terminator switch cgRNA (Mechanism 4A)

Mechanism 4A: Schematic

Mechanism 4A: Annotated Schematic

OFF State

ON State

Allosteric ON→OFF split-terminator switch cgRNA (Mechanisms 4B and 4C)

Mechanism 4B: Schematic

Mechanism 4B: Annotated Schematic

Mechanism 4C: Annotated Schematic

Interactions for allosteric ON→OFF terminator switch cgRNA

ON State
(absence of trigger X)

In the absence of trigger X, the cgRNA mediates Cas activity on target gene Y

OFF State
(presence of trigger X)

cgRNA:trigger
complex

Trigger X inactivates the cgRNA

Interactions for allosteric ON→OFF splinted switch cgRNA

ON State
(absence of trigger X)

In the absence of trigger X, the cgRNA mediates Cas activity on target gene Y

OFF State
(presence of trigger X)

Trigger X inactivates the cgRNA

Interactions for allosteric OFF→ON split-terminator switch cgRNA

OFF State
(absence of Trigger X)

cgRNA

In the absence of trigger X, the cgRNA is inactive

ON State
(presence of Trigger X)

cgRNA    trigger X    Cas9    target gene Y
or dCas9
or Cas cgRNA:trigger:Cas:target complex Trigger X activates the cgRNA to mediate Cas activity on target gene Y

Allosteric ON→OFF terminator switch cgRNA

| cgRNAs | Sequence |
|---|---|
| cgRNA A | 5'-aactttcagtttagcggtctGTTTTAGAGCTAGAAATAGCAAGTTAAAATAAGGCTAGTCCCGATCAAACGGGTAAACAAACAGGATAATTAAGGAGGCAGTACCCGGGCACCGAGTCGGTGCTTTTTT-3' (SEQ ID NO: 1) |
| cgRNA B | 5'-aactttcagtttagcggtctGTTTTAGAGCTAGAAATAGCAAGTTAAAATAAGGCTAGTCCCGTATCATGGGGTTGTGTGTTGTAAGTGTGTGTGTTGCCCCGGCACCGAGTCGGTGCTTTTTT-3' (SEQ ID NO: 2) |
| cgRNA C | 5'-aactttcagtttagcggtctGTTTTAGAGCTAGAAATAGCAAGTTAAAATAAGGCTAGTCCCGAATATAGGGGAAGAGAAAGAAGAAGAGAAGAGAAAGATGTCCCCGGCACCGAGTCGGTGCTTTTTT-3' (SEQ ID NO: 3) |
| Triggers | |
| Trigger X$_A$ | 5'-TACTGCCTCCTTAATTATCCTGTTTGTTTACCCGTTTGAT-3' (SEQ ID NO: 4) |
| Trigger X$_B$ | 5'-CAACACACACACACTTACAACAACACACAACCCCATGATA-3' (SEQ ID NO: 5) |
| Trigger X$_C$ | 5'-ACATCTTTCTCTTCTCTTCTTCTTTCTCTTCCCCTATATT-3' (SEQ ID NO: 6) |

FIG. 11F

Allosteric ON→OFF splinted switch cgRNA

ON OFF logic
"if not X then not Y"

| cgRNAs | Sequence |
|---|---|
| cgRNA A | 5'-catctaattcaacaagaattGTTTTAGAGCTACACCTTACG CCGGTTCAATTCCAAGTCCCTTCCAGTAGCAAGTTAAAATAAGG CTAGTCCGTTATCAACTTAACACCCTTTACAAACCTTCCTCTTC CTTTACCCTAAGTGGCACCGAGTCGGTGCTTTTTTT-3' (SEQ ID NO: 7) |
| cgRNA B | 5'-catctaattcaacaagaattGTTTTAGAGCTAGTAATCGAA TCATAGTAAATTTCCCATCGTCATAATAGCAAGTTAAAATAAGG CTAGTCCGTTATCAACTTCATACGGGTCTGAAGTAGTTCATTCT TATACAGTCAAGTGGCACCGAGTCGGTGCTTTTTTT-3' (SEQ ID NO: 8) |
| cgRNA C | 5'-catctaattcaacaagaattGTTTTAGAGCTAGTCGTTACC TTATCAATATCAACCTCCGCATACACTAGCAAGTTAAAATAAGG CTAGTCCGTTATCAACTTGCACATAGGACCCAACATGCCAACAG AGAAGAGTTAAGTGGCACCGAGTCGGTGCTTTTTTT-3' (SEQ ID NO: 9) |
| Triggers | |
| Trigger X$_A$ | 5'-AGGGTAAAGGAAGAGGAAGGTTTGTAAAGGGTGTTCTGGAA GGGACTTGGAATTGAACCGGCGTAAGGTG-3' (SEQ ID NO: 10) |
| Trigger X$_B$ | 5'-GACTGTATAAGAATGAACTACTTCAGACCCGTATGTTATGA CGATGGGAAATTTACTATGATTCGATTAC-3' (SEQ ID NO: 11) |
| Trigger X$_C$ | 5'-AACTCTTCTCTGTTGGCATGTTGGGTCCTATGTGCGTGTAT GCGGAGGTTGATATTGATAAGGTAACGAC-3' (SEQ ID NO: 12) |

FIG. 12F

Allosteric ON → OFF terminator switch cgRNA

ON → OFF logic
"if not X then Y"

| cgRNAs | Sequence |
|---|---|
| cgRNA Q | 5'-gagtcgcgtgtagcgaagcaGTTTAAGAGCTAGAAATAGCAAGTTAAAATAAGGCTAGTCCGATCTTTGCGCGTTAGTTTCGTTCGTATTTCTGTCATGTTTGCGCGGCACCGAGTCGGTGCtttttttt-3' (SEQ ID NO: 13) |
| cgRNA R | 5'-gagtcgcgtgtagcgaagcaGTTTAAGAGCTAGAAATAGCAAGTTAAAATAAGGCTAGTCCGTATCGCCGGGTTCAAGCAGATGTGGCATTTCAGTGTAGTTCCCGGGCACCGAGTCGGTGCtttttttt-3' (SEQ ID NO: 14) |
| cgRNA S | 5'-gagtcgcgtgtagcgaagcaGTTTAAGAGCTAGAAATAGCAAGTTAAAATAAGGCTAGTCCGTCCATTCGGGTTTACTATTACAATCTTACGTGTTCTCATTCCCGGGCACCGAGTCGGTGCtttttttt-3' (SEQ ID NO: 15) |
| cgRNA T | 5'-gagtcgcgtgtagcgaagcaGTTTAAGAGCTAGAAATAGCAAGTTAAAATAAGGCTAGTCCGGATAAAGGGAAAGATGAAGTGATGTGAAGATAGAGTTGGATCCCGGCACCGAGTCGGTGCtttttttt-3' (SEQ ID NO: 16) |
| Triggers | |
| Trigger X$_Q$ | 5'-AGTCAGGCCACTTGTGCCACGGTTTGAGCAAACCGTGCTGCCTGTAGCTCCGCCAATAATGGGAGGCGTAAACATGACAGAAATACGAACGAAACTAACGCGCAAAGATCtttttttt-3' (SEQ ID NO: 17) |
| Trigger X$_R$ | 5'-AGTCAGGCCACTTGTGCCACGGTTTGAGCAAACCGTGCTGCCTGTAGCTCCGCCAATAATGGGAGGCGTAACTACACTGAAATGCCACATCTGCTTGAACCCGGCGATACtttttttt-3' (SEQ ID NO: 18) |
| Trigger X$_S$ | 5'-AGTCAGGCCACTTGTGCCACGGTTTGAGCAAACCGTGCTGCCTGTAGCTCCGCCAATAATGGGAGGCGTAATGAGAACACGTAAGATTGTAATAGTAAACCCGAATGGACtttttttt-3' (SEQ ID NO: 19) |
| Trigger X$_T$ | 5'-AGTCAGGCCACTTGTGCCACGGTTTGAGCAAACCGTGCTGCCTGTAGCTCCGCCAATAATGGGAGGCGTTCCAACTCTATCTTCACATCACTTCATCTTTCCCTTTATCCtttttttt-3' (SEQ ID NO: 20) |

FIG. 13H

| Trigger $X_Q$ | |
|---|---|
| 40 nt | 5'-AGTCAGGCCACTTGTGCCACGGTTTGAGCAAACCGTGCTGCCT GTAGCTCCGCCAATAATGGGAGGCGT*AAACATGACAGAAATACGAA CGAAACTAACGCGCAAAGAT*Ctttttttt-3' (SEQ ID NO: 21) |
| 50 nt Triggers | |
| Center | 5'-AGTCAGGCCACTTGTGCCACGGTTTGAGCAAACCGTGCTGCCT GTAGCTCCGCCAATAATGGGAGGCGT*GCCGAAAACATGACAGAAAT ACGAACGAAACTAACGCGCAAAGATTCCAG*Ctttttttt-3' (SEQ ID NO: 22) |
| 40 nt $X_Q$ at 3' | 5'-AGTCAGGCCACTTGTGCCACGGTTTGAGCAAACCGTGCTGCCT GTAGCTCCGCCAATAATGGGAGGCGT*GCCGATCCAGAAACATGACA GAAATACGAACGAAACTAACGCGCAAAGAT*Ctttttttt-3' (SEQ ID NO: 23) |
| 40 nt $X_Q$ at 5' | 5'-AGTCAGGCCACTTGTGCCACGGTTTGAGCAAACCGTGCTGCCT GTAGCTCCGCCAATAATGGGAGGCGT*AAACATGACAGAAATACGAA CGAAACTAACGCGCAAAGATGCCGATCCAG*Ctttttttt-3' (SEQ ID NO: 24) |
| 70 nt Triggers | |
| Center | 5'-AGTCAGGCCACTTGTGCCACGGTTTGAGCAAACCGTGCTGCCT GTAGCTCCGCCAATAATGGGAGGCGT*GCCGAGCCGAGCCGAAAACA TGACAGAAATACGAACGAAACTAACGCGCAAAGATGCCGAGCCGAT CCAG*Ctttttttt-3' (SEQ ID NO: 25) |
| 40 nt $X_Q$ at 3' | 5'-AGTCAGGCCACTTGTGCCACGGTTTGAGCAAACCGTGCTGCCT GTAGCTCCGCCAATAATGGGAGGCGT*GCCGATCCAGGCCGATCCAG GCCGATCCAGAAACATGACAGAAATACGAACGAAACTAACGCGCAA AGAT*Ctttttttt-3' (SEQ ID NO: 26) |
| 40 nt $X_Q$ at 5' | 5'-AGTCAGGCCACTTGTGCCACGGTTTGAGCAAACCGTGCTGCCT GTAGCTCCGCCAATAATGGGAGGCGT*AAACATGACAGAAATACGAA CGAAACTAACGCGCAAAGATGCCGATCCAGGCCGATCCAGGCCGAT CCAG*Ctttttttt-3' (SEQ ID NO: 27) |
| 100 nt Triggers | |
| Center | 5'-AGTCAGGCCACTTGTGCCACGGTTTGAGCAAACCGTGCTGCCT GTAGCTCCGCCAATAATGGGAGGCGT*GCCGATCCAGGCCGATCCAG GCCGATCCAGAAACATGACAGAAATACGAACGAAACTAACGCGCAA AGATGCCGATCCAGGCCGATCCAGGCCGATCCAG*Ctttttttt-3' (SEQ ID NO: 28) |

FIG. 13J

| 100 nt Triggers | |
|---|---|
| 40 nt X$_Q$ at 3' | 5'-AGTCAGGCCACTTGTGCCACGGTTTGAGCAAACCGTGCTGCCT<br>GTAGCTCCGCCAATAATGGGAGGCGT*GCCGATCCAGGCCGATCCAG<br>GCCGATCCAGGCCGATCCAGGCCGATCCAGGCCGATCCAG*<u>*AAACAT<br>GACAGAAATACGAACGAAACTAACGCGCAAAGAT*</u>Cttttttt-3'<br>(SEQ ID NO: 29) |
| 40 nt X$_Q$ at 5' | 5'-AGTCAGGCCACTTGTGCCACGGTTTGAGCAAACCGTGCTGCCT<br>GTAGCTCCGCCAATAATGGGAGGCGT<u>*AAACATGACAGAAATACGAA<br>CGAAACTAACGCGCAAAGAT*</u>*GCCGATCCAGGCCGATCCAGGCCGAT<br>CCAGGCCGATCCAGGCCGATCCAGGCCGATCCAGC*ttttttt-3'<br>(SEQ ID NO: 30) |
| 150 nt Triggers | |
| Center | 5'-AGTCAGGCCACTTGTGCCACGGTTTGAGCAAACCGTGCTGCCT<br>GTAGCTCCGCCAATAATGGGAGGCGT*GCCGATCCAGGCCGATCCAG<br>GCCGAGCCGATCCAGGCCGATCCAGGCCGATCCAG*<u>*AAACATGACAG<br>AAATACGAACGAAACTAACGCGCAAAGAT*</u>*GCCGATCCAGGCCGATC<br>CAGGCCGAGCCGATCCAGGCCGATCCAGGCCGATCCAGC*ttttttt<br>-3' (SEQ ID NO: 31) |
| 40 nt X$_Q$ at 3' | 5'-AGTCAGGCCACTTGTGCCACGGTTTGAGCAAACCGTGCTGCCT<br>GTAGCTCCGCCAATAATGGGAGGCGT*GCCGATCCAGGCCGATCCAG<br>GCCGATCCAGGCCGATCCAGGCCGATCCAGGCCGATCCAGGCCGAT<br>CCAGGCCGATCCAGGCCGATCCAGGCCGATCCAGGCCGATCCAG*<u>*AA<br>ACATGACAGAAATACGAACGAAACTAACGCGCAAAGAT*</u>Cttttttt<br>-3' (SEQ ID NO: 32) |
| 40 nt X$_Q$ at 5' | 5'-AGTCAGGCCACTTGTGCCACGGTTTGAGCAAACCGTGCTGCCT<br>GTAGCTCCGCCAATAATGGGAGGCGT<u>*AAACATGACAGAAATACGAA<br>CGAAACTAACGCGCAAAGAT*</u>*GCCGATCCAGGCCGATCCAGGCCGAT<br>CCAGGCCGATCCAGGCCGATCCAGGCCGATCCAGGCCGATCCAGGC<br>CGATCCAGGCCGATCCAGGCCGATCCAGGCCGATCCAGC*ttttttt<br>-3' (SEQ ID NO: 33) |

FIG. 13J (CONTINUED)

Allosteric OFF→ON terminator switch cgRNA

OFF→ON logic
"if X then Y"

······ No-target gRNA (Ideal OFF state)
--- cgRNA (OFF state)
······ cgRNA + trigger (ON state)
—— Standard gRNA (Ideal ON state)

| cgRNAs | Sequence |
|---|---|
| cgRNA M | 5'-gagtcgcgtgtagcgaagcaGTTTAAGAGCTATGCTGGAAA CAGCATAGCAAGTTTAAATAAGGCTAGTCCGTTATCAGCACCtt ttttt-3' (SEQ ID NO: 34) |
| cgRNA N | 5'-gagtcgcgtgtagcgaagcaGTTTAAGAGCTATGCTGGAAA CAGCATAGCAAGTTTAAATAAGGCTAGTCCGTTATCAGGCCCtt ttttt-3' (SEQ ID NO: 35) |
| cgRNA O | 5'-gagtcgcgtgtagcgaagcaGTTTAAGAGCTATGCTGGAAA CAGCATAGCAAGTTTAAATAAGGCTAGTCCGTTATCACCCACtt ttttt-3' (SEQ ID NO: 36) |
| Triggers | |
| Trigger X$_M$ | 5'-GTGCGGCACCGAGTCGGTGCttttttt-3' (SEQ ID NO: 37) |
| Trigger X$_N$ | 5'-GGCCGGCACCGAGTCGGTGCttttttt-3' (SEQ ID NO: 38) |
| Trigger X$_O$ | 5'-TGGGGGCACCGAGTCGGTGCttttttt-3' (SEQ ID NO: 39) |

FIG. 14H

| cgRNAs | Sequence |
|---|---|
| cgRNA M | 5'-gagtcgcgtgtagcgaagcaGTTTAAGAGCTATGCTGGAAA CAGCATAGCAAGTTTAAATAAGGCTAGTCCGTTATCAGCACATC CCACtttttttt-3' (SEQ ID NO: 40) |
| cgRNA N | 5'-gagtcgcgtgtagcgaagcaGTTTAAGAGCTATGCTGGAAA CAGCATAGCAAGTTTAAATAAGGCTAGTCCGTTATCAGGCCAGG TTCCtttttttt-3' (SEQ ID NO: 41) |
| cgRNA O | 5'-gagtcgcgtgtagcgaagcaGTTTAAGAGCTATGCTGGAAA CAGCATAGCAAGTTTAAATAAGGCTAGTCCGTTATCACCCAGAA CACCtttttttt-3' (SEQ ID NO: 42) |
| Triggers | |
| Trigger X$_M$ | 5'-AGTCAGGCCACTTGTGCCACGGTTTGAGCAAACCGTGCTGC CTGTAGCTCCGCCAATAATGGGAGGCGTTGGGATGTGCGGCACC GAGTCGGTGCtttttttt-3' (SEQ ID NO: 43) |
| Trigger X$_N$ | 5'-AGTCAGGCCACTTGTGCCACGGTTTGAGCAAACCGTGCTGC CTGTAGCTCCGCCAATAATGGGAGGCGTGAACCTGGCCGGCACC GAGTCGGTGCtttttttt-3' (SEQ ID NO: 44) |
| Trigger X$_O$ | 5'-AGTCAGGCCACTTGTGCCACGGTTTGAGCAAACCGTGCTGC CTGTAGCTCCGCCAATAATGGGAGGCGTGTGTTCTGGGGGCACC GAGTCGGTGCtttttttt-3' (SEQ ID NO: 45) |

FIG. 15H

Allosteric OFF→ON terminator switch cgRNAs
with different terminator duplex lengths

|d| ∈ {4, 6, 8, 10} nt

|d| ∈ {10, 20, 30, 40} nt

| cgRNAs and Triggers with Idl = 10 nt | |
|---|---|
| cgRNAs | Sequence |
| cgRNA M | 5'-gagtcgcgtgtagcgaagcaGTTAAGAGCTATGCTGAAA CAGCATAGCAAGTTTAATAAGGCTAGTCCGTTATCA*GCACATC CCA*ctttttttt-3' (SEQ ID NO: 46) |
| cgRNA N | 5'-gagtcgcgtgtagcgaagcaGTTAAGAGCTATGCTGAAA CAGCATAGCAAGTTTAATAAGGCTAGTCCGTTATCA*GGCCAGG TTCC*ctttttttt-3' (SEQ ID NO: 47) |
| cgRNA O | 5'-gagtcgcgtgtagcgaagcaGTTAAGAGCTATGCTGAAA CAGCATAGCAAGTTTAATAAGGCTAGTCCGTTATCA*CCCAGAA CACC*ctttttttt-3' (SEQ ID NO: 48) |
| Triggers | |
| Trigger X$_M$ | 5'-AGTCAGGCCACTTGTGCCACGGTTTGAGCAAACCGTGCTGC CTGTAGCTCCGCCAATAATGGGAGGCGT*TGGGATGTGC*TGATGCA AGCTCGTGCtttttttt-3' (SEQ ID NO: 49) |
| Trigger X$_N$ | 5'-AGTCAGGCCACTTGTGCCACGGTTTGAGCAAACCGTGCTGC CTGTAGCTCCGCCAATAATGGGAGGCGT*GAACCTGGCC*TGATGCA AGCTCGTGCtttttttt-3' (SEQ ID NO: 50) |
| Trigger X$_O$ | 5'-AGTCAGGCCACTTGTGCCACGGTTTGAGCAAACCGTGCTGC CTGTAGCTCCGCCAATAATGGGAGGCGT*GTGTTCTGGG*TGATGCA AGCTCGTGCtttttttt-3' (SEQ ID NO: 51) |
| cgRNAs and Triggers with Idl = 8 nt | |
| cgRNAs | Sequence |
| cgRNA M | 5'-gagtcgcgtgtagcgaagcaGTTAAGAGCTATGCTGAAA CAGCATAGCAAGTTTAATAAGGCTAGTCCGTTATCA*GCACATC CC*ctttttttt-3' (SEQ ID NO: 52) |
| cgRNA N | 5'-gagtcgcgtgtagcgaagcaGTTAAGAGCTATGCTGAAA CAGCATAGCAAGTTTAATAAGGCTAGTCCGTTATCA*GGCCAGG TC*ctttttttt-3' (SEQ ID NO: 53) |
| cgRNA O | 5'-gagtcgcgtgtagcgaagcaGTTAAGAGCTATGCTGAAA CAGCATAGCAAGTTTAATAAGGCTAGTCCGTTATCA*CCCAGAA CC*ctttttttt-3' (SEQ ID NO: 54) |
| Triggers | |
| Trigger X$_M$ | 5'-AGTCAGGCCACTTGTGCCACGGTTTGAGCAAACCGTGCTGC CTGTAGCTCCGCCAATAATGGGAGGCGT*GGATGTGC*TGATGCA GCTCGTGCtttttttt-3' (SEQ ID NO: 55) |
| Trigger X$_N$ | 5'-AGTCAGGCCACTTGTGCCACGGTTTGAGCAAACCGTGCTGC CTGTAGCTCCGCCAATAATGGGAGGCGT*ACCTGGCC*TGATGCA GCTCGTGCtttttttt-3' (SEQ ID NO: 56) |
| Trigger X$_O$ | 5'-AGTCAGGCCACTTGTGCCACGGTTTGAGCAAACCGTGCTGC CTGTAGCTCCGCCAATAATGGGAGGCGT*GTTCTGGG*TGATGCA GCTCGTGCtttttttt-3' (SEQ ID NO: 57) |
| cgRNAs and Triggers with Idl = 6 nt | |
| cgRNAs | Sequence |
| cgRNA M | 5'-gagtcgcgtgtagcgaagcaGTTAAGAGCTATGCTGAAA CAGCATAGCAAGTTTAATAAGGCTAGTCCGTTATCA*GCACATC* ttttttt-3' (SEQ ID NO: 58) |
| cgRNA N | 5'-gagtcgcgtgtagcgaagcaGTTAAGAGCTATGCTGAAA CAGCATAGCAAGTTTAATAAGGCTAGTCCGTTATCA*GGCCAGC* ttttttt-3' (SEQ ID NO: 59) |
| cgRNA O | 5'-gagtcgcgtgtagcgaagcaGTTAAGAGCTATGCTGAAA CAGCATAGCAAGTTTAATAAGGCTAGTCCGTTATCA*CCCAGAC* ttttttt-3' (SEQ ID NO: 60) |
| Triggers | |
| Trigger X$_M$ | 5'-AGTCAGGCCACTTGTGCCACGGTTTGAGCAAACCGTGCTGC CTGTAGCTCCGCCAATAATGGGAGGCGT*ATGTGC*TGATGCAAGCT CGTGCtttttttt-3' (SEQ ID NO: 61) |
| Trigger X$_N$ | 5'-AGTCAGGCCACTTGTGCCACGGTTTGAGCAAACCGTGCTGC CTGTAGCTCCGCCAATAATGGGAGGCGT*CTGGCC*TGATGCAAGCT CGTGCtttttttt-3' (SEQ ID NO: 62) |
| Trigger X$_O$ | 5'-AGTCAGGCCACTTGTGCCACGGTTTGAGCAAACCGTGCTGC CTGTAGCTCCGCCAATAATGGGAGGCGT*TCTGGG*TGATGCAAGCT CGTGCtttttttt-3' (SEQ ID NO: 63) |

FIG. 16D

| cgRNAs with ldl = {40, 30, 20, 10} nt | Sequence |
|---|---|
| cgRNA 40 | 5'-agtcgcgtgtagcgaagca GTTTAAGAGCTATGCTGGAAAC AGCATAGCAAGTTTAAATAAGGCTAGTCCGTTATCA*CATATCCC ATCCACCTCCACCTCCACCTCCACATTCCCACCtttttttt-3'* (SEQ ID NO: 64) |
| cgRNA 30 | 5'-agtcgcgtgtagcgaagca GTTTAAGAGCTATGCTGGAAAC AGCATAGCAAGTTTAAATAAGGCTAGTCCGTTATCA*CATATCCC ATCCACCTCCACCTCCACCTCCCtttttttt-3'* (SEQ ID NO: 65) |
| cgRNA 20 | 5'-agtcgcgtgtagcgaagca GTTTAAGAGCTATGCTGGAAAC AGCATAGCAAGTTTAAATAAGGCTAGTCCGTTATCA*CATATCCC ATCCACCTCCACCtttttttt-3'* (SEQ ID NO: 66) |
| cgRNA 10 | 5'-agtcgcgtgtagcgaagca GTTTAAGAGCTATGCTGGAAAC AGCATAGCAAGTTTAAATAAGGCTAGTCCGTTATCA*CATATCCC ATCtttttttt-3'* (SEQ ID NO: 67) |
| Triggers with ldl = {40, 30, 20, 10} nt | |
| Trigger X$_{40}$ | 5'-AGTCAGGCCACTTGTGCCACGGTTTGAGCAAACCGTGCTGC CTGTAGCTCCGCCAATAATGGGAGGCGT*GTGGAATGTGGAGGT GGAGGTGGAGGTGGATGGGATATG*GGCACCGAGTCGGTGCtttt ttt-3' (SEQ ID NO: 68) |
| Trigger X$_{30}$ | 5'-AGTCAGGCCACTTGTGCCACGGTTTGAGCAAACCGTGCTGC CTGTAGCTCCGCCAATAATGGGAGGCGT*GGAGGTGGAGGTGGAG GTGGATGGGATATG*GGCACCGAGTCGGTGCtttttttt-3' (SEQ ID NO: 69) |
| Trigger X$_{20}$ | 5'-AGTCAGGCCACTTGTGCCACGGTTTGAGCAAACCGTGCTGC CTGTAGCTCCGCCAATAATGGGAGGCGT*GTGGAGGTGGATGGGA TATG*GGCACCGAGTCGGTGCtttttttt-3' (SEQ ID NO: 70) |
| Trigger X$_{10}$ | 5'-AGTCAGGCCACTTGTGCCACGGTTTGAGCAAACCGTGCTGC CTGTAGCTCCGCCAATAATGGGAGGCGTA*TGGGATATG*GGCACC GAGTCGGTGCtttttttt-3' (SEQ ID NO: 71) |

FIG. 16E

| gRNAs | Sequence |
|---|---|
| Standard gRNA | 5'-gagtcgcgtgtagcgaagcaGTTTTAGAGCTAGAAATAGCAAGTTAAAATAAGGCTAGTCCGTTATCAACTTGAAAAAGTGGCACCGAGTCGGTGCttttttt-3' (SEQ ID NO: 72) |
| No-target gRNA | 5'-GTTTTAGAGCTAGAAATAGCAAGTTAAAATAAGGCTAGTCCGTTATCAACTTGAAAAAGTGGCACCGAGTCGGTGCttttttt-3' (SEQ ID NO: 73) |
| 8 nt deletion | 5'-gagtcgcgtgtagcgaagcaGTTTTAGAGCTAGAAATAGCAAGTTAAAATAAGGCTAGTCCGTTATCAACTTGAAAAAGTGGCACCGCttttttt-3' (SEQ ID NO: 74) |
| 23 nt deletion | 5'-gagtcgcgtgtagcgaagcaGTTTTAGAGCTAGAAATAGCAAGTTAAAATAAGGCTAGTCCGTTATCAACTTCttttttt-3' (SEQ ID NO: 75) |
| 32 nt deletion | 5'-gagtcgcgtgtagcgaagcaGTTTTAGAGCTAGAAATAGCAAGTTAAAATAAGGCTAGTCCGTCttttttt-3' (SEQ ID NO: 76) |
| 45 nt deletion | 5'-gagtcgcgtgtagcgaagcaGTTTTAGAGCTAGAAATAGCAAGTTAAAATCttttttt-3' (SEQ ID NO: 77) |

FIG. 17C

Allosteric ON→OFF terminator switch cgRNA with mRNA trigger

| cgRNAs | Sequence |
|---|---|
| cgRNA A | 5'-aactttcagtttagcggtct<span style="color:gray">ttttagagctagaaatagca agttaaaataaggctagtccc</span>ATCAAACGGGTAAACAAACAGGA TAATTAAGGAGGCAGTACCCG<span style="color:gray">gcaccgagtcggtgcttttttt</span>-3' (SEQ ID NO: 78) |
| cgRNA E | 5'-aactttcagtttagcggtct<span style="color:gray">ttttagagctagaaatagca agttaaaataaggctagtccc</span>ACACAAGGGGAAATTAACAACAC AACACACACAACACAGGCCCC<span style="color:gray">gcaccgagtcggtgcttttttt</span>-3' (SEQ ID NO: 79) |
| Triggers | |
| Trigger X_A | 5'-tggctaaagaaagaggagaaaaggtttatggtagcaggtca tgcctctggcagcccgcattcgggaccgcctctcattcgaatt gcgaacatgaagagatccacctcgccggctcgatccagccgcat ggcgcgcttctggtcgtcagcgaacatgatcatcgcgtcatcca ggccagcgccaacgccgcggaatttctgaatctcggaagcgtac tcggcgttccgctcgccgagatcgacggcgatctgttgatcaag atcctgccgcatctcgatcccaccgccgaaggcatgccggtcgc ggtgcgctgccggatcggcaatccctctacggagtactgcggtc tgatgcatcggcctccggaaggcgggctgatcatcgaactcgaa cgtgccggccgtcgatcgatctgtcaggcacgctggcgccggc gctggagcggatccgcacggcgggttcactgcgcgcgctgtgcg atgacaccgtgctgctgtttcagcagtgcaccggctacgaccgg gtgatggtgtatcgtttcgatgagcaaggccacggcctggtatt ctccgagtgccatgtgcctgggctcgaatcctatttcggcaacc gctatccgtcgtcgactgtcccgcagatggcgcggcagctgtac gtgcggcagcgcgtccgcgtgctggtcgacgtcacctatcagcc ggtgccgctggagccgcggctgtcgccgctgaccgggcgcgatc tcgacatgtcgggctgcttcctgcgctcgatgtcgccgtgccat ctgcagttcctgaaggacatgggcgtgcgcgccaccctggcggt gtcgctggtggtcggcggcaagctgtggggcctggttgtctgtc accattatctgccgcgcttcatccgtttcgagctgcgggcgatc tgcaaacggctcgccgaaaggatcgcgacgcggatcaccgcgct tgagagcgaattcggtggtggtggttctggtggtggtggttcta tgagtgtcaacttagcttcccagttgcgggaagggacgaaaaaa tcccactccatggcggagaacgtcggctttgtcaaatgcttcct caagggcgttgtcgagaaaaattcctaccgtaagctggttggca atctctactttgtctacagtgccatggaagaggaaatggcaaaa tttaaggaccatcccatcctcagccacatttacttccccgaact caaccgcaaacaaagcctagagcaagacctgcaattctattacg gctccaactggcggcaagaagtgaaaatttctgccgctggccaa gcctatgtggaccgagtccggcaagtggccgctacggcccctga attgttggtggcccattcctacacccgttacctggggatctttt ccggcggtcaaattctcaagaaaattgcccaaaatgccatgaat ctccacgatggtggcacagctttctatgaatttgccgacattga tgacgaaaaggcttttaaaaatacctaccgtcaagctatgaatg atctgcccattgaccaagccaccgccgaacggattgtggatgaa gccaatgacgcctttgccatgaacatgaaaatgttcaacgaact tgaaggcaacctgatcaaggcgatcggcattatggtgttcaaca gcctcacccgtcgccgcagtcaaggcagcaccgaagttggcctc gccacctccgaaggctagtaaacgtcgactctcgagtgagattg ttgacggtaccgtatttTACTGCCTCCTTAATTATCCTGTTTG TTTACCCGTTTGATcgcaaaaaacccgcttcggcggggtttt tcgc-3' (SEQ ID NO: 80) |

FIG. 18E

| | |
|---|---|
| Trigger X$_E$ | 5'-tggctaaagaaagaggagaaaaggtttatggtagcaggtca<br>tgcctctggcagcccgcattcgggaccgcctctcattcgaatt<br>gcgaacatgaagagatccacctcgccggctcgatccagccgcat<br>ggcgcgcttctggtcgtcagcgaacatgatcatcgcgtcatcca<br>ggccagcgccaacgcgcggaatttctgaatctcggaagcgtac<br>tcggcgttccgctcgccgagatcgacggcgatctgttgatcaag<br>atcctgccgcatctcgatcccaccgcgaaggcatgccggtcgc<br>ggtgcgctgccggatcggcaatccctctacggagtactgcggtc<br>tgatgcatcggcctccggaaggcgggctgatcatcgaactcgaa<br>cgtgccggcccgtcgatcgatctgtcaggcacgctggcgccggc<br>gctggagcggatccgcacggcgggttcactgcgcgcgctgtgcg<br>atgacaccgtgctgctgtttcagcagtgcaccggctacgaccgg<br>gtgatggtgtatcgtttcgatgagcaaggccacggcctggtatt<br>ctccgagtgccatgtgcctgggctcgaatcctatttcggcaacc<br>gctatccgtcgtcgactgtcccgcagatggcgcggcagctgtac<br>gtgcggcagcgcgtccgcgtgctggtcgacgtcacctatcagcc<br>ggtgccgctggagccgcggctgtcgccgctgaccgggcgcgatc<br>tcgacatgtcgggctgcttcctgcgctcgatgtcgccgtgccat<br>ctgcagttcctgaaggacatgggcgtgcgcgccaccctggcggt<br>gtcgctggtggtcggcggcaagctgtggggcctggttgtctgtc<br>accattatctgccgcgcttcatccgtttcgagctgcgggcgatc<br>tgcaaacggctcgccgaaaggatcgcgacgcggatcaccgcgct<br>tgagagcgaattcggtggtggtggttctggtggtggtggttcta<br>tgagtgtcaacttagcttcccagttgcgggaagggacgaaaaaa<br>tcccactccatggcggagaacgtcggctttgtcaaatgcttcct<br>caagggcgttgtcgagaaaaattcctaccgtaagctggttggca<br>atctctactttgtctacagtgccatggaagaggaaatggcaaaa<br>tttaaggaccatcccatcctcagccacatttacttccccgaact<br>caaccgcaaacaaagcctagagcaagacctgcaattctattacg<br>gctccaactggcggcaagaagtgaaaatttctgccgctggccaa<br>gcctatgtggaccgagtccggcaagtggccgctacggcccctga<br>attgttggtggcccattcctacacccgttacctggggatcttt<br>ccggcggtcaaattctcaagaaaattgcccaaaatgccatgaat<br>ctccacgatggtggcacagctttctatgaatttgccgacattga<br>tgacgaaaaggcttttaaaaatacctaccgtcaagctatgaatg<br>atctgcccattgaccaagccaccgccgaacggattgtggatgaa<br>gccaatgacgcctttgccatgaacatgaaaatgttcaacgaact<br>tgaaggcaacctgatcaaggcgatcggcattatggtgttcaaca<br>gcctcacccgtcgccgcagtcaaggcagcaccgaagttggcctc<br>gccacctccgaaggctagtaaacgtcgactctcgagtgagattg<br>ttgacggtaccgtattt*CCTGTGTTGTGTGTTGTGTTGTTA<br>ATTTCCCCTTGTGT*cgcaaaaaacccgcttcggcggggttttt<br>tcgc-3' (SEQ ID NO: 81) |

FIG. 18F

Allosteric ON → OFF terminator switch cgRNA

Sequence Constraints

— Constrained by target gene
····· Constrained by dCas9
····· Constrained by hU6 terminator
— Designed sequence Allosteric OFF→ ON split-terminator switch cgRNA Sequence Constraints — Constrained by target gene
⋯ Constrained by dCas9
⋯ Constrained by hU6 terminator
— Designed sequence ON → OFF logic
"if not X then Y"

| cgRNAs | Sequence |
|---|---|
| cgRNA | 5'-gagtcgcgtgtagcgaagcaGTTTAAGAGCTAGAAATAGCAAGTTAAAATAAGGCTAGTCCGTCCATTCGGGTTTACTATTACAATCTTACGTGTTCTCATTCCCGGGCACCGAGTCGGTGCtttttttt-3' (SEQ ID NO: 82) |
| Triggers | |
| Non-cognate trigger (X´) | 5'-AGTCAGGCCACTTGTGCCACGGTTTGAGCAAACCGTGCTGCCTGTAGCTCCGCCAATAATGGGAGGCGTAAACATGACAGAAATACGAACGAAACTAACGCGCAAAGATCtttttttt-3' (SEQ ID NO: 83) |
| Cognate-trigger (X) | 5'-AGTCAGGCCACTTGTGCCACGGTTTGAGCAAACCGTGCTGCCTGTAGCTCCGCCAATAATGGGAGGCGTAATGAGAACACGTAAGATTGTAATAGTAAACCCGAATGGACtttttttt-3' (SEQ ID NO: 84) |

FIG. 21E

| cgRNAs | Sequence |
|---|---|
| cgRNA | 5'-gagtcgcgtgtagcgaagcaGTTTAAGAGCTATGCTGGAAA CAGCATAGCAAGTTTAAATAAGGCTAGTCCGTTATCAGGCCAGG TTCCttttttt-3' (SEQ ID NO: 85) |
| Triggers | |
| Non-cognate trigger (X') | 5'-AGTCAGGCCACTTGTGCCACGGTTTGAGCAAACCGTGCTGC CTGTAGCTCCGCCAATAATGGGAGGCGTTGGGATGTGCGGCACC GAGTCGGTGCttttttt-3' (SEQ ID NO: 86) |
| Cognate trigger (X) | 5'-AGTCAGGCCACTTGTGCCACGGTTTGAGCAAACCGTGCTGC CTGTAGCTCCGCCAATAATGGGAGGCGTGAACCTGGCCGGCACC GAGTCGGTGCttttttt-3' (SEQ ID NO: 87) |

FIG. 22E

Allosteric ON→OFF tandem switch cgRNA (Mechanism 3A)

---

Mechanism 3A: Schematic

Mechanism 3A: Annotated Schematic

Allosteric OFF→ON tandem switch cgRNA (Mechanism 3B)

Mechanism 3B: Schematic

Mechanism 3B: Annotated Schematic

Allosteric OFF→ON 5'-inhibited split-terminator switch cgRNA (Mechanism 5)

OFF→ON logic
"if X then regulate Y"

---

Mechanism 5: Schematic

OFF State

ON State

Allosteric OFF→ON 3'-inhibited split-terminator switch cgRNA
(Mechanism 6)

OFF→ON logic
"if X then regulate Y"

---

Mechanism 6: Schematic

OFF State

5' fragment cg5

3' fragment cg3 a* b* c* d*
RNA trigger X trigger:cg3 cg5

ON State trigger:cg5:cg3

Target gene Y

Mechanism 6: Annotated Schematic

Allosteric OFF→ON 5'- and 3'-inhibited split-terminator switch cgRNA (Mechanism 7)

Mechanism 7: Schematic

OFF State

ON State

Mechanism 7: Annotated Schematic

OFF State

ON State

Allosteric OFF→ON 5'- and 3'-inhibited split-terminator switch cgRNA (Mechanism 8)

Mechanism 8: Annotated Schematic

OFF State (continued top of next page)

Allosteric OFF→ON 5'- and 3'-inhibited split-terminator switch cgRNA
(Mechanism 9)

---

Mechanism 9: Schematic

OFF State

RNA trigger X trigger:cg5

ON State

Allosteric OFF→ON split-terminator switch cgRNA

OFF→ON logic
"if X then not Y"

| cgRNAs | Sequence |
|---|---|
| cgRNA M | 5'-catctaattcaacaagaattGTTTTAGAGCTAGAAATAGCAAGTTAAAATAAGGCTAGTCCGTTATCAGCAC-3' (SEQ ID NO: 88) |
| cgRNA N | 5'-catctaattcaacaagaattGTTTTAGAGCTAGAAATAGCAAGTTAAAATAAGGCTAGTCCGTTATCAGGCC-3' (SEQ ID NO: 89) |
| cgRNA O | 5'-catctaattcaacaagaattGTTTTAGAGCTAGAAATAGCAAGTTAAAATAAGGCTAGTCCGTTATCACCCA-3' (SEQ ID NO: 90) |
| Triggers | |
| Trigger $X_M$ | 5'-GTGCGGCACCGAGTCGGTG-3' (SEQ ID NO: 91) |
| Trigger $X_N$ | 5'-GGCCGGCACCGAGTCGGTG-3' (SEQ ID NO: 92) |
| Trigger $X_O$ | 5'-TGGGGGCACCGAGTCGGTG-3' (SEQ ID NO: 93) |

FIG. 30D

Allosteric ON→OFF split-terminator switch cgRNA (Mechanism 4B)

Allosteric ON→OFF split-terminator switch cgRNA (Mechanism 4C)

| Mechanism 4B | |
|---|---|
| cg5 | 5'-gagtcgcgtgtagcgaagca*TTTTAGAGCTAGAAATAGCAAG TTAAAATAAGGCTAGTCCG*TCCCATCGTCCGTCCCATCAATTTCCC tttttttt-3' (SEQ ID NO: 94) |
| cg3 | 5'- *AATATAATACGGGACGGACG*GGCACCGAGTCGGTGCtttttt t-3' (SEQ ID NO: 95) |
| Trigger | 5'-AGTCAGGCCACTTGTGCCACGGTTTGAGCAAACCGTGCTGCCT GTAGCTCCGCCAATAATGGGAGGCGT*CGTCCGTCCCGTATTATATT*C tttttttt-3' (SEQ ID NO: 96) |
| Mechanism 4C | |
| cg5 | 5'-gagtcgcgtgtagcgaagca*TTTTAGAGCTAGAAATAGCAAG TTAAAATAAGGCTAGTCCGATATATACAAACACAACACACACAA CAACAAACAC*tttttttt-3' (SEQ ID NO: 97) |
| cg3 | 5'-AGTCAGGCCACTTGTGCCACGGTTTGAGCAAACCGTGCTGCCT GTAGCTCCGCCAATAATGGGAGGCGT*TGTCTAGAATTGTTTGTTGT TGTGTGTGTGTTGTGTTTGT*GGCACCGAGTCGGTGCtttttttt-3' (SEQ ID NO: 98) |
| Trigger | 5'-AGTCAGGCCACTTGTGCCACGGTTTGAGCAAACCGTGCTGCCT GTAGCTCCGCCAATAATGGGAGGCGT*ACAAACACAACACACACA ACAACAAACAATTCTAGACAC*tttttttt-3' (SEQ ID NO: 99) |

FIG. 31E

**Allosteric ON→OFF split-terminator switch cgRNA
(Mechanism 4B)**

**Allosteric ON→OFF split-terminator switch cgRNA
(Mechanism 4C)**

| cgRNAs | Sequence |
|---|---|
| cg5 | 5'-aactttcagtttagcggtctGTTTTAGAGCTAGAAATAGCAAGTTAAAATAAGGCTAGTCCGATATATACAAACACAACACACACACAACAACAAACACAACCCAACCagagcgcaaaaaaccccgcttcggcggggttttttcgc-3' (SEQ ID NO: 100) |
| cg3 | 5'-TGTCTAGAATTGTTTGTTGTTGTGTGTGTTGTGTTTGTgcaccgagtcggtgcttttttttcgcc-3' (SEQ ID NO: 101) |
| Triggers | |
| No-trigger control | 5'-cgcaaaaaaccccgcttcggcggggttttttcgc-3' (SEQ ID NO: 102) |
| Trigger X (Mechanism 4B) | 5'-GGTTGGGTTGTGTTTGTTGTTGTGTGTGTTGTGTTTGTcgcaaaaaaccccgcttcggcggggttttttcgc-3' (SEQ ID NO: 103) |
| Trigger X (Mechanism 4C) | 5'-ACAAACACAACACACACACAACAACAAACAATTCTAGACAcgcaaaaaaccccgcttcggcggggttttttcgc-3' (SEQ ID NO: 104) |

FIG. 32F

Allosteric OFF→ON 5' and 3'inhibited split-terminator switch cgRNA (Mechanism 7)

| cgRNAs | Sequence |
|---|---|
| cg5 | 5'-*TTGTTTAAGGCTATGGTGAG*aactttcagtttagcggtct ??????????????????????????????????????*TAA ATAAAAGCCCACCCTCACCATAG*agagcgcaaaaaaccccgctt cggcggggttttttcgc-3' (SEQ ID NO: 105) |
| cg3 | 5'-*CCACCCTCACCATAGGTGCTATGGTGAGGGTGGGCTTT*ggc accgagtcggtgcttttttttcgcaaaaaaccccgcttcggcggg gttttttcgc-3' (SEQ ID NO: 106) |
| Triggers | |
| No-trigger control | 5'-cgcaaaaaaccccgcttcggcggggttttttcgc-3' (SEQ ID NO: 107) |
| Trigger X | 5'-*CTCACCATAGCCTTGAACAA*cgcaaaaaaccccgctt cggcggggttttttcgc-3' (SEQ ID NO: 108) |

SEQUENCE LISTING

```
Sequence total quantity: 108
SEQ ID NO: 1                moltype = DNA   length = 129
FEATURE                     Location/Qualifiers
misc_feature                1..129
                            note = cgRNA A
source                      1..129
                            mol_type = other DNA
                            organism = synthetic construct
SEQUENCE: 1
aactttcagt ttagcggtct gttttagagc tagaaatagc aagttaaaat aaggctagtc   60
cgatcaaacg ggtaaacaaa caggataatt aaggaggcag tacccgggca ccgagtcggt  120
gctttttt                                                           129

SEQ ID NO: 2                moltype = DNA   length = 129
FEATURE                     Location/Qualifiers
misc_feature                1..129
                            note = cgRNA B
source                      1..129
                            mol_type = other DNA
                            organism = synthetic construct
SEQUENCE: 2
aactttcagt ttagcggtct gttttagagc tagaaatagc aagttaaaat aaggctagtc   60
cgtatcatgg ggttgtgtgt tgttgtaagt gtgtgtgtgt tgccccggca ccgagtcggt  120
gctttttt                                                           129

SEQ ID NO: 3                moltype = DNA   length = 129
FEATURE                     Location/Qualifiers
misc_feature                1..129
                            note = cgRNA C
source                      1..129
                            mol_type = other DNA
                            organism = synthetic construct
SEQUENCE: 3
aactttcagt ttagcggtct gttttagagc tagaaatagc aagttaaaat aaggctagtc   60
cgaatatagg ggaagagaaa gaagaagaga agagaaagat gtccccggca ccgagtcggt  120
gctttttt                                                           129

SEQ ID NO: 4                moltype = DNA   length = 40
FEATURE                     Location/Qualifiers
misc_feature                1..40
                            note = Trigger XA
source                      1..40
                            mol_type = other DNA
                            organism = synthetic construct
SEQUENCE: 4
tactgcctcc ttaattatcc tgtttgttta cccgtttgat                         40

SEQ ID NO: 5                moltype = DNA   length = 40
FEATURE                     Location/Qualifiers
misc_feature                1..40
                            note = Trigger XB
source                      1..40
                            mol_type = other DNA
                            organism = synthetic construct
SEQUENCE: 5
caacacacac acacttacaa caacacacaa ccccatgata                         40

SEQ ID NO: 6                moltype = DNA   length = 40
FEATURE                     Location/Qualifiers
misc_feature                1..40
                            note = Trigger XC
source                      1..40
                            mol_type = other DNA
                            organism = synthetic construct
SEQUENCE: 6
acatctttct cttctcttct tctttctctt ccccctatatt                        40

SEQ ID NO: 7                moltype = DNA   length = 165
FEATURE                     Location/Qualifiers
misc_feature                1..165
                            note = cgRNA A
source                      1..165
                            mol_type = other DNA
                            organism = synthetic construct
SEQUENCE: 7
catctaattc aacaagaatt gttttagagc tacaccttac gccggttcaa ttccaagtcc   60
cttccagtag caagttaaaa taaggctagt ccgttatcaa cttaacaccc tttacaaacc  120
ttcctcttcc tttaccctaa gtggcaccga gtcggtgctt ttttt                  165
```

```
SEQ ID NO: 8              moltype = DNA   length = 165
FEATURE                   Location/Qualifiers
misc_feature              1..165
                          note = cgRNA B
source                    1..165
                          mol_type = other DNA
                          organism = synthetic construct
SEQUENCE: 8
catctaattc aacaagaatt gttttagagc tagtaatcga atcatagtaa atttcccatc    60
gtcataatag caagttaaaa taaggctagt ccgttatcaa cttcatacgg gtctgaagta   120
gttcattctt atacagtcaa gtggcaccga gtcggtgctt ttttt                   165

SEQ ID NO: 9              moltype = DNA   length = 165
FEATURE                   Location/Qualifiers
misc_feature              1..165
                          note = cgRNA C
source                    1..165
                          mol_type = other DNA
                          organism = synthetic construct
SEQUENCE: 9
catctaattc aacaagaatt gttttagagc tagtcgttac cttatcaata tcaacctccg    60
catacactag caagttaaaa taaggctagt ccgttatcaa cttgcacata ggacccaaca   120
tgccaacaga gaagagttaa gtggcaccga gtcggtgctt ttttt                   165

SEQ ID NO: 10             moltype = DNA   length = 70
FEATURE                   Location/Qualifiers
misc_feature              1..70
                          note = Trigger XA
source                    1..70
                          mol_type = other DNA
                          organism = synthetic construct
SEQUENCE: 10
agggtaaagg aagaggaagg tttgtaaagg gtgttctgga agggacttgg aattgaaccg    60
gcgtaaggtg                                                           70

SEQ ID NO: 11             moltype = DNA   length = 70
FEATURE                   Location/Qualifiers
misc_feature              1..70
                          note = Trigger XB
source                    1..70
                          mol_type = other DNA
                          organism = synthetic construct
SEQUENCE: 11
gactgtataa gaatgaacta cttcagaccc gtatgttatg acgatgggaa atttactatg    60
attcgattac                                                           70

SEQ ID NO: 12             moltype = DNA   length = 70
FEATURE                   Location/Qualifiers
misc_feature              1..70
                          note = Trigger XC
source                    1..70
                          mol_type = other DNA
                          organism = synthetic construct
SEQUENCE: 12
aactcttctc tgttggcatg ttgggtccta tgtgcgtgta tgcggaggtt gatattgata    60
aggtaacgac                                                           70

SEQ ID NO: 13             moltype = DNA   length = 129
FEATURE                   Location/Qualifiers
misc_feature              1..129
                          note = cgRNA Q
source                    1..129
                          mol_type = other DNA
                          organism = synthetic construct
SEQUENCE: 13
gagtcgcgtg tagcgaagca gttttagagc tagaaatagc aagttaaaat aaggctagtc    60
cgatctttgc gcgttagttt cgttcgtatt tctgtcatgt ttgcgcggca ccgagtcggt   120
gcttttttt                                                           129

SEQ ID NO: 14             moltype = DNA   length = 129
FEATURE                   Location/Qualifiers
misc_feature              1..129
                          note = cgRNA R
source                    1..129
                          mol_type = other DNA
                          organism = synthetic construct
SEQUENCE: 14
gagtcgcgtg tagcgaagca gttttagagc tagaaatagc aagttaaaat aaggctagtc    60
```

```
cgtatcgccg ggttcaagca gatgtggcat tcagtgtag ttcccgggca ccgagtcggt    120
gcttttttt                                                           129

SEQ ID NO: 15           moltype = DNA   length = 129
FEATURE                 Location/Qualifiers
misc_feature            1..129
                        note = cgRNA S
source                  1..129
                        mol_type = other DNA
                        organism = synthetic construct
SEQUENCE: 15
gagtcgcgtg tagcgaagca gttttagagc tagaaatagc aagttaaaat aaggctagtc    60
cgtccattcg ggtttactat tacaatctta cgtgttctca ttcccgggca ccgagtcggt    120
gcttttttt                                                           129

SEQ ID NO: 16           moltype = DNA   length = 129
FEATURE                 Location/Qualifiers
misc_feature            1..129
                        note = cgRNA T
source                  1..129
                        mol_type = other DNA
                        organism = synthetic construct
SEQUENCE: 16
gagtcgcgtg tagcgaagca gttttagagc tagaaatagc aagttaaaat aaggctagtc    60
cggataaagg gaaagatgaa gtgatgtgaa gatagagttg gatcccggca ccgagtcggt    120
gcttttttt                                                           129

SEQ ID NO: 17           moltype = DNA   length = 117
FEATURE                 Location/Qualifiers
misc_feature            1..117
                        note = Trigger XQ
source                  1..117
                        mol_type = other DNA
                        organism = synthetic construct
SEQUENCE: 17
agtcaggcca cttgtgccac ggtttgagca aaccgtgctg cctgtagctc cgccaataat    60
gggaggcgta aacatgacag aaatacgaac gaaactaacg cgcaaagatc tttttt       117

SEQ ID NO: 18           moltype = DNA   length = 117
FEATURE                 Location/Qualifiers
misc_feature            1..117
                        note = Trigger XR
source                  1..117
                        mol_type = other DNA
                        organism = synthetic construct
SEQUENCE: 18
agtcaggcca cttgtgccac ggtttgagca aaccgtgctg cctgtagctc cgccaataat    60
gggaggcgta actacactga aatgccacat ctgcttgaac ccggcgatac tttttt       117

SEQ ID NO: 19           moltype = DNA   length = 117
FEATURE                 Location/Qualifiers
misc_feature            1..117
                        note = Trigger XS
source                  1..117
                        mol_type = other DNA
                        organism = synthetic construct
SEQUENCE: 19
agtcaggcca cttgtgccac ggtttgagca aaccgtgctg cctgtagctc cgccaataat    60
gggaggcgta atgagaacac gtaagattgt aatagtaaac ccgaatggac tttttt       117

SEQ ID NO: 20           moltype = DNA   length = 117
FEATURE                 Location/Qualifiers
misc_feature            1..117
                        note = Trigger XT
source                  1..117
                        mol_type = other DNA
                        organism = synthetic construct
SEQUENCE: 20
agtcaggcca cttgtgccac ggtttgagca aaccgtgctg cctgtagctc cgccaataat    60
gggaggcgtt ccaactctat cttcacatca cttcatcttt ccctttatcc tttttt       117

SEQ ID NO: 21           moltype = DNA   length = 117
FEATURE                 Location/Qualifiers
misc_feature            1..117
                        note = Trigger XQ - 40 nt
source                  1..117
                        mol_type = other DNA
                        organism = synthetic construct
SEQUENCE: 21
```

```
agtcaggcca cttgtgccac ggtttgagca aaccgtgctg cctgtagctc cgccaataat    60
gggaggcgta aacatgacag aaatacgaac gaaactaacg cgcaaagatc ttttttt     117

SEQ ID NO: 22           moltype = DNA   length = 127
FEATURE                 Location/Qualifiers
misc_feature            1..127
                        note = 50 nt Trigger - Center
source                  1..127
                        mol_type = other DNA
                        organism = synthetic construct
SEQUENCE: 22
agtcaggcca cttgtgccac ggtttgagca aaccgtgctg cctgtagctc cgccaataat    60
gggaggcgtg ccgaaaacat gacagaaata cgaacgaaac taacgcgcaa agattccagc   120
ttttttt                                                            127

SEQ ID NO: 23           moltype = DNA   length = 127
FEATURE                 Location/Qualifiers
misc_feature            1..127
                        note = 50 nt Trigger - 40 nt XQ at 3'
source                  1..127
                        mol_type = other DNA
                        organism = synthetic construct
SEQUENCE: 23
agtcaggcca cttgtgccac ggtttgagca aaccgtgctg cctgtagctc cgccaataat    60
gggaggcgtg ccgatccaga aacatgacag aaatacgaac gaaactaacg cgcaaagatc   120
ttttttt                                                            127

SEQ ID NO: 24           moltype = DNA   length = 127
FEATURE                 Location/Qualifiers
misc_feature            1..127
                        note = 50 nt Trigger - 40 nt XQ at 5'
source                  1..127
                        mol_type = other DNA
                        organism = synthetic construct
SEQUENCE: 24
agtcaggcca cttgtgccac ggtttgagca aaccgtgctg cctgtagctc cgccaataat    60
gggaggcgta aacatgacag aaatacgaac gaaactaacg cgcaaagatg ccgatccagc   120
ttttttt                                                            127

SEQ ID NO: 25           moltype = DNA   length = 147
FEATURE                 Location/Qualifiers
misc_feature            1..147
                        note = 70 nt Trigger - Center
source                  1..147
                        mol_type = other DNA
                        organism = synthetic construct
SEQUENCE: 25
agtcaggcca cttgtgccac ggtttgagca aaccgtgctg cctgtagctc cgccaataat    60
gggaggcgtg ccgagccgag ccgaaaacat gacagaaata cgaacgaaac taacgcgcaa   120
agatgccgag ccgatccagc ttttttt                                      147

SEQ ID NO: 26           moltype = DNA   length = 147
FEATURE                 Location/Qualifiers
misc_feature            1..147
                        note = 70 nt Trigger - 40 nt XQ at 3'
source                  1..147
                        mol_type = other DNA
                        organism = synthetic construct
SEQUENCE: 26
agtcaggcca cttgtgccac ggtttgagca aaccgtgctg cctgtagctc cgccaataat    60
gggaggcgtg ccgatccagg ccgatccagg ccgatccaga aacatgacag aaatacgaac   120
gaaactaacg cgcaaagatc ttttttt                                      147

SEQ ID NO: 27           moltype = DNA   length = 147
FEATURE                 Location/Qualifiers
misc_feature            1..147
                        note = 70 nt Trigger - 40 nt XQ at 5'
source                  1..147
                        mol_type = other DNA
                        organism = synthetic construct
SEQUENCE: 27
agtcaggcca cttgtgccac ggtttgagca aaccgtgctg cctgtagctc cgccaataat    60
gggaggcgta aacatgacag aaatacgaac gaaactaacg cgcaaagatg ccgatccagg   120
ccgatccagg ccgatccagc ttttttt                                      147

SEQ ID NO: 28           moltype = DNA   length = 177
FEATURE                 Location/Qualifiers
misc_feature            1..177
                        note = 100 nt Trigger - Center
```

```
source                          1..177
                                mol_type = other DNA
                                organism = synthetic construct
SEQUENCE: 28
agtcaggcca cttgtgccac ggtttgagca aaccgtgctg cctgtagctc cgccaataat    60
gggaggcgtg ccgatccagg ccgatccagg ccgatccaga aacatgacag aaatacgaac   120
gaaactaacg cgcaaagatg ccgatccagg ccgatccagg ccgatccagc tttttt       177

SEQ ID NO: 29                   moltype = DNA   length = 177
FEATURE                         Location/Qualifiers
misc_feature                    1..177
                                note = 100 nt Trigger - 40 nt XQ at 3'
source                          1..177
                                mol_type = other DNA
                                organism = synthetic construct
SEQUENCE: 29
agtcaggcca cttgtgccac ggtttgagca aaccgtgctg cctgtagctc cgccaataat    60
gggaggcgtg ccgatccagg ccgatccagg ccgatccagg ccgatccagg ccgatccagg   120
ccgatccaga aacatgacag aaatacgaac gaaactaacg cgcaaagatc tttttt       177

SEQ ID NO: 30                   moltype = DNA   length = 177
FEATURE                         Location/Qualifiers
misc_feature                    1..177
                                note = 100 nt Trigger - 40 nt XQ at 5'
source                          1..177
                                mol_type = other DNA
                                organism = synthetic construct
SEQUENCE: 30
agtcaggcca cttgtgccac ggtttgagca aaccgtgctg cctgtagctc cgccaataat    60
gggaggcgta aacatgacag aaatacgaac gaaactaacg cgcaaagatg ccgatccagg   120
ccgatccagg ccgatccagg ccgatccagg ccgatccagg ccgatccagc tttttt       177

SEQ ID NO: 31                   moltype = DNA   length = 227
FEATURE                         Location/Qualifiers
misc_feature                    1..227
                                note = 150 nt Trigger - Center
source                          1..227
                                mol_type = other DNA
                                organism = synthetic construct
SEQUENCE: 31
agtcaggcca cttgtgccac ggtttgagca aaccgtgctg cctgtagctc cgccaataat    60
gggaggcgtg ccgatccagg ccgatccagg ccgagccgat ccaggccgat ccaggccgat   120
ccagaaacat gacagaaata cgaacgaaac taacgcgcaa agatgccgat ccaggccgat   180
ccaggccgag ccgatccagg ccgatccagg ccgatccagc tttttt                  227

SEQ ID NO: 32                   moltype = DNA   length = 227
FEATURE                         Location/Qualifiers
misc_feature                    1..227
                                note = 150 nt Trigger - 40 nt XQ at 3'
source                          1..227
                                mol_type = other DNA
                                organism = synthetic construct
SEQUENCE: 32
agtcaggcca cttgtgccac ggtttgagca aaccgtgctg cctgtagctc cgccaataat    60
gggaggcgtg ccgatccagg ccgatccagg ccgatccagg ccgatccagg ccgatccagg   120
ccgatccagg ccgatccagg ccgatccagg ccgatccagg ccgatccagg ccgatccaga   180
aacatgacag aaatacgaac gaaactaacg cgcaaagatc tttttt                  227

SEQ ID NO: 33                   moltype = DNA   length = 227
FEATURE                         Location/Qualifiers
misc_feature                    1..227
                                note = 150 nt Trigger - 40 nt XQ at 5'
source                          1..227
                                mol_type = other DNA
                                organism = synthetic construct
SEQUENCE: 33
agtcaggcca cttgtgccac ggtttgagca aaccgtgctg cctgtagctc cgccaataat    60
gggaggcgta aacatgacag aaatacgaac gaaactaacg cgcaaagatg ccgatccagg   120
ccgatccagg ccgatccagg ccgatccagg ccgatccagg ccgatccagg ccgatccagg   180
ccgatccagg ccgatccagg ccgatccagg ccgatccagc tttttt                  227

SEQ ID NO: 34                   moltype = DNA   length = 90
FEATURE                         Location/Qualifiers
misc_feature                    1..90
                                note = cgRNA M
source                          1..90
                                mol_type = other DNA
                                organism = synthetic construct
SEQUENCE: 34
```

```
gagtcgcgtg tagcgaagca gtttaagagc tatgctggaa acagcatagc aagtttaaat    60
aaggctagtc cgttatcagc accttttttt                                    90

SEQ ID NO: 35          moltype = DNA  length = 90
FEATURE                Location/Qualifiers
misc_feature           1..90
                       note = cgRNA N
source                 1..90
                       mol_type = other DNA
                       organism = synthetic construct
SEQUENCE: 35
gagtcgcgtg tagcgaagca gtttaagagc tatgctggaa acagcatagc aagtttaaat    60
aaggctagtc cgttatcagg cccttttttt                                    90

SEQ ID NO: 36          moltype = DNA  length = 90
FEATURE                Location/Qualifiers
misc_feature           1..90
                       note = cgRNA O
source                 1..90
                       mol_type = other DNA
                       organism = synthetic construct
SEQUENCE: 36
gagtcgcgtg tagcgaagca gtttaagagc tatgctggaa acagcatagc aagtttaaat    60
aaggctagtc cgttatcacc cactttttt                                     90

SEQ ID NO: 37          moltype = DNA  length = 27
FEATURE                Location/Qualifiers
misc_feature           1..27
                       note = Trigger XM
source                 1..27
                       mol_type = other DNA
                       organism = synthetic construct
SEQUENCE: 37
gtgcggcacc gagtcggtgc ttttttt                                       27

SEQ ID NO: 38          moltype = DNA  length = 27
FEATURE                Location/Qualifiers
misc_feature           1..27
                       note = Trigger XN
source                 1..27
                       mol_type = other DNA
                       organism = synthetic construct
SEQUENCE: 38
ggccggcacc gagtcggtgc ttttttt                                       27

SEQ ID NO: 39          moltype = DNA  length = 27
FEATURE                Location/Qualifiers
misc_feature           1..27
                       note = Trigger XO
source                 1..27
                       mol_type = other DNA
                       organism = synthetic construct
SEQUENCE: 39
tgggggcacc gagtcggtgc ttttttt                                       27

SEQ ID NO: 40          moltype = DNA  length = 96
FEATURE                Location/Qualifiers
misc_feature           1..96
                       note = cgRNA M
source                 1..96
                       mol_type = other DNA
                       organism = synthetic construct
SEQUENCE: 40
gagtcgcgtg tagcgaagca gtttaagagc tatgctggaa acagcatagc aagtttaaat    60
aaggctagtc cgttatcagc acatcccact tttttt                             96

SEQ ID NO: 41          moltype = DNA  length = 96
FEATURE                Location/Qualifiers
misc_feature           1..96
                       note = cgRNA N
source                 1..96
                       mol_type = other DNA
                       organism = synthetic construct
SEQUENCE: 41
gagtcgcgtg tagcgaagca gtttaagagc tatgctggaa acagcatagc aagtttaaat    60
aaggctagtc cgttatcagg ccaggttcct tttttt                             96

SEQ ID NO: 42          moltype = DNA  length = 96
FEATURE                Location/Qualifiers
```

```
misc_feature              1..96
                          note = cgRNA O
source                    1..96
                          mol_type = other DNA
                          organism = synthetic construct
SEQUENCE: 42
gagtcgcgtg tagcgaagca gtttaagagc tatgctggaa acagcatagc aagtttaaat    60
aaggctagtc cgttatcacc cagaacacct tttttt                              96

SEQ ID NO: 43             moltype = DNA  length = 102
FEATURE                   Location/Qualifiers
misc_feature              1..102
                          note = Trigger XM
source                    1..102
                          mol_type = other DNA
                          organism = synthetic construct
SEQUENCE: 43
agtcaggcca cttgtgccac ggtttgagca aaccgtgctg cctgtagctc cgccaataat    60
gggaggcgtt gggatgtgcg gcaccgagtc ggtgcttttt tt                      102

SEQ ID NO: 44             moltype = DNA  length = 102
FEATURE                   Location/Qualifiers
misc_feature              1..102
                          note = Trigger XN
source                    1..102
                          mol_type = other DNA
                          organism = synthetic construct
SEQUENCE: 44
agtcaggcca cttgtgccac ggtttgagca aaccgtgctg cctgtagctc cgccaataat    60
gggaggcgtg aacctggccg gcaccgagtc ggtgcttttt tt                      102

SEQ ID NO: 45             moltype = DNA  length = 102
FEATURE                   Location/Qualifiers
misc_feature              1..102
                          note = Trigger XO
source                    1..102
                          mol_type = other DNA
                          organism = synthetic construct
SEQUENCE: 45
agtcaggcca cttgtgccac ggtttgagca aaccgtgctg cctgtagctc cgccaataat    60
gggaggcgtg tgttctgggg gcaccgagtc ggtgcttttt tt                      102

SEQ ID NO: 46             moltype = DNA  length = 96
FEATURE                   Location/Qualifiers
misc_feature              1..96
                          note = cgRNA M
source                    1..96
                          mol_type = other DNA
                          organism = synthetic construct
SEQUENCE: 46
gagtcgcgtg tagcgaagca gtttaagagc tatgctggaa acagcatagc aagtttaaat    60
aaggctagtc cgttatcagc acatcccact tttttt                              96

SEQ ID NO: 47             moltype = DNA  length = 96
FEATURE                   Location/Qualifiers
misc_feature              1..96
                          note = cgRNA N
source                    1..96
                          mol_type = other DNA
                          organism = synthetic construct
SEQUENCE: 47
gagtcgcgtg tagcgaagca gtttaagagc tatgctggaa acagcatagc aagtttaaat    60
aaggctagtc cgttatcagg ccaggttcct tttttt                              96

SEQ ID NO: 48             moltype = DNA  length = 96
FEATURE                   Location/Qualifiers
misc_feature              1..96
                          note = cgRNA O
source                    1..96
                          mol_type = other DNA
                          organism = synthetic construct
SEQUENCE: 48
gagtcgcgtg tagcgaagca gtttaagagc tatgctggaa acagcatagc aagtttaaat    60
aaggctagtc cgttatcacc cagaacacct tttttt                              96

SEQ ID NO: 49             moltype = DNA  length = 102
FEATURE                   Location/Qualifiers
misc_feature              1..102
                          note = Trigger XM
```

```
                        source              1..102
                                            mol_type = other DNA
                                            organism = synthetic construct
SEQUENCE: 49
agtcaggcca cttgtgccac ggtttgagca aaccgtgctg cctgtagctc cgccaataat    60
gggaggcgtt gggatgtgcg gcaccgagtc ggtgcttttt tt                      102

SEQ ID NO: 50           moltype = DNA   length = 102
FEATURE                 Location/Qualifiers
misc_feature            1..102
                        note = Trigger XN
source                  1..102
                        mol_type = other DNA
                        organism = synthetic construct
SEQUENCE: 50
agtcaggcca cttgtgccac ggtttgagca aaccgtgctg cctgtagctc cgccaataat    60
gggaggcgtg aacctggccg gcaccgagtc ggtgcttttt tt                      102

SEQ ID NO: 51           moltype = DNA   length = 102
FEATURE                 Location/Qualifiers
misc_feature            1..102
                        note = Trigger XO
source                  1..102
                        mol_type = other DNA
                        organism = synthetic construct
SEQUENCE: 51
agtcaggcca cttgtgccac ggtttgagca aaccgtgctg cctgtagctc cgccaataat    60
gggaggcgtg tgttctgggg gcaccgagtc ggtgcttttt tt                      102

SEQ ID NO: 52           moltype = DNA   length = 94
FEATURE                 Location/Qualifiers
misc_feature            1..94
                        note = cgRNA M
source                  1..94
                        mol_type = other DNA
                        organism = synthetic construct
SEQUENCE: 52
gagtcgcgtg tagcgaagca gtttaagagc tatgctggaa acagcatagc aagtttaaat    60
aaggctagtc cgttatcagc acatcccttt tttt                                94

SEQ ID NO: 53           moltype = DNA   length = 94
FEATURE                 Location/Qualifiers
misc_feature            1..94
                        note = cgRNA N
source                  1..94
                        mol_type = other DNA
                        organism = synthetic construct
SEQUENCE: 53
gagtcgcgtg tagcgaagca gtttaagagc tatgctggaa acagcatagc aagtttaaat    60
aaggctagtc cgttatcagg ccaggtcttt tttt                                94

SEQ ID NO: 54           moltype = DNA   length = 94
FEATURE                 Location/Qualifiers
misc_feature            1..94
                        note = cgRNA O
source                  1..94
                        mol_type = other DNA
                        organism = synthetic construct
SEQUENCE: 54
gagtcgcgtg tagcgaagca gtttaagagc tatgctggaa acagcatagc aagtttaaat    60
aaggctagtc cgttatcacc cagaaccttt tttt                                94

SEQ ID NO: 55           moltype = DNA   length = 100
FEATURE                 Location/Qualifiers
misc_feature            1..100
                        note = Trigger XM
source                  1..100
                        mol_type = other DNA
                        organism = synthetic construct
SEQUENCE: 55
agtcaggcca cttgtgccac ggtttgagca aaccgtgctg cctgtagctc cgccaataat    60
gggaggcgtg gatgtgcggc accgagtcgg tgctttttt                          100

SEQ ID NO: 56           moltype = DNA   length = 100
FEATURE                 Location/Qualifiers
misc_feature            1..100
                        note = Trigger XN
source                  1..100
                        mol_type = other DNA
```

```
                        organism = synthetic construct
SEQUENCE: 56
agtcaggcca cttgtgccac ggtttgagca aaccgtgctg cctgtagctc cgccaataat   60
gggaggcgta cctggccggc accgagtcgg tgcttttttt                        100

SEQ ID NO: 57           moltype = DNA   length = 100
FEATURE                 Location/Qualifiers
misc_feature            1..100
                        note = Trigger XO
source                  1..100
                        mol_type = other DNA
                        organism = synthetic construct
SEQUENCE: 57
agtcaggcca cttgtgccac ggtttgagca aaccgtgctg cctgtagctc cgccaataat   60
gggaggcgtg ttctgggggc accgagtcgg tgcttttttt                        100

SEQ ID NO: 58           moltype = DNA   length = 92
FEATURE                 Location/Qualifiers
misc_feature            1..92
                        note = cgRNA M
source                  1..92
                        mol_type = other DNA
                        organism = synthetic construct
SEQUENCE: 58
gagtcgcgtg tagcgaagca gtttaagagc tatgctggaa acagcatagc aagtttaaat   60
aaggctagtc cgttatcagc acatcttttt tt                                92

SEQ ID NO: 59           moltype = DNA   length = 92
FEATURE                 Location/Qualifiers
misc_feature            1..92
                        note = cgRNA N
source                  1..92
                        mol_type = other DNA
                        organism = synthetic construct
SEQUENCE: 59
gagtcgcgtg tagcgaagca gtttaagagc tatgctggaa acagcatagc aagtttaaat   60
aaggctagtc cgttatcagg ccagcttttt tt                                92

SEQ ID NO: 60           moltype = DNA   length = 92
FEATURE                 Location/Qualifiers
misc_feature            1..92
                        note = cgRNA O
source                  1..92
                        mol_type = other DNA
                        organism = synthetic construct
SEQUENCE: 60
gagtcgcgtg tagcgaagca gtttaagagc tatgctggaa acagcatagc aagtttaaat   60
aaggctagtc cgttatcacc cagacttttt tt                                92

SEQ ID NO: 61           moltype = DNA   length = 98
FEATURE                 Location/Qualifiers
misc_feature            1..98
                        note = Trigger XM
source                  1..98
                        mol_type = other DNA
                        organism = synthetic construct
SEQUENCE: 61
agtcaggcca cttgtgccac ggtttgagca aaccgtgctg cctgtagctc cgccaataat   60
gggaggcgta tgtgcggcac cgagtcggtg ctttttt                           98

SEQ ID NO: 62           moltype = DNA   length = 98
FEATURE                 Location/Qualifiers
misc_feature            1..98
                        note = Trigger XN
source                  1..98
                        mol_type = other DNA
                        organism = synthetic construct
SEQUENCE: 62
agtcaggcca cttgtgccac ggtttgagca aaccgtgctg cctgtagctc cgccaataat   60
gggaggcgtc tggccggcac cgagtcggtg ctttttt                           98

SEQ ID NO: 63           moltype = DNA   length = 98
FEATURE                 Location/Qualifiers
misc_feature            1..98
                        note = Trigger XO
source                  1..98
                        mol_type = other DNA
                        organism = synthetic construct
SEQUENCE: 63
```

```
agtcaggcca cttgtgccac ggtttgagca aaccgtgctg cctgtagctc cgccaataat   60
gggaggcgtt ctggggcac cgagtcggtg cttttttt                            98

SEQ ID NO: 64           moltype = DNA   length = 125
FEATURE                 Location/Qualifiers
misc_feature            1..125
                        note = cgRNA 40
source                  1..125
                        mol_type = other DNA
                        organism = synthetic construct
SEQUENCE: 64
agtcgcgtgt agcgaagcag tttaagagct atgctggaaa cagcatagca agtttaaata   60
aggctagtcc gttatcacat atcccatcca cctccacctc cacctccaca ttcccacctt  120
ttttt                                                              125

SEQ ID NO: 65           moltype = DNA   length = 115
FEATURE                 Location/Qualifiers
misc_feature            1..115
                        note = cgRNA 30
source                  1..115
                        mol_type = other DNA
                        organism = synthetic construct
SEQUENCE: 65
agtcgcgtgt agcgaagcag tttaagagct atgctggaaa cagcatagca agtttaaata   60
aggctagtcc gttatcacat atcccatcca cctccacctc cacctccctt ttttt       115

SEQ ID NO: 66           moltype = DNA   length = 105
FEATURE                 Location/Qualifiers
misc_feature            1..105
                        note = cgRNA 20
source                  1..105
                        mol_type = other DNA
                        organism = synthetic construct
SEQUENCE: 66
agtcgcgtgt agcgaagcag tttaagagct atgctggaaa cagcatagca agtttaaata   60
aggctagtcc gttatcacat atcccatcca cctccacctt ttttt                  105

SEQ ID NO: 67           moltype = DNA   length = 95
FEATURE                 Location/Qualifiers
misc_feature            1..95
                        note = cgRNA 10
source                  1..95
                        mol_type = other DNA
                        organism = synthetic construct
SEQUENCE: 67
agtcgcgtgt agcgaagcag tttaagagct atgctggaaa cagcatagca agtttaaata   60
aggctagtcc gttatcacat atcccatctt ttttt                              95

SEQ ID NO: 68           moltype = DNA   length = 132
FEATURE                 Location/Qualifiers
misc_feature            1..132
                        note = Trigger X40
source                  1..132
                        mol_type = other DNA
                        organism = synthetic construct
SEQUENCE: 68
agtcaggcca cttgtgccac ggtttgagca aaccgtgctg cctgtagctc cgccaataat   60
gggaggcgtg tgggaatgtg gaggtggagg tggaggtgga tgggatatgg gcaccgagtc  120
ggtgcttttt tt                                                      132

SEQ ID NO: 69           moltype = DNA   length = 122
FEATURE                 Location/Qualifiers
misc_feature            1..122
                        note = Trigger X30
source                  1..122
                        mol_type = other DNA
                        organism = synthetic construct
SEQUENCE: 69
agtcaggcca cttgtgccac ggtttgagca aaccgtgctg cctgtagctc cgccaataat   60
gggaggcgtg gaggtggagg tggaggtgga tgggatatgg gcaccgagtc ggtgctttt   120
tt                                                                 122

SEQ ID NO: 70           moltype = DNA   length = 113
FEATURE                 Location/Qualifiers
misc_feature            1..113
                        note = Trigger X20
source                  1..113
                        mol_type = other DNA
                        organism = synthetic construct
```

-continued

```
SEQUENCE: 70
agtcaggcca cttgtgccac ggtttgagca aaccgtgctg cctgtagctc cgccaataat    60
gggaggcgtg tggaggtgga tgggatatgg gcaccgagtc ggtgcttttt ttt          113

SEQ ID NO: 71           moltype = DNA   length = 102
FEATURE                 Location/Qualifiers
misc_feature            1..102
                        note = Trigger X10
source                  1..102
                        mol_type = other DNA
                        organism = synthetic construct
SEQUENCE: 71
agtcaggcca cttgtgccac ggtttgagca aaccgtgctg cctgtagctc cgccaataat    60
gggaggcgta tgggatatgg gcaccgagtc ggtgcttttt tt                      102

SEQ ID NO: 72           moltype = DNA   length = 103
FEATURE                 Location/Qualifiers
misc_feature            1..103
                        note = Standard gRNA
source                  1..103
                        mol_type = other DNA
                        organism = synthetic construct
SEQUENCE: 72
gagtcgcgtg tagcgaagca gttttagagc tagaaatagc aagttaaaat aaggctagtc    60
cgttatcaac ttgaaaaagt ggcaccgagt cggtgctttt ttt                     103

SEQ ID NO: 73           moltype = DNA   length = 83
FEATURE                 Location/Qualifiers
misc_feature            1..83
                        note = No-target gRNA
source                  1..83
                        mol_type = other DNA
                        organism = synthetic construct
SEQUENCE: 73
gttttagagc tagaaatagc aagttaaaat aaggctagtc cgttatcaac ttgaaaaagt    60
ggcaccgagt cggtgctttt ttt                                           83

SEQ ID NO: 74           moltype = DNA   length = 95
FEATURE                 Location/Qualifiers
misc_feature            1..95
                        note = 8 nt deletion
source                  1..95
                        mol_type = other DNA
                        organism = synthetic construct
SEQUENCE: 74
gagtcgcgtg tagcgaagca gttttagagc tagaaatagc aagttaaaat aaggctagtc    60
cgttatcaac ttgaaaaagt ggcaccgctt ttttt                              95

SEQ ID NO: 75           moltype = DNA   length = 80
FEATURE                 Location/Qualifiers
misc_feature            1..80
                        note = 23 nt deletion
source                  1..80
                        mol_type = other DNA
                        organism = synthetic construct
SEQUENCE: 75
gagtcgcgtg tagcgaagca gttttagagc tagaaatagc aagttaaaat aaggctagtc    60
cgttatcaac ttctttttt                                                80

SEQ ID NO: 76           moltype = DNA   length = 71
FEATURE                 Location/Qualifiers
misc_feature            1..71
                        note = 32 nt deletion
source                  1..71
                        mol_type = other DNA
                        organism = synthetic construct
SEQUENCE: 76
gagtcgcgtg tagcgaagca gttttagagc tagaaatagc aagttaaaat aaggctagtc    60
cgtcttttt t                                                         71

SEQ ID NO: 77           moltype = DNA   length = 58
FEATURE                 Location/Qualifiers
misc_feature            1..58
                        note = 45 nt deletion
source                  1..58
                        mol_type = other DNA
                        organism = synthetic construct
SEQUENCE: 77
gagtcgcgtg tagcgaagca gttttagagc tagaaatagc aagttaaaat cttttttt     58
```

```
SEQ ID NO: 78            moltype = DNA  length = 129
FEATURE                  Location/Qualifiers
misc_feature             1..129
                         note = cgRNAA
source                   1..129
                         mol_type = other DNA
                         organism = synthetic construct
SEQUENCE: 78
aactttcagt ttagcggtct gttttagagc tagaaatagc aagttaaaat aaggctagtc    60
cgatcaaacg ggtaaacaaa caggataatt aaggaggcag tacccgggca ccgagtcggt   120
gcttttttt                                                           129

SEQ ID NO: 79            moltype = DNA  length = 129
FEATURE                  Location/Qualifiers
misc_feature             1..129
                         note = cgRNA E
source                   1..129
                         mol_type = other DNA
                         organism = synthetic construct
SEQUENCE: 79
aactttcagt ttagcggtct gttttagagc tagaaatagc aagttaaaat aaggctagtc    60
cgacacaagg ggaaattaac aacacaacac acacaacaca ggccccggca ccgagtcggt   120
gcttttttt                                                           129

SEQ ID NO: 80            moltype = DNA  length = 1849
FEATURE                  Location/Qualifiers
misc_feature             1..1849
                         note = Trigger XA
source                   1..1849
                         mol_type = other DNA
                         organism = synthetic construct
SEQUENCE: 80
tggctaaaga aagaggagaa aaggtttatg gtagcaggtc atgcctctgg cagccccgca    60
ttcgggaccg cctctcattc gaattgcgaa catgaagaga tccacctcgc cggctcgatc   120
cagccgcatg gcgcgcttct ggtcgtcagc gaacatgatc atcgcgtcat ccaggccagc   180
gccaacgccg cggaatttct gaatctcgga agcgtactcg gcgttccgct cgccgagatc   240
gacggcgatc tgttgatcaa gatcctgccg catctcgatc ccaccgccga aggcatgccg   300
gtcgcggtgc gctgccggat cggcaatccc tctacggagt actgcggtct gatgcatcgg   360
cctccggaag gcgggctgat catcgaactc gaacgtgccg gccgtcgat cgatctgtca   420
ggcacgctgg cgccggcgct ggagcggatc cgcacggcgg gttcactgcg cgcgctgtgc   480
gatgacaccg tgctgctgtt tcagcagtgc accggctacg accgggtgat ggtgtatcgt   540
ttcgatgagc aaggccacgg cctggttatc tccgagtgcg atgtgcctgg gctcgaatcc   600
tatttcggca accgctatcc gtcgtcgact gtcccgcaga tggcgcggca gctgtacgtg   660
cggcagcgcg tccgcgtgct ggtcgacgtc acctatcagc cggtgccgct ggagccgcgg   720
ctgtcgccgc tgaccgggcg cgatctcgac atgtcgggct gcttcctgcg ctcgatgtcg   780
ccgtgccatc tgcagttcct gaaggacatg ggcgtgccgc ccaccctggc ggtgtcgctg   840
gtggtcggcg gcaagctgtg gggcctggtt gtctgtcacc attatctgcc gcgcttcatc   900
cgtttcgagc tgcgggcgat ctgcaaacgc tcgccgaaaa ggatcgcgac gcggatcacc   960
gcgcttgaga gcgaattcgg tggtggtggt tctggtggtg gtggtctat gagtgtcaac  1020
ttagcttccc agttgcggga agggacgaaa aaatcccact ccatggcgca gaacgtcggc  1080
tttgtcaaat gcttcctcaa gggcgttgtc gagaaaaatt cctaccgtaa gctggttggc  1140
aatctctact ttgtctacag tgccatgaaa gaggaaatgg caaaatttaa ggaccatccc  1200
atcctcagcc acatttactt cccccgaactc aaccgcaaac aaagcctaga gcaagacctg  1260
caattctatt acggctccaa ctggcggcaa gaagtgaaaa tttctgccgc tggccaagcc  1320
tatgtggacc gagtccggca agtgccgct acgccccctg aattgttggt ggccccattcc  1380
tacacccgtt acctgggga tctttccggc ggtcaaattc tcaagaaaat tgcccaaaat  1440
gccatgaatc tccacgatgg tggcacagct ttctatgaat tgccgacat tgatgacgaa  1500
aaggctttta aaaataccta ccgtcaagct atgaatgct tgcccattga ccaagccacc  1560
gccgaacgga ttgtggatga agccaatgac gccttttgcca tgaacatgaa aatgttcaac  1620
gaacttgaag caaccgtgat caaggcgatc ggcattatgg tgttcaacag cctcacccgt  1680
cgccgcagtc aaggcagcac cgaagttggc ctcgccacct ccgaaggcta gtaaacgtcg  1740
actctcgagt gagattgttg acggtaccgt attttactg cctccttaat tatcctgttt  1800
gtttaccccgt ttgatcgcaa aaaaccccgc ttcggcgggg tttttcgc               1849

SEQ ID NO: 81            moltype = DNA  length = 1849
FEATURE                  Location/Qualifiers
misc_feature             1..1849
                         note = Trigger XE
source                   1..1849
                         mol_type = other DNA
                         organism = synthetic construct
SEQUENCE: 81
tggctaaaga aagaggagaa aaggtttatg gtagcaggtc atgcctctgg cagccccgca    60
ttcgggaccg cctctcattc gaattgcgaa catgaagaga tccacctcgc cggctcgatc   120
cagccgcatg gcgcgcttct ggtcgtcagc gaacatgatc atcgcgtcat ccaggccagc   180
gccaacgccg cggaatttct gaatctcgga agcgtactcg gcgttccgct cgccgagatc   240
gacggcgatc tgttgatcaa gatcctgccg catctcgatc ccaccgccga aggcatgccg   300
gtcgcggtgc gctgccggat cggcaatccc tctacggagt actgcggtct gatgcatcgg   360
```

```
cctccggaag gcgggctgat catcgaactc gaacgtgccg gcccgtcgat cgatctgtca    420
ggcacgctgg cgccgcgct ggagcggatc cgcacggcgg gttcactgcg cgcgctgtgc    480
gatgacaccg tgctgctgtt tcagcagtgc accggctacg accgggtgat ggtgtatcgt    540
ttcgatgagc aaggccacgg cctggtattc tccgagtgcc atgtgcctgg gctcgaatcc    600
tatttcggca accgctatcc gtcgtcgact gtcccgcagg ggtcgcggca ggtgtacgtg    660
cggcagcgcg tccgcgtgct ggtcgacgtc acctatcagc cggtgccgct ggagccgcgg    720
ctgtcgccgc tgaccgggcg cgatctcgac atgtcgggct gcttcctgcg ctcgatgtcg    780
ccgtgccatc tgcagttcct gaaggacatg ggcgtgcgcg ccaccctggc ggtgtcgctg    840
gtggtcggcg gcaagctgtg gggcctggtt gtctgtcacc attatctgcc gcgcttcatc    900
cgtttcgagc tgcgggcgat ctgcaaacgg ctcgccgaaa ggatcgcgac gcggatcacc    960
gcgcttgaga gcgaattcgg tggtggtggt tctggtggtg gtggttctat gagtgtcaac   1020
ttagcttccc agttgcggga agggacgaaa aaatcccact ccatggcgga gaacgtcggc   1080
tttgtcaaat gcttcctcaa gggcgttgtc gagaaaaatt cctaccgtaa gctggttggc   1140
aatctctact ttgtctacag tgccatggaa gaggaaatgg caaaatttaa ggaccatccc   1200
atcctcagcc acatttactt ccccgaactc aaccgcaaaa aaagcctaga gcaagacctg   1260
caattctatt acggctccaa ctggcggcaa gaagtgaaaa tttctgccgc tggccaagcc   1320
tatgtggacc gagtccggca gtggccgct acggcccctg aattgttggt ggcccattcc   1380
tacacccgtt acctggggga tctttccggc ggtcaaattc tcaagaaaat tgcccaaaat   1440
gccatgaatc tccacgatgg tggcacagct ttctatgaat ttgccgacat tgatgacgaa   1500
aaggctttta aaaataccta ccgtcaagct atgaatgatc tgcccattga ccaagccacc   1560
gccgaacgga ttgtggatga agccaatgac gcctttgcca tgaacatgaa aatgttcaac   1620
gaacttgaag gcaacctgat caaggcgatc ggcattatgg tgttcaacag cctcacccgt   1680
cgccgcagtc aaggcagcac cgaagttggc ctcgccacct ccgaaggcta gtaaacgtcg   1740
actctcgagt gagattgttg acggtaccgt attttcctgt gttgtgtgtg ttgtgttgtt   1800
aatttcccct tgtgtcgcaa aaaccccgc ttcggcgggg ttttttcgc                1849

SEQ ID NO: 82         moltype = DNA  length = 129
FEATURE               Location/Qualifiers
misc_feature          1..129
                      note = cgRNA
source                1..129
                      mol_type = other DNA
                      organism = synthetic construct
SEQUENCE: 82
gagtcgcgtg tagcgaagca gttttagagc tagaaatagc aagttaaaat aaggctagtc     60
cgtccattcg ggtttactat tacaatctta cgtgttctca ttcccgggca ccgagtcggt    120
gctttttt                                                             129

SEQ ID NO: 83         moltype = DNA  length = 117
FEATURE               Location/Qualifiers
misc_feature          1..117
                      note = Non-cognate trigger (X')
source                1..117
                      mol_type = other DNA
                      organism = synthetic construct
SEQUENCE: 83
agtcaggcca cttgtgccac ggtttgagca aaccgtgctg cctgtagctc cgccaataat     60
gggaggcgta aacatgacag aaatacgaac gaaactaacg cgcaaagatc tttttttt     117

SEQ ID NO: 84         moltype = DNA  length = 117
FEATURE               Location/Qualifiers
misc_feature          1..117
                      note = Cognate-trigger (X)
source                1..117
                      mol_type = other DNA
                      organism = synthetic construct
SEQUENCE: 84
agtcaggcca cttgtgccac ggtttgagca aaccgtgctg cctgtagctc cgccaataat     60
gggaggcgta atgagaacac gtaagattgt aatagtaaac ccgaatggac ttttttt      117

SEQ ID NO: 85         moltype = DNA  length = 96
FEATURE               Location/Qualifiers
misc_feature          1..96
                      note = cgRNA
source                1..96
                      mol_type = other DNA
                      organism = synthetic construct
SEQUENCE: 85
gagtcgcgtg tagcgaagca gtttaagagc tatgctggaa acagcatagc aagtttaaat     60
aaggctagtc cgttatcagg ccaggttcct tttttt                               96

SEQ ID NO: 86         moltype = DNA  length = 102
FEATURE               Location/Qualifiers
misc_feature          1..102
                      note = Non-cognate trigger (X')
source                1..102
                      mol_type = other DNA
                      organism = synthetic construct
SEQUENCE: 86
```

```
agtcaggcca cttgtgccac ggtttgagca aaccgtgctg cctgtagctc cgccaataat    60
gggaggcgtt gggatgtgcg gcaccgagtc ggtgcttttt tt                      102

SEQ ID NO: 87          moltype = DNA   length = 102
FEATURE                Location/Qualifiers
misc_feature           1..102
                       note = Cognate trigger (X)
source                 1..102
                       mol_type = other DNA
                       organism = synthetic construct
SEQUENCE: 87
agtcaggcca cttgtgccac ggtttgagca aaccgtgctg cctgtagctc cgccaataat    60
gggaggcgtg aacctggccg gcaccgagtc ggtgcttttt tt                      102

SEQ ID NO: 88          moltype = DNA   length = 72
FEATURE                Location/Qualifiers
misc_feature           1..72
                       note = cgRNA M
source                 1..72
                       mol_type = other DNA
                       organism = synthetic construct
SEQUENCE: 88
catctaattc aacaagaatt gttttagagc tagaaatagc aagttaaaat aaggctagtc    60
cgttatcagc ac                                                       72

SEQ ID NO: 89          moltype = DNA   length = 72
FEATURE                Location/Qualifiers
misc_feature           1..72
                       note = cgRNA N
source                 1..72
                       mol_type = other DNA
                       organism = synthetic construct
SEQUENCE: 89
catctaattc aacaagaatt gttttagagc tagaaatagc aagttaaaat aaggctagtc    60
cgttatcagg cc                                                       72

SEQ ID NO: 90          moltype = DNA   length = 72
FEATURE                Location/Qualifiers
misc_feature           1..72
                       note = cgRNA O
source                 1..72
                       mol_type = other DNA
                       organism = synthetic construct
SEQUENCE: 90
catctaattc aacaagaatt gttttagagc tagaaatagc aagttaaaat aaggctagtc    60
cgttatcacc ca                                                       72

SEQ ID NO: 91          moltype = DNA   length = 19
FEATURE                Location/Qualifiers
misc_feature           1..19
                       note = Trigger XM
source                 1..19
                       mol_type = other DNA
                       organism = synthetic construct
SEQUENCE: 91
gtgcggcacc gagtcggtg                                                19

SEQ ID NO: 92          moltype = DNA   length = 19
FEATURE                Location/Qualifiers
misc_feature           1..19
                       note = Trigger XN
source                 1..19
                       mol_type = other DNA
                       organism = synthetic construct
SEQUENCE: 92
ggccggcacc gagtcggtg                                                19

SEQ ID NO: 93          moltype = DNA   length = 19
FEATURE                Location/Qualifiers
misc_feature           1..19
                       note = Trigger XO
source                 1..19
                       mol_type = other DNA
                       organism = synthetic construct
SEQUENCE: 93
tgggggcacc gagtcggtg                                                19

SEQ ID NO: 94          moltype = DNA   length = 96
FEATURE                Location/Qualifiers
```

```
misc_feature             1..96
                         note = cg5
source                   1..96
                         mol_type = other DNA
                         organism = synthetic construct
SEQUENCE: 94
gagtcgcgtg tagcgaagca gttttagagc tagaaatagc aagttaaaat aaggctagtc   60
cgtcccatcg tccgtcccat caatttccct tttttt                             96

SEQ ID NO: 95            moltype = DNA   length = 43
FEATURE                  Location/Qualifiers
misc_feature             1..43
                         note = cg3
source                   1..43
                         mol_type = other DNA
                         organism = synthetic construct
SEQUENCE: 95
aatataatac gggacggacg ggcaccgagt cggtgctttt ttt                     43

SEQ ID NO: 96            moltype = DNA   length = 97
FEATURE                  Location/Qualifiers
misc_feature             1..97
                         note = Trigger
source                   1..97
                         mol_type = other DNA
                         organism = synthetic construct
SEQUENCE: 96
agtcaggcca cttgtgccac ggtttgagca aaccgtgctg cctgtagctc cgccaataat   60
gggaggcgtc gtccgtcccg tattatattc tttttttt                           97

SEQ ID NO: 97            moltype = DNA   length = 106
FEATURE                  Location/Qualifiers
misc_feature             1..106
                         note = cg5
source                   1..106
                         mol_type = other DNA
                         organism = synthetic construct
SEQUENCE: 97
gagtcgcgtg tagcgaagca gttttagagc tagaaatagc aagttaaaat aaggctagtc   60
cgatatatac aaacacaaca cacacacaac aacaaacact tttttt                  106

SEQ ID NO: 98            moltype = DNA   length = 132
FEATURE                  Location/Qualifiers
misc_feature             1..132
                         note = cg3
source                   1..132
                         mol_type = other DNA
                         organism = synthetic construct
SEQUENCE: 98
agtcaggcca cttgtgccac ggtttgagca aaccgtgctg cctgtagctc cgccaataat   60
gggaggcgtt gtctagaatt gtttgttgtt gtgtgtgtgt tgtgtttgtg gcaccgagtc   120
ggtgcttttt tt                                                       132

SEQ ID NO: 99            moltype = DNA   length = 117
FEATURE                  Location/Qualifiers
misc_feature             1..117
                         note = Trigger
source                   1..117
                         mol_type = other DNA
                         organism = synthetic construct
SEQUENCE: 99
agtcaggcca cttgtgccac ggtttgagca aaccgtgctg cctgtagctc cgccaataat   60
gggaggcgta caaacacaac acacacacaa caacaaacaa ttctagacac tttttt       117

SEQ ID NO: 100           moltype = DNA   length = 146
FEATURE                  Location/Qualifiers
misc_feature             1..146
                         note = cg5
source                   1..146
                         mol_type = other DNA
                         organism = synthetic construct
SEQUENCE: 100
aactttcagt ttagcggtct gttttagagc tagaaatagc aagttaaaat aaggctagtc   60
cgatatatac aaacacaaca cacacacaac aacaaacaca acccaaccag agcgcaaaaa   120
accccgcttc ggcggggttt tttcgc                                        146

SEQ ID NO: 101           moltype = DNA   length = 67
FEATURE                  Location/Qualifiers
misc_feature             1..67
```

```
                    note = cg3
source              1..67
                    mol_type = other DNA
                    organism = synthetic construct
SEQUENCE: 101
tgtctagaat tgtttgttgt tgtgtgtgtg ttgtgtttgt ggcaccgagt cggtgctttt    60
tttcgcc                                                               67

SEQ ID NO: 102      moltype = DNA   length = 34
FEATURE             Location/Qualifiers
misc_feature        1..34
                    note = No-trigger control
source              1..34
                    mol_type = other DNA
                    organism = synthetic construct
SEQUENCE: 102
cgcaaaaaac cccgcttcgg cggggttttt tcgc                                 34

SEQ ID NO: 103      moltype = DNA   length = 74
FEATURE             Location/Qualifiers
misc_feature        1..74
                    note = Trigger X (Mechanism 4B)
source              1..74
                    mol_type = other DNA
                    organism = synthetic construct
SEQUENCE: 103
ggttgggttg tgtttgttgt tgtgtgtgtg ttgtgtttgt cgcaaaaaac cccgcttcgg    60
cggggttttt tcgc                                                       74

SEQ ID NO: 104      moltype = DNA   length = 74
FEATURE             Location/Qualifiers
misc_feature        1..74
                    note = Trigger X (Mechanism 4C)
source              1..74
                    mol_type = other DNA
                    organism = synthetic construct
SEQUENCE: 104
acaaacacaa cacacacaca acaacaaaca attctagaca cgcaaaaaac cccgcttcgg    60
cggggttttt tcgc                                                       74

SEQ ID NO: 105      moltype = DNA   length = 146
FEATURE             Location/Qualifiers
misc_feature        1..146
                    note = cg5
source              1..146
                    mol_type = other DNA
                    organism = synthetic construct
SEQUENCE: 105
ttgtttaagg ctatggtgag aactttcagt ttagcggtct gttttagagc tagaaatagc    60
aagttaaaat aaggctagtc cgtaaataaa agcccaccct caccatagag agcgcaaaaa   120
accccgcttc ggcggggttt tttcgc                                         146

SEQ ID NO: 106      moltype = DNA   length = 95
FEATURE             Location/Qualifiers
misc_feature        1..95
                    note = cg3
source              1..95
                    mol_type = other DNA
                    organism = synthetic construct
SEQUENCE: 106
ccaccctcac cataggtgct atggtgaggg tgggctttgg caccgagtcg gtgcttttt     60
tcgcaaaaaa ccccgcttcg gcggggtttt ttcgc                                95

SEQ ID NO: 107      moltype = DNA   length = 34
FEATURE             Location/Qualifiers
misc_feature        1..34
                    note = No-trigger control
source              1..34
                    mol_type = other DNA
                    organism = synthetic construct
SEQUENCE: 107
cgcaaaaaac cccgcttcgg cggggttttt tcgc                                 34

SEQ ID NO: 108      moltype = DNA   length = 54
FEATURE             Location/Qualifiers
misc_feature        1..54
                    note = Trigger X
source              1..54
                    mol_type = other DNA
```

```
                        organism = synthetic construct
SEQUENCE: 108
ctcaccatag cctttgaacaa cgcaaaaaac cccgcttcgg cggggttttt tcgc          54
```

ALLOSTERIC CONDITIONAL GUIDE RNAS FOR CELL-SELECTIVE REGULATION OF CRISPR/CAS

STATEMENT REGARDING FEDERALLY SPONSORED R&D

This invention was made with government support under Grant No. HR0011-17-2-0008 awarded by DARPA, under Grant No. 7000000323 and Grant No. NNX16AO69A awarded by NASA. The government has certain rights in the invention.

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

REFERENCE TO SEQUENCE LISTING, TABLE, OR COMPUTER PROGRAM LISTING

The present application is being filed along with a Sequence Listing in electronic format. The Sequence Listing is provided as a file entitled CALTE157D1_ST.26.XML created on Dec. 12, 2023 and is 149,550 bytes in size. The information in the electronic format of the Sequence Listing is incorporated herein by reference in its entirety.

BACKGROUND

Programmable guide RNAs (gRNAs) play a central role in the CRISPR revolution sweeping biology and medicine by directing the function of Cas protein effectors to a target gene of choice, providing a versatile programmable platform for engineering diverse modes of synthetic regulation in organisms ranging from bacteria to humans. Wildtype Cas9 and Cas12a allow genome editing[1-4] while mutated catalytically dead Cas9 (dCas9) and nickase variants allow gene editing, silencing, induction,[5-8] binding, epigenome editing,[9] chromatin interaction mapping[10] and regulation,[11] and imaging.[12] Hence, gRNA-mediated CRISPR/Cas combines the rich functional vocabulary of different Cas effectors (edit, silence, induce, bind, etc) and the programmability of the gRNA. To target a new gene of choice, all that is needed is to change the sequence of the gRNA.

However, it can be challenging to confine gRNA activity to a desired location and time within an organism. Strategies for achieving temporal control include modulation of gRNA activity using antisense RNAs[13] and small-molecule induction of gRNAs[14,15] or Cas9.[16] Spatiotemporal control can be achieved in photoaccessible tissues using light to uncage gRNAs,[17,18] cleave antisense DNAs,[19] or regulate Cas9.[20] Alternatively, Cas9 can be regulated using tissue-specific promoters[21,22] or microRNAs.[23] Cas9 tolerates, to varying degrees, a variety of modifications to the standard gRNA structure,[24-26] allowing for introduction of auxiliary domains to provide hooks for regulation by small-molecules,[27-29] protein-bound RNAs,[30] nucleases,[31] or nuclease-recruiting DNAs or miRNAs.[31,32]

SUMMARY OF THE INVENTION

In accordance with some implementations, there is an allosteric conditional guide RNA (cgRNA) comprising a target-binding region and a trigger-binding region, wherein the target-binding region is non-overlapping with the trigger-binding region, wherein the cgRNA is active in the absence of a cognate RNA trigger, wherein the cgRNA is configured to mediate the function of a Cas protein effector on a target gene that binds the target-binding region, and wherein upon hybridization to the cognate RNA trigger, the cgRNA is inactivated, inhibiting further mediation of Cas function on the target gene. In accordance with certain implementations, the allosteric cgRNA may further comprise a Cas handle wherein the target-binding region is 5' of the Cas handle and the trigger-binding region is 3' of the Cas handle. In accordance with certain implementations, the allosteric cgRNA may further comprise a first terminator hairpin with an extended loop comprising 5 or more nucleotides wherein the trigger-binding region comprises zero, one, or more nucleotides of a linker 5'-adjacent to the first terminator hairpin, zero, one, or more nucleotides in a 5' portion of a stem of the first terminator hairpin, and one or more nucleotides in the extended loop of the first terminator hairpin, wherein the cgRNA is inactivated upon hybridization of the cognate RNA trigger to the cgRNA. In accordance with some implementations, the allosteric cgRNA may further comprise a Cas handle with an extended loop wherein the target-binding region is 5' of the Cas handle and the trigger-binding region comprises a portion of the extended loop of the Cas handle and no nucleotides 5' of the Cas handle. In accordance with some implementations, the allosteric cgRNA may further comprise a first terminator hairpin with an extended loop comprising 5 or more nucleotides such that the trigger-binding region comprises one or more nucleotides in the extended loop of the Cas handle, and one or more nucleotides in the extended loop of the first terminator hairpin, wherein upon hybridization of the cognate RNA trigger to the cgRNA, the cgRNA is inactivated. In accordance with some implementations, the allosteric cgRNA may further comprise a first terminator hairpin with an extended loop comprising 5 or more nucleotides wherein the trigger-binding region further comprises zero, one, or more nucleotides of a linker 5'-adjacent to the first terminator hairpin, zero, one, or more nucleotides in a 5' portion of a stem of the first terminator hairpin, and one or more nucleotides in the extended loop of the first terminator hairpin, wherein the cgRNA is inactivated upon hybridization of the cognate RNA trigger to the cgRNA.

In accordance with some implementations, there is an allosteric conditional guide RNA (cgRNA) and an RNA inhibitor strand, wherein the cgRNA comprises a target-binding region and an inhibitor-binding region, and the RNA inhibitor strand comprises a trigger-binding region, wherein the cgRNA is configured to bind to a portion of the trigger-binding region to form a cgRNA:inhibitor complex: wherein the target-binding region is not base-paired to the trigger-binding region in the cgRNA:inhibitor complex; wherein the cgRNA:inhibitor complex is inactive in the absence of a cognate RNA trigger; and wherein upon hybridization of a cognate RNA trigger to the inhibitor, the cgRNA is activated, mediating the function of a Cas protein effector on a target gene that binds the target-binding region. In accordance with some implementations, the cgRNA further comprises a Cas handle wherein the target-binding region is 5' of the Cas handle and the inhibitor-binding region is 3' of the Cas handle. In accordance with some implementations, the inhibitor further comprises a toehold of one or more unpaired nucleotides at one or both ends, the cgRNA further comprising a first terminator hairpin with an extended loop comprising 5 or more nucleotides, the cgRNA further comprising an inhibitor-binding region comprising: zero, one, or more nucleotides of a linker 5'-adjacent to the first terminator hairpin; zero, one, or more nucleotides in a 5' portion of a stem of the first terminator hairpin; and one or more nucleotides in the extended loop of the first terminator hairpin; wherein the cgRNA is inactive in the cgRNA:inhibitor complex, and wherein hybridization of the cognate RNA trigger to the inhibitor displaces the cgRNA from the inhibitor, thereby activating the cgRNA. In accordance with some implementations, the cgRNA further comprises a Cas handle with an extended loop wherein the target-binding region is 5' of the Cas handle, and wherein the inhibitor-binding region comprises a portion of the extended loop of the Cas handle and no nucleotides 5' of the Cas handle. In accordance with some implementations, the inhibitor further comprises a toehold of one or more unpaired nucleotides at one or both ends, the cgRNA further comprising a first terminator hairpin with an extended loop comprising 5 or more nucleotides, and the inhibitor-binding region comprising: one or more nucleotides in the extended loop of the Cas handle; and one or more nucleotides in the extended loop of the first terminator hairpin; wherein the cgRNA is inactive in the cgRNA:inhibitor complex, and wherein hybridization of the cognate RNA trigger to the inhibitor displaces the cgRNA from the inhibitor, thereby activating the cgRNA. In accordance with some implementations, the inhibitor comprises a toehold of one or more unpaired nucleotides at one or both ends, the cgRNA further comprising a first terminator hairpin with an extended loop comprising 5 or more nucleotides, and the inhibitor-binding region comprising: one or more nucleotides in the extended loop of the Cas handle; zero, one, or more nucleotides of a linker 5'-adjacent to the first terminator hairpin; zero, one, or more nucleotides of a 5' portion of a stem of the first terminator hairpin; and one or more nucleotides in the extended loop of the first terminator hairpin; wherein the cgRNA is inactive in the cgRNA:inhibitor complex, and wherein hybridization of the cognate trigger to the inhibitor displaces the cgRNA from the inhibitor, thereby activating the cgRNA.

In accordance with some implementations, there is an allosteric conditional guide RNA (cgRNA) comprising a 5' fragment (cg5) and a 3' fragment (cg3), cg5 comprising a target-binding region and a trigger-binding region, and cg3 comprising a cognate RNA trigger: wherein the target-binding region is non-overlapping with the trigger-binding region; wherein cg5 and cg3 are inactive when not bound to each other; and wherein upon hybridization of cg3 to cg5 to form a cg5:cg3 complex, the cgRNA is activated, mediating the function of a Cas protein effector on a target gene that binds the target-binding region. In accordance with some implementations, the fragment cg5 further comprises a Cas handle wherein the target-binding region is 5' of the Cas handle and the trigger-binding region is 3' of the Cas handle. In accordance with some implementations, the fragment cg5 further comprises a trigger-binding region comprising a 5' portion of a stem of a terminator duplex and the fragment cg3 further comprises a 3' portion of a stem of the terminator duplex, wherein hybridization of cg5 to cg3 forms the terminator duplex, activating the cgRNA.

In accordance with some implementations, there is an allosteric conditional guide RNA (cgRNA) comprising a 5' fragment (cg5) and a 3' fragment (cg3), cg5 comprising a target-binding region and a trigger-binding region, and cg3 configured to bind to a portion of the trigger-binding region to form a cg5:cg3 complex: wherein the target-binding region is non-overlapping with the trigger-binding region; wherein the cg5:cg3 complex is active in the absence of a cognate RNA trigger, mediating the function of a Cas protein effector on a target gene that binds the target-binding region; wherein cg5 and cg3 are inactive when not bound to each other; and wherein hybridization of the cognate RNA trigger to cg5 displaces cg3 from cg5, thereby inhibiting further mediation of Cas function on the target gene. In accordance with some implementations, the fragment cg5 further comprises a Cas handle wherein the target-binding region is 5' of the Cas handle and the trigger-binding region is 3' of the Cas handle. In accordance with some implementations, the fragment cg5 further comprises a trigger-binding region comprising: a 5' portion of a stem of a terminator duplex; zero, one, or more nucleotides of a linker 5'-adjacent to the 5' portion of the stem of the terminator duplex, and a toehold comprising zero, one, or more nucleotides 3'-adjacent to 5' portion of the stem of the terminator duplex, wherein the fragment cg3 further comprises a 3' portion of the stem of the terminator duplex, wherein hybridization of cg5 to cg3 forms the terminator duplex within the cg5:cg3 complex, and wherein hybridization of the trigger to cg5 displaces cg3 from cg5, thereby breaking the terminator duplex and inactivating the cgRNA.

In accordance with some implementations, there is an allosteric conditional guide RNA (cgRNA) comprising: a 5' fragment (cg5) and a 3' fragment (cg3), cg5 comprising a target-binding region; and cg3 comprising a trigger-binding region, wherein cg5 is configured to bind to a portion of the trigger-binding region to form a cg5:cg3 complex: wherein the target-binding region is not base-paired to the trigger-binding region in the cg5:cg3 complex; wherein the cg5:cg3 complex is active in the absence of a cognate RNA trigger, mediating the function of a Cas protein effector on a target gene that binds the target-binding region; wherein cg5 and cg3 are inactive when not bound to each other; and wherein hybridization of the cognate RNA trigger to cg3 displaces cg5 from cg3, thereby inhibiting further mediation of Cas function on the target gene. In accordance with some implementations, the fragment cg5 further comprises a Cas handle wherein the target-binding region is 5' of the Cas handle, and wherein the fragment cg3 binds to cg5 3' of the Cas handle. In accordance with some implementations, the fragment cg3 further comprises a trigger-binding region comprising a 3' portion of a stem of a terminator duplex, and a toehold comprising zero, one, or more nucleotides 5'-adjacent to the 3' portion of the stem of the terminator duplex; the fragment cg5 further comprises a 5' portion of the stem of the terminator duplex; and wherein hybridization of cg5 to cg3 forms the terminator duplex within the cg5:cg3 complex, and wherein hybridization of the cognate RNA trigger to cg3 displaces cg5 from cg3, thereby breaking the terminator duplex and inactivating the cgRNA.

In accordance with some implementations, there is an allosteric conditional guide RNA (cgRNA) comprising a 5' fragment (cg5) and a 3' fragment (cg3): wherein cg5 comprises a Cas handle, a target-binding region 5' of the Cas handle, and a cg3-binding region 3' of the Cas handle, wherein cg3 comprises a cg5-binding region, and wherein either cg5 or cg3 comprises a trigger-binding region: wherein the target-binding region is non-overlapping with the trigger-binding region and is configured not to bind to the trigger-binding region; wherein cg5 and cg3 are inactive when not bound to each other, wherein in the absence of a cognate RNA trigger, cg5 and cg3 are configured to be inhibited from binding to each other, and wherein upon hybridization of the cognate RNA trigger to either cg5 or cg3, cg5 and cg3 hybridize to form a trigger:cg5:cg3 complex that activates the cgRNA, thereby mediating the function of a Cas protein effector on a target gene that binds the target-binding region. In accordance with some implementations, the fragment cg5 further comprises: a trigger-binding region comprising a first inhibitor region, and a second inhibitor region, wherein in the absence of the cognate RNA trigger, the first inhibitor region is configured to bind to the second inhibitor region, thereby inhibiting binding between cg5 and cg3. In accordance with some implementations, the cognate RNA trigger comprises a cg5-binding region; the trigger-binding region further comprises a toehold of one or more unpaired nucleotides at one or both ends; the cg3-binding region of cg5 comprises a 5' portion of a stem of a terminator duplex; and the cg5-binding region of cg3 comprises a 3' portion of the stem of the terminator duplex; wherein upon hybridization of the cognate RNA trigger to cg5, cg5 hybridizes to cg3 to form the terminator duplex, thereby activating the cgRNA. In accordance with some implementations, cg3 further comprises: a trigger-binding region comprising a first inhibitor region, and a second inhibitor region, wherein in the absence of the cognate RNA trigger, the first inhibitor region is configured to bind the second inhibitor region, thereby inhibiting binding between cg5 and cg3. In accordance with some implementations, the cognate RNA trigger comprises a cg3-binding region; the trigger-binding region further comprises a toehold of one or more unpaired nucleotides at one or both ends; the cg5-binding region of cg3 comprises a 3' portion of a stem of a terminator duplex; and the cg3-binding region of cg5 comprises a 5' portion of the stem of the terminator duplex, wherein upon hybridization of the cognate RNA trigger to cg3, cg3 hybridizes to cg5 to form the terminator duplex, thereby activating the cgRNA. In accordance with some implementations, cg5 further comprises: a trigger-binding region comprising a first inhibitor region and a second inhibitor region; and wherein cg3 further comprises a third inhibitor region and a fourth inhibitor region, wherein in the absence of a cognate RNA trigger, the first inhibitor region is configured to bind the second inhibitor region and the third inhibitor region is configured to bind to the fourth inhibitor region, thereby inhibiting binding between cg5 and cg3. In accordance with some implementations, the cognate RNA trigger comprises a cg5-binding region; the trigger-binding region of cg5 further comprises a toehold of one or more unpaired nucleotides at one or both ends; the cg3-binding region of cg5 comprises a 5' portion of a stem of a terminator duplex; and the cg5-binding region of cg3 comprises a 3' portion of the stem of the terminator duplex comprising a toehold of one or more unpaired nucleotides at one or both ends, wherein upon hybridization of the cognate RNA trigger to cg5, cg5 hybridizes to cg3 to form the terminator duplex, thereby activating the cgRNA. In accordance with some implementations, the trigger-binding region of cg5 is 5' of the target-binding region. In accordance with some implementations, cg3 comprises a trigger mimic region having a sequence identical to that of the cg5-binding region of the cognate RNA trigger, wherein upon activation of the cgRNA by the cognate RNA trigger, the trigger mimic region is exposed and capable of serving as the cognate RNA trigger for a new copy of the cgRNA comprising a new copy of the 5' fragment cg5 and a new copy of the 3' fragment cg3. In accordance with some implementations, the trigger-binding region of cg5 is 3' of the Cas handle. In accordance with some implementations, the cgRNA additionally comprises a splint as a third fragment wherein the splint comprises a cg3-binding region comprising a fifth inhibitor region and further comprising a toehold of one or more unpaired nucleotides at one or both ends; and a cg5-binding region comprising a sixth inhibitor region; wherein in the absence of a cognate RNA trigger, the fifth inhibitor region is configured to bind the sixth inhibitor region, inhibiting binding of the splint to cg5 and cg5, and wherein upon activation of the cgRNA by the cognate RNA trigger, cg3 hybridizes to the cg3-binding region of the splint and the cg5-binding region of the splint hybridizes to cg5, displacing the trigger from cg5, and catalytically regenerating the trigger which then serves as the cognate RNA trigger for a new copy of the cgRNA comprising a new copy of the 5' fragment cg5 and a new copy of the 3' fragment cg3. In accordance with some implementations, the catalytically regenerated trigger serves as the cognate RNA trigger for a new copy of the cgRNA which further comprises a new copy of the splint fragment. In accordance with some implementations, cg3 comprises a trigger mimic region having a sequence identical to that of the cg5-binding region of the cognate RNA trigger, wherein upon activation of the cgRNA by the cognate RNA trigger, the trigger mimic region hybridizes to the trigger-binding region of cg5, displacing the trigger from cg5, and catalytically regenerating the trigger which can then serve as the cognate RNA trigger for a new copy of the cgRNA comprising a new copy of the 5' fragment cg5 and a new copy of the 3' fragment cg3.

In accordance with some implementations, there is a method of conditionally inhibiting mediation of Cas function on a target gene, comprising: providing an allosteric conditional guide RNA (cgRNA); and combining the cgRNA with a system comprising a target gene and a Cas protein effector; wherein the cgRNA is active in mediating the function of the Cas protein effector on the target gene in the absence of a cognate RNA trigger, and wherein upon hybridization to the cognate RNA trigger, the cgRNA is inactivated, inhibiting further mediation of Cas function on the target gene.

In accordance with some implementations, there is a method of conditionally mediating the function of a Cas protein effector on a target gene, comprising: providing an allosteric conditional guide RNA (cgRNA) and an RNA inhibitor strand; and combining the cgRNA and RNA inhibitor strand with a system comprising a target gene and a Cas protein effector; wherein in the absence of a cognate RNA trigger, the inhibitor is bound to the cgRNA and the cgRNA is inactive; and wherein upon hybridization of a cognate RNA trigger to the inhibitor, the cgRNA is activated, mediating the function of a Cas protein effector on the target gene.

In accordance with some implementations, there is a method of conditionally mediating the function of a Cas protein effector on a target gene, comprising: providing an allosteric conditional guide RNA (cgRNA) comprising a 5' fragment (cg5) and a 3' fragment (cg3); and combining the cgRNA with a system comprising a target gene and a Cas protein effector; wherein cg5 and cg3 are inactive when not bound to each other; and wherein upon hybridization of cg3 to cg5, the cgRNA is activated, mediating the function of a Cas protein effector on the target gene.

In accordance with some implementations, there is a method of conditionally inhibiting mediation of Cas function on a target gene, comprising: providing an allosteric conditional guide RNA (cgRNA) comprising a 5' fragment (cg5) and a 3' fragment (cg3); and combining the cgRNA with a system comprising a target gene and a Cas protein effector; wherein in the absence of a cognate RNA trigger cg5 is bound to cg3 and the cgRNA is active; and wherein hybridization of the cognate RNA trigger to cg5 displaces cg3 from cg5, thereby inhibiting further mediation of Cas function on the target gene.

In accordance with some implementations, there is a method of conditionally inhibiting mediation of Cas function on a target gene, comprising: providing an allosteric conditional guide RNA (cgRNA) comprising a 5' fragment (cg5) and a 3' fragment (cg3); and combining the cgRNA with a system comprising a target gene and a Cas protein effector; wherein in the absence of a cognate RNA trigger cg5 is bound to cg3 and the cgRNA is active; and wherein hybridization of the cognate RNA trigger to cg3 displaces cg5 from cg3, thereby inhibiting further mediation of Cas function on the target gene.

In accordance with some implementations, there is a method of conditionally mediating the function of a Cas protein effector on a target gene, comprising: providing an allosteric conditional guide RNA (cgRNA) comprising a 5' fragment (cg5) and a 3' fragment (cg3); and combining the cgRNA with a system comprising a target gene and a Cas protein effector; wherein in the absence of a cognate RNA trigger, cg5 and cg3 are inhibited from binding to each other and the cgRNA is inactive; and wherein upon hybridization of the cognate RNA trigger to either cg5 or cg3, cg5 and cg3 hybridize to form a trigger:cg5:cg3 complex that activates the cgRNA, thereby mediating the function of a Cas protein effector on the target gene.

In accordance with some implementations of any of the foregoing, one or more of the following may also be present: the trigger is an RNA; the trigger is or is a subsequence of an mRNA, an rRNA, a lncRNA, a miRNA, or a tRNA; the cgRNA is expressed in a cell; the cgRNA is chemically synthesized; the cgRNA, cgRNA fragment, RNA inhibitor strand, and/or trigger further comprises one or more additional regions at the 5' and/or the 3' end; the cgRNA, cgRNA fragment, RNA inhibitor strand, and/or trigger further comprises one or more chemical modifications that alter one or more of degradation properties, affinity, biological activity, and/or delivery properties of the cgRNA; the cgRNA, cgRNA fragment, RNA inhibitor strand, and/or trigger comprises one or more chemical modifications selected from the group consisting of arabino nucleic acids (ANA), locked nucleic acids (LNA), peptide nucleic acids (PNA), phosphoroamidate DNA analogues, phosphorodiamidate morpholino oligomers (PMO), cyclohexene nucleic acids (CeNA), tricycloDNA (tcDNA), bridged nucleic acids (BNA), phosphorothioate modification, 2'-fluoro (2'-F) modification, 2'-fluoroarabino (2'-FANA) modification, 2'O-Methyl (2'O-Me) modification, and 2'O-(2-methoxyethyl) (2'O-MOE) modification; and the cgRNA works in conjunction with Cas to mediate cell-selective induction, silencing, editing, or binding of a target gene.

In accordance with some implementations of any of the foregoing, the allosteric cgRNA wherein an RNA trigger, RNA helper, and/or RNA inhibitor further comprises a protective element (PEL), wherein none, some, or all of the PEL sequence is derived from a component of a viral xrRNA sequence, and wherein the PEL reduces degradation of the RNA trigger, RNA helper, and/or RNA inhibitor in a prokaryotic or eukaryotic cell. In accordance with some implementations of any of the foregoing, the allosteric cgRNA further wherein the cgRNA and/or one or more cgRNA fragments further comprise a protective element (PEL), wherein none, some, or all of the PEL sequence is derived from a component of a viral xrRNA, and wherein the PEL reduces degradation of the cgRNA in a prokaryotic or eukaryotic cell.

BRIEF DESCRIPTION OF THE DRAWINGS

FIGS. 11A-11F demonstrate ON→OFF conditional logic in bacteria using allosteric terminator switch cgRNAs.

FIG. 12A-12F demonstrate ON→OFF conditional logic in bacteria using allosteric splinted switch cgRNAs.

FIG. 13A-13J demonstrate ON→OFF conditional logic in human cells using allosteric terminator switch cgRNAs.

FIG. 14A-14H demonstrate OFF→ON conditional logic in human cells using allosteric split-terminator switch cgRNAs with a 4-bp terminator duplex.

FIG. 15A-15H demonstrate OFF→ON conditional logic in human cells using allosteric split-terminator switch cgRNAs with a 10-bp terminator duplex.

FIG. 16A-16E demonstrate OFF→ON conditional logic in human cells using allosteric split-terminator switch cgRNAs with terminator duplexes of different lengths (40, 30, 20, 10, 8, 6, 4 bp).

FIG. 17A-17C demonstrate that 3' truncation of a standard gRNA can lead to complete inactivation, providing the basis for engineering cgRNAs with a clean OFF state.

FIGS. 18A-18F demonstrate ON→OFF conditional logic in bacteria using allosteric terminator switch cgRNAs and mRNA triggers.

FIGS. 21A-21E demonstrate an allosteric ON→OFF cgRNA functioning in a multicellular organism FIGS. 22A-22E demonstrate an allosteric OFF→ON cgRNA functioning in a multicellular organism

FIGS. 30A-30D demonstrate allosteric OFF→ON split-terminator switch cgRNAs functioning in bacteria.

FIGS. 31A-31E demonstrate allosteric ON→OFF split-terminator switch cgRNAs functioning in human cells.

FIGS. 32A-32F demonstrate allosteric ON→OFF split-terminator switch cgRNAs functioning in bacteria.

FIGS. 33A-33D demonstrate allosteric OFF→ON 5'- and 3'-inhibited split-terminator switch cgRNAs functioning in bacteria.

DETAILED DESCRIPTION OF THE PREFERRED EMBODIMENT

Programmable guide RNAs (gRNAs) play a central role in the CRISPR revolution sweeping biology and medicine by directing the function of Cas protein effectors to a target gene of choice (FIG. 1A), providing a versatile programmable platform for engineering diverse modes of synthetic regulation in organisms ranging from bacteria to humans. Wildtype Cas9 and Cas12a allow for genome editing[1-4] while mutated catalytically dead Cas9 (dCas9) and nickase variants allow for gene editing, silencing, induction,[5-8] binding, epigenome editing,[9] chromatin interaction mapping[10] and regulation,[11] and imaging.[12] Hence, gRNA-mediated CRISPR/Cas combines the rich functional vocabulary of different Cas effectors (edit, silence, induce, bind, etc) and the programmability of the gRNA. To target a new gene of choice, all that is needed is to change the sequence of the gRNA.

However, the fact that gRNAs are constitutively active is a significant limitation, making it challenging to confine gRNA activity to a desired location and time within an organism. Strategies for achieving temporal control include modulation of gRNA activity using antisense RNAs[13] and small-molecule induction of gRNAs[14,15] or Cas9.[16] Spatiotemporal control can be achieved in photoaccessible tissues using light to uncage gRNAs,[17,18] cleave antisense DNAs,[19] or regulate Cas9.[20] Alternatively, Cas9 can be regulated using tissue-specific promoters[21,22] or microRNAs.[23] Cas9 tolerates, to varying degrees, a variety of modifications to the standard gRNA structure (FIG. 1B),[24-26] allowing for introduction of auxiliary domains to provide hooks for regulation by small-molecules,[27-29] protein-bound RNAs,[30] nucleases,[31] or nuclease-recruiting DNAs or miRNAs.[31,32] As appreciated herein, for generality, it can be desirable to control gRNA regulatory scope in a manner that is both conditional and programmable, and for simplicity, to leverage dynamic RNA nanotechnology without relying on the functionality of additional pathways.

Figure 2A:
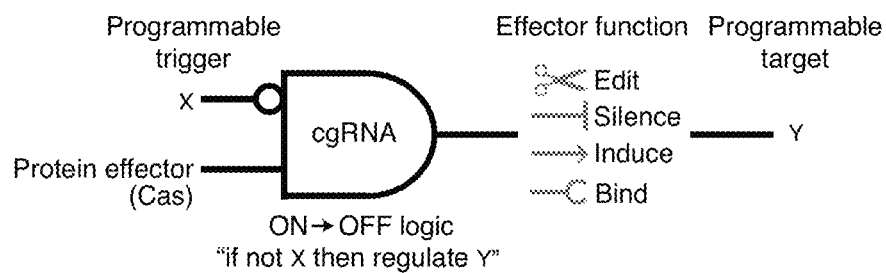
FIGS. 2A-2B depict the logic and function of a conditional guide RNA (cgRNA).
Figure 2B:
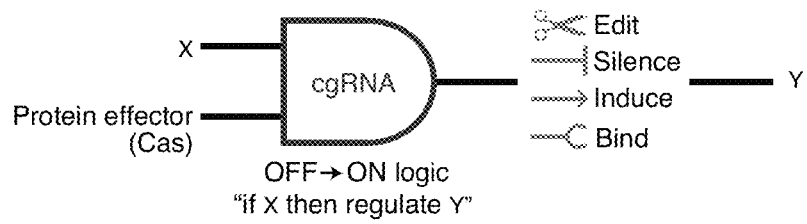

To exert programmable control over the scope of gRNA activity, conditional guide RNAs (cgRNAs) change conformation in response to an RNA trigger X, conditionally directing the function of Cas to a target gene Y (FIG. 2).[26,33,34] Unlike a standard gRNA, a cgRNA is programmable at two levels, with the trigger-binding sequence controlling the scope of cgRNA activity and the target-binding sequence determining the subject of Cas activity. Hybridizing to the trigger changes the cgRNA conformation to perform sequence transduction between X and Y and shape transduction between active/inactive states. The disclosure herein relates to cgRNAs that are allosteric so that the sequence of the target gene Y places no restriction on the sequence of the RNA trigger X, allowing for independent control over the regulatory scope (using X) and the regulatory target (using Y). In some embodiments, cgRNA mechanisms implement ON→OFF logic (conditional inactivation by trigger X; FIG. 2A). In some embodiments, cgRNA mechanisms implement OFF→ON logic (conditional activation by trigger X; FIG. 2B). In some embodiments, cgRNAs work in concert with Cas variants that either edit, silence, induce, or bind the target Y (FIG. 2), creating opportunities for diverse modes of tissue-selective spatiotemporal control over regulation (see for example FIG. 3). In some embodiments, cgRNAs work in concert with Cas variants that mediate induction, silencing, editing, binding, epigenome editing, chromatin interaction mapping and regulation, or imaging of a target gene.

Figure 3A:
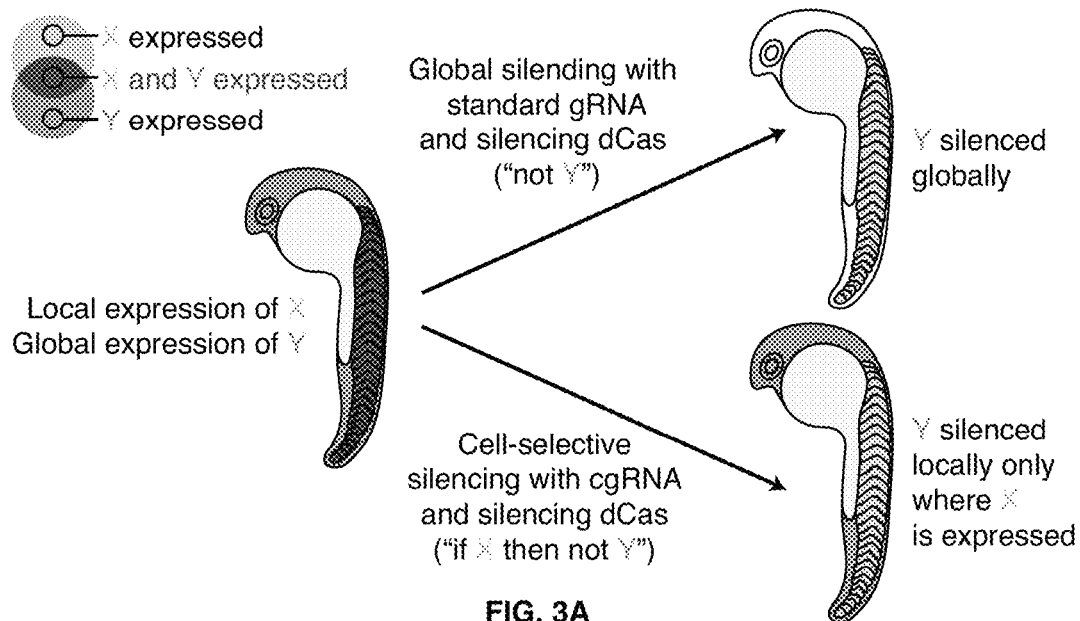
FIGS. 3A-3E depict applications of cell-selection spatiotemporal control of CRISPR/Cas regulation.
Figure 3B:
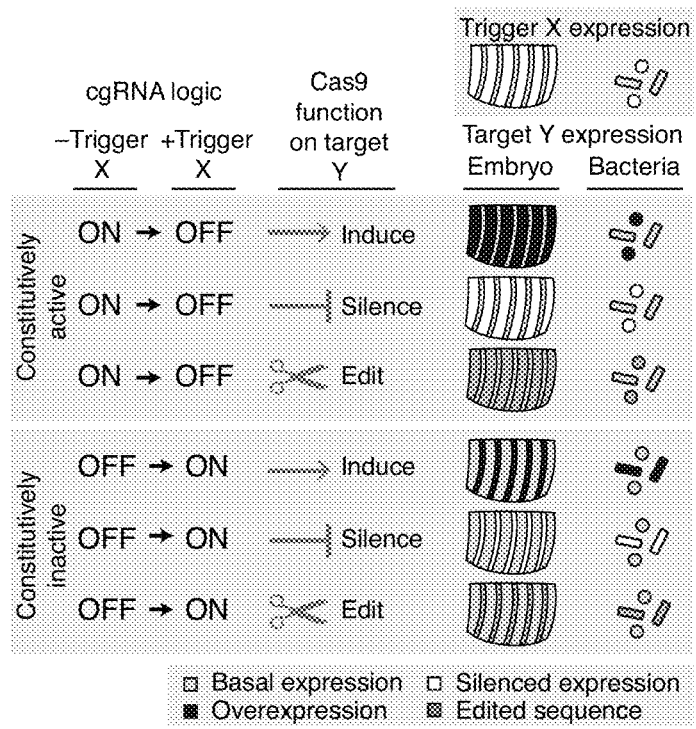
Figure 3C:
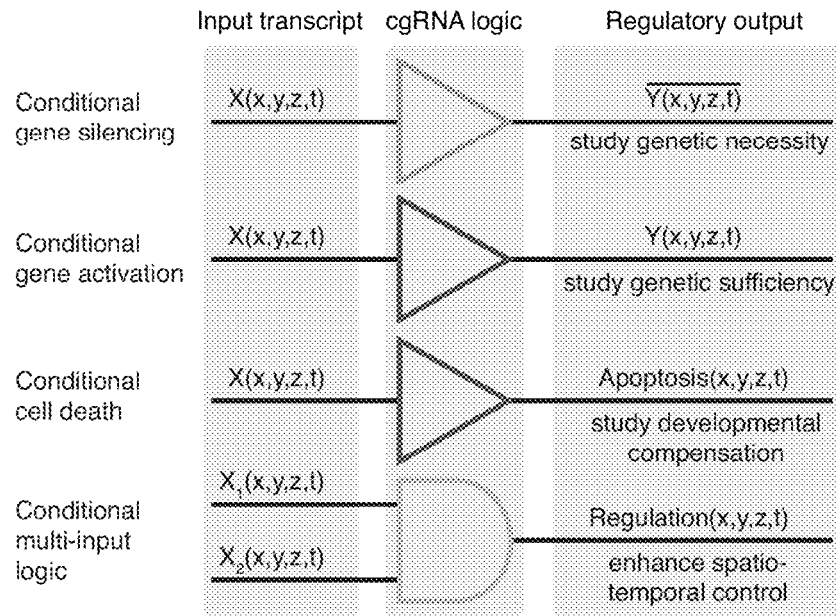
Figure 3D:
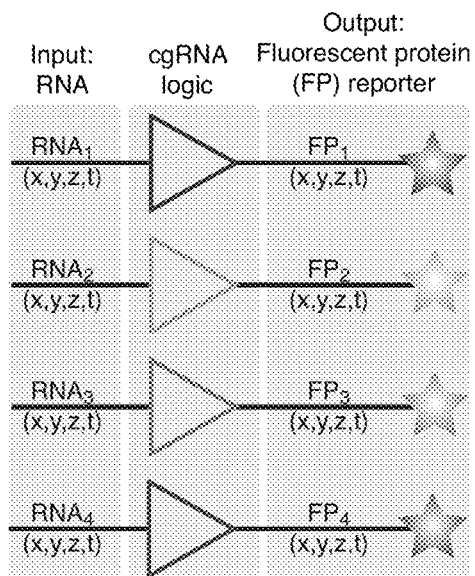
Figure 3E:
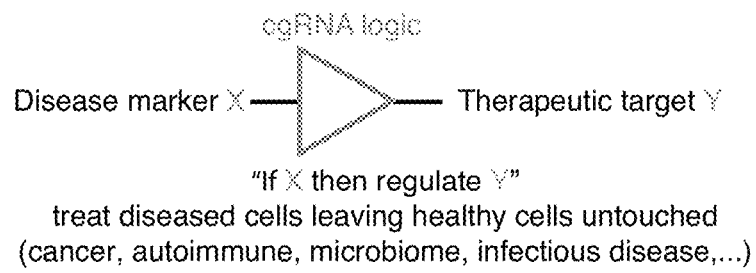

In some embodiments, cgRNAs open the possibility of restricting synthetic regulation to a desired cell type, tissue, or organ. This can be achieved by selecting an endogenous RNA trigger X with the desired spatial and temporal expression profile, allowing for spatiotemporal control over regulation (FIG. 3A). In some embodiments, cgRNAs open the possibility of restricting synthetic regulation to a desired cell type, tissue, or organ without engineering the organism. FIG. 3B illustrates a variety of modes of cell-selective spatiotemporal regulatory control that can be implemented by combining the conditionality of cgRNA logic (ON→OFF and OFF→ON) and the functionality of Cas variants (edit, silence, induce, bind, etc). In some embodiments, cgRNAs can be used as cell-selective and tissue-selective research tools (FIG. 3C): conditional gene silencing would probe genetic necessity, conditional gene induction would probe genetic sufficiency, conditional cell death would probe developmental compensation. In some embodiments, to shift conditional regulation to a different tissue or developmental stage, the sequence of a cgRNA is simply redesigned to recognize a different input X with the desired spatial and temporal expression profile. In some embodiments, cgRNAs can be used to mediate in vivo imaging of a target RNA using the cgRNA to recognize the RNA of interest and mediate expression of a fluorescent protein reporter. In some embodiments, multiple cgRNAs recognizing different target RNAs and inducing spectrally distinct different fluorescent protein reporters can be used for multiplexed in vivo RNA imaging. In some embodiments, in a model organism with N fluorescent proteins integrated into the genome, a set of N target RNAs can be imaged in vivo using a set of N cgRNAs to induce the fluorescent proteins upon detection of the corresponding target RNAs. In some embodiments, to switch to imaging a new set of N target RNAs, no genome engineering is required as this can be achieved simply by using a new set of N cgRNAs. In some embodiments, cgRNAs also provide a framework for conditional chemotherapies ("if X then regulate Y") with X as a programmable disease marker and Y as an independent programmable therapeutic pathway, allowing for selective treatment or killing of diseased cells leaving healthy cells untouched (FIG. 3E).

The repurposing of RNA-guided CRISPR effectors through development of modified guide RNAs (gRNAs) and CRISPR-associated (Cas) proteins has yielded a suite of powerful tools for biological research, synthetic biology, and medicine. Precision genome editing has been achieved in a variety of organisms using gRNAs to direct the nuclease activity of Cas9 and Cas12a (Cpf1) to a target gene of choice.[1-4] Mutation of the nuclease domains to produce a catalytically dead Cas9 (dCas9) has allowed for silencing of genetic expression via inhibition of transcriptional elongation,[5,6] or induction (or silencing) of genetic expression using dCas9 fusions that incorporate transcriptional regulatory domains.[7] Other dCas9 fusions have mediated target-binding to allow for visualization of genomic loci,[35,36] epigenetic modification,[37] and single-base editing at a specific genomic locus,[4,38] chromatin interaction mapping[10] and regulation,[11] and imaging.[12] Hence, gRNA:effector complexes combine the benefits of the rich functional vocabulary of the protein effector (edit, silence, induce, bind) and the programmability of the gRNA in targeting effector activity to a gene of choice.

Because gRNAs are constitutively active, additional measures are needed to restrict effector activity to a desired location and time. Temporal control can be achieved by small-molecule induction of gRNAs[14,15] or Cas9,[16] but this comes with limitations in terms of multiplexing and spatial control. In some settings, spatiotemporal control can be achieved by regulation of Cas9 via photoactivation[20] or via tissue-specific promoters[21,22] or microRNAs,[23] which comes with the unwelcome restriction that all gRNAs are subject to the same regulatory scope. Cas9 activity is tolerant to significant modifications to the standard gRNA structure.[24-26] The introduction of auxiliary domains can allow for conditional control of gRNA activity via structural changes induced by small-molecules,[27-29] protein-bound RNAs,[30] nucleases,[31] or nuclease-recruiting DNAs.[31] Alternatively, the activity of standard gRNAs can be modulated by antisense RNAs[13] or by photolysis of antisense DNAs incorporating photocleavable groups.[19]

For generality, it is useful to control the regulatory scope of a gRNA in a manner that is both conditional and programmable. Conditional guide RNAs (cgRNAs) achieve this goal by changing conformation in response to an RNA trigger X to conditionally direct the function of a Cas effector to a target gene Y.[26,33,34,39] Unlike a standard gRNA, a cgRNA is programmable at two levels, with the trigger-binding sequence controlling the scope of cgRNA activity and the target-binding sequence determining the subject of effector activity. Functionally, the cgRNA performs sequence transduction between X and Y as well as shape transduction between active/inactive conformations. cgRNA activity can be engineered to toggle either ON→OFF or OFF→ON in response to a cognate RNA trigger X; this conditional control can be exerted over Cas (for example, Cas9 or dCas9) variants that either, for example, edit, silence, induce, or bind the target Y (FIG. 2). For example, by selecting an endogenous transcript X with a desired spatiotemporal expression profile during development, the downstream regulatory effect on target Y could be restricted to a desired tissue and developmental stage within a model organism (FIGS. 3A and 3B). Alternatively, in a therapeutic context, X can be a disease marker and Y an independent therapeutic target, allowing for selective treatment or killing of diseased cells leaving healthy cells untouched (FIG. 3E).

Figure 1A:
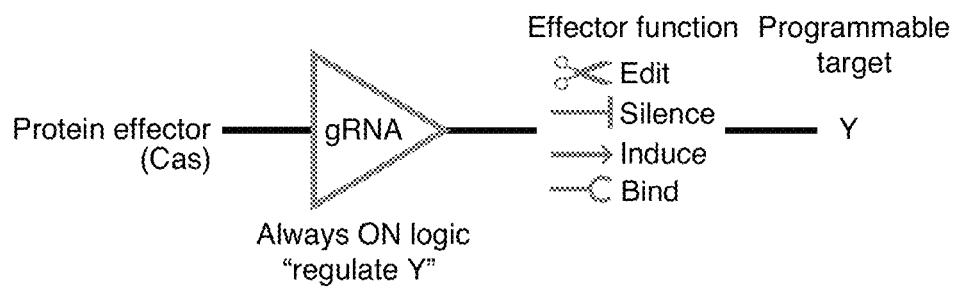
FIGS. 1A-1B depict the logic, function, structure, and interactions of a standard guide RNA (gRNA).
Figure 1B:
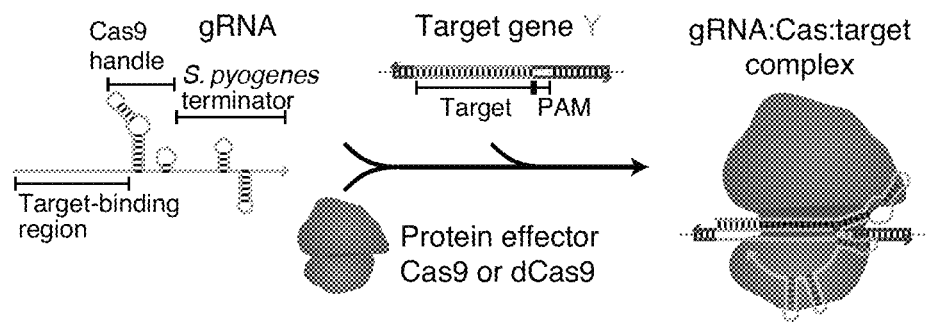

FIG. 1A depicts the logic and function of a standard guide RNA (gRNA). A standard gRNA is always ON, unconditionally directing the activity of a protein effector to a target Y; different Cas9, dCas9, and/or Cas variants implement different functions (for example, edit, silence, induce, bind). FIG. 1B depicts structure and interactions of a standard gRNA. From 5' to 3', a standard gRNA comprises: a target-binding region, a Cas handle recognized by the protein effector, and a terminator region.

For some embodiments, FIG. 2 depicts the logic and function of a conditional guide RNA (cgRNA). For some embodiments, a cgRNA changes conformation in response to a programmable trigger X to conditionally direct the activity of a protein effector to a programmable target Y. For some embodiments, FIG. 2A depicts ON→OFF logic with a constitutively active cgRNA that is conditionally inactivated by X. For some embodiments, FIG. 2B depicts OFF→ON logic with a constitutively inactive cgRNA that is conditionally activated by X.

For some embodiments, FIG. 3 illustrates applications of cell-selective regulation of CRISPR/Cas function using cgRNAs. FIG. 3A contrasts global silencing (top arrow) of target gene Y using silencing dCas9 and a standard gRNA that implements the unconditional logic "silence Y" to cell-selective silencing (bottom arrow) of target gene Y using silencing dCas9 and a conditional cgRNA, such that Y is silenced locally only where X is expressed. For some embodiments, FIG. 3B illustrates diverse modes of cell-selective spatiotemporal regulatory control using cgRNA conditional logic (ON→OFF or OFF→ON) and different Cas9 functional variants (induce, silence, edit, bind, etc). ON→OFF and OFF→ON cgRNAs produce inverted regulatory patterns on target Y in response to a given pattern for trigger X. For some embodiments, FIG. 3C illustrates cell-selective and tissue-selective tools. For example, conditional gene silencing ("if gene X is transcribed, silence independent gene Y") can be used to probe genetic necessity, conditional gene activation ("if gene X is transcribed, activate independent gene Y") can be used to probe genetic sufficiency, and conditional cell death ("if gene X is transcribed, induce apoptosis") can be used to probe developmental compensation. In each case, conditional regulation is mediated by a cgRNA whose activity is toggled by a programmable trigger X. For some embodiments, by selecting a trigger X with the desired spatial and temporal expression profiles, the regulatory function is restricted to a desired cell type, tissue, or organ within an organism, mixture of cells, or ecosystem. For some embodiments, to shift conditional regulation to a different tissue type or time point, the cgRNAs can be programmed to recognize a different trigger X. For some embodiments, to enhance cell-selective spatiotemporal control in multi-cellular settings (e.g., within embryos or bacterial mixtures), multi-input conditional logic (operating on two or more inputs $X_1, X_2, \ldots$) using AND gates can be used to narrow the scope of regulation on Y; alternatively, OR gates can be used to broaden the scope of regulation on Y. In some embodiments, AND logic is implemented using split-cgRNAs that are functional only in the presence of both $X_1$ and $X_2$. In some embodiments, OR logic is executed using multiple cgRNA variants that accept different inputs ($X_1, X_2, \ldots$) but target the same output Y. FIG. 3D illustrates cgRNA-mediated cell-selective reporter regulation for multiplexed in vivo RNA imaging. In some embodiments, 4 cgRNAs each detect a different mRNA input ($mRNA_1, mRNA_2, mRNA_3, mRNA_4$) that serves as an RNA trigger, activating the corresponding cgRNA to induce the corresponding spectrally distinct FP reporter ($FP_1, FP_2, FP_3, FP_4$). In some embodiments, after once optimizing a plasmid-based reporter system expressing inducing dCas9, the 4 FP reporters, and the 4 cgRNAs, imaging a new set of mRNAs requires only updating the sequences of the cgRNAs to accept new mRNAs as triggers. In some embodiments, this cgRNA approach offers important conceptual advantages relative to FP fusion methods, which have revolutionized the study of genetic expression,[43-45] but have the well-known drawbacks that a new fusion must be engineered for each gene of interest, that it is difficult to determine whether fusions affect the expression or function of target proteins, and that fusion methods are not applicable to imaging non-protein gene products such as coding and non-coding RNAs. In some embodiments, cgRNAs eliminate these issues by replacing the conventional physical link of FP fusion approaches with a logical link executed by cgRNAs that execute conditional gene induction, allowing for spatiotemporal monitoring of gene expression levels in living chick embryos without the need to modify the imaged molecules ($mRNA_1$, $mRNA_2$, $mRNA_3$, $mRNA_4$) in any way. FIG. 3E depicts the conditional logic using cgRNAs as conditional chemotherapies: "if disease marker X then regulate therapeutic target Y". In some embodiments, X is a programmable disease marker and Y is an independent therapeutic target, allowing for selective treatment or killing of diseased cells (the subset of cells containing X) while leaving healthy cells untouched (the subset of cells lacking X). In some embodiments, cgRNAs allow for independent diagnosis (detection of disease marker X) and treatment (regulation or editing of independent therapeutic target Y).

For some embodiments, FIG. 10 depicts interactions between allosteric cgRNAs, RNA triggers, and Cas9, dCas9 or Cas. For some embodiments, FIG. 10A depicts interactions for an allosteric ON→OFF terminator switch cgRNA. In the ON state, the terminator switch cgRNA is constitutively active, directing the function of protein effector Cas9, dCas9, or Cas to a target gene Y in the absence of trigger. The extended loop and modified sequence domains in the terminator region are intended not to interfere with the activity of the cgRNA:Cas complex. In the OFF state, in the presence of RNA trigger X, hybridization of the trigger forms a structure incompatible with cgRNA mediation of Cas9, dCas9, and/or Cas function. For some embodiments, FIG. 10B depicts interactions for an allosteric ON→OFF splinted switch cgRNA. In the ON state, the splinted switch cgRNA is constitutively active, directing the function of protein effector Cas9, dCas9, or Cas to a target gene Y in the absence of trigger. The extended loops in the Cas9 handle and terminator region are intended not to interfere with the activity of the cgRNA:Cas complex. In the OFF state, in the presence of RNA trigger X, hybridization of the trigger forms a splint that is structurally incompatible with cgRNA mediation of Cas9, dCas9, and/or Cas function. For some embodiments, FIG. 10C depicts interactions for an allosteric OFF→ON split-terminator switch cgRNA. In the OFF state, the split-terminator switch cgRNA is constitutively inactive. In the absence of RNA trigger X, the cgRNA is incapable of directing the function of the protein effector Cas9, dCas9, and/or Cas. In the ON state, the complex of cgRNA and trigger X mediates the function of the protein effector Cas9, dCas9, or Cas on the target gene Y. The modified sequence domains in the terminator duplex do not to interfere with the activity of the cgRNA:trigger:Cas complex.

Definitions

"Nucleic acids" as used herein includes oligomers of RNA, DNA, 2'OMe-RNA, LNA, PNA, XNA, chemically modifications thereof, synthetic analogs of RNA or DNA, any other material capable of base-pairing, one or more chemical linkers not capable of base-pairing, or any combination thereof. Nucleic acids may include analogs of DNA or RNA having modifications to either the bases or the backbone. For example, nucleic acid, as used herein, includes the use of peptide nucleic acids (PNA). The term "nucleic acids" also includes chimeric molecules. The phrase includes artificial constructs as well as derivatives etc. The phrase includes, for example, any one or more of DNA, RNA, 2'OMe-RNA, LNA, XNA, synthetic nucleic acid analogs, and PNA. The phrase also includes oligomers of RNA, DNA, 2'OMe-RNA, LNA, PNA, XNA and/or other nucleic acid analogs with or without chemical linkers between nucleic acid segments.

Figure 4A:
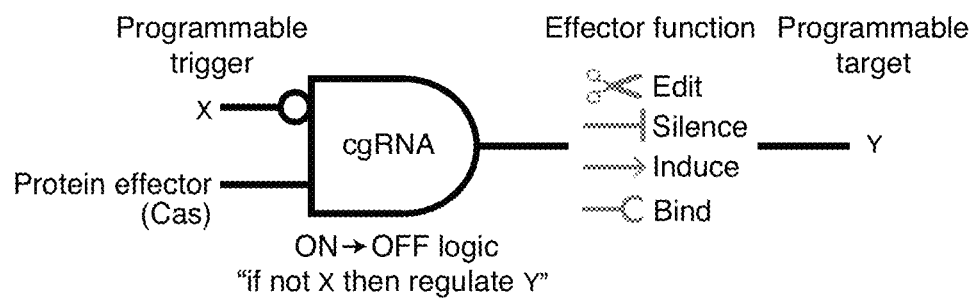
FIGS. 4A-4C depict the logic, function, and mechanism of allosteric ON→OFF terminator switch cgRNAs (Mechanism 1A).

A "nucleic acid strand" refers to an oligomer of nucleotides (typically listed from 5' to 3'). In diagrams, a nucleic acid strand is depicted with an arrowhead at the 3' end. A nucleic acid strand may comprise one or more "regions" and/or "sequence domains" (equivalently "domains"). For example, FIG. 4C depicts a nucleic acid strand (labeled "Allosteric cgRNA") containing a "target-binding region" comprising domain "u", a "Cas handle" region, a "trigger binding region" comprising domains "d", "e", and "f", and other regions and domains. A "secondary structure" of a nucleic acid strand is defined by a set of base pairs (for example, Watson-Crick base pairs [A-U or C-G] or wobble base pairs [G-U] for RNA).

Two "complementary" sequence domains can base-pair to each other (i.e., hybridize) to form a "duplex" or "stem", representing one or more consecutive base pairs between two regions (or equivalently, one or more consecutive base pairs between two sequence domains). For example, in FIG. 4C, domain "e*" is complementary to sequence domain "e", allowing for hybridization to form a "duplex" or "stem". In some settings it is convenient to designate complementary sequence domains using matching domain names with and without an asterisk (for example, domain "e*" complementary to domain "e"). Complementarity may also be specified independent of the sequence domain names. For example, domain "b" may be specified as complementary to domain "c". The complementarity between two complementary sequence domains may be partial, such that when they base-pair to each other to form a duplex (or stem), the base pairs within the duplex (or stem) may have one or more mismatches interspersed between them (i.e., one or more unpaired bases interspersed between the base pairs within the duplex). In some embodiments, a duplex (or stem) comprises, consists, or consists essentially of 1, 2, 3, 4, 5, 6, 7, 8, 9, 10, 11, 12, 13, 14, 15, 16, 17, 18, 19, 20, or more consecutive base pairs between two segments. In some embodiments a duplex (or stem) comprises, consists, or consists essentially of 5, 10, 15, 20, 25, 30, 35, 40, 45, or 50 consecutive base pairs (or any integer number of consecutive base pairs in between any of these values) between two segments. In some embodiments a duplex (or stem) comprises, consists, or consists essentially of 10, 20, 30, 40, 50, 60, 70, 80, 90, or 100 consecutive base pairs (or any integer number of consecutive base pairs in between any of these values) between two segments). In some embodiments a duplex (or stem) comprises, consists, or consists essentially of 100, 200, 300, 400, or 500 consecutive base pairs (or any integer number of consecutive base pairs in between any of these values) between two segments. In some embodiments, a duplex (or stem) comprises, consists, or consists essentially of 2, 3, 4, 5, 6, 7, 8, 9, 10, 11, 12, 13, 14, 15, 16, 17, 18, 19, 20, or more base pairs between two segments wherein 1, 2, 3, 4, 5, 6, 7, 8, 9, 10, 11, 12, 13, 14, 15, 16, 17, 18, 19, 20, or more unpaired bases are interspersed at one or more locations between the base pairs. In some embodiments a duplex (or stem) comprises, consists, or consists essentially of 5, 10, 15, 20, 25, 30, 35, 40, 45, or 50 base pairs (or any integer number of base pairs in between any of these values) between two segments wherein 1, 5, 10, 15, 20, 25, 30, 35, 40, 45, or 40 unpaired bases (or any integer number of unpaired bases between any of these values) are interspersed at one or more locations between the base pairs. In some embodiments a duplex (or stem) comprises, consists, or consists essentially of 10, 20, 30, 40, 50, 60, 70, 80, 90, or 100 base pairs (or any integer number of base pairs in between any of these values) between two segments wherein 1, 10, 20, 30, 40, 50, 60, 70, 80, 90, or 100 unpaired bases (or any integer number of unpaired bases between any of these values) are interspersed at one or more locations between the base pairs. In some embodiments a duplex (or stem) comprises, consists, or consists essentially of 100, 200, 300, 400, or 500 base pairs (or any integer number of base pairs in between any of these values) between two segments wherein 1, 100, 200, 300, 400, or 500 unpaired bases (or any integer number of unpaired bases between any of these values) are interspersed at one or more locations between the base pairs. In some embodiments, a duplex (or stem) comprising N base pairs between 2 segments further comprises 1, 2, 3, 4, 5, 6, 7, 8, 9, 10 or more mismatches corresponding to bases that are unpaired. In some embodiments, a duplex (or stem) comprising N base pairs between 2 segments further comprises 0% N, 1% N, 2% N, 5% N, 10% N, 20% N, 50% N, 100% N, or 200% N or more mismatches (or any percentage of N mismatches intermediate to the stated values) corresponding to bases that are unpaired.

A "hairpin" is a nucleic acid secondary structure comprising from 5' to 3': a 5' portion of a stem, an unpaired (single-stranded) loop, and a 3' portion of the stem, wherein the 5' portion of the stem is base-paired to the 3' portion of the stem.

Within a nucleic acid secondary structure, a "toehold" is a region or domain comprising one or more unpaired nucleotides, wherein the toehold serves as a nucleation site for binding another nucleic acid strand.

A "Cas handle" is a binding site for a Cas protein effector.

A "conditional guide RNA (cgRNA)" conditionally mediates the function of a Cas protein effector on a target gene depending on the presence/absence of a cognate RNA trigger. In some embodiments, cgRNAs implement ON→OFF logic (conditional inactivation by a cognate RNA trigger; for example FIG. 2A). In some embodiments, cgRNAs implement OFF→ON logic (conditional activation by a cognate RNA trigger; for example FIG. 2B). In some embodiments, cgRNAs work in concert with Cas variants that either edit, silence, induce, or bind the target gene (for example, FIG. 2).

A cgRNA is termed "allosteric" if the cognate RNA trigger toggles the activity of the cgRNA without interacting with the target-binding site within the cgRNA, allowing for the sequence of the cognate RNA trigger to be selected independently of the sequence of the target gene.

As used herein, "combining" encompasses any act or situation where at least two elements are able to interact, including, for example, adding one to the other, allowing the two elements to interact, exposing the two elements to each other, placing or having arranged the elements in a situation where they can interact, etc.

As used herein, the term "providing" encompasses any way to provide the denoted material, including for example, having, obtaining, creating, causing to be created, suppling, etc. the denoted material. This can be done directly (such as the provision of an RNA molecule itself) or indirectly (such as the provision of an DNA molecule that is to be transcribed into the RNA molecule). In some embodiments, this process can be an independent process (such as by obtaining an RNA segment), or it can be part of another process in the method (such as by providing an DNA sequence that is then transcribed into an RNA sequence).

As used in some embodiments herein, the term "mediating" can include one or more of facilitating, directing, or enabling.

In some embodiments, an "inactive" cgRNA is said to be "activated" by a cognate RNA trigger if the trigger increases the cgRNA-mediated function of a Cas protein effector on a target gene by 20%, 50%, 90%, 100%, 200%, 500%, 1000%, or more, or any percentage intermediate to the stated values. In some embodiments, an "inactive" cgRNA is said to be "activated" by a cognate RNA trigger if the trigger increases the cgRNA-mediated function of a Cas protein effector on a target gene by 1.2-fold, 1.5-fold, 2-fold, 5-fold, 10-fold, 20-fold, 50-fold, 100-fold, 200-fold, 500-fold, 1000-fold, 2000-fold, 5000-fold, 10,000-fold, 100,000-fold or more, or any fold change intermediate to these values.

In some embodiments, an "active" cgRNA is said to be "inactivated" by a cognate RNA trigger if the trigger decreases the cgRNA-mediated function of a Cas protein effector on a target gene by 20%, 50%, 90%, 95%, 99%, 99.9%, 99.99%, 99.999%, or 100%, or any percentage intermediate to the stated values. In some embodiments, an "active" cgRNA is said to be "inactivated" by a cognate RNA trigger if the trigger decreases the cgRNA-mediated function of a Cas protein effector on a target gene by 1.5-fold, 2-fold, 5-fold, 10-fold, 20-fold, 50-fold, 100-fold, 200-fold, 500-fold, 1000-fold, 2000-fold, 5000-fold, 10,000-fold, 100,000-fold or more, or any fold change intermediate to these values.

The section headings used herein are for organizational purposes only and are not to be construed as limiting the described subject matter in any way. All literature and similar materials cited in this application, including but not limited to, patents, patent applications, articles, books, treatises, and internet web pages are expressly incorporated by reference in their entirety for any purpose. When definitions of terms in incorporated references appear to differ from the definitions provided in the present teachings, the definition provided in the present teachings shall control. It will be appreciated that there is an implied "about" prior to the temperatures, concentrations, times, etc discussed in the present teachings, such that slight and insubstantial deviations are within the scope of the present teachings herein. In this application, the use of the singular includes the plural unless specifically stated otherwise. Also, the use of "comprise", "comprises", "comprising", "contain", "contains", "containing", "include", "includes", and "including" are not intended to be limiting. It is to be understood that both the foregoing general description and the following detailed description are exemplary and explanatory only and are not restrictive. Unless defined otherwise, technical and scientific terms used herein have the same meaning as commonly understood by one of ordinary skill in the art to which this invention belongs. See, for example Singleton et al., Dictionary of Microbiology and Molecular Biology 2nd ed., J. Wiley & Sons (New York, N.Y. 1994); Sambrook et al., Molecular Cloning, A Laboratory Manual, Cold Springs Harbor Press (Cold Springs Harbor, N.Y. 1989). It is to be understood that both the general description and the detailed description are exemplary and explanatory only and are not restrictive of the invention as claimed. In this application, the use of the singular includes the plural unless specifically stated otherwise. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise. Also, the use of the term "portion" can include part of a moiety or the entire moiety. Also, the term "embodiment" as used herein refers to an aspect or an implementation of what is disclosed herein, and embodiments may be combined with one another.

Allosteric ON→OFF Terminator Switch cgRNAs (Mechanism 1A)

Figure 4B:
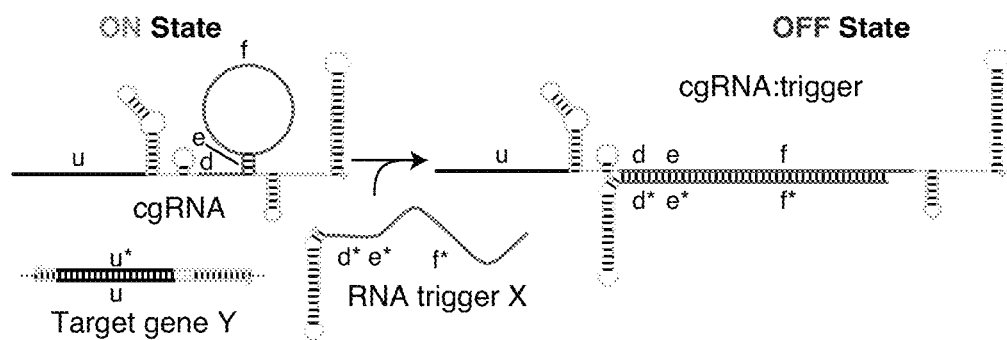
Figure 4C:
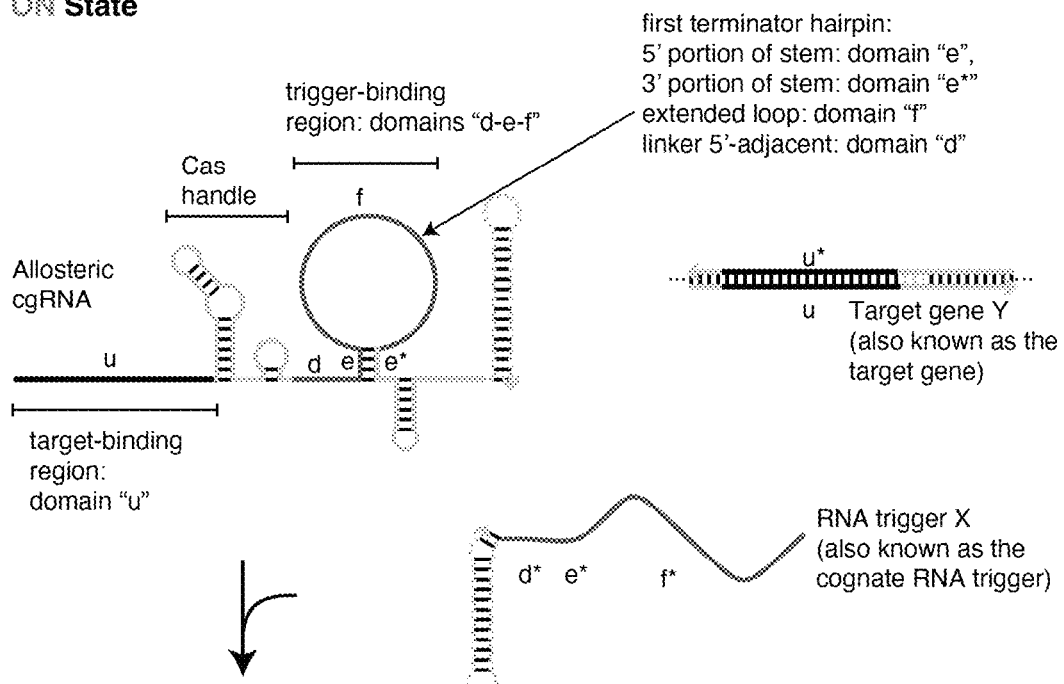
Figure 4C:
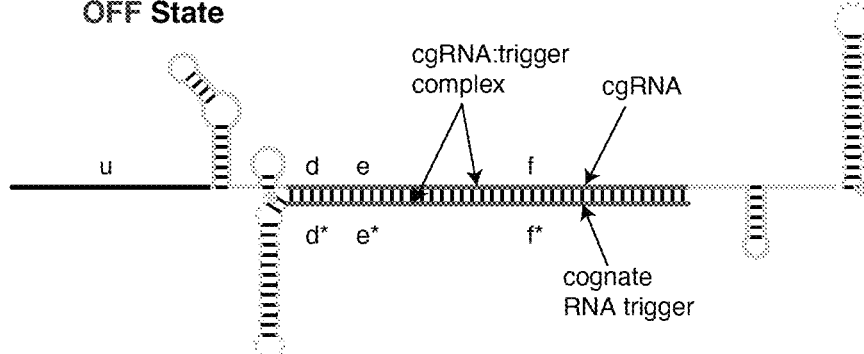
Figure 10A:
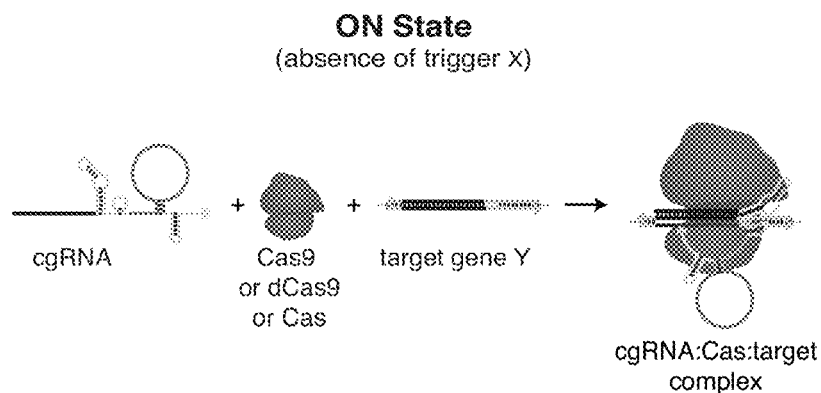
FIGS. 10A-10C depict the interactions between allosteric cgRNAs, triggers, and Cas.
Figure 10A:
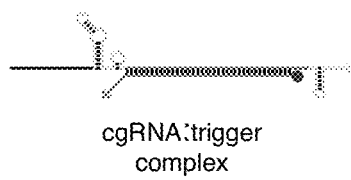

In some embodiments, allosteric ON→OFF cgRNA logic (FIG. 4A) is implemented using an allosteric ON→OFF terminator switch cgRNA mechanism (FIGS. 4B and 4C). The ON→OFF terminator switch cgRNA of FIGS. 4B and 4C is conditionally inactivated by RNA trigger X (the cognate RNA trigger). Compared to a standard gRNA (FIG. 1), in some embodiments the ON→OFF terminator switch cgRNA has a modified terminator region with an extended loop and rationally designed sequence domains "d-e-f". In some embodiments, the cgRNA comprises a target-binding region (domain "u"), a Cas handle, a trigger-binding region (domains "d-e-f"), a first terminator hairpin, and a linker 5'-adjacent to the first terminator hairpin (domain "d"); wherein the first terminator hairpin comprises a 5' portion of the stem (domain "e"), a 3' portion of the stem (domain "e*"), and an extended loop (domain "f"). In some embodiments, to toggle to the OFF state, hybridization of the RNA trigger X (the cognate RNA trigger) to the trigger-binding region of the cgRNA (forming the cgRNA:trigger complex) disrupts the structure of the first terminator hairpin to form a structure incompatible with cgRNA mediation of Cas9, dCas9, and/or Cas function (FIG. 10A). In some embodiments, the mechanism is allosteric because the trigger down-regulates cgRNA:Cas function not by sequestering the target-binding region (domain "u" in FIGS. 4B and 4C), but by hybridizing to the distal trigger-binding region (domains "d-e-f" in FIGS. 4B and 4C). Hence, the sequences of the RNA trigger X and the regulatory target Y (the target gene) are fully independent. In some embodiments, domain "d" in the cgRNA is constrained to a wild-type subsequence of the standard gRNA. In some embodiments, domain "e" in the cgRNA is constrained to a wild-type subsequence of the standard gRNA. In some embodiments, a partial subsequence of domain "f" in the cgRNA is constrained to a wild-type subsequence of the standard gRNA. In some embodiments, domain "d*" in the trigger is optional. In some embodiments, domain "e*" in the trigger is optional. In some embodiments, the extended terminator loop comprises or comprises, consists, or consists essentially of 4 nt, or 5 nt, or 6 nt, or 8 nt, or 10 nt, or 20 nt, or 30 nt, or 40 nt, or 50 nt, or 100 nt, or 200 nt, or more, or any number of nucleotides intermediate to any of the preceding values.

Allosteric OFF→ON Terminator Switch cgRNAs (Mechanism 1B)

Figure 5A:
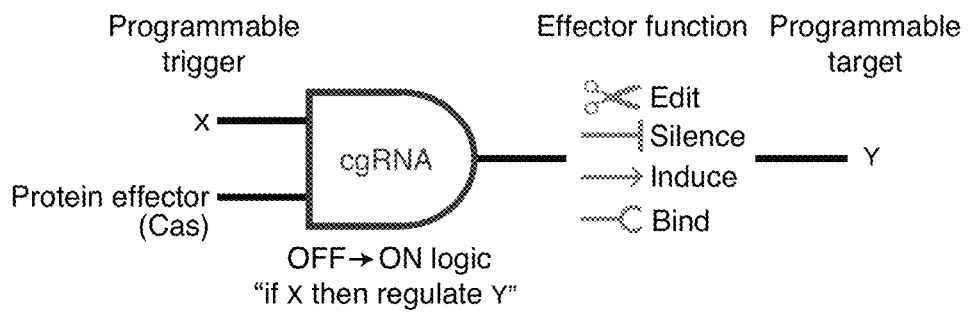
FIGS. 5A-5C depict the logic, function, and mechanism of allosteric OFF→ON terminator switch cgRNAs (Mechanism 1B).
Figure 5B:
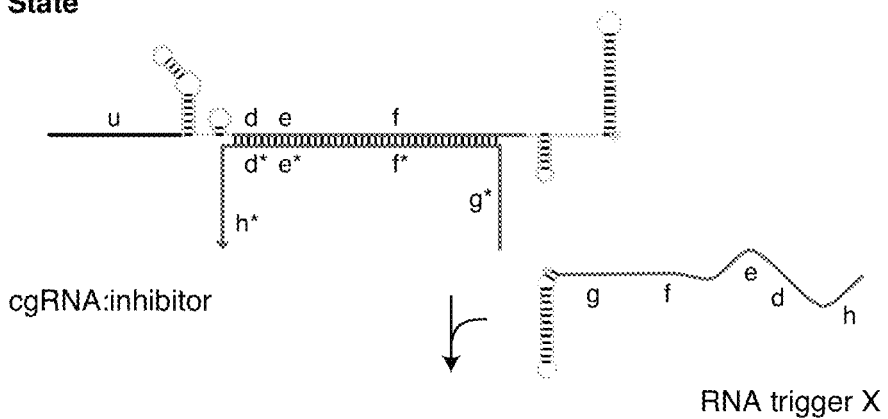
Figure 5B:
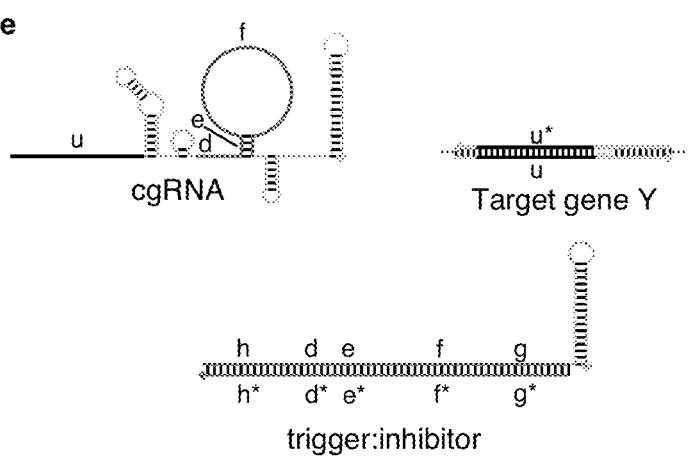
Figure 5C:
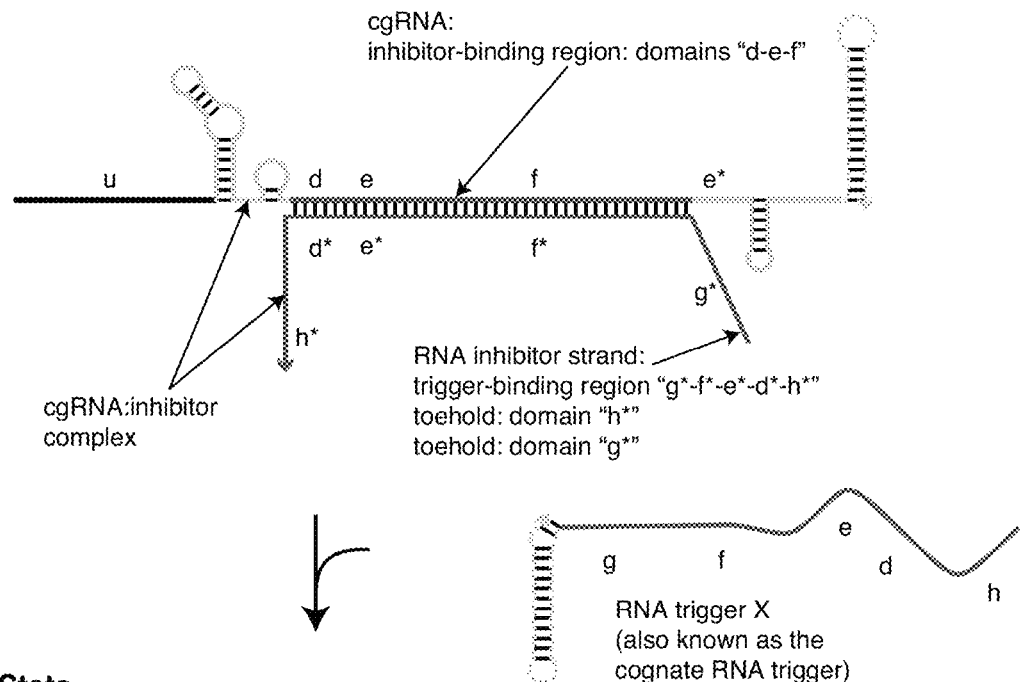
Figure 5C:
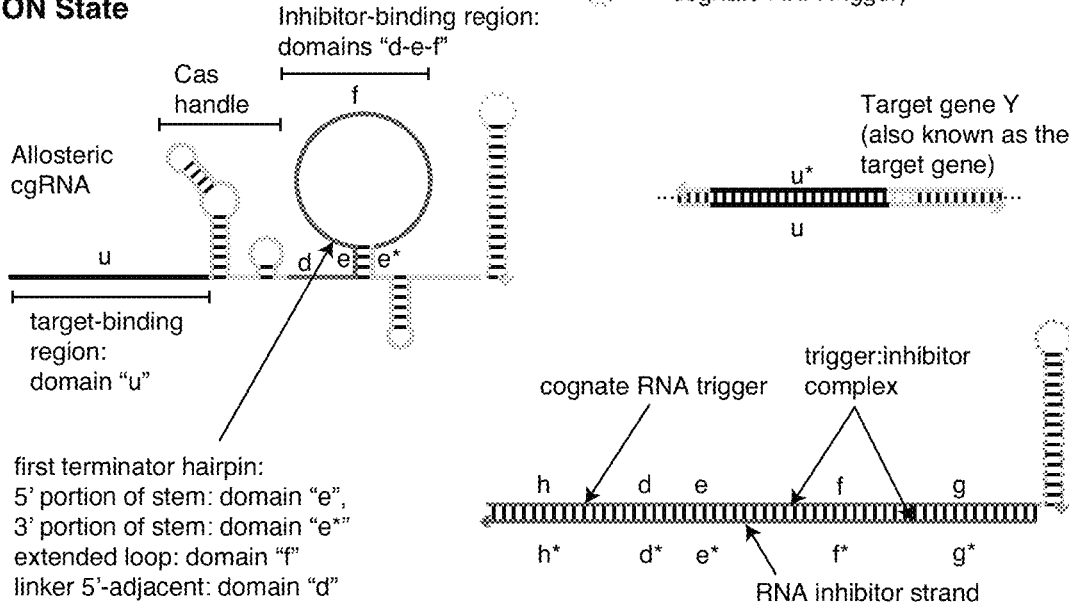

In some embodiments, allosteric OFF→ON cgRNA logic (FIG. 5A) is implemented using an allosteric OFF→ON terminator switch cgRNA mechanism (FIGS. 5B and 5C). The OFF→ON terminator switch cgRNA of FIGS. 5B and 5C is conditionally activated by RNA trigger X (the cognate RNA trigger), which binds to the inhibitor to remove the inhibitor from the cgRNA. Compared to a standard gRNA (FIG. 1), in some embodiments the OFF→ON terminator switch cgRNA has a modified terminator region with an extended loop and rationally designed sequence domains "d-e-f". In some embodiments, the cgRNA comprises a target-binding region (domain "u"), a Cas handle, an inhibitor-binding region (domains "d-e-f"), a first terminator hairpin, and a linker 5'-adjacent to the first terminator hairpin (domain "d"); wherein the first terminator hairpin comprises a 5' portion of the stem (domain "e"), a 3' portion of the stem (domain "e*"), and an extended loop (domain "f"). In some embodiments, the RNA inhibitor strand comprises a trigger-binding region (domains "g*-f*-e*-d*-h*") and a toehold at one or both ends (domains "g*" and/or "h*"). In some embodiments, in the OFF state, the inhibitor is hybridized to the inhibitor-binding region of the cgRNA (forming the cgRNA:inhibitor complex) to disrupt the structure of the first terminator hairpin and form a structure incompatible with cgRNA mediation of Cas9, dCas9, and/or Cas function. In some embodiments, to toggle the cgRNA to the ON state, the RNA trigger X (the cognate RNA trigger) displaces the inhibitor from the cgRNA via toehold-mediated strand displacement in which the trigger first nucleates with the inhibitor by binding to the exposed toehold domain "g*" on the inhibitor, and then hybridizes to domains "f*-e*-d*-h*" to displace the inhibitor from the cgRNA (forming the trigger:inhibitor complex). In some embodiments, to toggle the cgRNA to the ON state, the RNA trigger X (the cognate RNA trigger) displaces the inhibitor from the cgRNA via toehold-mediated strand displacement in which the trigger first nucleates with the inhibitor by binding to the exposed toehold domain "h*" on the inhibitor, and then hybridizes to domains "d*", "e*", "f*", and "g*" to displace the inhibitor from the cgRNA (forming the trigger:inhibitor complex). In some embodiments, domain "g" in the trigger is optional. In some embodiments, domain "g*" in the inhibitor is optional. In some embodiments, domain "h" in the trigger is optional. In some embodiments, domain "h*" in the inhibitor is optional. In some embodiments, the mechanism is allosteric because the inhibitor down-regulates cgRNA:Cas function not by sequestering the target-binding region (domain "u" in FIGS. 5B and 5C), but by hybridizing to the distal terminator region comprising domains "d-e-f" in FIGS. 5B and 5C. As a result, the sequence of the RNA trigger X (which binds to the inhibitor to up-regulate cgRNA:Cas function) is independent of domain "u", yielding full sequence independence between trigger X and regulatory target Y (the target gene). In some embodiments, the extended terminator loop comprises, consists, or consists essentially of 4 nt, or 5 nt, or 6 nt, or 8 nt, or 10 nt, or 20 nt, or 30 nt, or 40 nt, or 50 nt, or 100 nt, or 200 nt, or more, or any number of nucleotides intermediate to any of the preceding values. In some embodiments, a toehold domain comprises, consists, or consists essentially of 4 nt, or 10 nt, or 20 nt, or 30 nt, or 40 nt, or 50 nt, or 100 nt, or 200 nt, or more, or any number of nucleotides intermediate to any of the preceding values.

Allosteric ON→OFF Splinted Switch cgRNAs (Mechanism 2A)

Figure 6A:
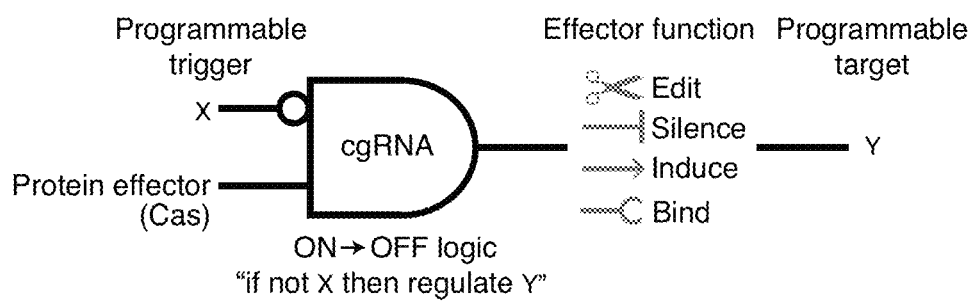
FIGS. 6A-6C depict the logic, function, and mechanism of allosteric ON→OFF splinted switch cgRNAs (Mechanism 2A).
Figure 6B:
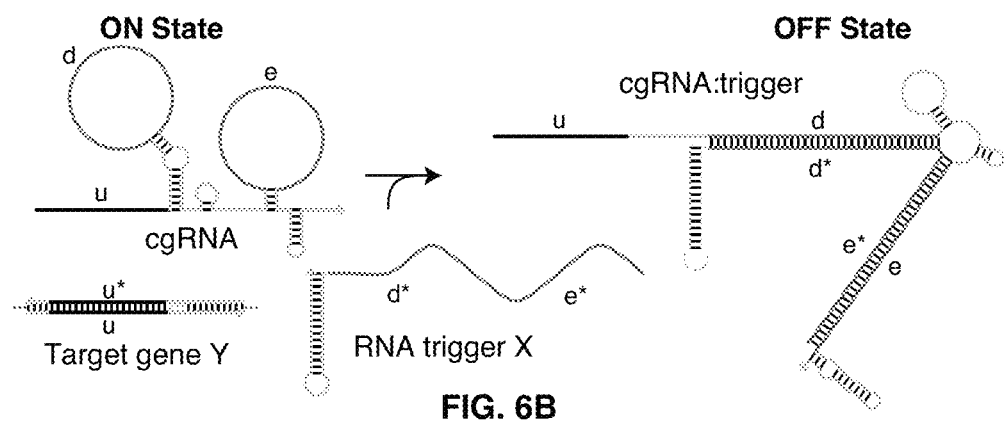
Figure 6C:
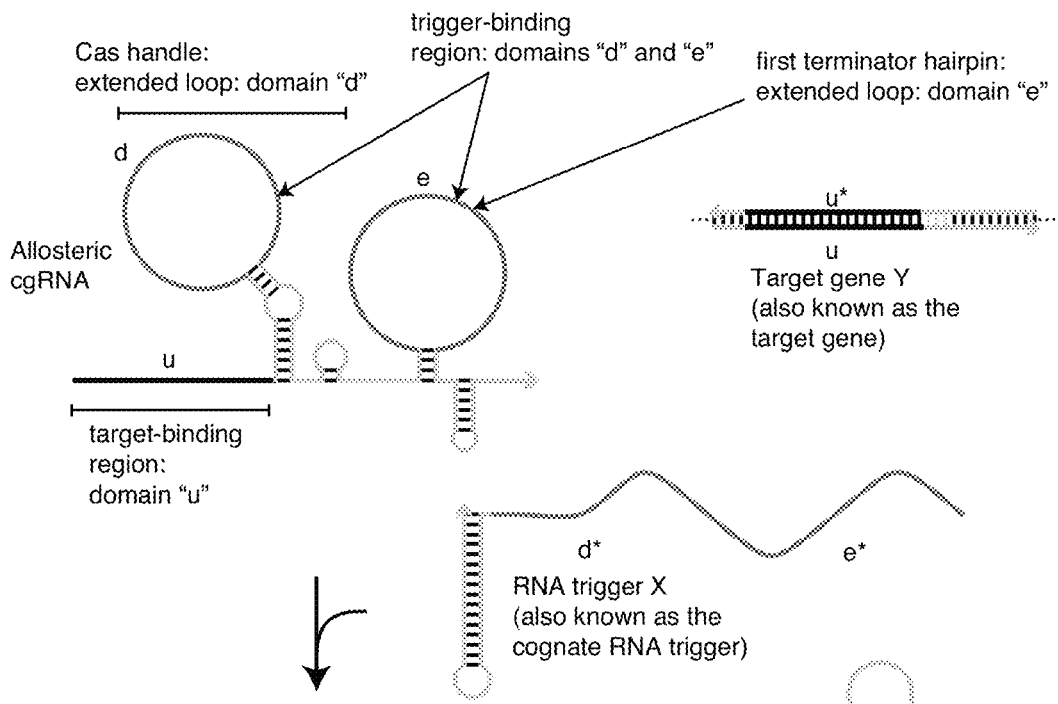
Figure 6C:
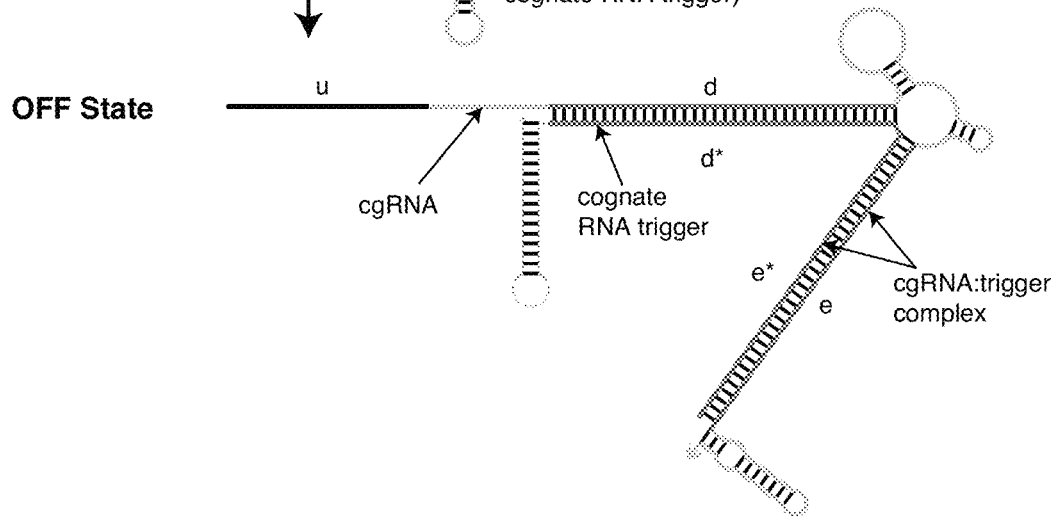
Figure 10B:
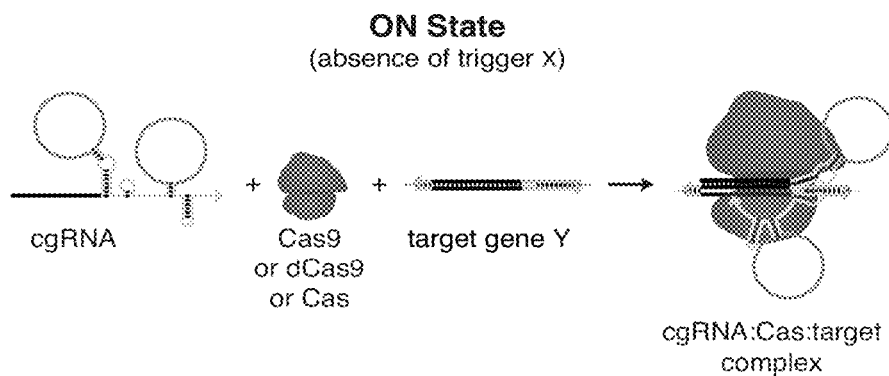
Figure 10B:
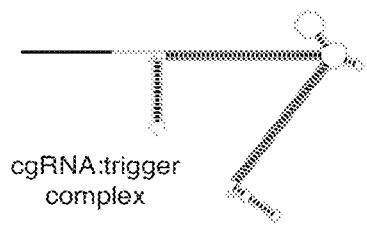

In some embodiments, allosteric ON→OFF cgRNA logic (FIG. 6A) is implemented using an allosteric ON→OFF splinted switch cgRNA mechanism (FIGS. 6B and 6C). The ON→OFF splinted switch cgRNA of FIGS. 6B and 6C is conditionally inactivated by RNA trigger X (the cognate RNA trigger). Compared to a standard gRNA (FIG. 1), in some embodiments the ON→OFF splinted switch cgRNA has extended loops in both the Cas9 handle (domain "d") and terminator (domain "e"). In some embodiments, the cgRNA comprises a target-binding region (domain "u"), a Cas handle with an extended loop (domain "d"), a trigger binding region (domains "d" and "e"), and a first terminator hairpin with an extended loop (domain "e"). In some embodiments, to toggle to the OFF state, hybridization of RNA trigger X (the cognate RNA trigger) to the trigger-binding region of the cgRNA (forming the cgRNA:trigger complex) disrupts the structure of the Cas handle and the first terminator hairpin to form a structure incompatible with cgRNA mediation of Cas9, dCas9, and/or Cas function (FIG. 10B). In some embodiments, the mechanism is allosteric because the trigger down-regulates cgRNA:Cas function by hybridizing to extended loops (domains "d" and "e" in FIGS. 6B and 6C) distal to the target-binding region (domain "u" in FIGS. 6B and 6C). The resulting full sequence independence between RNA trigger X (the cognate RNA trigger) and target gene Y (the target gene) provides the flexibility for X to control regulatory scope (also known as the scope of activity) independent of the choice of Y. In some embodiments, the extended Cas handle comprises, consists, or consists essentially of 4 nt, or 5 nt, or 6 nt, or 8 nt, or 10 nt, or 20 nt, or 30 nt, or 40 nt, or 50 nt, or 100 nt, or 200 nt, or more, or any number of nucleotides intermediate to any of the preceding values. In some embodiments, the extended terminator loop comprises, consists, or consists essentially of 4 nt, or 5 nt, or 6 nt, or 8 nt, or 10 nt, or 20 nt, or 30 nt, or 40 nt, or 50 nt, or 100 nt, or 200 nt, or more, or any number of nucleotides intermediate to any of the preceding values.

Allosteric OFF→ON Splinted Switch cgRNAs (Mechanism 2B)

Figure 7A:
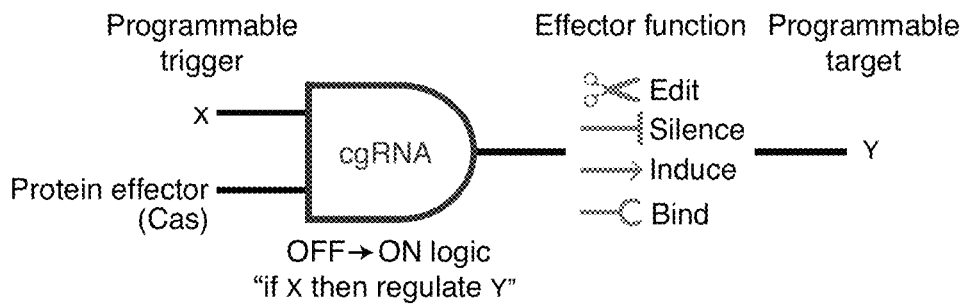
FIGS. 7A-7C depict the logic, function, and mechanism of allosteric OFF→ON splinted switch cgRNAs (Mechanism 2B).
Figure 7B:
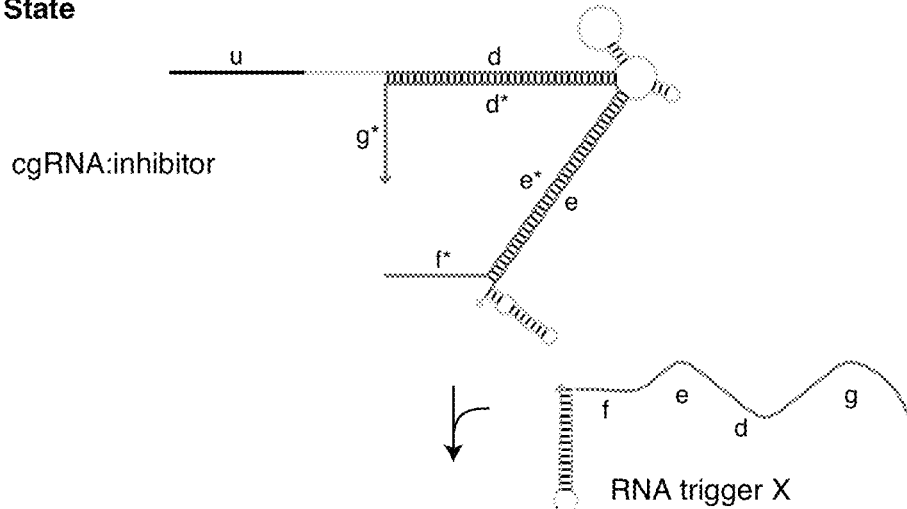
Figure 7B:
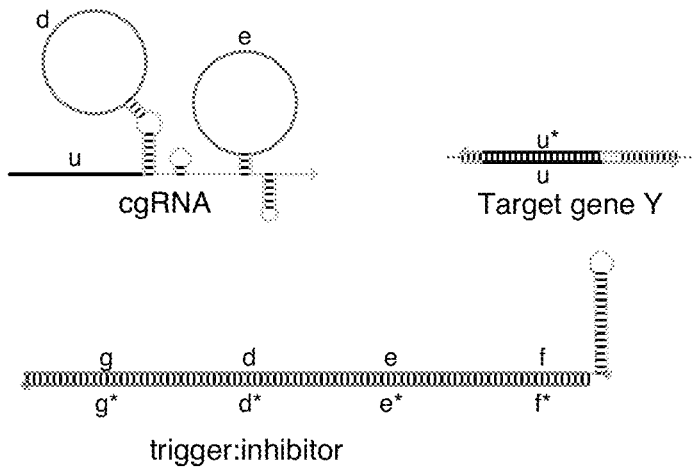
Figure 7C:
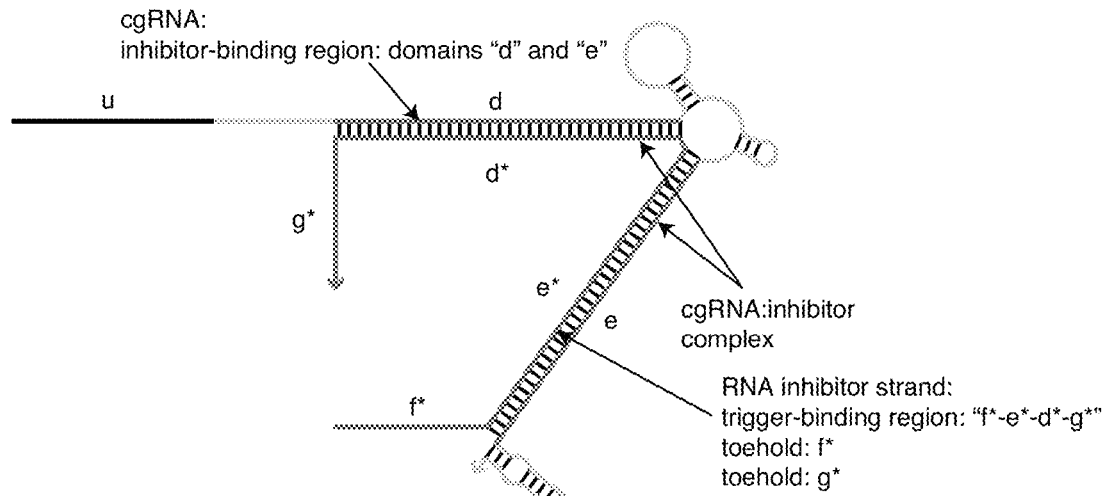
Figure 7C:
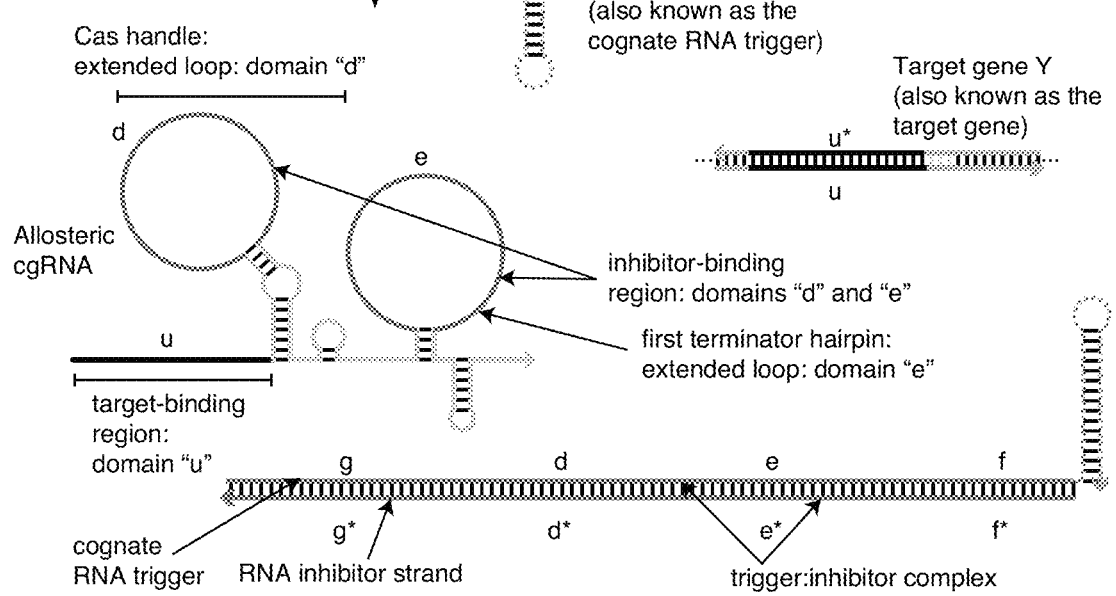

In some embodiments, allosteric OFF→ON cgRNA logic (FIG. 7A) is implemented using an allosteric OFF→ON splinted switch cgRNA mechanism (FIGS. 7B and 7C). The OFF→ON splinted switch cgRNA of FIGS. 7B and 7C is conditionally activated by RNA trigger X (the cognate RNA trigger), which binds to the inhibitor to remove the inhibitor from the cgRNA. Compared to a standard gRNA (FIG. 1), in some embodiments, the OFF→ON splinted switch cgRNA has extended loops in both the Cas9 handle (domain "d") and terminator (domain "e"). In some embodiments, the cgRNA comprises a target-binding region (domain "u"), a Cas handle with an extended loop (domain "d"), an inhibitor-binding region (domains "d" and "e"), and a first terminator hairpin with an extended loop (domain "e"). In some embodiments, the RNA inhibitor strand comprises a trigger-binding region (domains "f*-e*-d*-g*") and a toehold at one or both ends (domains "f*" and/or "g*"). In some embodiments, in the OFF state, the inhibitor is hybridized to the inhibitor-binding region of the cgRNA (forming the cgRNA:inhibitor complex) to disrupt the structure of the Cas handle and the first terminator hairpin and form a structure incompatible with cgRNA mediation of Cas9, dCas9, and/or Cas function. In some embodiments, to toggle the cgRNA to the ON state, the RNA trigger X (the cognate RNA trigger) displaces the inhibitor from the cgRNA via toehold-mediated strand displacement in which the trigger first nucleates with the inhibitor by binding to the exposed toehold domain "f*" on the inhibitor, and then hybridizes to domains "e*-d*-g*" to displace the inhibitor from the cgRNA (forming the trigger:inhibitor complex). In some embodiments, to toggle the cgRNA to the ON state, the RNA trigger X (the cognate RNA trigger) displaces the inhibitor from the cgRNA via toehold-mediated strand displacement in which the trigger first nucleates with the inhibitor by binding to the exposed toehold domain "g*" on the inhibitor, and then hybridizes to domains "d*", "e*" and "f*" to displace the inhibitor from the cgRNA (forming the trigger:inhibitor complex). In some embodiments, domain "f" in the trigger is optional. In some embodiments, domain "f*" in the inhibitor is optional. In some embodiments, domain "g" in the trigger is optional. In some embodiments, domain "g*" in the inhibitor is optional. In some embodiments, the mechanism is allosteric because the inhibitor down-regulates cgRNA:Cas function by hybridizing to extended loops (domains "d" and "e" in FIGS. 7B and 7C) distal to the target-binding region (domain "u" in FIGS. 7B and 7C). As a result, the sequence of the RNA trigger X (which binds to the inhibitor to up-regulate cgRNA:Cas function) is independent of domain "u", yielding full sequence independence between trigger X (the cognate RNA trigger) and regulatory target Y (the target gene). In some embodiments, the extended Cas handle comprises, consists, or consists essentially of 4 nt, or 5 nt, or 6 nt, or 8 nt, or 10 nt, or 20 nt, or 30 nt, or 40 nt, or 50 nt, or 100 nt, or 200 nt, or more, or any number of nucleotides intermediate to any of the preceding values. In some embodiments, the extended terminator loop comprises, consists, or consists essentially of 4 nt, or 5 nt, or 6 nt, or 8 nt, or 10 nt, or 20 nt, or 30 nt, or 40 nt, or 50 nt, or 100 nt, or 200 nt, or more, or any number of nucleotides intermediate to any of the preceding values. In some embodiments, a toehold domain comprises, consists, or consists essentially of 4 nt, or 10 nt, or 20 nt, or 30 nt, or 40 nt, or 50 nt, or 100 nt, or 200 nt, or more, or any number of nucleotides intermediate to any of the preceding values.

Allosteric ON→OFF Tandem Switch cgRNAs (Mechanism 3A)

Figure 23A:
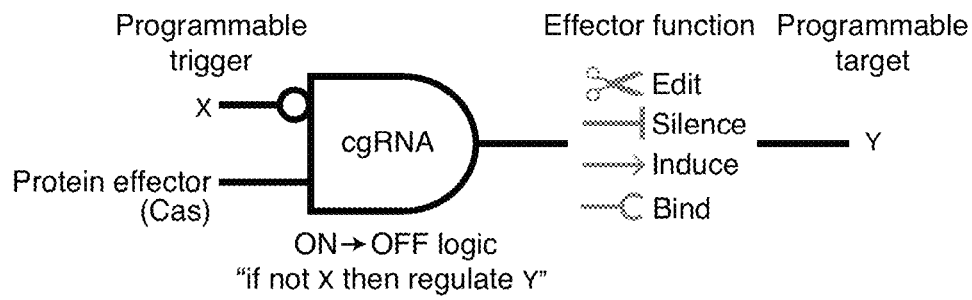
FIGS. 23A-23C depict the logic, function, and mechanism of allosteric ON→OFF tandem switch cgRNAs (Mechanism 3A).
Figure 23B:
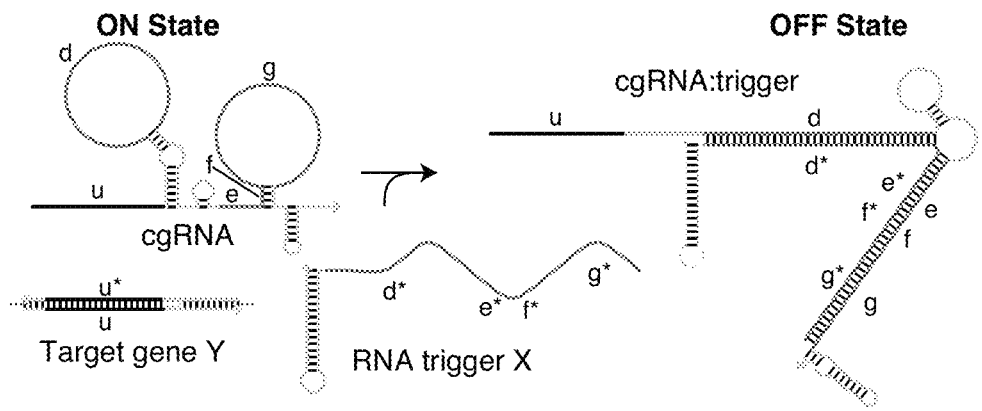
Figure 23C:
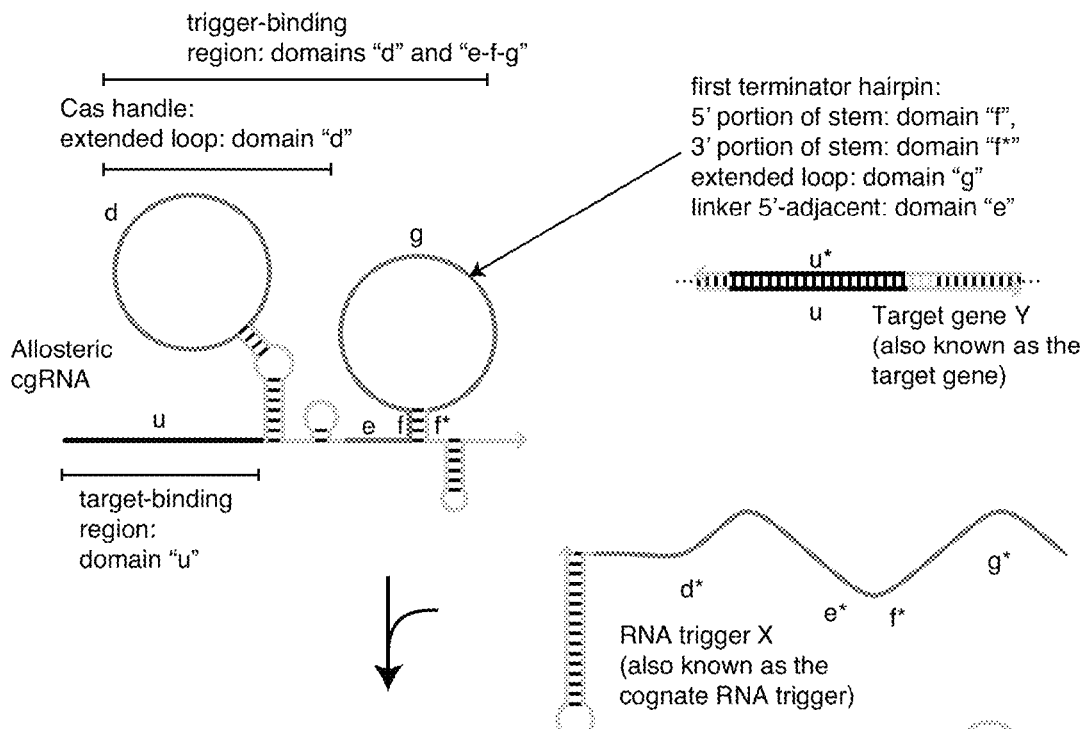
Figure 23C:
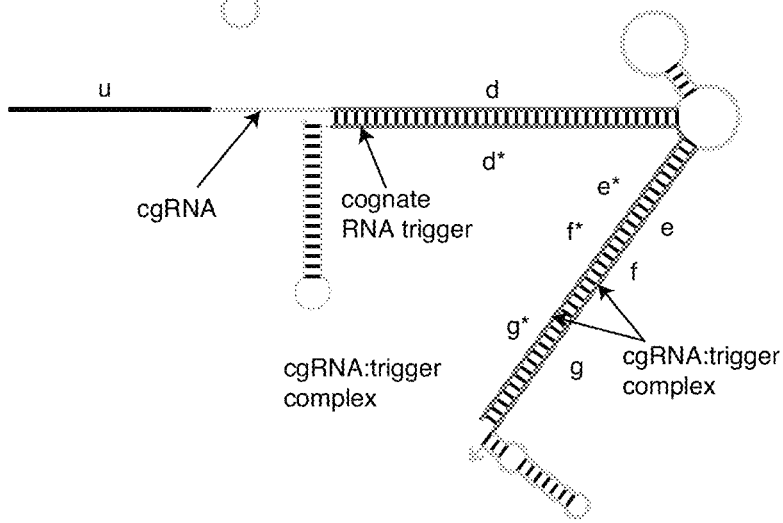

In some embodiments, allosteric ON→OFF cgRNA logic (FIG. 23A) is implemented using an allosteric ON→OFF tandem switch cgRNA mechanism (FIGS. 23B and 23C). The ON→OFF terminator switch cgRNA of FIGS. 23B and 23C is conditionally inactivated by RNA trigger X (the cognate RNA trigger). Compared to a standard gRNA (FIG. 1), in some embodiments the ON→OFF tandem switch cgRNA has an extended loop in the Cas9 handle (domain "d") and a modified terminator region with an extended loop and rationally designed sequence domains "e-f-g". In some embodiments, the cgRNA comprises a target-binding region (domain "u"), a Cas handle with an extended loop (domain "d"), a trigger-binding region (domain "d" and "e-f-g"), a first terminator hairpin, and a linker 5'-adjacent to the first terminator hairpin (domain "e"); wherein the first terminator hairpin comprises a 5' portion of the stem (domain "f"), a 3' portion of the stem (domain "f*"), and an extended loop (domain "g"). In some embodiments, to toggle to the OFF state, hybridization of the RNA trigger X (the cognate RNA trigger) to the trigger-binding region of the cgRNA (forming the cgRNA:trigger complex) disrupts the structure of the Cas handle and the first terminator hairpin to form a structure incompatible with cgRNA mediation of Cas9, dCas9, and/or Cas function. In some embodiments, the mechanism is allosteric because the trigger down-regulates cgRNA:Cas function not by sequestering the target-binding region (domain "u" in FIGS. 23B and 23C), but by hybridizing to the distal trigger-binding region (domain "d" and domains "e-f-g" in FIGS. 23B and 23C). Hence, the sequences of the RNA trigger X (the cognate RNA trigger) and the regulatory target Y (the target gene) are fully independent. In some embodiments, domain "e" in the cgRNA is constrained to a wild-type subsequence of the standard gRNA. In some embodiments, domain "f" in the cgRNA is constrained to a wild-type subsequence of the standard gRNA. In some embodiments, a partial subsequence of domain "g" in the cgRNA is constrained to a wild-type subsequence of the standard gRNA. In some embodiments, a partial subsequence of domain "d" in the cgRNA is constrained to a wild-type subsequence of the standard gRNA. In some embodiments, domain "e*" in the trigger is optional. In some embodiments, domain "f*" in the trigger is optional. In some embodiments, the extended Cas handle comprises, consists, or consists essentially of 4 nt, or 5 nt, or 6 nt, or 8 nt, or 10 nt, or 20 nt, or 30 nt, or 40 nt, or 50 nt, or 100 nt, or 200 nt, or more, or any number of nucleotides intermediate to any of the preceding values. In some embodiments, the extended terminator loop comprises, consists, or consists essentially of 4 nt, or 5 nt, or 6 nt, or 8 nt, or 10 nt, or 20 nt, or 30 nt, or 40 nt, or 50 nt, or 100 nt, or 200 nt, or more, or any number of nucleotides intermediate to any of the preceding values.

Allosteric OFF→ON Tandem Switch cgRNAs (Mechanism 3B)

Figure 24A:
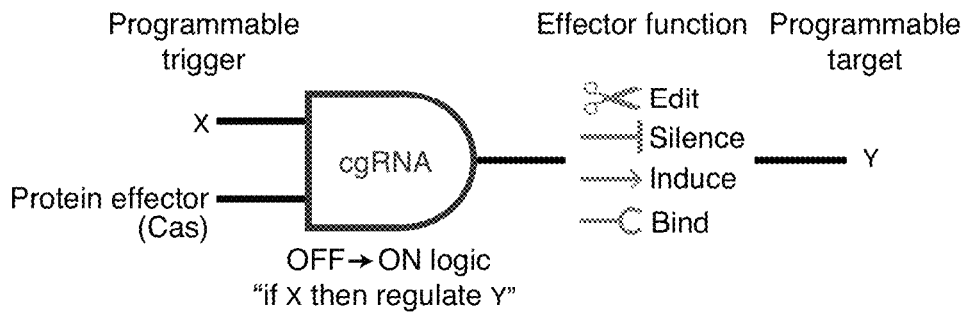
FIGS. 24A-24C depict the logic, function, and mechanism of allosteric OFF→ON tandem switch cgRNAs (Mechanism 3B).
Figure 24B:
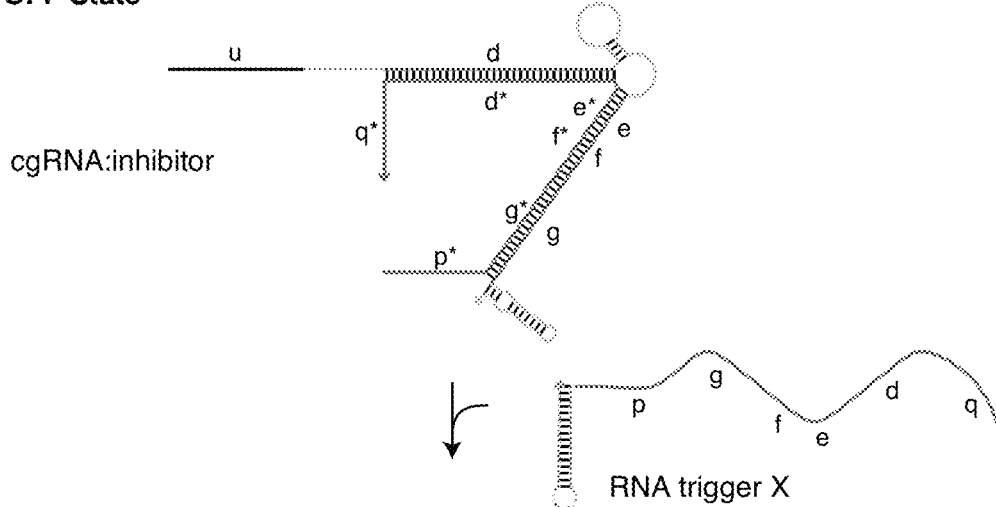
Figure 24B:
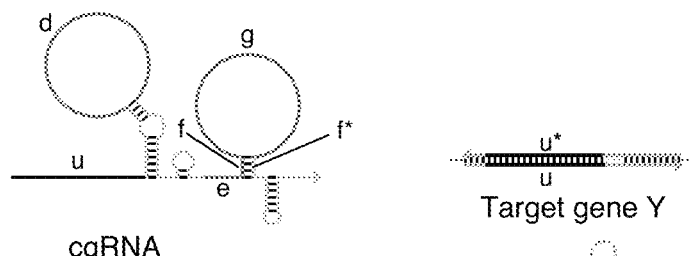
Figure 24B:
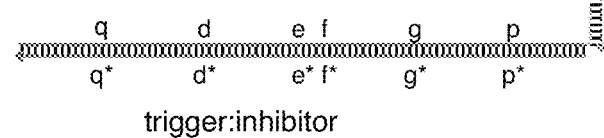
Figure 24C:
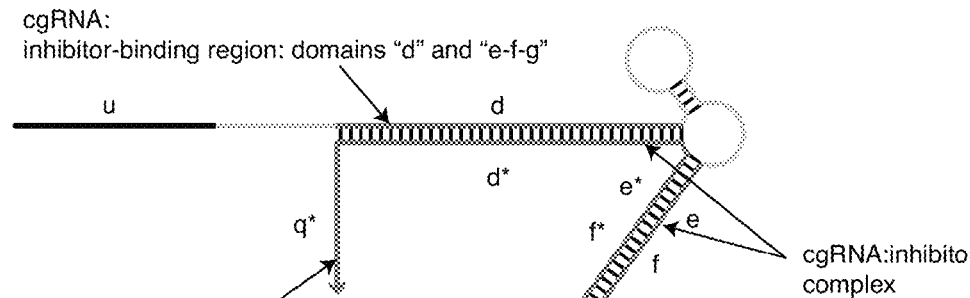
Figure 24C:
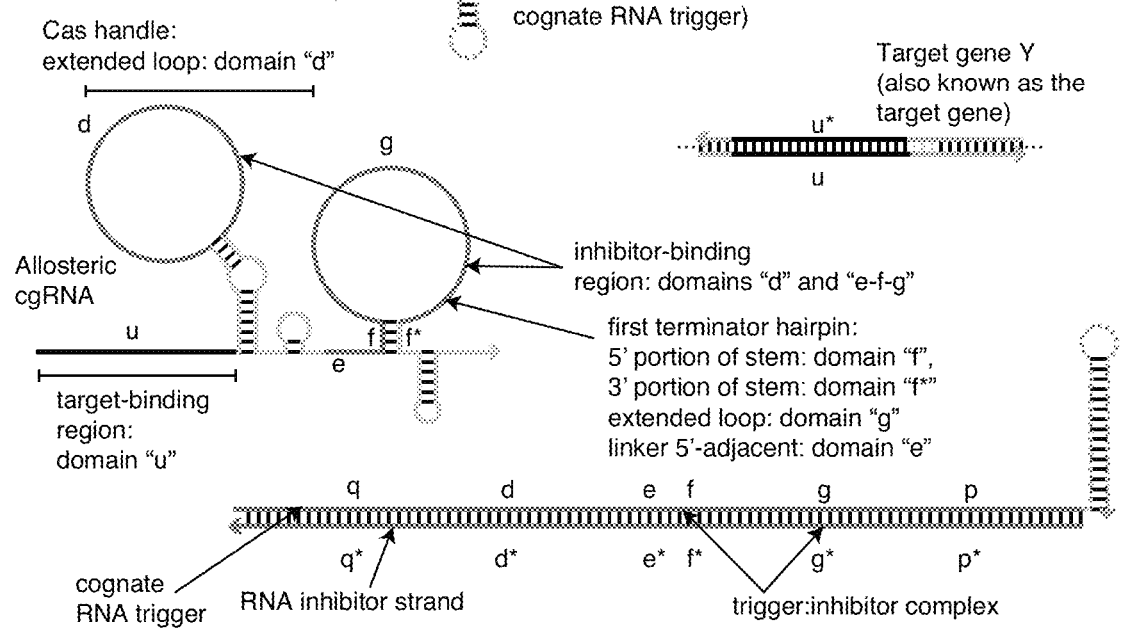

In some embodiments, allosteric OFF→ON cgRNA logic (FIG. 24A) is implemented using an allosteric OFF→ON tandem switch cgRNA mechanism (FIGS. 24B and 24C). The OFF→ON tandem switch cgRNA of FIGS. 24B and 24C is conditionally activated by RNA trigger X (the cognate RNA trigger), which binds to the inhibitor to remove the inhibitor from the cgRNA. Compared to a standard gRNA (FIG. 1), in some embodiments the OFF→ON tandem switch cgRNA has an extended loop in the Cas9 handle (domain "d") and a modified terminator region with an extended loop and rationally designed sequence domains "e-f-g". In some embodiments, the cgRNA comprises a target-binding region (domain "u"), a Cas handle with an extended loop (domain "d"), an inhibitor-binding region (domains "d" and "e-f-g"), a first terminator hairpin, and a linker 5'-adjacent to the first terminator hairpin (domain "e"); wherein the first terminator hairpin comprises a 5' portion of the stem (domain "f"), a 3' portion of the stem (domain "f*"), and an extended loop (domain "g"). In some embodiments, the RNA inhibitor strand comprises a trigger-binding region (domains "p*-g*-f*-e*-d*-q*") with a toehold at one or both ends (domains "p*" and/or "q*"). In the OFF state, the inhibitor is hybridized to the inhibitor-binding region of the cgRNA (forming the cgRNA:inhibitor complex) to disrupt the structure of the Cas handle and the first terminator hairpin and form a structure incompatible with cgRNA mediation of Cas9, dCas9, and/or Cas function. In some embodiments, to toggle the cgRNA to the ON state, the RNA trigger X (the cognate RNA trigger) displaces the inhibitor from the cgRNA via toehold-mediated strand displacement in which the trigger first nucleates with the inhibitor by binding to the exposed toehold domain "p*" on the inhibitor, and then hybridizes to domains "g*-f*-e*-d*-q*" to displace the inhibitor from the cgRNA (forming the trigger:inhibitor complex). In some embodiments, to toggle the cgRNA to the ON state, the RNA trigger X (the cognate RNA trigger) displaces the inhibitor from the cgRNA via toehold-mediated strand displacement in which the trigger first nucleates with the inhibitor by binding to the exposed toehold domain "q*" on the inhibitor, and then hybridizes to domains "d*", "e*", "f*", "g*", and "p*" to displace the inhibitor from the cgRNA (forming the trigger:inhibitor complex). In some embodiments, domain "p" in the trigger is optional. In some embodiments, domain "p*" in the inhibitor is optional. In some embodiments, domain "q" in the trigger is optional. In some embodiments, domain "q*" in the inhibitor is optional. In some embodiments, the mechanism is allosteric because the inhibitor down-regulates cgRNA:Cas function not by sequestering the target-binding region (domain "u" in FIGS. 24B and 24C), but by hybridizing to the distal terminator region comprising domains "d" and "e-f-g" in FIGS. 24B and 24C. As a result, the sequence of the RNA trigger X (which binds to the inhibitor to up-regulate cgRNA:Cas function) is independent of domain "u", yielding full sequence independence between trigger X (the cognate RNA trigger) and regulatory target Y (the target gene). In some embodiments, the extended Cas handle comprises, consists, or consists essentially of 4 nt, or 5 nt, or 6 nt, or 8 nt, or 10 nt, or 20 nt, or 30 nt, or 40 nt, or 50 nt, or 100 nt, or 200 nt, or more, or any number of nucleotides intermediate to any of the preceding values. In some embodiments, the extended terminator loop comprises, consists, or consists essentially of 4 nt, or 5 nt, or 6 nt, or 8 nt, or 10 nt, or 20 nt, or 30 nt, or 40 nt, or 50 nt, or 100 nt, or 200 nt, or more, or any number of nucleotides intermediate to any of the preceding values. In some embodiments, a toehold domain comprises, consists, or consists essentially of 4 nt, or 10 nt, or 20 nt, or 30 nt, or 40 nt, or 50 nt, or 100 nt, or 200 nt, or more, or any number of nucleotides intermediate to any of the preceding values.

Allosteric OFF→ON Split-Terminator Switch cgRNAs (Mechanism 4A)

Figure 8A:
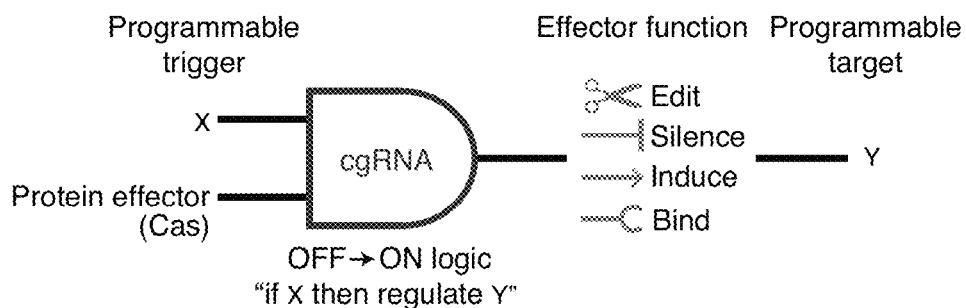
FIGS. 8A-8C depict the logic, function, and mechanism of allosteric OFF→ON split-terminator switch cgRNAs (Mechanism 4A).
Figure 8B:
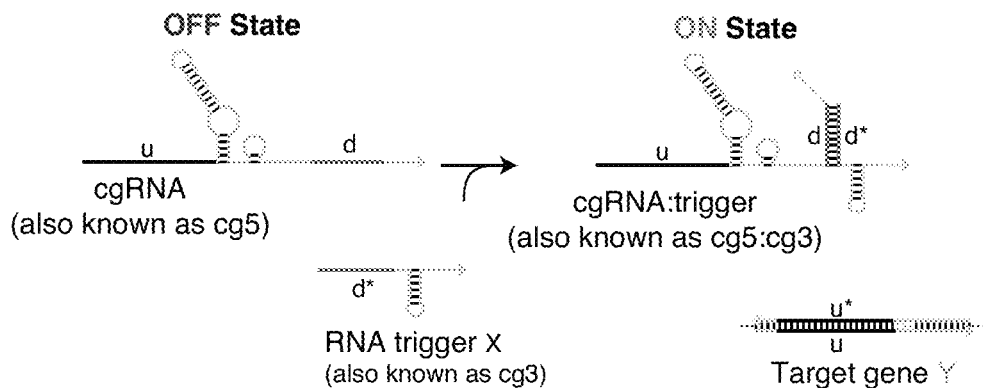
Figure 8C:
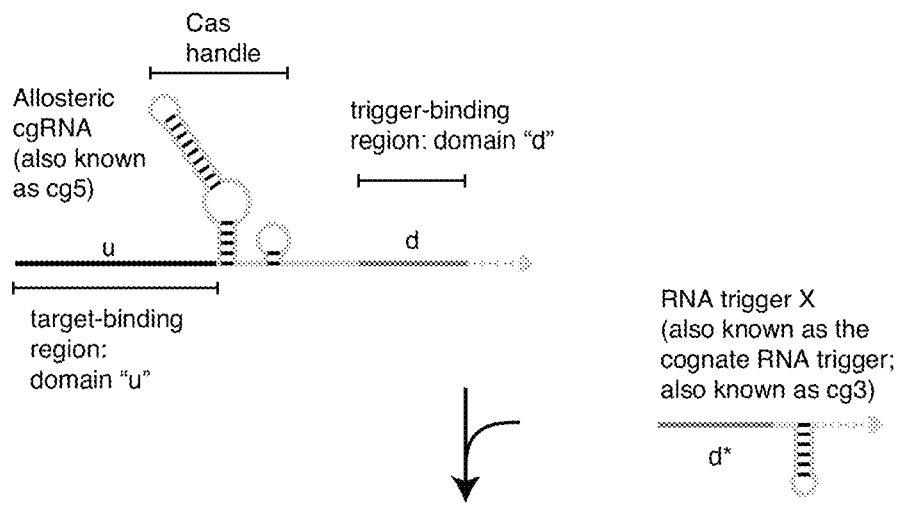
Figure 8C:
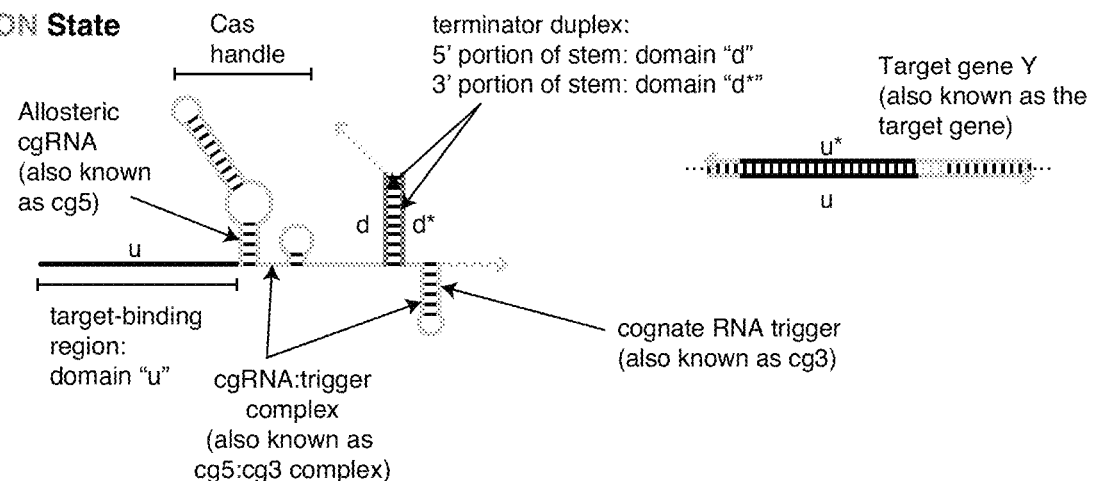
Figure 10C:
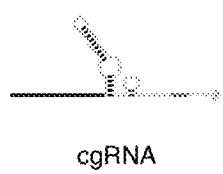
Figure 10C:
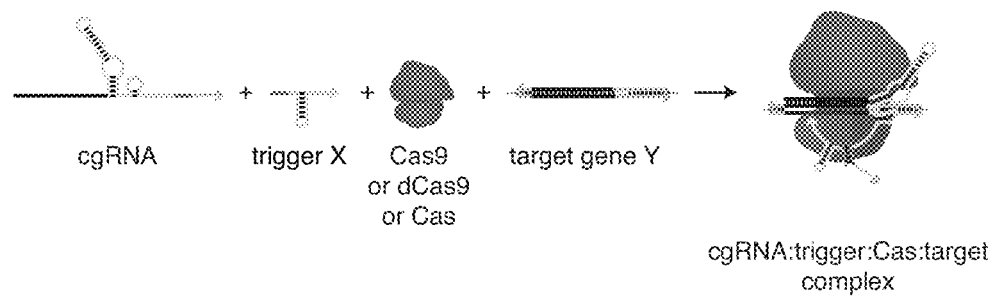

In some embodiments, allosteric OFF→ON cgRNA logic (FIG. 8A) is implemented using an allosteric OFF→ON split-terminator switch cgRNA mechanism (FIGS. 8B and 8C). The OFF→ON split-terminator switch cgRNA of FIGS. 8B and 8C is conditionally activated by RNA trigger X (the cognate RNA trigger). Equivalently, the cgRNA may be interpreted as a 5' fragment (cg5) and the trigger may be interpreted as a 3' fragment (cg3), such that cg5 and cg3 are inactive when not bound to each other, but such that upon binding to each other to form the complex cg5:cg3, this complex constitutes an activated conditional guide RNA capable of mediating Cas9, dCas9, and/or Cas function. Compared to a standard gRNA (FIG. 1), in some embodiments the OFF→ON split-terminator switch cgRNA (also known as cg5) is incomplete, containing only one half of the stem region of the 5' terminator hairpin (sequence domain "d"). In some embodiments, the cgRNA (also known as cg5) comprises a target-binding region (domain "u"), a Cas handle, and a trigger-binding region (domain "d"). In some embodiments, to toggle to the ON state, hybridization of the RNA trigger X (the cognate RNA trigger; also known as cg3) to the trigger-binding region of the cgRNA (also known as cg5) to form the cgRNA:trigger complex (also known as the cg5:cg3 complex) yields a terminator duplex that activates the cgRNA (or equivalently yields a terminator duplex that activates the complex cg5:cg3), allowing for mediation of Cas function (FIG. 10C). In some embodiments, the terminator duplex comprises a 5' portion of the stem (domain "d") and a 3' portion of the stem (domain "d*"). In some embodiments, the mechanism is allosteric because the trigger (also known as cg3) and cgRNA (also known as cg5) interact via a terminator duplex (domains "d" and "d*" in FIGS. 8B and 8C) distal to the target-binding region (domain "u" in FIGS. 8B and 8C). The resulting full sequence independence between RNA trigger X (the cognate RNA trigger; also known as cg3) and target gene Y (the target gene) provides the flexibility for X to control regulatory scope (also known as the scope of activity) independent of the choice of Y. In some embodiments, the terminator duplex comprises, consists, or consists essentially of 2 bp, or 4 bp, or 6 bp, or 8 bp, or 10 bp, or 20 bp, or 30 bp, or 40 bp, or 50 bp, or 100 bp, or 200 bp, or more, or any number of base pairs intermediate to any of the preceding values.

In some embodiments, the cgRNA (also known as cg5) comprises one or more substrate domains 5'-adjacent to domain "d" and the cognate RNA trigger (also known as cg3) comprises one or more substrate domains 5'-adjacent to domain "d*". In some embodiments, an additional bridge strand hybridizes to a substrate on the cgRNA (also known as cg5) and to a substrate on the helper strand (also known as cg3) for the purpose of holding the cgRNA (also known as cg5) and helper strand (also known as cg3) together in a complex (cg5:cg3:bridge). In some embodiments, an inhibitor strand hybridizes to one or more substrates on the cgRNA (also known as cg5) and one or more substrates on the cognate RNA trigger (also known as cg3) so as to form a junction that disrupts the structure of the terminator duplex, wherein the structure of the cgRNA:trigger:inhibitor complex (also known as the cg5:cg3:inhibitor complex) is incompatible with mediation of Cas9, dCas9, and/or Cas function. In some embodiments, the cgRNA (also known as cg5) can be activated (OFF→ON logic) by the trigger (also known as cg3) and then later inactivated by the inhibitor (ON→OFF logic) corresponding overall to (OFF→ON→OFF) logic. In some embodiments, a cgRNA can be activated and then subsequently inactivated. In some embodiments, the activity of a cgRNA can be repeatedly toggled between the OFF and ON states by successive interactions with a first trigger, a first inhibitor, a second trigger, a second inhibitor, and so on.

Allosteric ON→OFF Split-Terminator Switch cgRNAs (Mechanism 4B)

Figure 9A:
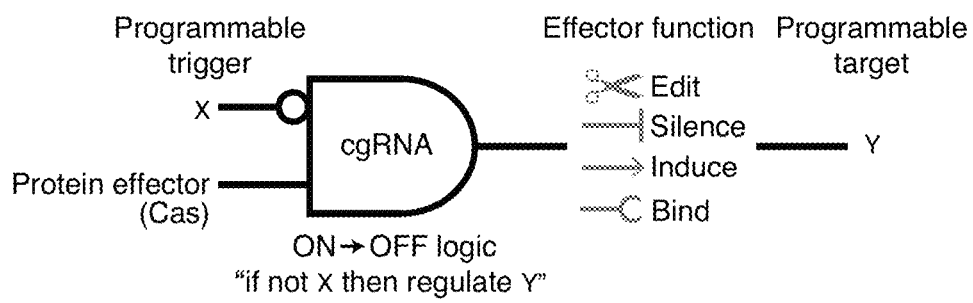
FIGS. 9A-9E depict the logic, function, and mechanism of allosteric ON→OFF split-terminator switch cgRNAs (Mechanisms 4B and 4C).
Figure 9B:
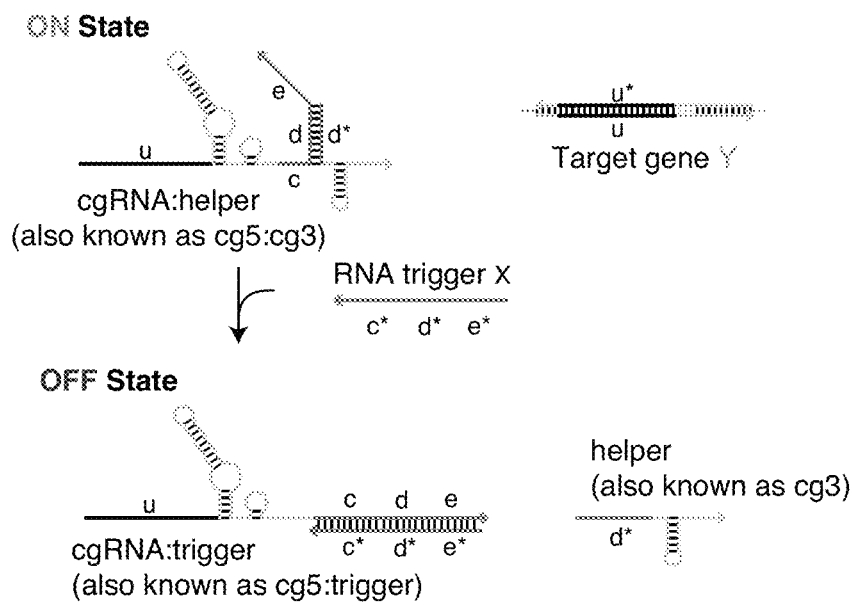
Figure 9C:
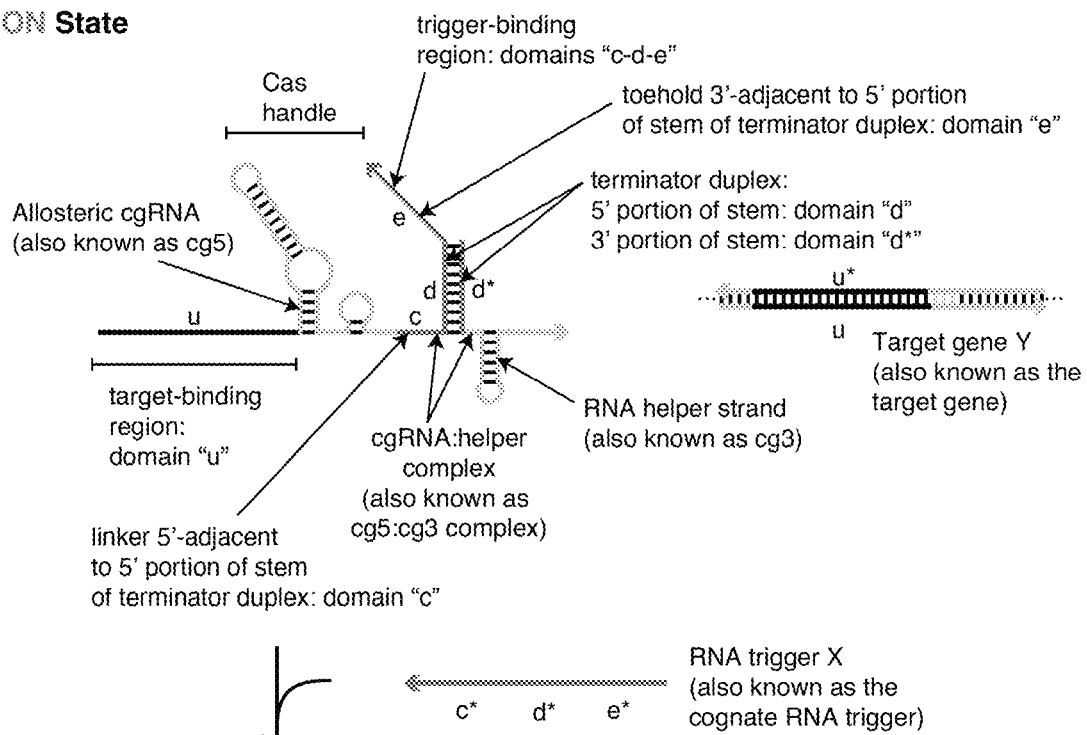
Figure 9C:
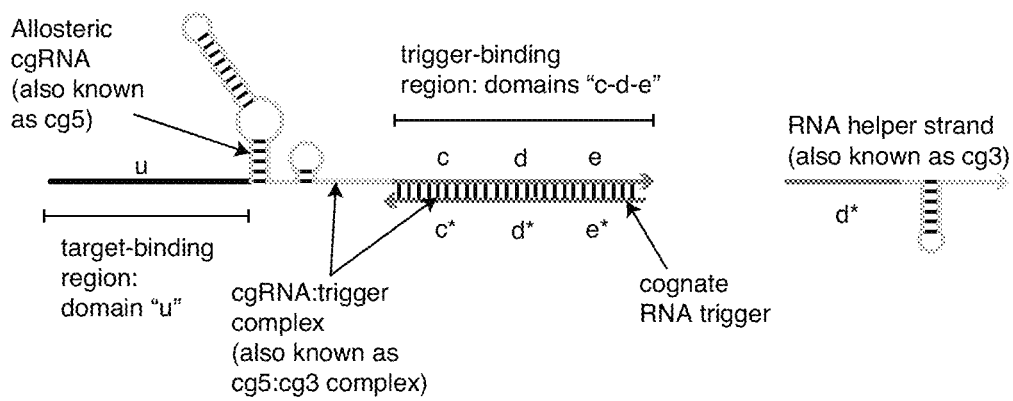

In some embodiments, allosteric ON→OFF cgRNA logic (FIG. 9A) is implemented using an allosteric ON→OFF split-terminator switch cgRNA mechanism (FIGS. 9B and 9C). In some embodiments, the ON→OFF split-terminator switch cgRNA (also known as cg5) of FIGS. 9B and 9C is conditionally inactivated by RNA trigger X (cognate RNA trigger), which binds to the cgRNA to displace the RNA helper strand (also known as cg3) and form a structure incompatible with cgRNA mediation of Cas9, dCas9, and/or Cas function. Equivalently, in some embodiments, the functional conditional guide RNA can be interpreted as a complex of two fragments (complex cg5:cg3 comprising 5'-fragment cg5 and 3'-fragment cg3; FIGS. 9B and 9C) that is conditionally inactivated by RNA trigger X (cognate RNA trigger), which binds to the complex to displace cg3 and form complex cg5:trigger, wherein both cg5:trigger and cg3 are structurally incompatible with mediation of Cas9, dCas9, and/or Cas function. Compared to a standard gRNA (FIG. 1), in some embodiments the ON→OFF split-terminator switch cgRNA (also known as cg5) is incomplete, containing only one half of the stem region of the 5' terminator hairpin (sequence domain "d"). In some embodiments, in the ON state, hybridization of the RNA helper strand (also known as cg3) to domain "d" forms a terminator duplex (domain "d" base-paired to domain "d*") such that the cgRNA:helper complex (also known as the cg5:cg3 complex) is active. In some embodiments, the cgRNA (also known as cg5) comprises a target-binding region (domain "u"), a Cas handle, and a trigger-binding region (domains "c-d-e"); wherein the trigger-binding region comprises a 5' portion of the stem of the terminator duplex (domain "d"), a linker 5'-adjacent to the 5' portion of the stem of the terminator duplex (domain "c"), and a toehold 3'-adjacent to the 5' portion of the stem of the terminator duplex (domain "e"). In some embodiments, the RNA helper strand (also known as cg3) comprises a 3' portion of the stem of the terminator duplex (domain "d*"). In some embodiments, to toggle the cgRNA (also known as cg5) to the OFF state, the RNA trigger X (cognate RNA trigger) displaces the helper (also known as cg3) from the cgRNA (also known as cg5) via toehold-mediated strand displacement in which the trigger first nucleates with the cgRNA (also known as cg5) by binding to the exposed toehold domain "e" on the cgRNA, and then hybridizes to domains "d" and "c" to displace the helper (also known as cg3) from the cgRNA (forming the cgRNA:trigger complex; also known as the cg5:trigger complex), yielding a structure with a disrupted linker (domain "c") and lacking the remainder of the terminator region present in the RNA helper strand (also known as cg3), wherein the structure is incompatible with cgRNA mediation of Cas9, dCas9, and/or Cas function. In some embodiments, to toggle the cgRNA to the OFF state, the RNA trigger X (cognate RNA trigger) displaces the helper (also known as cg3) from the cgRNA (also known as cg5) via toehold-mediated strand displacement in which the trigger first nucleates with the cgRNA (also known as cg5) by binding to the exposed toehold domain "c" (also known as the linker domain "c") on the cgRNA (also known as cg5), and then hybridizes to domains "d" and "e" to displace the helper (also known as cg3) from the cgRNA, yielding a cgRNA:trigger complex (also known as the cg5:trigger complex) that is structurally incompatible with cgRNA mediation of Cas9, dCas9, and/or Cas function. In some embodiments, the mechanism is allosteric because the cgRNA and helper interact via a terminator duplex (domains "d" and "d*" in FIGS. 9B and 9C) distal to the target-binding region (domain "u" in FIGS. 9B and 9C). As a result, the sequence of the RNA trigger X (which binds to the cgRNA domains "c-d-e" to down-regulate Cas function) is also independent of domain "u", yielding full sequence independence between trigger X (the cognate RNA trigger) and regulatory target Y (the target gene). In some embodiments, domain "c*" in the trigger is optional. In some embodiments, domain "e*" in the trigger is optional. In some embodiments, domain "e" in the cgRNA is optional. In some embodiments, domain "c" in the cgRNA is constrained to a wild-type subsequence of the standard gRNA. In some embodiments, the terminator duplex comprises, consists, or consists essentially of 2 bp, or 4 bp, 6 bp, or 8 bp, or 10 bp, or 20 bp, or 30 bp, or 40 bp, or 50 bp, or 100 bp, or 200 bp, or more, or any number of base pairs intermediate to any of the preceding values. In some embodiments, a toehold domain comprises, consists, or consists essentially of 4 nt, or 10 nt, or 20 nt, or 30 nt, or 40 nt, or 50 nt, or 100 nt, or 200 nt, or more, or any number of nucleotides intermediate to any of the preceding values.

Allosteric ON→OFF Split-Terminator Switch cgRNAs (Mechanism 4C)

Figure 9D:
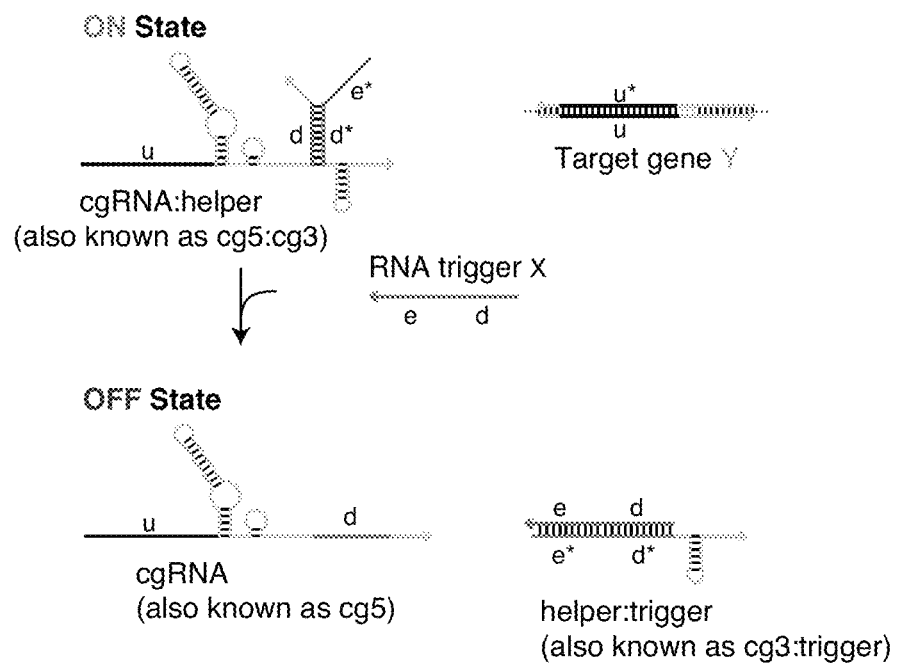
Figure 9E:
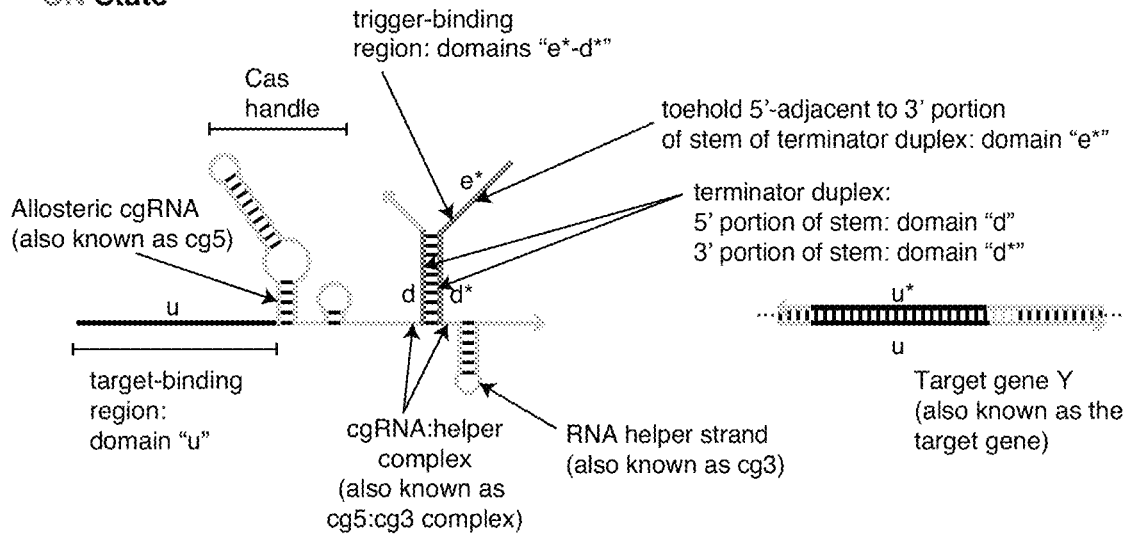
Figure 9E:
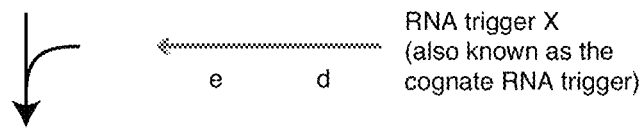
Figure 9E:
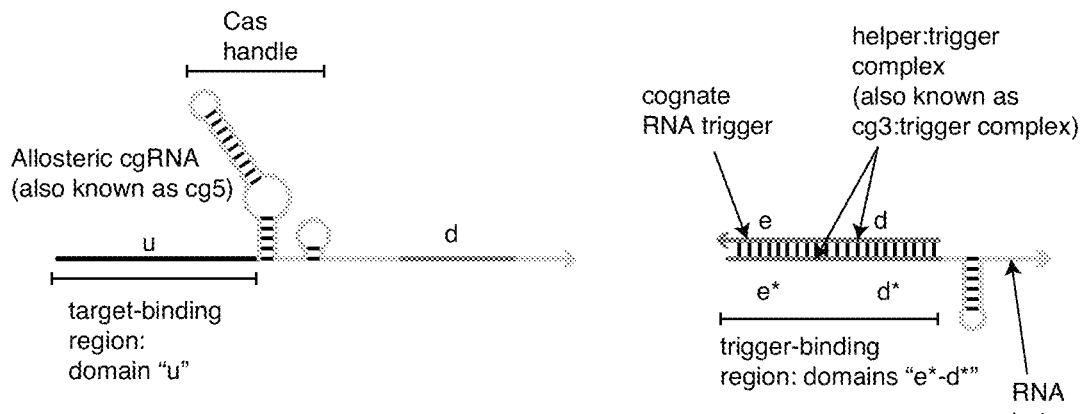

In some embodiments, allosteric ON→OFF cgRNA logic (FIG. 9A) is implemented using an allosteric ON→OFF split-terminator switch cgRNA mechanism (FIGS. 9D and 9E). In some embodiments, the ON→OFF split-terminator switch cgRNA (also known as cg5) of FIGS. 9D and 9E is conditionally inactivated by RNA trigger X (the cognate RNA trigger), which binds to the RNA helper strand (also known as cg3) to remove it from the cgRNA (also known as cg5), which then lacks the terminator duplex and the remainder of the terminator region, yielding a structure incompatible with mediation of Cas9, dCas9, and/or Cas function. Equivalently, in some embodiments, the functional conditional guide RNA can be interpreted as a complex of two fragments (complex cg5:cg3 comprising 5'-fragment cg5 and 3'-fragment cg3; FIGS. 9D and 9E) that is conditionally inactivated by RNA trigger X (cognate RNA trigger), which binds to the complex to displace cg5 and form the cg3:trigger complex, wherein both cg3:trigger and cg5 are structurally incompatible with mediation of Cas9, dCas9, and/or Cas function. Compared to a standard gRNA (FIG. 1), in some embodiments the ON→OFF split-terminator switch cgRNA (also known as cg5) is incomplete, containing only one half of the stem region of the 5' terminator hairpin (sequence domain "d"). In the ON state, hybridization of the RNA helper strand (also known as cg3) to domain "d" forms a terminator duplex (domain "d" base-paired to domain "d*") such that the cgRNA:helper complex (also known as the cg5:cg3 complex) is active. In some embodiments, the cgRNA (also known as cg5) comprises a target-binding region (domain "u"), a Cas handle, and a 5' portion of the stem of the terminator duplex (domain "d"). In some embodiments, the RNA helper strand (also known as cg3) comprises a trigger-binding region (domains "e*-d*"); wherein the trigger-binding region comprises a 3' portion of the stem of the terminator duplex (domain "d*") and a toehold 5'-adjacent to the 3' portion of the stem of the terminator duplex (domain "e*"). In some embodiments, to toggle the cgRNA (also known as cg5) to the OFF state, the RNA trigger X (the cognate RNA trigger) displaces the RNA helper strand (also known as cg3) from the cgRNA (also known as cg5) via toehold-mediated strand displacement in which the trigger first nucleates with the helper (also known as cg3) by binding to the exposed toehold domain "e*" on the helper (also known as cg3), and then hybridizes to domain "d*" to displace the helper (also known as cg3) from the cgRNA (also known as cg5), forming the helper:trigger complex (also known as the cg3:trigger complex). This yields an incomplete cgRNA (also known as cg5) lacking the terminator duplex, wherein the cgRNA (also known as cg5) is structurally incompatible with mediation of Cas9, dCas9, and or Cas function. In some embodiments, the mechanism is allosteric because the cgRNA (also known as cg5) and helper (also known as cg3) interact via a terminator duplex (domains "d" and "d*" in FIGS. 9D and 9E) distal to the target-binding region (domain "u" in FIGS. 9D and 9E). As a result, the sequence of the RNA trigger X (which binds to the helper domains "e*-d*" to down-regulate Cas function) is independent of domain "u", yielding full sequence independence between trigger X (the cognate RNA trigger) and regulatory target Y (the target gene). In some embodiments, the terminator duplex comprises, consists, or consists essentially of 2 bp, or 4 bp, 6 bp, or 8 bp, or 10 bp, or 20 bp, or 30 bp, or 40 bp, or 50 bp, or 100 bp, or 200 bp, or more, or any number of base pairs intermediate to any of the preceding values. In some embodiments, a toehold domain comprises, consists, or consists essentially of 4 nt, or 10 nt, or 20 nt, or 30 nt, or 40 nt, or 50 nt, or 100 nt, or 200 nt, or more, or any number of nucleotides intermediate to any of the preceding values.

In some embodiments, the RNA helper strand (also known as cg3) comprises one or more additional domains 5'-adjacent to domain "d*". In some embodiments, one or more of these additional domains functions as a toehold to nucleate interactions with an auxiliary trigger that hybridizes to the helper strand (also known as cg3) to remove the helper strand (also known as cg3) from the cgRNA (also known as cg5). In some embodiments, one or more of these additional domains functions as a substrate to provide a binding site for an additional strand that hybridizes to both the substrate and to the cgRNA (also known as cg5) for the purpose of holding the cgRNA (also known as cg5) and helper strand (also known as cg3) together in complex (cg5:cg3: additional-strand). In some embodiments, the RNA helper strand (also known as cg3) comprises one or more additional domains 3'-adjacent to domain "d*". In some embodiments, one or more of these additional domains functions as a toehold to nucleate interactions with an auxiliary trigger that hybridizes to the helper strand (also known as cg3) to remove the helper strand (also known as cg3) from the cgRNA (also known as cg5). In some embodiments, the cgRNA (also known as cg5) comprises one or more substrate domains 3'-adjacent to domain "d" and the RNA helper strand (also known as cg3) comprises one or more substrate domains 5'-adjacent to domain "d*". In some embodiments, the trigger hybridizes to one or more substrates on the cgRNA (also known as cg5) and one or more substrates on the helper strand (also known as cg3) so as to form a 3-way junction that disrupts the structure of the terminator duplex, wherein the structure of the cgRNA:helper:trigger complex (also known as the cg5:cg3:trigger complex) is incompatible with mediation of Cas9, dCas9, and/or Cas function.

Allosteric OFF→ON 5'-Inhibited Split-Terminator Switch cgRNAs (Mechanism 5)

Figure 25A:
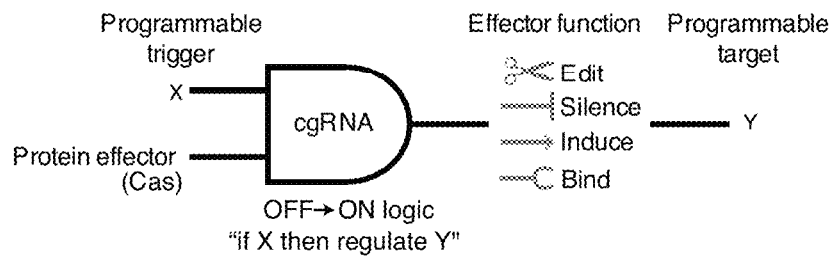
FIGS. 25A-25C depict the logic, function, and mechanism of allosteric OFF→ON 5'-inhibited split-terminator switch cgRNAs (Mechanism 5).
Figure 25B:
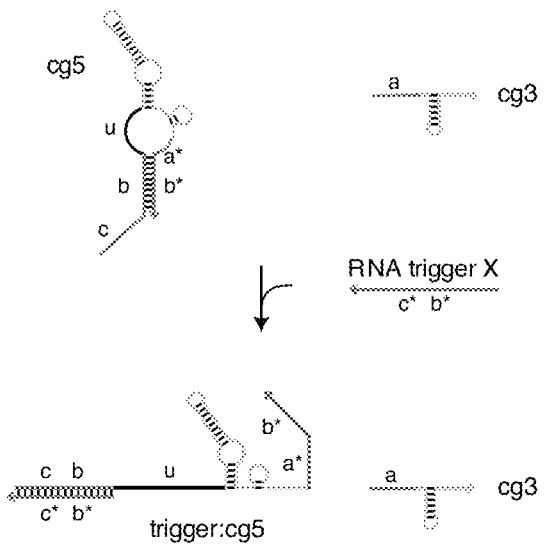
Figure 25B:
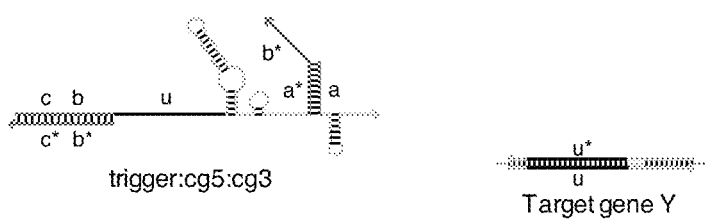
Figure 25C:
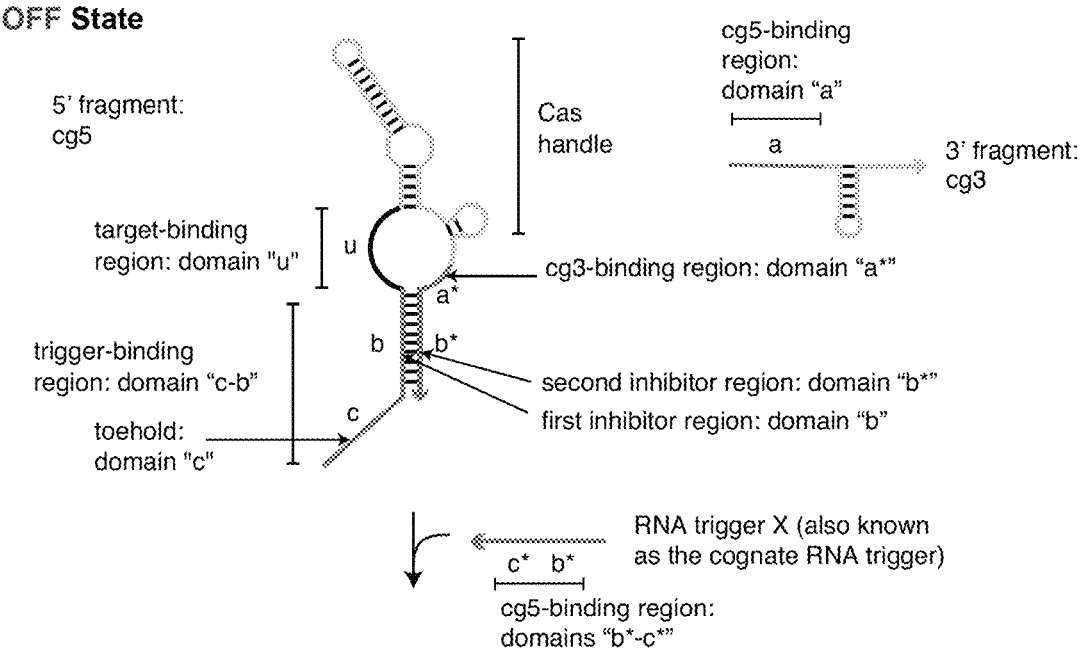
Figure 25C:
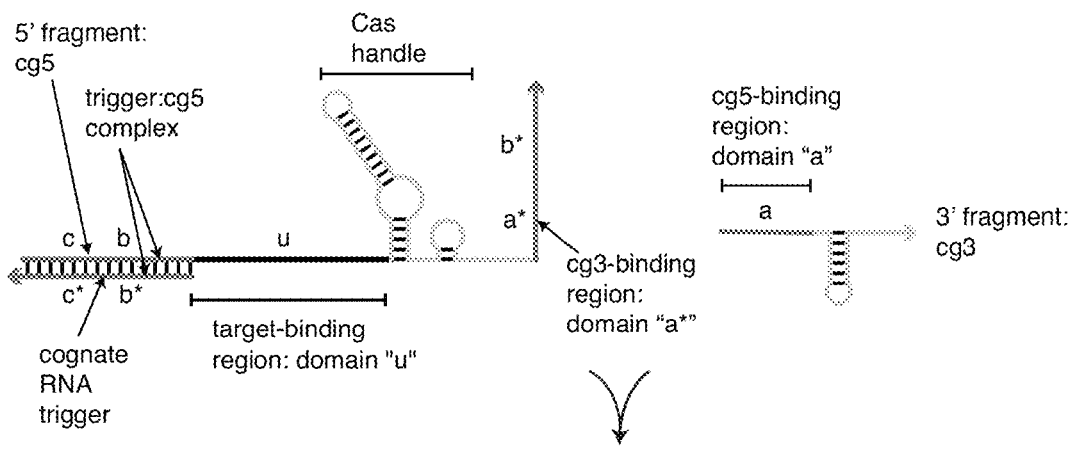
Figure 25C:
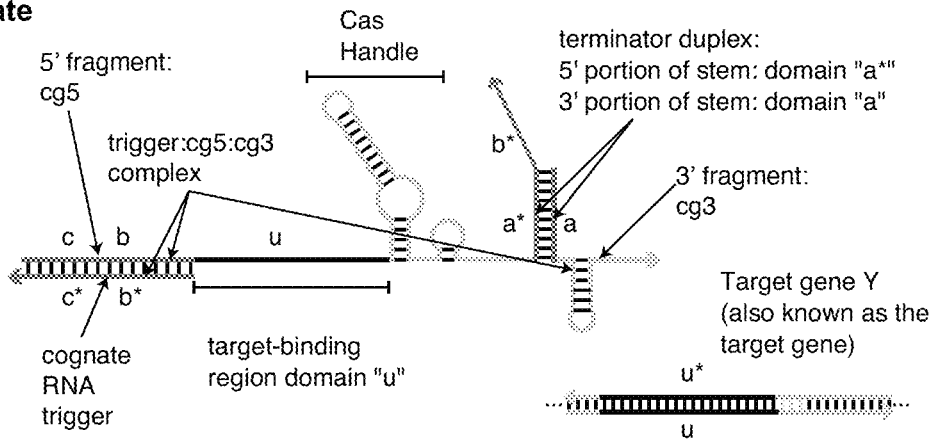

In some embodiments, allosteric OFF→ON cgRNA logic (FIG. 25A) is implemented using an allosteric OFF→ON 5'-inhibited split-terminator switch cgRNA mechanism (FIGS. 25B and 25C). In some embodiments, the OFF→ON 5'-inhibited split-terminator switch cgRNA (FIGS. 25B and 25C) comprises two inactive cgRNA fragments (cg5 and cg3) that are conditionally activated by RNA trigger X (the cognate RNA trigger), which binds to cg5 to allow for formation of the trigger:cg5:cg3 complex that activates the cgRNA, mediating the function of a Cas protein effector on a target gene (Y). In some embodiments, the OFF→ON 5'-sequestered split-terminator switch cgRNA comprises two fragments (FIGS. 25B and 25C), a 5'-fragment (cg5) and a 3'-fragment (cg3), that are inactive when not bound to each other (OFF state). In some embodiments, cg5 comprises a Cas handle, a target-binding region (sequence domain "u") 5' of the Cas handle, and a cg3-binding region (sequence domain "a*") 3' of the Cas handle. In some embodiments, cg3 comprises a cg5-binding region (sequence domain "a"). In some embodiments, cg5 further comprises a trigger-binding region (sequence domains "c-b") comprising a first inhibitor region (sequence domain "b"), and a second inhibitor region (sequence domain "b*"), such that in the absence of the cognate RNA trigger, the first inhibitor region (sequence domain "b") is configured to bind to the second inhibitor region (sequence domain "b*"), inhibiting binding between cg5 and cg3 by sequestering the cg3-binding region of cg5 (sequence domain "a*") in a loop. In some embodiments, the cognate RNA trigger comprises a cg5-binding region (sequence domains "b*-c*"), the trigger-binding region further comprises a toehold of one or more unpaired nucleotides at one or both ends (for example, domain "c"), the cg3-binding region of cg5 comprises the 5' portion of the stem of a terminator duplex (sequence domain "d"), and the cg5-binding region of cg3 comprises the 3' portion of the stem of the terminator duplex (sequence domain "d*"), such that upon hybridization of the cognate RNA trigger to cg5, cg5 hybridizes to cg3 to form the terminator duplex, activating the cgRNA (ON state). In some embodiments, the target-binding region (sequence domain "u") is non-overlapping with the trigger-binding region (sequence domains "c-b") and is configured not to bind to the trigger-binding region, allowing for allosteric signal transduction, in which the sequence of the cognate RNA trigger (X) can be selected independently of the sequence of the target gene (Y). In some embodiments, the cognate RNA trigger comprises additional flanking nucleotides 5' and/or 3' of the cg5-binding region. In some embodiments, to toggle the cgRNA from the OFF state to the ON state, the RNA trigger X (cognate RNA trigger) opens up the sequestering loop in cg5 via toehold-mediated strand displacement in which the trigger first nucleates with cg5 by hybridizing to the exposed toehold "c" on cg5 and then hybridizes to domain "b" to open the loop containing domain "a*", facilitating hybridization between domain "a*" in cg5 and domain "a" in cg3 to form the terminator duplex and activate the cgRNA, allowing for mediation of Cas function on the target gene (FIG. 25C). In some embodiments, the mechanism is allosteric because the trigger and cg5 interact via domains "c-b" in cg5 and "b*-c*" in the trigger (see FIGS. 25B and 25C) that are independent of the target-binding region (domain "u" in FIGS. 25B and 25C). The resulting full sequence independence between RNA trigger X (the cognate RNA trigger) and target gene Y (the target gene) provides the flexibility for X to control regulatory scope (also known as the scope of activity) independent of the choice of Y. In some embodiments, the terminator duplex comprises, consists, or consists essentially of 2 bp, or 4 bp, 6 bp, or 8 bp, or 10 bp, or 20 bp, or 30 bp, or 40 bp, or 50 bp, or 100 bp, or 200 bp, or more, or any number of base pairs intermediate to any of the preceding values.

Allosteric OFF→ON 3'-Inhibited Split-Terminator Switch cgRNAs (Mechanism 6)

Figure 26A:
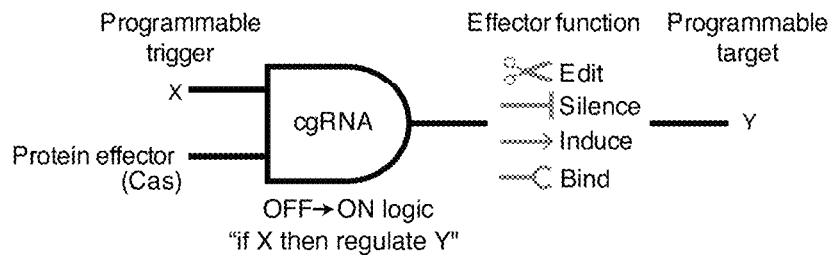
FIGS. 26A-26C depict the logic, function, and mechanism of allosteric OFF→ON 3'-inhibited split-terminator switch cgRNAs (Mechanism 6).
Figure 26B:
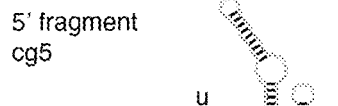
Figure 26B:
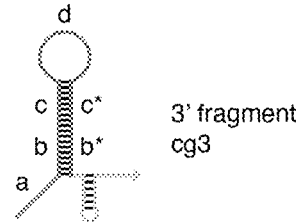
Figure 26B:
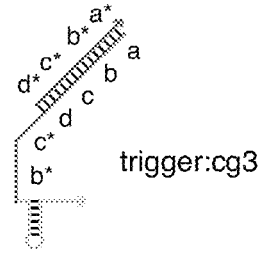
Figure 26B:
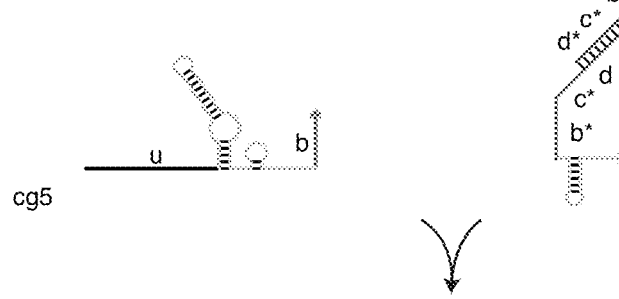
Figure 26B:
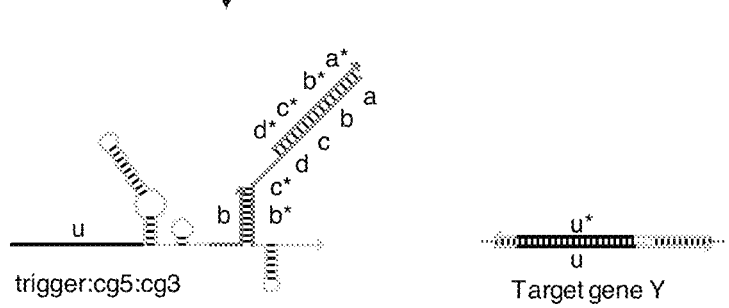
Figure 26C:
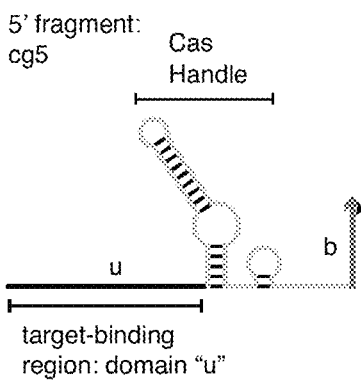
Figure 26C:
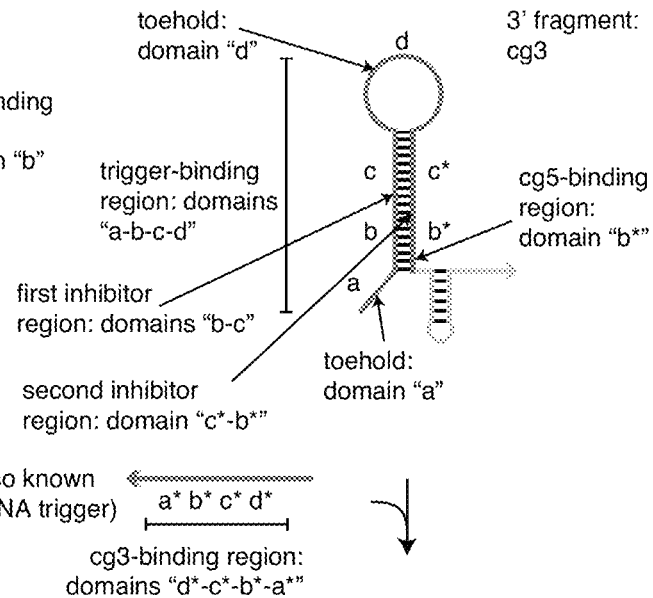
Figure 26C:
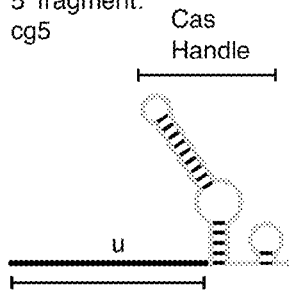
Figure 26C:
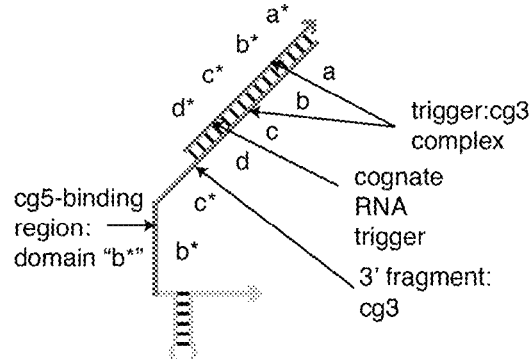

In some embodiments, allosteric OFF→ON cgRNA logic (FIG. 26A) is implemented using an allosteric OFF→ON 3'-inhibited split-terminator switch cgRNA mechanism (FIGS. 26B and 26C). In some embodiments, the OFF→ON 3'-inhibited split-terminator switch cgRNA (FIGS. 26B and 26C) comprises two inactive cgRNA fragments (cg5 and cg3) that are conditionally activated by RNA trigger X (the cognate RNA trigger), which binds to cg3 to allow for formation of the trigger:cg5:cg3 complex that activates the cgRNA, mediating the function of a Cas protein effector on a target gene (Y). In some embodiments, the OFF→ON 3'-sequestered split-terminator switch cgRNA comprises two fragments (FIGS. 26B and 26C), a 5'-fragment (cg5) and a 3'-fragment (cg3), that are inactive when not bound to each other (OFF state). In some embodiments, cg5 comprises a Cas handle, a target-binding region (sequence domain "u") 5' of the Cas handle, and a cg3-binding region (sequence domain "b") 3' of the Cas handle. In some embodiments, cg3 comprises a cg5-binding region (sequence domain "b*"). In some embodiments, cg3 further comprises a trigger-binding region (sequence domains "a-b-c-d") comprising a first inhibitor region (sequence domains "b-c"), and a second inhibitor region (sequence domain "c*-b*"), such that in the absence of the cognate RNA trigger, the first inhibitor region (sequence domains "b-c") is configured to bind to the second inhibitor region (sequence domain "c*-b*"), inhibiting binding between cg3 and cg5 by sequestering the cg5-binding region of cg3 (sequence domain "b*") in a duplex (i.e., the duplex formed by base-pairing between domains "b" and "b*" within cg3). In some embodiments, the cognate RNA trigger comprises a cg3-binding region (sequence domains "d*-c*-b*-a*"), the trigger-binding region further comprises a toehold of one or more unpaired nucleotides at one or both ends (for example, domain "a" and/or domain "d"), the cg3-binding region of cg5 comprises the 5' portion of the stem of a terminator duplex (sequence domain "b"), and the cg5-binding region of cg3 comprises the 3' portion of the stem of the terminator duplex (sequence domain "b*"), such that upon hybridization of the cognate RNA trigger to cg3, cg3 hybridizes to cg5 to form the terminator duplex, activating the cgRNA (ON state). In some embodiments, the target-binding region (sequence domain "u") is non-overlapping with the trigger-binding region (sequence domains "a-b-c-d") and is configured not to bind to the trigger-binding region, allowing for allosteric signal transduction, in which the sequence of the cognate RNA trigger (X) can be selected independently of the sequence of the target gene (Y). In some embodiments, the cognate RNA trigger comprises additional flanking nucleotides 5' and/or 3' of the cg3-binding region. In some embodiments, to toggle the cgRNA from the OFF state to the ON state, the RNA trigger X (cognate RNA trigger) opens up the duplex in cg3 via toehold-mediated strand displacement in which the trigger first nucleates with cg3 by hybridizing to the exposed toehold "a" on cg3 (and/or the exposed toehold "d") and then hybridizes to domains "b-c" to open the duplex sequestering domain "b*", facilitating hybridization between domain "b*" in cg3 and domain "b" in cg5 to form the terminator duplex and activate the cgRNA, allowing for mediation of Cas function on the target gene (FIG. 26C). In some embodiments, the mechanism is allosteric because the trigger and cg3 interact via domains "a-b-c-d" in cg3 and "d*-c*-b*-a*" in the trigger (see FIGS. 26B and 26C) that are independent of the target-binding region (domain "u" in cg5; FIGS. 26B and 26C). The resulting full sequence independence between RNA trigger X (the cognate RNA trigger) and target gene Y (the target gene) provides the flexibility for X to control regulatory scope (also known as the scope of activity) independent of the choice of Y. In some embodiments, the terminator duplex comprises, consists, or consists essentially of 2 bp, or 4 bp, 6 bp, or 8 bp, or 10 bp, or 20 bp, or 30 bp, or 40 bp, or 50 bp, or 100 bp, or 200 bp, or more, or any number of base pairs intermediate to any of the preceding values.

Allosteric OFF→ON 5'- and 3'-Inhibited Split-Terminator Switch cgRNAs (Mechanism 7)

Figure 27A:
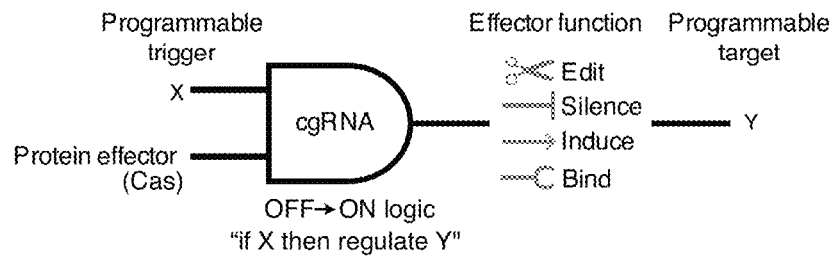
FIGS. 27A-27C depict the logic, function, and mechanism of allosteric OFF→ON 5'- and 3'-inhibited split-terminator switch cgRNAs (Mechanism 7).
Figure 27B:
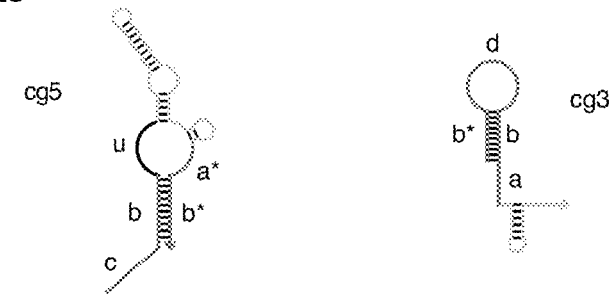
Figure 27B:
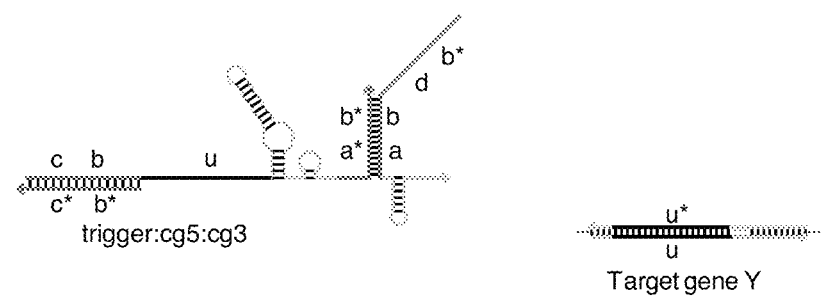
Figure 27C:
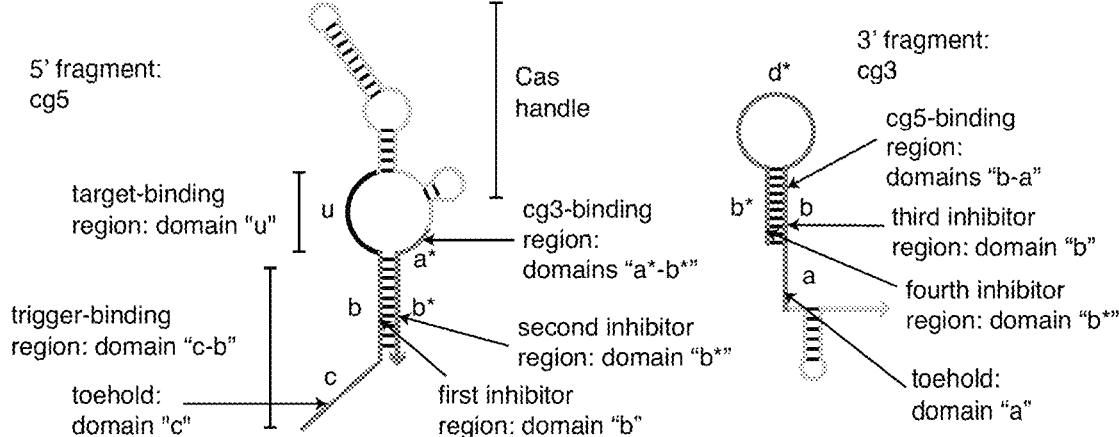
Figure 27C:
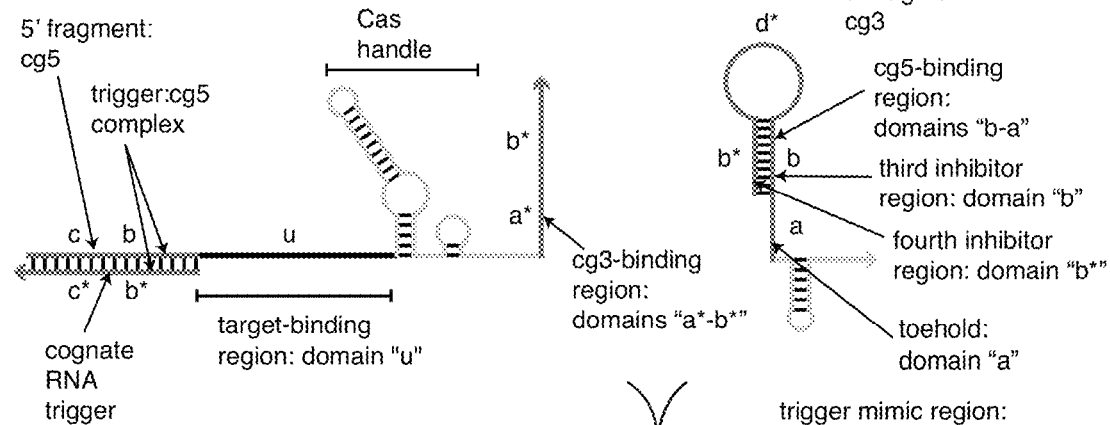
Figure 27C:
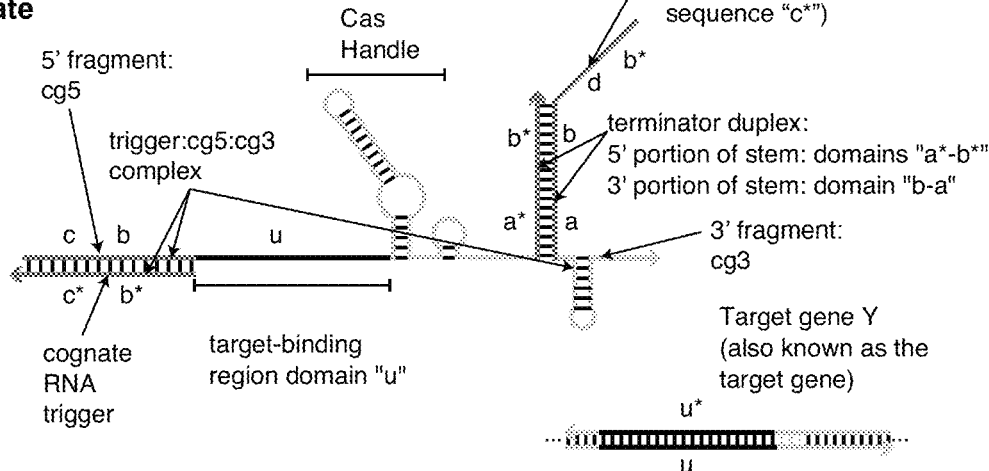

In some embodiments, allosteric OFF→ON cgRNA logic (FIG. 27A) is implemented using an allosteric OFF→ON 5'- and 3'-inhibited split-terminator switch cgRNA mechanism (Mechanism 7; FIGS. 27B and 27C). In some embodiments, the OFF→ON 5'- and 3'-inhibited split-terminator switch cgRNA (Mechanism 7; FIGS. 27B and 27C) comprises two inactive cgRNA fragments (cg5 and cg3) that are conditionally activated by RNA trigger X (the cognate RNA trigger), which binds to cg5 to allow for formation of the trigger:cg5:cg3 complex that activates the cgRNA, mediating the function of a Cas protein effector on a target gene (Y). In some embodiments, the OFF→ON 5'- and 3'-inhibited split-terminator switch cgRNA (Mechanism 7) comprises two fragments (FIGS. 27B and 27C), a 5'-fragment (cg5) and a 3'-fragment (cg3), that are inactive when not bound to each other (OFF state). In some embodiments, cg5 comprises a Cas handle, a target-binding region (sequence domain "u") 5' of the Cas handle, and a cg3-binding region (sequence domains "a*-b*") 3' of the Cas handle. In some embodiments, cg3 comprises a cg5-binding region (sequence domains "b-a"). In some embodiments, cg5 further comprises: 1) a trigger-binding region (sequence domains "c-b") comprising a first inhibitor region (sequence domain "b" in cg5), 2) and a second inhibitor region (sequence domain "b*" in cg5); and cg3 further comprises a third inhibitor region (sequence domain "b" in cg3) and a fourth inhibitor region (sequence domain "b*" in cg3); such that in the absence of the cognate RNA trigger, the first inhibitor region (sequence domain "b" in cg5) is configured to bind to the second inhibitor region (sequence domain "b*" in cg5) and the third inhibitor region (sequence domain "b" in cg3) is configured to bind to the fourth inhibitor region (sequence domain "b*" in cg3), inhibiting binding between cg5 and cg3 by sequestering the cg3-binding region of cg5 (sequence domains "a*-b*") in a loop and duplex ("a*" is sequestered in a loop and "b*'" is sequestered in a duplex; FIGS. 27B and 27C) and by sequestering a portion of the cg5-binding region of cg3 (sequence domain "b") in a duplex. In some embodiments, the cognate RNA trigger comprises a cg5-binding region (sequence domains "b*-c*'"), the trigger-binding region of cg5 further comprises a toehold of one or more unpaired nucleotides at one or both ends (for example, domain "c"), the cg3-binding region of cg5 comprises the 5' portion of the stem of a terminator duplex (sequence domains "a*-b*'"), and the cg5-binding region of cg3 comprises the 3' portion of the stem of the terminator duplex (sequence domain "b-a"), such that upon hybridization of the cognate RNA trigger to cg5, cg5 hybridizes to cg3 to form the terminator duplex, activating the cgRNA (ON state). In some embodiments, the target-binding region (sequence domain "u") is non-overlapping with the trigger-binding region (sequence domains "c-b") and is configured not to bind to the trigger-binding region, allowing for allosteric signal transduction, in which the sequence of the cognate RNA trigger (X) can be selected independently of the sequence of the target gene (Y). In some embodiments, the cognate RNA trigger comprises additional flanking nucleotides 5' and/or 3' of the cg5-binding region. In some embodiments, to toggle the cgRNA from the OFF state to the ON state, the RNA trigger X (cognate RNA trigger) opens up the sequestering loop and duplex in cg5 via toehold-mediated strand displacement in which the trigger first nucleates with cg5 by hybridizing to the exposed toehold "c" on cg5 and then hybridizes to domain "b" to open the loop containing domain "a*'" and the duplex containing domain "b*'", facilitating hybridization between domains "a*-b*'" in cg5 and domains "b-a" in cg3 to form the terminator duplex and activate the cgRNA, allowing for mediation of Cas function on the target gene (FIG. 27C). In some embodiments, once the cognate RNA trigger binds to cg5 to form complex trigger:cg5 and expose domains "a*-b*'", cg5 opens up the sequestering duplex in cg3 via toehold-mediated strand displacement in which cg5 first nucleates with cg3 by hybridizing to the exposed toehold "a" on cg3 and then hybridizes to domain "b" to open the duplex containing domain "b*'". In some embodiments, the mechanism is allosteric because the trigger and cg5 interact via domains "c-b" in cg5 and "b*-c*'" in the trigger (see FIGS. 27B and 27C) that are independent of the target-binding region (domain "u" in FIGS. 27B and 27C). The resulting full sequence independence between RNA trigger X (the cognate RNA trigger) and target gene Y (the target gene) provides the flexibility for X to control regulatory scope (also known as the scope of activity) independent of the choice of Y. In some embodiments, the terminator duplex comprises, consists, or consists essentially of 2 bp, or 4 bp, 6 bp, or 8 bp, or 10 bp, or 20 bp, or 30 bp, or 40 bp, or 50 bp, or 100 bp, or 200 bp, or more, or any number of base pairs intermediate to any of the preceding values.

In some embodiments (Mechanism 7; FIGS. 27B and 27C), cg3 further comprises a trigger mimic region (sequence domains "b*-d") with the same sequence as the cg5-binding region of the cognate RNA trigger (sequence domains "b*-c*'") (that is, in some embodiments, the sequence of domain "d" is specified to be the same as the sequence of domain "c*'"), such that upon activation of the cgRNA by the cognate RNA trigger, the trigger mimic region (sequence domains "b*-d" with the sequence of domain "d" defined to be the same as the sequence of domain "c*'") is exposed. In some embodiments, this exposed trigger mimic region is then capable of serving as the cognate RNA trigger for a new copy of the cgRNA comprising a new copy of the 5' fragment cg5 and a new copy of the 3' fragment cg3. In some embodiments, the original cognate RNA trigger molecule is capable of triggering the ON state of a first cgRNA, which in turn is capable of trigger the ON state of a second cgRNA, which in turn is capable of trigger the ON state of a third cgRNA, and so on; this situation is equivalent to catalytic activation of multiple cgRNAs by a single cognate RNA trigger molecule.

Allosteric OFF→ON 5'- and 3'-Inhibited Split-Terminator Switch cgRNAs (Mechanism 8)

Figure 28A:
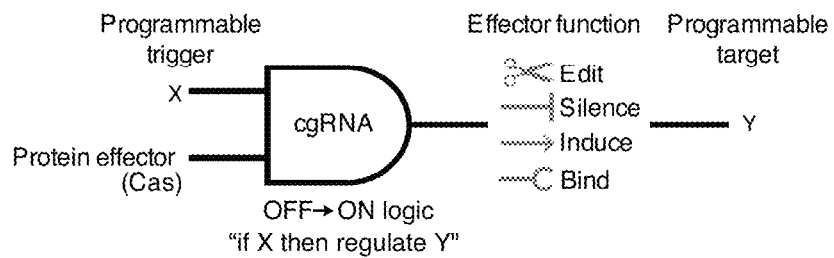
FIGS. 28A-28D depict the logic, function, and mechanism of allosteric OFF→ON 5'- and 3'-inhibited split-terminator switch cgRNAs (Mechanism 8).
Figure 28B:
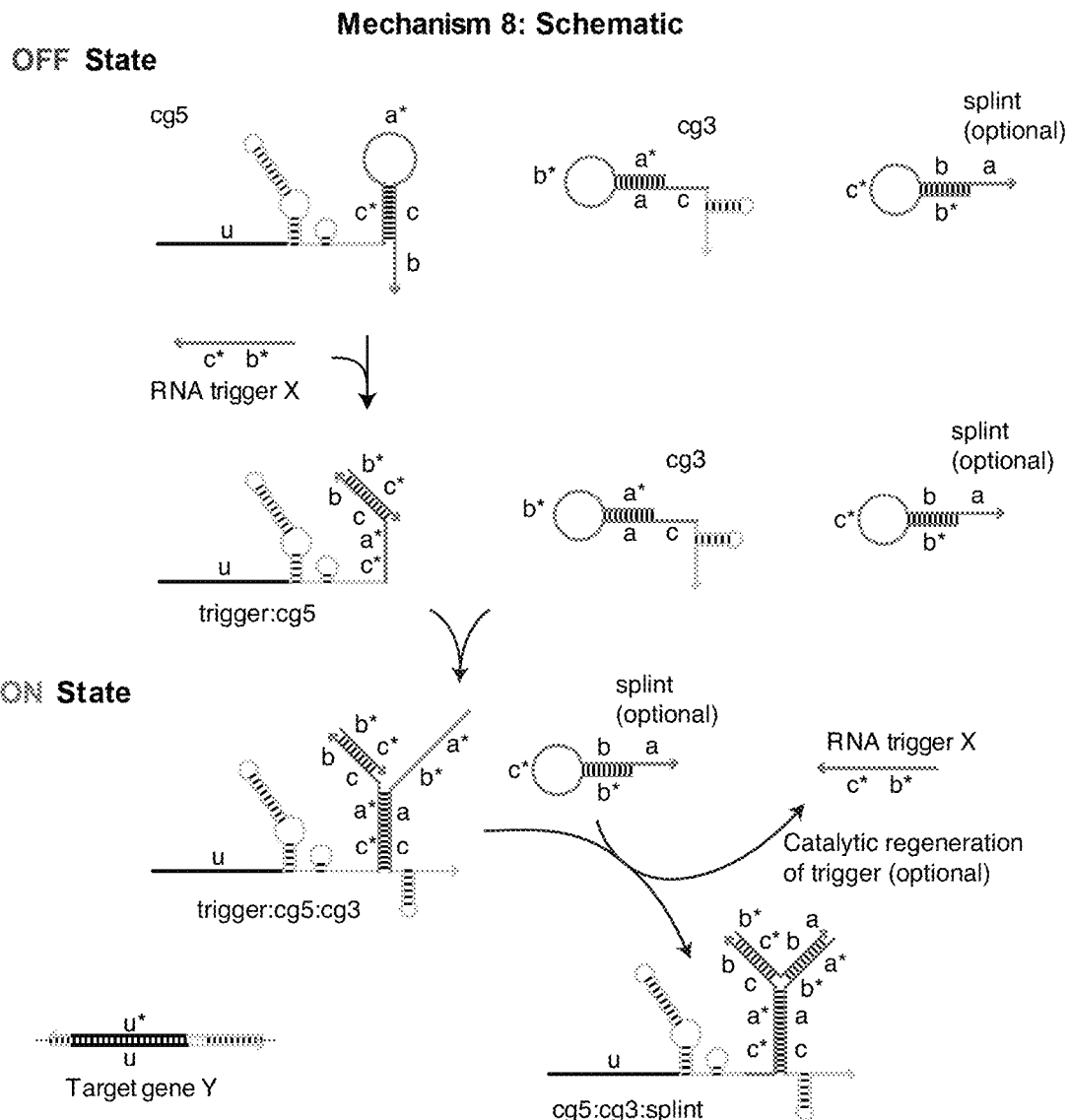
Figure 28C:
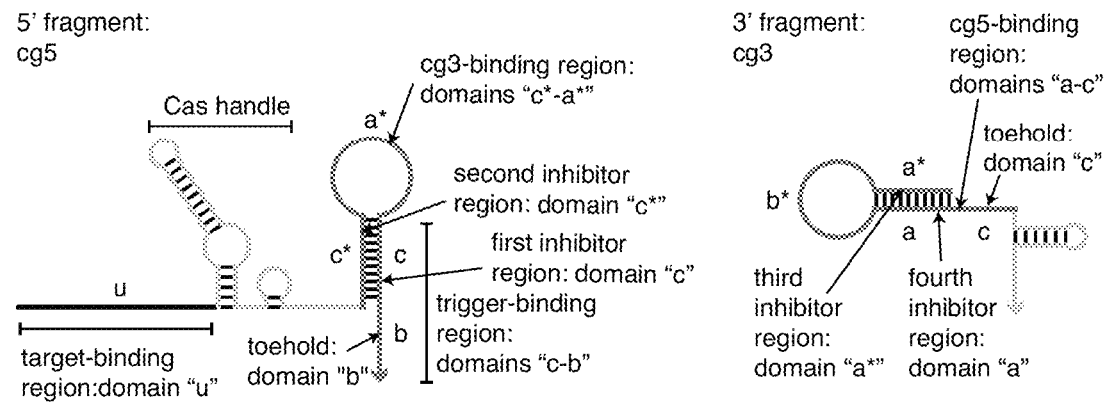
Figure 28C:
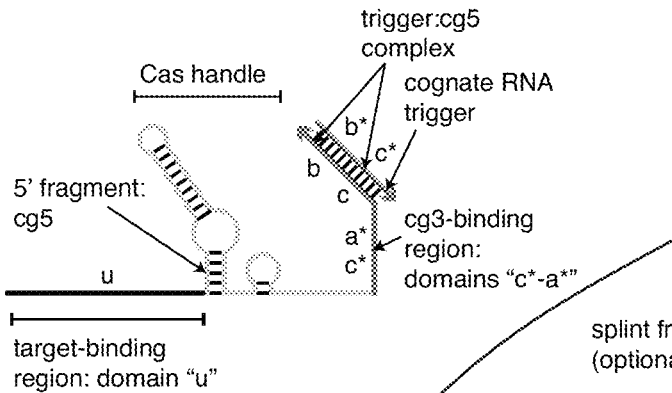
Figure 28C:
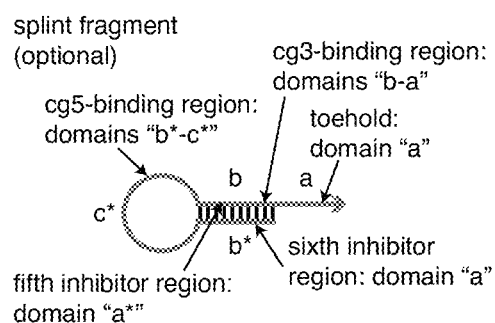

In some embodiments, allosteric OFF→ON cgRNA logic (FIG. 28A) is implemented using an allosteric OFF→ON 5'- and 3'-inhibited split-terminator switch cgRNA mechanism (Mechanism 8; FIGS. 28B, 28C and 28D). In some embodiments, the OFF→ON 5'- and 3'-inhibited split-terminator switch cgRNA (Mechanism 8; FIGS. 28B, 28C and 28D) comprises two inactive cgRNA fragments (cg5 and cg3) that are conditionally activated by RNA trigger X (the cognate RNA trigger), which binds to cg5 to allow for formation of the trigger:cg5:cg3 complex that activates the cgRNA, mediating the function of a Cas protein effector on a target gene (Y). In some embodiments, the OFF→ON 5'- and 3'-inhibited split-terminator switch cgRNA (Mechanism 8) comprises two fragments (FIGS. 28B 28C and 28D), a 5'-fragment (cg5) and a 3'-fragment (cg3), that are inactive when not bound to each other (OFF state). In some embodiments, cg5 comprises a Cas handle, a target-binding region (sequence domain "u") 5' of the Cas handle, and a cg3-binding region (sequence domains "c*-a*'") 3' of the Cas handle. In some embodiments, cg3 comprises a cg5-binding region (sequence domains "a-c"). In some embodiments, cg5 further comprises: 1) a trigger-binding region (sequence domains "c-b") comprising a first inhibitor region (sequence domain "c" in cg5), 2) and a second inhibitor region (sequence domain "c*'" in cg5); and cg3 further comprises a third inhibitor region (sequence domain "a*'" in cg3) and a fourth inhibitor region (sequence domain "a" in cg3); such that in the absence of the cognate RNA trigger, the first inhibitor region (sequence domain "c" in cg5) is configured to bind to the second inhibitor region (sequence domain "c*'" in cg5) and the third inhibitor region (sequence domain "a*'" in cg3) is configured to bind to the fourth inhibitor region (sequence domain "a" in cg3), inhibiting binding between cg5 and cg3 by sequestering the cg3-binding region of cg5 (sequence domains "c*-a*'") in a loop and duplex ("a*'" is sequestered in a loop and "c*'" is sequestered in a duplex; FIGS. 28B, 28C and 28D) and by sequestering a portion of the cg5-binding region of cg3 in a duplex (the sequestered portion corresponds to domain "a" which is base paired to domain "a*'" in a duplex). In some embodiments, the cognate RNA trigger comprises a cg5-binding region (sequence domains "b*-c*'"), the trigger-binding region of cg5 further comprises a toehold of one or more unpaired nucleotides at one or both ends (for example, domain "b"), the cg3-binding region of cg5 comprises the 5' portion of the stem of a terminator duplex (sequence domains "c*-a*'"), and the cg5-binding region of cg3 comprises the 3' portion of the stem of the terminator duplex (sequence domain "a-c"), such that upon hybridization of the cognate RNA trigger to cg5, cg5 hybridizes to cg3 to form the terminator duplex, activating the cgRNA (ON state). In some embodiments, the target-binding region (sequence domain "u") is non-overlapping with the trigger-binding region (sequence domains "c-b") and is configured not to bind to the trigger-binding region, allowing for allosteric signal transduction, in which the sequence of the cognate RNA trigger (X) can be selected independently of the sequence of the target gene (Y). In some embodiments, the cognate RNA trigger comprises additional flanking nucleotides 5' and/or 3' of the cg5-binding region. In some embodiments, to toggle the cgRNA from the OFF state to the ON state, the RNA trigger X (cognate RNA trigger) opens up the sequestering loop and duplex in cg5 via toehold-mediated strand displacement in which the trigger first nucleates with cg5 by hybridizing to the exposed toehold "b" on cg5 and then hybridizes to domain "c" to open the loop containing domain "a*" and the duplex containing domain "c*", facilitating hybridization between domains "c*-a*" in cg5 and domains "a-c" in cg3 to form the terminator duplex and activate the cgRNA, allowing for mediation of Cas function on the target gene (FIGS. 28C and 28D). In some embodiments, once the cognate RNA trigger binds to cg5 to form complex trigger: cg5 and expose domains "c*-a*", cg5 opens up the sequestering duplex in cg3 via toehold-mediated strand displacement in which cg5 first nucleates with cg3 by hybridizing to the exposed toehold "c" on cg3 and then hybridizes to domain "a" to open the duplex containing domain "a*". In some embodiments, the mechanism is allosteric because the trigger and cg5 interact via domains "c-b" in cg5 and "b*-c*" in the trigger (see FIGS. 28B, 28C and 28D) that are independent of the target-binding region (domain "u" in FIGS. 28B, 28C and 28D). The resulting full sequence independence between RNA trigger X (the cognate RNA trigger) and target gene Y (the target gene) provides the flexibility for X to control regulatory scope (also known as the scope of activity) independent of the choice of Y. In some embodiments, the terminator duplex comprises, consists, or consists essentially of 2 bp, or 4 bp, 6 bp, or 8 bp, or 10 bp, or 20 bp, or 30 bp, or 40 bp, or 50 bp, or 100 bp, or 200 bp, or more, or any number of base pairs intermediate to any of the preceding values.

In some embodiments (Mechanism 8; FIGS. 28B, 28C and 28D), cg3 additionally comprises a third fragment (known as the splint fragment) comprising a cg3-binding region (sequence domains "b-a") comprising a fifth inhibitor region (sequence domain "b") and a cg5-binding region (sequence domains "b*-c") comprising a sixth inhibitor region (sequence domains "b*") such that in the absence of the cognate RNA trigger, the fifth inhibitor region is configured to bind to the sixth inhibitor region, inhibiting binding of the splint to cg5 and cg3, and such that upon activation of the cgRNA by the cognate RNA trigger, cg3 hybridizes to the cg3-binding region of the splint (sequence domains "b-a") and cg5 hybridizes to the cg5-binding region of the splint (sequence domains "b*-c*"), displacing the trigger from cg5, corresponding to catalytic regeneration of the trigger, which can then serve as the cognate RNA trigger for a new copy of the cgRNA comprising a new copy of the 5' fragment cg5, a new copy of the 3' fragment cg3, and a new copy of the splint. In some embodiments, the original cognate RNA trigger molecule is capable of triggering the ON state of a first cgRNA, which in turn is capable of trigger the ON state of a second cgRNA, which in turn is capable of trigger the ON state of a third cgRNA, and so on; this situation corresponds to catalytic activation of multiple cgRNAs by a single cognate RNA trigger molecule. In some embodiments, after the cognate RNA trigger actives the cgRNA, cg3 opens up the sequestering duplex in the splint via toehold-mediated strand displacement in which cg3 first nucleates with the splint by hybridizing to the exposed toehold "a" on the splint and then hybridizes to domain "b" to open the duplex containing domain "b*"; in some embodiments, the exposed cg5-binding region (sequence domains "b*-c*") in the splint then hybridizes to cg5 to displace the cognate RNA trigger.

Allosteric OFF→ON 5'- and 3'-Inhibited Split-Terminator Switch cgRNAs (Mechanism 9)

Figure 29A:
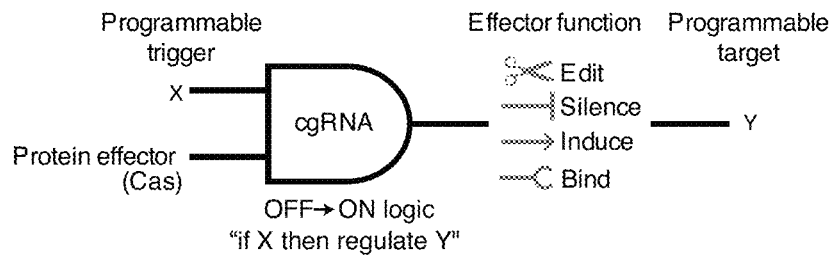
FIGS. 29A-29D depict the logic, function, and mechanism of allosteric OFF→ON 5'- and 3'-inhibited split-terminator switch cgRNAs (Mechanism 9).
Figure 29B:
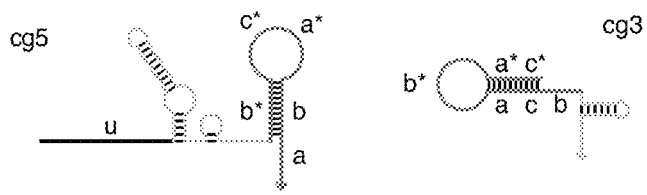
Figure 29B:
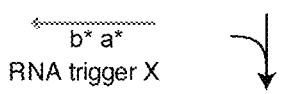
Figure 29B:
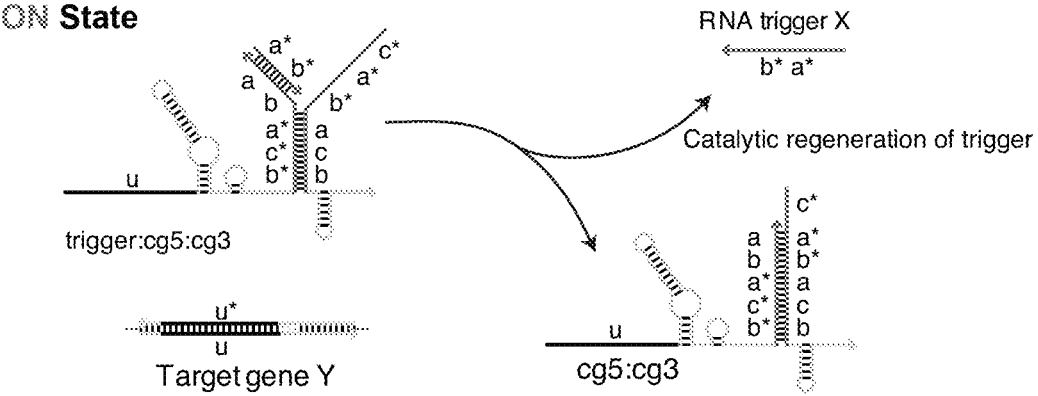
Figure 29C:
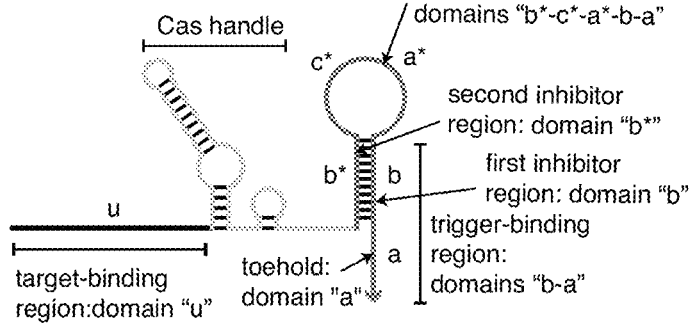
Figure 29C:
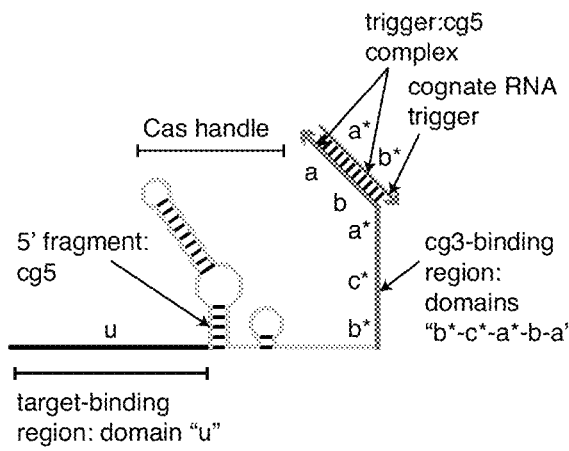

In some embodiments, allosteric OFF→ON cgRNA logic (FIG. 29A) is implemented using an allosteric OFF→ON 5'- and 3'-inhibited split-terminator switch cgRNA mechanism (Mechanism 9; FIGS. 29B, 29C and 29D). In some embodiments, the OFF→ON 5'- and 3'-inhibited split-terminator switch cgRNA (Mechanism 9; FIGS. 29B, 29C and 29D) comprises two inactive cgRNA fragments (cg5 and cg3) that are conditionally activated by RNA trigger X (the cognate RNA trigger), which binds to cg5 to allow for formation of the trigger:cg5:cg3 complex that activates the cgRNA, mediating the function of a Cas protein effector on a target gene (Y). In some embodiments, the OFF→ON 5'- and 3'-inhibited split-terminator switch cgRNA (Mechanism 9) comprises two fragments (FIGS. 29B, 29C and 29D), a 5'-fragment (cg5) and a 3'-fragment (cg3), that are inactive when not bound to each other (OFF state). In some embodiments, cg5 comprises a Cas handle, a target-binding region (sequence domain "u") 5' of the Cas handle, and a cg3-binding region (sequence domains "b*-c*-a*") 3' of the Cas handle. In some embodiments, cg3 comprises a cg5-binding region (sequence domains "a-c-b"). In some embodiments, cg5 further comprises: 1) a trigger-binding region (sequence domains "b-a") comprising a first inhibitor region (sequence domain "b" in cg5), 2) and a second inhibitor region (sequence domain "b*" in cg5); and cg3 further comprises a third inhibitor region (sequence domains "c*-a*" in cg3) and a fourth inhibitor region (sequence domains "a-c" in cg3); such that in the absence of the cognate RNA trigger, the first inhibitor region (sequence domain "b" in cg5) is configured to bind to the second inhibitor region (sequence domain "b*" in cg5) and the third inhibitor region (sequence domains "c*-a*" in cg3) is configured to bind to the fourth inhibitor region (sequence domain "a-c" in cg3), inhibiting binding between cg5 and cg3 by sequestering the cg3-binding region of cg5 (sequence domains "b*-c*-a*") in a loop and duplex ("c*-a*" is sequestered in a loop and "b*" is sequestered in a duplex; FIGS. 29B, 29C and 29D) and by sequestering a portion of the cg5-binding region of cg3 in a duplex (the sequestered portion corresponds to domains "a-c" which are base paired to domain "c*-a*" in a duplex). In some embodiments, the cognate RNA trigger comprises a cg5-binding region (sequence domains "a*-b*"), the trigger-binding region in cg5 further comprises a toehold of one or more unpaired nucleotides at one or both ends (for example, domain "a"), the cg3-binding region of cg5 comprises the 5' portion of the stem of a terminator duplex (sequence domains "b*-c*-a*"), and the cg5-binding region of cg3 comprises the 3' portion of the stem of the terminator duplex (sequence domain "a-c-b"), such that upon hybridization of the cognate RNA trigger to cg5, cg5 hybridizes to cg3 to form the terminator duplex, activating the cgRNA (ON state). In some embodiments, the target-binding region (sequence domain "u") is non-overlapping with the trigger-binding region (sequence domains "b-a") and is configured not to bind to the trigger-binding region, allowing for allosteric signal transduction, in which the sequence of the cognate RNA trigger (X) can be selected independently of the sequence of the target gene (Y). In some embodiments, the cognate RNA trigger comprises additional flanking nucleotides 5' and/or 3' of the cg5-binding region. In some embodiments, to toggle the cgRNA from the OFF state to the ON state, the RNA trigger X (cognate RNA trigger) opens up the sequestering loop and duplex in cg5 via toehold-mediated strand displacement in which the trigger first nucleates with cg5 by hybridizing to the exposed toehold "a" on cg5 and then hybridizes to domain "b" to open the loop containing domains "c*-a*" and the duplex containing domain "b", facilitating hybridization between domains "b*-c*-a*" in cg5 and domains "a-c-b" in cg3 to form the terminator duplex and activate the cgRNA, allowing for mediation of Cas function on the target gene (FIGS. 29C and 29D). In some embodiments, once the cognate RNA trigger binds to cg5 to form complex trigger:cg5 and expose domains "b*-c*-a*", cg5 opens up the sequestering duplex in cg3 via toehold-mediated strand displacement in which cg5 first nucleates with cg3 by hybridizing to the exposed toehold "b" on cg3 and then hybridizes to domains "c-a" to open the duplex containing domains "c*-a*". In some embodiments, the mechanism is allosteric because the trigger and cg5 interact via domains "b-a" in cg5 and "a*-b*" in the trigger (see FIGS. 29B, 29C and 29D) that are independent of the target-binding region (domain "u" in FIGS. 29B, 29C and 29D). The resulting full sequence independence between RNA trigger X (the cognate RNA trigger) and target gene Y (the target gene) provides the flexibility for X to control regulatory scope (also known as the scope of activity) independent of the choice of Y. In some embodiments, the terminator duplex comprises, consists, or consists essentially of 2 bp, or 4 bp, 6 bp, or 8 bp, or 10 bp, or 20 bp, or 30 bp, or 40 bp, or 50 bp, or 100 bp, or 200 bp, or more, or any number of base pairs intermediate to any of the preceding values.

In some embodiments, the cg3-binding region of cg5 comprises sequence domains "b*-c*-a*-b-a" and the cg5-binding region of cg3 comprises sequence domains "a*-b*-a-c-b". In some embodiments, the cg3-binding region of cg5 comprises the 5' portion of the stem of a terminator duplex (sequence domains "b*-c*-a*-b-a"), and the cg5-binding region of cg3 comprises the 3' portion of the stem of the terminator duplex (sequence domain "a*-b*-a-c-b"), such that upon hybridization of the cognate RNA trigger to cg5, cg5 hybridizes to cg3 to form the terminator duplex, activating the cgRNA (ON state). In some embodiments (Mechanism 9; FIGS. 29B, 29C and 29D), cg3 comprises a trigger mimic region (sequence domains "a*-b") with the same sequence as the cg5-binding region of the cognate RNA trigger (sequence domains "a*-b*") such that upon activation of the cgRNA by the cognate RNA trigger, the trigger mimic region (sequence domains "a*-b") hybridizes to the trigger-binding region of cg5 (sequence domains "b-a"), displacing the trigger from cg5, corresponding to catalytic regeneration of the trigger which can then serve as the cognate RNA trigger for a new copy of the cgRNA comprising a new copy of the 5' fragment cg5 and a new copy of the 3' fragment cg3. In some embodiments, the original cognate RNA trigger molecule is capable of triggering the ON state of a first cgRNA, which in turn is capable of trigger the ON state of a second cgRNA, which in turn is capable of trigger the ON state of a third cgRNA, and so on; this situation corresponds to catalytic activation of multiple cgRNAs by a single cognate RNA trigger molecule. In some embodiments, the sequence of domain "b*" in cg3 is modified to be only partially complementary to domain "b" in cg5 (or to be non-complementary to domain "b" in cg5) so that cg3 does not displace the trigger from cg5 and the trigger is not catalytically regenerated.

Conditional Guide RNAs

In some embodiments, the trigger comprises any of RNA, DNA, PNA, XNA, 2'OMe-RNA, amino acids, artificial amino acids, chemically modified nucleic acids, chemically modified amino acids, synthetic nucleic acid analogs, and/or chemical linkers. In some embodiments, the trigger is a combination of two or more materials. In some embodiments, the trigger molecule contains a trigger domain that is capable of toggling the activity of a cgRNA from ON→OFF or OFF→ON via a binding event. In some embodiments, the trigger molecule is an mRNA and the trigger domain is a subsequence of the mRNA. In some embodiments, the trigger molecule is an mRNA, an rRNA, a lncRNA, a miRNA, a tRNA, or any other type of endogenous or exogenous RNA comprising a subsequence that is a trigger domain capable of toggling the activity of a cgRNA (from ON→OFF or OFF→ON). In some embodiments, the trigger is a DNA molecule comprising a subsequence that is a trigger domain capable of toggling the activity of a cgRNA (from ON→OFF or OFF→ON). In some embodiments, the trigger molecule is a synthetic nucleic acid comprising a subsequence that is a trigger domain capable of toggling the activity of a cgRNA (from ON→OFF or OFF→ON). In some embodiments, the trigger molecule is expressed and comprises a subsequence that is a trigger domain capable of toggling the activity of a cgRNA (from ON→OFF or OFF→ON). In some embodiments, the trigger molecule is chemically synthesized and comprises a subsequence that is a trigger domain capable of toggling the activity of a cgRNA (from ON→OFF or OFF→ON).

In some embodiments one or more of the nucleotides in the cgRNA and/or trigger sequences is rationally designed. In some embodiments, cgRNA and/or trigger sequences are designed using the reaction pathway designer within the NUPACK® the software suite,[40,41] another piece of software, or a computational algorithm. In some embodiments, sequence design is formulated as a multistate optimization problem using a set of target test tubes to represent elementary steps in the reaction pathway as well as to model global crosstalk.[41] In some embodiments, each elementary step tube contains a set of desired on-target complexes (each with a target secondary structure and target concentration), corresponding to the on-pathway hybridization products for a given step, and a set of undesired off-target complexes (each with vanishing target concentration), corresponding to on-pathway reactants and off-pathway hybridization crosstalk for a given step;[41] in this scenario, these elementary step tubes promote full conversion of cognate reactants into cognate products and against local hybridization crosstalk between these same reactants. In some embodiments, to simultaneously design N orthogonal systems, elementary step tubes are specified for each orthogonal system. In some embodiments, to design against off-pathway interactions between systems, a single global crosstalk tube is also specified.[41] In some embodiments, in the global crosstalk tube, the on-target complexes correspond to all reactive species generated during all elementary steps for all systems (for example, single-stranded domains). In some embodiments, in the global crosstalk tube, the off-target complexes correspond to noncognate interactions between these reactive species. In some embodiments, the global crosstalk tube ensemble omits the cognate products that the reactive species are intended to form (they appear as neither on-targets nor off-targets); in this scenario, all reactive species in the global crosstalk tube can be forced to either perform no reaction (remaining as desired on-targets) or to undergo a crosstalk reaction (forming undesired off-targets), providing the basis for minimization of global crosstalk during sequence optimization. In some embodiments, sequence design is performed subject to complementarity constraints including any combination of: 1) sequence constraints inherent to the reaction pathway (for example in FIG. 4B, domain "d" complementary to domain "d*", etc), 2) sequence constraints imposed by the trigger sequence X, 3) sequence constraints imposed by the target Y, 4) sequence constraints imposed by the protein effector (for example, Cas, dCas, Cas9, dCas9, etc), 5) sequence constraints imposed by a synthetic terminator,[41] other sequence constraints. In some embodiments, sequences are optimized by reducing the ensemble defect quantifying the average fraction of incorrectly paired nucleotides over the multi-tube ensemble.[41] In some embodiments, defect weights are applied within the ensemble defect to prioritize design effort.[41] In some embodiments, optimization of the ensemble defect implements both a positive design paradigm, explicitly design for on-pathway elementary steps, and a negative design paradigm, explicitly design against off-pathway crosstalk.[41]

In some embodiments, the cgRNA and/or trigger sequence is engineered using directed evolution. In some embodiments, the cgRNA and/or trigger sequence is engineered using a combination of rational design and directed evolution. In some embodiments, the cgRNA and/or trigger sequence is engineered using machine learning. In some embodiments, the cgRNA and/or trigger sequence is engineered using machine learning and directed evolution. In some embodiments, the cgRNA and/or trigger sequence is engineered using a combination of rational design, machine learning, and/or directed evolution.

In some embodiments, the cgRNA comprises one or more chemical modifications that alter one or more of degradation properties, affinity, biological activity, and/or delivery properties of the cgRNA, optionally wherein the one or more chemical modifications is selected from the group consisting of arabino nucleic acids (ANA), locked nucleic acids (LNA), peptide nucleic acids (PNA), phosphoroamidate DNA analogues, phosphorodiamidate morpholino oligomers (PMO), cyclohexene nucleic acids (CeNA), tricycloDNA (tcDNA), bridged nucleic acids (BNA), phosphorothioate modification, 2'-fluoro (2'-F) modification, 2'-fluoroarabino (2'-FANA) modification, 2'O-Methyl (2'O-Me) modification, and 2'O-(2-methoxyethyl) (ZO-MOE) modification.

In some embodiments, the trigger comprises one or more chemical modifications that alter one or more of degradation properties, affinity, biological activity, and delivery properties of the trigger, optionally wherein the one or more chemical modifications is selected from the group consisting of arabino nucleic acids (ANA), locked nucleic acids (LNA), peptide nucleic acids (PNA), phosphoroamidate DNA analogues, phosphorodiamidate morpholino oligomers (PMO), cyclohexene nucleic acids (CeNA), tricycloDNA (tcDNA), bridged nucleic acids (BNA), phosphorothioate modification, 2'-fluoro (2'-F) modification, 2'-fluoroarabino (2'-FANA) modification, 2'O-Methyl (ZO-Me) modification, and 2'O-(2-methoxyethyl) (ZO-MOE) modification.

In some embodiments, the sequence of the cgRNA is a subsequence of a longer RNA, DNA, or any polymer capable of base-pairing. In some embodiments, the polymer containing the cgRNA includes chemical linkers that are not capable of base-pairing. In some embodiments, the sequence of the trigger is a subsequence of a longer RNA, DNA, or any polymer capable of base-pairing. In some embodiments, the polymer containing the trigger includes chemical linkers that are not capable of base-pairing.

In some embodiments, one or more duplexes (or stems) formed by complementary or partially complementary domains of the cgRNA, 5' fragment cg5, 3' fragment cg3, cgRNA:inhibitor complex, cgRNA:helper complex, cg5:cg3 complex, trigger:cg5:cg3 complex, cg3:trigger complex, inhibitor:trigger complex, and/or cgRNA:trigger complex (or any of the cgRNA molecules, cgRNA fragments, triggers, inhibitors, helpers and/or complexes thereof) may contain zero, one, or more of mismatches, loops, multiloops, bulge loops, interior loops, or nicks between strands.

In some embodiments, the cgRNA, cgRNA fragments, inhibitor, and/or helper is expressed in the cells, living organisms, or artificial settings in which it interacts with effector, input, and/or target. In some embodiments, the trigger is expressed in the cells, living organisms or artificial settings in which it interacts with effector, input, and/or target. In some embodiments, the cgRNA, inhibitor, and/or helper is artificially synthesized or exogenously expressed and delivered to the cells, living organisms or artificial settings in which it interacts with effector, input, and/or target. In some embodiments, the trigger is artificially synthesized or exogenously expressed and delivered to the cells, living organisms or artificial settings in which it interacts with effector, input, and/or target. In some embodiments, the effector is expressed in the cells, living organisms or artificial settings in which it interacts with cgRNA, input, and/or target. In some embodiments, the effector is artificially synthesized or exogenously expressed and delivered to the cells, living organisms or artificial settings in which it interacts with effector, input, and/or target. In some embodiments, any of the cgRNA, cgRNA fragments, inhibitor, helper, and/or effector are delivered as a plasmid and expressed. In some embodiments, any of the cgRNA, cgRNA fragments, inhibitor, helper, and/or effector are delivered by a virus, by electroporation, by transfection, by lateral gene transfer, by microinjection, or by nanoparticle delivery. In some embodiments, any of the cgRNA, cgRNA fragments, inhibitor, helper, and/or effector are delivered as DNA and expressed.

In some embodiments, one or more of the cgRNA, cgRNA fragments, inhibitor, and/or helper strands is expressed with a self-cleaving ribozyme at one or both ends that cleaves the transcript to create the cgRNA, cgRNA fragments, inhibitor, and/or helper strands.

In some embodiments, one or more of the cgRNA, cgRNA fragments, inhibitor, and/or helper strands contains a protective element (PEL) at one or both ends, or internally, to inhibit degradation of the strand by ribonucleases.

In some embodiments, the target nucleic acid is endogenous RNA, DNA, or another polymer capable of base-pairing, whether the polymer is coding or non-coding. In some embodiments, the target nucleic acid is exogenous RNA, DNA, or another polymer capable of base-pairing, whether the polymer is coding or non-coding.

In some embodiments, the RNA guided effector is selected from the group consisting of Cas9, nickase Cas9, dCas9, silencing dCas9, inducing dCas9, catalytically dead dCas9, Cas12a, Cas13d, protein fusions or derivatives thereof, RNA-guided CRISPR effector protein or protein complex, or any protein from a similar pathway.

In some embodiments, the cgRNA conditionally performs a downstream function on a target nucleic acid in a living organism, ecosystem, tissue extract, cell lysate, and/or artificial system of reconstituted biological components. In some embodiments, the downstream effector function is the downregulation of the expression of a target nucleic acid. In some embodiments, the downstream effector function is the upregulation of the expression of a target nucleic acid. In some embodiments, the downstream effector function is the editing of the sequence of a target nucleic acid without template. In some embodiments, the downstream effector function is the editing of the sequence of a target nucleic acid with template. In some embodiments, the expression of a therapeutic target is conditionally downregulated in diseased cells or tissues. In some embodiments, the expression of a therapeutic target is conditionally upregulated in diseased cells or tissues. In some embodiments, the sequence of a therapeutic target is conditionally edited in diseased cells or tissues. In some embodiments, the regulation and/or editing of a target gene mediated by a cgRNA results in the conditional death of diseased cells or tissues. In some embodiments, the expression of a target gene is conditionally downregulated in selected prokaryotes. In some embodiments, the expression of a target gene is conditionally upregulated in selected prokaryotes. In some embodiments, the sequence of a target gene is conditionally edited in selected prokaryotes. In some embodiments, the regulation and/or editing of a target gene mediated by a cgRNA results in the conditional death of selected prokaryotes. In some embodiments, the expression of a target gene is conditionally downregulated in selected cells within a plant. In some embodiments, the expression of a target gene is conditionally upregulated in selected sells within a plant. In some embodiments, the sequence of a target gene is conditionally edited in selected cells within a plant. In some embodiments, the regulation and/or editing of a target gene mediated by a cgRNA results in the conditional death of selected cells within a plant. In some embodiments, the expression of a target gene is conditionally downregulated in a sample. In some embodiments, the expression of a target gene is conditionally upregulated in a sample. In some embodiments, the sequence of a target gene is conditionally edited in a sample. In some embodiments, the regulation and/or editing of a target gene mediated by a cgRNA results in conditional cell death in a sample. In some embodiments, the expression of a target gene is conditionally downregulated in selected prokaryotes on or within a human, pet, livestock animal, or crop plant. In some embodiments, the expression of a target gene is conditionally upregulated in selected prokaryotes on or within a human, pet, livestock animal, or crop plant. In some embodiments, the sequence of a target gene is conditionally edited in selected prokaryotes on or within a human, pet, livestock animal, or crop plant. In some embodiments, the regulation and/or editing of a target gene mediated by a cgRNA results in the conditional death of selected prokaryotes on or within a human, pet, livestock animal, or crop plant. In some embodiments, the expression of a target gene is conditionally downregulated in selected eukaryotic cells. In some embodiments, the expression of a target gene is conditionally upregulated in selected eukaryotic cells. In some embodiments, the sequence of a target gene is conditionally edited in selected eukaryotic cells. In some embodiments, the regulation and/or editing of a target gene mediated by a cgRNA results in the conditional death of selected eukaryotic cells.

In schematics depicting allosteric cgRNAs, cgRNA fragments, cognate RNA triggers, target genes, RNA inhibitor strands, and/or RNA helper strands, and/or interactions between any of the above (for example, the schematics of FIGS. 4B, 4C, 5B, 5C, 6B, 6C, 7B, 7C, 8B, 8C, 9B, 9C, 9D, 9E, 10A, 10B, 10C, 23B, 23C, 24B, 24C, 25B, 25C, 26B, 26C, 27B, 27C, 28B, 28C, 28D, 29B, 29C, 29D), the 3' end of each strand is depicted with an arrowhead. In some embodiments, a base-paired region in a schematic depicting allosteric cgRNAs, cognate RNA triggers, target genes, RNA inhibitor strands, and/or RNA helper strands, and/or interactions between any of the above (for example, the schematics of FIGS. 4B, 4C, 5B, 5C, 6B, 6C, 7B, 7C, 8B, 8C, 9B, 9C, 9D, 9E, 10A, 10B, 10C, 23B, 23C, 24B, 24C, 25B, 25C, 26B, 26C, 27B, 27C, 28B, 28C, 28D, 29B, 29C, 29D), comprises 1, 2, or more base pairs. In some embodiments, a base-paired region in a schematic depicting allosteric cgRNAs, cgRNA fragments, cognate RNA triggers, target genes, RNA inhibitor strands, and/or RNA helper strands, and/or interactions between any of the above (for example, the schematics of FIGS. 4B, 4C, 5B, 5C, 6B, 6C, 7B, 7C, 8B, 8C, 9B, 9C, 9D, 9E, 10A, 10B, 10C, 23B, 23C, 24B, 24C, 25B, 25C, 26B, 26C, 27B, 27C, 28B, 28C, 28D, 29B, 29C, 29D), comprises a duplex (or stem) comprising 1, 2, or more base pairs. In some embodiments, a base-paired region in a schematic depicting allosteric cgRNAs, cgRNA fragments, cognate RNA triggers, target genes, RNA inhibitor strands, and/or RNA helper strands, and/or interactions between any of the above (for example, the schematics of FIGS. 4B, 4C, 5B, 5C, 6B, 6C, 7B, 7C, 8B, 8C, 9B, 9C, 9D, 9E, 0A, 10B, 10C, 23B, 23C, 24B, 24C, 25B, 25C, 26B, 26C, 27B, 27C, 28B, 28C, 28D, 29B, 29C, 29D), comprises a duplex (or stem) comprising 1, 2, or more consecutive base pairs. In some embodiments, a base-paired region in a schematic depicting allosteric cgRNAs, cgRNA fragments, cognate RNA triggers, target genes, RNA inhibitor strands, and/or RNA helper strands, and/or interactions between any of the above (for example, the schematics of FIGS. 4B, 4C, 5B, 5C, 6B, 6C, 7B, 7C, 8B, 8C, 9B, 9C, 9D, 9E, 10A, 10B, 10C, 23B, 23C, 24B, 24C, 25B, 25C, 26B, 26C, 27B, 27C, 28B, 28C, 28D, 29B, 29C, 29D) is optional. In some embodiments, any of allosteric cgRNAs, cgRNA fragments, cognate RNA triggers, RNA inhibitor strands, and/or RNA helper strands can be extended at either or both of the 5' or 3' ends (or internally) by zero, one, or more additional domains, wherein any additional domains may be unstructured, may serve as a protective element (PEL) to reduce RNA degradation, may serve as a toehold, may comprise additional base-pairs, or any combination of the above. In some embodiments, the cognate RNA trigger is a subsequence of an endogenous RNA. In some embodiments, any of allosteric cgRNAs, cgRNA fragments, cognate RNA triggers, RNA inhibitor strands, and/or RNA helper strands may include one or more chemically modified nucleotides or synthetic nucleic acid analogs or other materials capable of base-pairing (including but not limited to DNA, XNA, PNA, 2'OMe-RNA) and/or one or more chemical linkers that are not capable of base-pairing. In some embodiments, the Cas9 handle is a modified handle with a different structure and/or sequence relative to a wildtype Cas9 handle (for example, the "flip+extend" (FE)-modified Cas9 handle used in the experimental studies of FIGS. 14-16)[42]. In some embodiments, the structure and/or sequence of the Cas handle is modified relative to a wildtype Cas sequence via rational design, machine learning, directed evolution, or any combination thereof.

In some embodiments, additional regions or sequence domains may be added at either end of any of the depicted regions or sequence domains. In some embodiments, one or more depicted regions (e.g., sequence domains or nucleotides) are optional.

In some embodiments, an inactive cgRNA (for example, Mechanisms 1B, 2B, 3B, 4A, 5, 6, 7, 8, 9) can be activated by a first trigger sequence (OFF→ON logic). In some embodiments, a cgRNA that is activated by a first trigger sequence (OFF→ON logic) can later be inactivated by second trigger sequence (ON→OFF logic). In some embodiments, a cgRNA can be cycled between the ON and OFF states by first and second trigger sequences.

In some embodiments, an active cgRNA (for example, Mechanisms 1A, 2A, 3A, 4B, 4C) can be inactivated by a first trigger sequence (ON→OFF logic). In some embodiments, a cgRNA that is inactivated by a first trigger sequence (OFF→ON logic) can later be activated by second trigger sequence (ON→OFF logic). In some embodiments, a cgRNA can be cycled between the ON and OFF states by first and second trigger sequences.

In some embodiments, a cgRNA can catalytically regenerate the trigger sequence (for example, Mechanisms 7, 8, 9) so that one trigger molecule can toggle the state of multiple copies of the cgRNA.

Although the foregoing invention has been described in terms of certain preferred embodiments, other embodiments will be apparent to those of ordinary skill in the art. Additionally, other combinations, omissions, substitutions and modification will be apparent to the skilled artisan, in view of the disclosure herein. Accordingly, any invention herein is not intended to be limited by the recitation of the preferred embodiments, but is instead to be defined by reference to the appended claims. All references cited herein are incorporated by reference in their entirety.

Arrangements

In addition to the foregoing, some embodiments provide the following arrangements:

Arrangement 1: An allosteric conditional guide RNA (cgRNA) comprising a target-binding region and a trigger-binding region: a. wherein the target-binding region is non-overlapping with the trigger-binding region; b. wherein the cgRNA is active in the absence of a cognate RNA trigger, wherein the cgRNA is configured to mediate the function of a Cas protein effector on a target gene that binds the target-binding region; and c. wherein upon hybridization to the cognate RNA trigger, the cgRNA is inactivated, inhibiting further mediation of Cas function on the target gene.

Arrangement 2: The allosteric cgRNA of Arrangement 1, further comprising a Cas handle wherein the target-binding region is 5' of the Cas handle and the trigger-binding region is 3' of the Cas handle.

Arrangement 3: The allosteric cgRNA of Arrangement 1, the cgRNA further comprising a first terminator hairpin with an extended loop comprising 5 or more nucleotides wherein the trigger-binding region comprises: a. zero, one, or more nucleotides of a linker 5'-adjacent to the first terminator hairpin; b. zero, one, or more nucleotides in a 5' portion of a stem of the first terminator hairpin; and c. one or more nucleotides in the extended loop of the first terminator hairpin; wherein the cgRNA is inactivated upon hybridization of the cognate RNA trigger to the cgRNA.

Arrangement 4: The allosteric cgRNA of Arrangement 1, further comprising a Cas handle with an extended loop wherein the target-binding region is 5' of the Cas handle and the trigger-binding region comprises a portion of the extended loop of the Cas handle and no nucleotides 5' of the Cas handle.

Arrangement 5: The allosteric cgRNA of Arrangement 4, further comprising a first terminator hairpin with an extended loop comprising 5 or more nucleotides such that the trigger-binding region comprises: a. one or more nucleotides in the extended loop of the Cas handle; and b. one or more nucleotides in the extended loop of the first terminator hairpin, wherein upon hybridization of the cognate RNA trigger to the cgRNA, the cgRNA is inactivated.

Arrangement 6: The allosteric cgRNA of Arrangement 4, the cgRNA further comprising a first terminator hairpin with an extended loop comprising 5 or more nucleotides wherein the trigger-binding region further comprises: a. zero, one, or more nucleotides of a linker 5'-adjacent to the first terminator hairpin; b. zero, one, or more nucleotides in a 5' portion of a stem of the first terminator hairpin; and c. one or more nucleotides in the extended loop of the first terminator hairpin, wherein the cgRNA is inactivated upon hybridization of the cognate RNA trigger to the cgRNA.

Arrangement 7: An allosteric conditional guide RNA (cgRNA) and an RNA inhibitor strand, wherein the cgRNA comprises a target-binding region and an inhibitor-binding region, and the RNA inhibitor strand comprises a trigger-binding region, wherein the cgRNA is configured to bind to a portion of the trigger-binding region to form a cgRNA:inhibitor complex: a. wherein the target-binding region is not base-paired to the trigger-binding region in the cgRNA:inhibitor complex; b. wherein the cgRNA:inhibitor complex is inactive in the absence of a cognate RNA trigger; and c. wherein upon hybridization of a cognate RNA trigger to the inhibitor, the cgRNA is activated, mediating the function of a Cas protein effector on a target gene that binds the target-binding region.

Arrangement 8: The allosteric cgRNA and RNA inhibitor strand of Arrangement 7, the cgRNA further comprising a Cas handle wherein the target-binding region is 5' of the Cas handle and the inhibitor-binding region is 3' of the Cas handle.

Arrangement 9: The allosteric cgRNA and RNA inhibitor strand of Arrangement 7, the inhibitor further comprising a toehold of one or more unpaired nucleotides at one or both ends, the cgRNA further comprising a first terminator hairpin with an extended loop comprising 5 or more nucleotides, the cgRNA further comprising an inhibitor-binding region comprising: a. zero, one, or more nucleotides of a linker 5'-adjacent to the first terminator hairpin; b. zero, one, or more nucleotides in a 5' portion of a stem of the first terminator hairpin; and c. one or more nucleotides in the extended loop of the first terminator hairpin, wherein the cgRNA is inactive in the cgRNA:inhibitor complex, and wherein hybridization of the cognate RNA trigger to the inhibitor displaces the cgRNA from the inhibitor, thereby activating the cgRNA.

Arrangement 10: The allosteric cgRNA and RNA inhibitor strand of Arrangement 7, the cgRNA further comprising a Cas handle with an extended loop wherein the target-binding region is 5' of the Cas handle, and wherein the inhibitor-binding region comprises a portion of the extended loop of the Cas handle and no nucleotides 5' of the Cas handle.

Arrangement 11: The allosteric cgRNA and RNA inhibitor strand of Arrangement 10, the inhibitor further comprising a toehold of one or more unpaired nucleotides at one or both ends, the cgRNA further comprising a first terminator hairpin with an extended loop comprising 5 or more nucleotides, and the inhibitor-binding region comprising: a. one or more nucleotides in the extended loop of the Cas handle; and b. one or more nucleotides in the extended loop of the first terminator hairpin; wherein the cgRNA is inactive in the cgRNA:inhibitor complex, and wherein hybridization of the cognate RNA trigger to the inhibitor displaces the cgRNA from the inhibitor, thereby activating the cgRNA.

Arrangement 12: The allosteric cgRNA and RNA inhibitor strand of Arrangement 10, the inhibitor further comprising a toehold of one or more unpaired nucleotides at one or both ends, the cgRNA further comprising a first terminator hairpin with an extended loop comprising 5 or more nucleotides, and the inhibitor-binding region comprising: a. one or more nucleotides in the extended loop of the Cas handle; b. zero, one, or more nucleotides of a linker 5'-adjacent to the first terminator hairpin; c. zero, one, or more nucleotides of a 5' portion of a stem of the first terminator hairpin; and d.

one or more nucleotides in the extended loop of the first terminator hairpin; wherein the cgRNA is inactive in the cgRNA:inhibitor complex, and wherein hybridization of the cognate trigger to the inhibitor displaces the cgRNA from the inhibitor, thereby activating the cgRNA.

Arrangement 13: An allosteric conditional guide RNA (cgRNA) comprising a 5' fragment (cg5) and a 3' fragment (cg3), cg5 comprising a target-binding region and a trigger-binding region, and cg3 comprising a cognate RNA trigger: a. wherein the target-binding region is non-overlapping with the trigger-binding region; b. wherein cg5 and cg3 are inactive when not bound to each other; and c. wherein upon hybridization of cg3 to cg5 to form a cg5:cg3 complex, the cgRNA is activated, mediating the function of a Cas protein effector on a target gene that binds the target-binding region.

Arrangement 14: The allosteric cgRNA of Arrangement 13 wherein the fragment cg5 further comprises a Cas handle wherein the target-binding region is 5' of the Cas handle and the trigger-binding region is 3' of the Cas handle.

Arrangement 15: The allosteric cgRNA of Arrangement 13, wherein fragment cg5 further comprises a trigger-binding region comprising a 5' portion of a stem of a terminator duplex; and fragment cg3 further comprises a 3' portion of the stem of the terminator duplex, such that hybridization of cg5 to cg3 forms the terminator duplex, activating the cgRNA.

Arrangement 16: An allosteric conditional guide RNA (cgRNA) comprising a 5' fragment (cg5) and a 3' fragment (cg3), cg5 comprising a target-binding region and a trigger-binding region, and cg3 configured to bind to a portion of the trigger-binding region to form a cg5:cg3 complex: a. wherein the target-binding region is non-overlapping with the trigger-binding region; b. wherein the cg5:cg3 complex is active in the absence of a cognate RNA trigger, mediating the function of a Cas protein effector on a target gene that binds the target-binding region; c. wherein cg5 and cg3 are inactive when not bound to each other; and d. wherein hybridization of the cognate RNA trigger to cg5 displaces cg3 from cg5, thereby inhibiting further mediation of Cas function on the target gene.

Arrangement 17: The allosteric cgRNA of Arrangement 16, wherein the fragment cg5 further comprises a Cas handle wherein the target-binding region is 5' of the Cas handle and the trigger-binding region is 3' of the Cas handle.

Arrangement 18: The allosteric cgRNA of Arrangement 16, wherein the fragment cg5 further comprises a trigger-binding region comprising: a. a 5' portion of a stem of a terminator duplex; b. zero, one, or more nucleotides of a linker 5'-adjacent to the 5' portion of the stem of the terminator duplex; and c. a toehold comprising zero, one, or more nucleotides 3'-adjacent to the 5' portion of the stem of the terminator duplex; wherein the fragment cg3 further comprises a 3' portion of the stem of the terminator duplex, wherein hybridization of cg5 to cg3 forms the terminator duplex within the cg5:cg3 complex, and wherein hybridization of the trigger to cg5 displaces cg3 from cg5, thereby breaking the terminator duplex and inactivating the cgRNA.

Arrangement 19: An allosteric conditional guide RNA (cgRNA) comprising: a 5' fragment (cg5) and a 3' fragment (cg3), cg5 comprising a target-binding region; and cg3 comprising a trigger-binding region, wherein cg5 is configured to bind to a portion of the trigger-binding region to form a cg5:cg3 complex: a. wherein the target-binding region is not base-paired to the trigger-binding region in the cg5:cg3 complex; b. wherein the cg5:cg3 complex is active in the absence of a cognate RNA trigger, mediating the function of a Cas protein effector on a target gene that binds the target-binding region; c. wherein cg5 and cg3 are inactive when not bound to each other; and d. wherein hybridization of the cognate RNA trigger to cg3 displaces cg5 from cg3, thereby inhibiting further mediation of Cas function on the target gene.

Arrangement 20: The allosteric cgRNA of Arrangement 19, wherein the fragment cg5 further comprises a Cas handle wherein the target-binding region is 5' of the Cas handle, and wherein the fragment cg3 binds to cg5 3' of the Cas handle.

Arrangement 21: The allosteric cgRNA of Arrangement 19, wherein: the fragment cg3 further comprises a trigger-binding region comprising: a. a 3' portion of a stem of a terminator duplex, and b. a toehold comprising zero, one, or more nucleotides 5'-adjacent to the 3' portion of the stem of the terminator duplex; the fragment cg5 further comprises a 5' portion of the stem of the terminator duplex; and wherein hybridization of cg5 to cg3 forms the terminator duplex within the cg5:cg3 complex, and wherein hybridization of the cognate RNA trigger to cg3 displaces cg5 from cg3, thereby breaking the terminator duplex and inactivating the cgRNA.

Arrangement 22: An allosteric conditional guide RNA (cgRNA) comprising: a 5' fragment (cg5) and a 3' fragment (cg3), wherein cg5 comprises a Cas handle, a target-binding region 5' of the Cas handle, and a cg3-binding region 3' of the Cas handle, wherein cg3 comprises a cg5-binding region, and wherein either cg5 or cg3 comprises a trigger-binding region: a. wherein the target-binding region is non-overlapping with the trigger-binding region and is configured not to bind to the trigger-binding region; b. wherein cg5 and cg3 are inactive when not bound to each other; c. wherein in the absence of a cognate RNA trigger, cg5 and cg3 are configured to be inhibited from binding to each other; and d. wherein upon hybridization of the cognate RNA trigger to either cg5 or cg3, cg5 and cg3 hybridize to form a trigger:cg5:cg3 complex that activates the cgRNA, thereby mediating the function of a Cas protein effector on a target gene that binds the target-binding region.

Arrangement 23: The allosteric cgRNA of Arrangement 22, wherein the fragment cg5 further comprises: a. a trigger-binding region comprising a first inhibitor region, and b. a second inhibitor region; wherein in the absence of the cognate RNA trigger, the first inhibitor region is configured to bind to the second inhibitor region, thereby inhibiting binding between cg5 and cg3.

Arrangement 24: The allosteric cgRNA of Arrangement 23, wherein: a. the cognate RNA trigger comprises a cg5-binding region; b. the trigger-binding region further comprises a toehold of one or more unpaired nucleotides at one or both ends; c. the cg3-binding region of cg5 comprises a 5' portion of a stem of a terminator duplex; and d. the cg5-binding region of cg3 comprises a 3' portion of the stem of the terminator duplex; wherein upon hybridization of the cognate RNA trigger to cg5, cg5 hybridizes to cg3 to form the terminator duplex, thereby activating the cgRNA.

Arrangement 25: The allosteric cgRNA of Arrangement 22, wherein cg3 further comprises: a. a trigger-binding region comprising a first inhibitor region, and b. a second inhibitor region; wherein in the absence of the cognate RNA trigger, the first inhibitor region is configured to bind the second inhibitor region, thereby inhibiting binding between cg5 and cg3.

Arrangement 26: The allosteric cgRNA of Arrangement 25, wherein: a. the cognate RNA trigger comprises a cg3-binding region; b. the trigger-binding region further comprises a toehold of one or more unpaired nucleotides at one or both ends; c. the cg5-binding region of cg3 comprises a 3' portion of a stem of a terminator duplex; and d. the cg3-binding region of cg5 comprises a 5' portion of the stem of the terminator duplex; wherein upon hybridization of the cognate RNA trigger to cg3, cg3 hybridizes to cg5 to form the terminator duplex, thereby activating the cgRNA.

Arrangement 27: The allosteric cgRNA of Arrangement 22 wherein cg5 further comprises: a. a trigger-binding region comprising a first inhibitor region; and b. a second inhibitor region; and wherein cg3 further comprises: c. a third inhibitor region; and d. a fourth inhibitor region, wherein in the absence of a cognate RNA trigger, the first inhibitor region is configured to bind the second inhibitor region and the third inhibitor region is configured to bind to the fourth inhibitor region, thereby inhibiting binding between cg5 and cg3.

Arrangement 28: The allosteric cgRNA of Arrangement 27, wherein: a. the cognate RNA trigger comprises a cg5-binding region; b. the trigger-binding region of cg5 further comprises a toehold of one or more unpaired nucleotides at one or both ends; c. the cg3-binding region of cg5 comprises a 5' portion of a stem of a terminator duplex; and d. the cg5-binding region of cg3 comprises a 3' portion of the stem of the terminator duplex comprising a toehold of one or more unpaired nucleotides at one or both ends; wherein upon hybridization of the cognate RNA trigger to cg5, cg5 hybridizes to cg3 to form the terminator duplex, thereby activating the cgRNA.

Arrangement 29: The allosteric cgRNA of Arrangement 27 wherein the trigger-binding region of cg5 is 5' of the target-binding region.

Arrangement 30: The allosteric cgRNA of any one of Arrangements 27, 28, and 29, wherein cg3 comprises a trigger mimic region having a sequence identical to that of the cg5-binding region of the cognate RNA trigger, wherein upon activation of the cgRNA by the cognate RNA trigger, the trigger mimic region is exposed and capable of serving as the cognate RNA trigger for a new copy of the cgRNA comprising a new copy of the 5' fragment cg5 and a new copy of the 3' fragment cg3.

Arrangement 31: The allosteric cgRNA of Arrangement 27 wherein the trigger-binding region of cg5 is 3' of the Cas handle.

Arrangement 32: The allosteric cgRNA of any one of Arrangements 27, 28, and 31 wherein the cgRNA additionally comprises a splint as a third fragment wherein the splint comprises: a. a cg3-binding region comprising a fifth inhibitor region and further comprising a toehold of one or more unpaired nucleotides at one or both ends; and b. a cg5-binding region comprising a sixth inhibitor region; wherein in the absence of a cognate RNA trigger, the fifth inhibitor region is configured to bind the sixth inhibitor region, inhibiting binding of the splint to cg5 and cg3, and wherein upon activation of the cgRNA by the cognate RNA trigger, cg3 hybridizes to the cg3-binding region of the splint and the cg5-binding region of the splint hybridizes to cg5, displacing the trigger from cg5, and catalytically regenerating the trigger which then serves as the cognate RNA trigger for a new copy of the cgRNA comprising a new copy of the 5' fragment cg5 and a new copy of the 3' fragment cg3.

Arrangement 33: The allosteric cgRNA of Arrangement 32, wherein the catalytically regenerated trigger serves as the cognate RNA trigger for a new copy of the cgRNA that further comprises a new copy of the splint fragment.

Arrangement 34: The allosteric cgRNA of any one of Arrangements 27, 28, and 31, wherein cg3 comprises a trigger mimic region having a sequence identical to that of the cg5-binding region of the cognate RNA trigger, wherein upon activation of the cgRNA by the cognate RNA trigger, the trigger mimic region hybridizes to the trigger-binding region of cg5, displacing the trigger from cg5, and catalytically regenerating the trigger which can then serve as the cognate RNA trigger for a new copy of the cgRNA comprising a new copy of the 5' fragment cg5 and a new copy of the 3' fragment cg3.

Arrangement 35: The allosteric cgRNA of any one of Arrangements 1 to 34 where the trigger is an RNA.

Arrangement 36: The allosteric cgRNA of any one of Arrangements 1 to 34 where the trigger is or is a subsequence of an mRNA, an rRNA, a lncRNA, a miRNA, or a tRNA.

Arrangement 37: The allosteric cgRNA of any one of Arrangements 1 to 34 where the cgRNA is expressed in a cell.

Arrangement 38: The allosteric cgRNA of any one of Arrangements 1 to 34 where the cgRNA is chemically synthesized.

Arrangement 39: The allosteric cgRNA of any one of the preceding Arrangements, wherein the cgRNA, cgRNA fragment, RNA inhibitor strand, and/or trigger further comprises one or more additional regions at the 5' and/or the 3' end.

Arrangement 40: The allosteric cgRNA of any one of the preceding Arrangements, wherein the cgRNA, cgRNA fragment, RNA inhibitor strand, and/or trigger comprises one or more chemical modifications that alter one or more of degradation properties, affinity, biological activity, and/or delivery properties of the cgRNA.

Arrangement 41: The allosteric cgRNA of any one of the preceding Arrangements, wherein the cgRNA, cgRNA fragment, RNA inhibitor strand, and/or trigger comprises one or more chemical modifications selected from the group consisting of arabino nucleic acids (ANA), locked nucleic acids (LNA), peptide nucleic acids (PNA), phosphoroamidate DNA analogues, phosphorodiamidate morpholino oligomers (PMO), cyclohexene nucleic acids (CeNA), tricycloDNA (tcDNA), bridged nucleic acids (BNA), phosphorothioate modification, 2'-fluoro (2'-F) modification, 2'-fluoroarabino (2'-FANA) modification, 2'O-Methyl (2'O-Me) modification, and 2'O-(2-methoxyethyl) (2'O-MOE) modification.

Arrangement 42: The allosteric cgRNA of any one of the preceding Arrangements, wherein an RNA trigger, RNA helper, and/or RNA inhibitor further comprises a protective element (PEL), wherein none, some, or all of the PEL sequence is derived from a component of a viral xrRNA sequence, and wherein the PEL reduces degradation of the RNA trigger, RNA helper, and/or RNA inhibitor in a prokaryotic or eukaryotic cell.

Arrangement 43: The allosteric cgRNA of any one of the preceding Arrangements, wherein the cgRNA and/or one or more cgRNA fragments further comprise a protective element (PEL), wherein none, some, or all of the PEL sequence is derived from a component of a viral xrRNA, and wherein the PEL reduces degradation of the cgRNA and/or the cgRNA fragments in a prokaryotic or eukaryotic cell.

Arrangement 44: The allosteric cgRNA of any one of the preceding Arrangements, wherein the cgRNA works in conjunction with Cas to mediate cell-selective induction, silencing, editing, or binding of a target gene.

Arrangement 45: A method of conditionally inhibiting mediation of Cas function on a target gene, comprising: providing an allosteric conditional guide RNA (cgRNA) according to any one of Arrangements 1 to 6 and 35-44; and combining the cgRNA with a system comprising a target gene and a Cas protein effector; wherein the cgRNA is active in mediating the function of the Cas protein effector on the target gene in the absence of a cognate RNA trigger, and wherein upon hybridization to the cognate RNA trigger, the cgRNA is inactivated, inhibiting further mediation of Cas function on the target gene.

Arrangement 46: A method of conditionally mediating the function of a Cas protein effector on a target gene, comprising: providing an allosteric conditional guide RNA (cgRNA) and an RNA inhibitor strand according to any one of Arrangements 7 to 12 and 35-44; and combining the cgRNA and RNA inhibitor strand with a system comprising a target gene and a Cas protein effector; wherein in the absence of a cognate RNA trigger, the inhibitor is bound to the cgRNA and the cgRNA is inactive; and wherein upon hybridization of a cognate RNA trigger to the inhibitor, the cgRNA is activated, mediating the function of a Cas protein effector on the target gene.

Arrangement 47: A method of conditionally mediating the function of a Cas protein effector on a target gene, comprising: providing an allosteric conditional guide RNA (cgRNA) comprising a 5' fragment (cg5) and a 3' fragment (cg3) according to any one of Arrangements 13 to 15 and 35-44; and combining the cgRNA with a system comprising a target gene and a Cas protein effector; wherein cg5 and cg3 are inactive when not bound to each other; and wherein upon hybridization of cg3 to cg5, the cgRNA is activated, mediating the function of a Cas protein effector on the target gene.

Arrangement 48: A method of conditionally inhibiting mediation of Cas function on a target gene, comprising: providing an allosteric conditional guide RNA (cgRNA) comprising a 5' fragment (cg5) and a 3' fragment (cg3) according to any one of Arrangements 16 to 18 and 35-44; and combining the cgRNA with a system comprising a target gene and a Cas protein effector; wherein in the absence of a cognate RNA trigger cg5 is bound to cg3 and the cgRNA is active; and wherein hybridization of the cognate RNA trigger to cg5 displaces cg3 from cg5, thereby inhibiting further mediation of Cas function on the target gene.

Arrangement 49: A method of conditionally inhibiting mediation of Cas function on a target gene, comprising: providing an allosteric conditional guide RNA (cgRNA) comprising a 5' fragment (cg5) and a 3' fragment (cg3) according to any one of Arrangements 19 to 21 and 35-44; and combining the cgRNA with a system comprising a target gene and a Cas protein effector; wherein in the absence of a cognate RNA trigger cg5 is bound to cg3 and the cgRNA is active; and wherein hybridization of the cognate RNA trigger to cg3 displaces cg5 from cg3, thereby inhibiting further mediation of Cas function on the target gene.

Arrangement 50: A method of conditionally mediating the function of a Cas protein effector on a target gene, comprising: providing an allosteric conditional guide RNA (cgRNA) comprising a 5' fragment (cg5) and a 3' fragment (cg3) according to any one of Arrangements 22 to 34 and 35-44; and combining the cgRNA with a system comprising a target gene and a Cas protein effector; wherein in the absence of a cognate RNA trigger, cg5 and cg3 are inhibited from binding to each other and the cgRNA is inactive; and wherein upon hybridization of the cognate RNA trigger to either cg5 or cg3, cg5 and cg3 hybridize to form a trigger:cg5:cg3 complex that activates the cgRNA, thereby mediating the function of a Cas protein effector on the target gene.

EXAMPLES

Example—Logic, Function, Structure, and Interactions of a Standard Guide RNA (gRNA)

FIG. 1A depicts the logic and function of a standard guide RNA (gRNA). A standard gRNA is always ON, unconditionally directing the activity of a protein effector to a target Y; different Cas9, dCas9, and/or Cas variants implement different functions (for example, edit, silence, induce, bind). FIG. 1B depicts structure and interactions of a standard gRNA. From 5' to 3', a standard gRNA comprises: a target-binding region, a Cas handle recognized by the protein effector, and a terminator region.

Example—Logic and Function of a Conditional Guide RNA (cgRNA)

FIG. 2 depicts the logic and function of a conditional guide RNA (cgRNA) in which a cgRNA changes conformation in response to a programmable trigger X to conditionally direct the activity of a protein effector to a programmable target Y. FIG. 2A depicts ON→OFF logic with a constitutively active cgRNA that is conditionally inactivated by X. FIG. 2B depicts OFF→ON logic with a constitutively inactive cgRNA that is conditionally activated by X.

Example—Applications of Cell-Selective Control of Regulatory Control with cgRNAs FIG. 3 illustrates applications of cell-selective regulation of CRISPR/Cas function using cgRNAs. FIG. 3A contrasts global silencing (top arrow) of target gene Y using silencing dCas9 and a standard gRNA that implements the unconditional logic "silence Y" to cell-selective silencing (bottom arrow) of target gene Y using silencing dCas9 and a conditional cgRNA, such that Y is silenced locally only where X is expressed. FIG. 3B illustrates diverse modes of cell-selective spatiotemporal regulatory control using cgRNA conditional logic (ON→OFF or OFF→ON) and different Cas9 functional variants (induce, silence, edit, bind, etc). ON→OFF and OFF→ON cgRNAs produce inverted regulatory patterns on target Y in response to a given pattern for trigger X. FIG. 3C illustrates some cell-selective and tissue-selective tools. For example, conditional gene silencing ("if gene X is transcribed, silence independent gene Y") can be used to probe genetic necessity, conditional gene activation ("if gene X is transcribed, activate independent gene Y") can be used to probe genetic sufficiency, and conditional cell death ("if gene X is transcribed, induce apoptosis") can be used to probe developmental compensation. In each case, conditional regulation is mediated by a cgRNA whose activity is toggled by a programmable trigger X. For some embodiments, by selecting a trigger X with the desired spatial and temporal expression profiles, the regulatory function is restricted to a desired cell type, tissue, or organ within an organism, mixture of cells, or ecosystem. For some embodiments, to shift conditional regulation to a different tissue type or time point, the cgRNAs can be programmed to recognize a different trigger X. For some embodiments, to enhance cell-selective spatiotemporal control in multi-cellular settings (e.g., within embryos or bacterial mixtures), multi-input conditional logic (operating on two or more inputs $X_1, X_2, \ldots$) using AND gates can be used to narrow the scope of regulation on Y; alternatively, OR gates can be used to broaden the scope of regulation on Y. In some embodiments, AND logic is implemented using split-cgRNAs that are functional only in the presence of both $X_1$ and $X_2$. In some embodiments, OR logic is executed using multiple cgRNA variants that accept different inputs ($X_1, X_2, \ldots$) but target the same output Y. FIG. 3D illustrates one example of cgRNA-mediated cell-selective reporter regulation for multiplexed in vivo RNA imaging. Four cgRNAs each detect a different mRNA input ($mRNA_1$, mRNA$_2$, mRNA$_3$, mRNA$_4$) that serves as an RNA trigger, activating the corresponding cgRNA to induce the corresponding spectrally distinct FP reporter (FP$_1$, FP$_2$, FP$_3$, FP$_4$). After once optimizing a plasmid-based reporter system expressing inducing dCas9, the 4 FP reporters, and the 4 cgRNAs, imaging a new set of mRNAs requires only updating the sequences of the cgRNAs to accept new mRNAs as triggers. This cgRNA approach offers important conceptual advantages relative to FP fusion methods, which have revolutionized the study of genetic expression,[43-45] but have the well-known drawbacks that a new fusion must be engineered for each gene of interest, that it is difficult to determine whether fusions affect the expression or function of target proteins, and that fusion methods are not applicable to imaging non-protein gene products such as coding and non-coding RNAs. cgRNAs can eliminate these issues by replacing the conventional physical link of FP fusion approaches with a logical link executed by cgRNAs that execute conditional gene induction, allowing for spatiotemporal monitoring of gene expression levels in living chick embryos without the need to modify the imaged molecules (mRNA$_1$, mRNA$_2$, mRNA$_3$, mRNA$_4$) in any way. FIG. 3E depicts the conditional logic using cgRNAs as conditional chemotherapies: "if disease marker X then regulate therapeutic target Y". Here, X is a programmable disease marker and Y is an independent therapeutic target, allowing for selective treatment or killing of diseased cells (the subset of cells containing X) while leaving healthy cells untouched (the subset of cells lacking X). In this way, cgRNAs allow for independent diagnosis (detection of disease marker X) and treatment (regulation or editing of independent therapeutic target Y).

Example—Logic, Function, and Mechanism for Allosteric ON→OFF Terminator Switch cgRNAs (Mechanism 1A)

FIG. 4 depicts the logic, function, and mechanism for allosteric ON→OFF terminator switch cgRNAs. FIG. 4A depicts the conditional logic and function of an ON→OFF terminator switch cgRNA used in conjunction with different Cas protein effectors (for example, edit, silence, induce, bind): "if not X then regulate Y" (if trigger X is not detected, then edit, silence, induce, or bind target gene Y). FIGS. 4B and 4C depict a mechanism for an allosteric ON→OFF terminator switch cgRNA: the constitutively active cgRNA is inactivated by hybridization of RNA trigger X. This mechanism offers the flexibility to rationally design sequence domains (as well as their complementary domains) "d" (linker), "e" (stem), and "f" (extended loop) in the cgRNA, independent of the sequence of the target-binding region (domain "u").

Example—Logic, Function, and Mechanism for Allosteric OFF→ON Terminator Switch cgRNAs (Mechanism 1B)

FIG. 5 depicts the logic, function, and mechanism for allosteric OFF→ON terminator switch cgRNAs. FIG. 5A depicts the conditional logic and function of an OFF→ON terminator switch cgRNA used in conjunction with different Cas protein effectors (for example, edit, silence, induce, bind): "if X then regulate Y" (if trigger X is detected, then edit, silence, induce, or bind target gene Y depending on the Cas effector). FIGS. 5B and 5C depict a mechanism for an allosteric OFF→ON terminator switch cgRNA: the cgRNA: inhibitor complex is inactive; hybridization of RNA trigger X to the inhibitor displaces the inhibitor from the cgRNA, activating the cgRNA. This mechanism offers the flexibility to rationally design sequence domains (as well as their complementary domains) "d" (linker), "e" (stem), and "f" (extended loop) in the cgRNA, as well as toehold domains "g" and "h" in the trigger, independent of the sequence of the target-binding region (domain "u").

Example—Logic, Function, and Mechanisms for Allosteric ON→OFF Splinted Switch cgRNAs (Mechanism 2A)

FIG. 6 depicts the logic, function, and mechanism for allosteric ON→OFF splinted switch cgRNAs. FIG. 6A depicts the conditional logic and function of an ON→OFF splinted switch cgRNA used in conjunction with different Cas protein effectors (for example, edit, silence, induce, bind): "if not X then regulate Y" (if trigger X is not detected, then edit, silence, induce, or bind target gene Y depending on the Cas effector). FIGS. 6B and 6C depict a mechanism for an allosteric ON→OFF splinted switch cgRNA: the constitutively active cgRNA is inactivated by hybridization of RNA trigger X. This mechanism offers the flexibility to rationally design sequence domains (as well as their complementary domains) "d" (extended Cas9 handle loop) and "e" (extended terminator hairpin loop) in the cgRNA, independent of the sequence of the target-binding region (domain "u").

Example—Logic, Function, and Mechanisms for Allosteric OFF→ON Splinted Switch cgRNAs (Mechanism 2B)

FIG. 7 depicts the logic, function, and mechanism for allosteric OFF→ON splinted switch cgRNAs. FIG. 7A depicts the conditional logic and function of an OFF→ON splinted switch cgRNA used in conjunction with different Cas protein effectors (for example, edit, silence, induce, bind): "if X then regulate Y" (if trigger X is detected, then edit, silence, induce, or bind target gene Y depending on the Cas effector). FIGS. 7B and 7C depict a mechanism for an allosteric OFF→ON splinted switch cgRNA: the cgRNA: inhibitor complex is inactive; hybridization of RNA trigger X to the inhibitor displaces the inhibitor from the cgRNA, activating the cgRNA. This mechanism offers the flexibility to rationally design sequence domains (as well as their complementary domains) "d" (extended Cas9 handle loop) and "e" (extended terminator hairpin loop) in the cgRNA, as well as toehold domains "f" and "g" in the trigger, independent of the sequence of the target-binding region (domain "u").

Example—Logic, Function, and Mechanism for Allosteric ON→OFF Tandem Switch cgRNAs (Mechanism 3A)

FIG. 23 depicts the logic, function, and mechanism for allosteric ON→OFF tandem switch cgRNAs. FIG. 23A depicts the conditional logic and function of an ON→OFF tandem switch cgRNA used in conjunction with different Cas protein effectors (for example, edit, silence, induce, bind): "if not X then regulate Y" (if trigger X is not detected, then edit, silence, induce, or bind target gene Y). FIGS. 23B and 23C depict a mechanism for an allosteric ON→OFF tandem switch cgRNA: the constitutively active cgRNA is inactivated by hybridization of RNA trigger X. This mechanism offers the flexibility to rationally design sequence Example—Logic, Function, and Mechanism for
Allosteric OFF→ON Tandem Switch cgRNAs
(Mechanism 3B)

FIG. 24 depicts the logic, function, and mechanism for allosteric OFF→ON tandem switch cgRNAs. FIG. 24A depicts the conditional logic and function of an OFF→ON tandem switch cgRNA used in conjunction with different Cas protein effectors (for example, edit, silence, induce, bind): "if X then regulate Y" (if trigger X is detected, then edit, silence, induce, or bind target gene Y depending on the Cas effector). FIGS. 24B and 24C depict a mechanism for an allosteric OFF→ON tandem switch cgRNA: the cgRNA:inhibitor complex is inactive; hybridization of RNA trigger X to the inhibitor displaces the inhibitor from the cgRNA, activating the cgRNA. This mechanism offers the flexibility to rationally design sequence domains (as well as their complementary domains) "d" (extended Cas9 handle loop), "e" (linker), "f" (stem), and "g" (extended terminator hairpin loop) in the cgRNA, as well as toehold domains "p" and "q" in the trigger, independent of the sequence of the target-binding region (domain "u").

Example—Logic, Function, and Mechanism for
Allosteric OFF→ON Split-Terminator Switch
cgRNAs (Mechanism 4A)

FIG. 8 depicts the logic, function, and mechanism for allosteric OFF→ON split-terminator switch cgRNAs. FIG. 8A depicts the conditional logic and function for an OFF→ON split-terminator switch cgRNA used in conjunction with different Cas protein effectors (for example, edit, silence, induce, bind): "if X then regulate Y" (if trigger X is detected, then edit, silence, induce, or bind target gene Y depending on the Cas effector). FIGS. 8B and 8C depict a mechanism for an allosteric OFF→ON split-terminator switch cgRNA: the constitutively inactive cgRNA is activated by hybridization of RNA trigger X. Equivalently, the cgRNA may be interpreted as a 5' fragment (cg5) and the trigger may be interpreted as a 3' fragment (cg3), such that cg5 and cg3 are inactive when not bound to each other, but such that upon binding to each other to form the complex cg5:cg3, this complex constitutes an activated conditional guide RNA capable of mediating Cas9 or dCas9 function. This mechanism offers the flexibility to rationally design the sequence of the terminator duplex (cgRNA domain "d" and trigger domain "d*"), independent of the sequence of the target-binding region (domain "u").

Example—Logic, Function, and Mechanisms for
Allosteric ON→OFF Split-Terminator Switch
cgRNA (Mechanisms 4B and 4C)

FIG. 9 depicts the logic, function, and mechanism for allosteric ON→OFF split-terminator switch cgRNAs. FIG. 9A depicts the conditional logic and function for an ON→OFF split-terminator switch cgRNA used in conjunction with different Cas protein effectors (for example, edit, silence, induce, bind): "if X then regulate Y" (if trigger X is detected, then edit, silence, induce, or bind target gene Y depending on the Cas effector). FIGS. 9B and 9C depict one mechanism for an allosteric ON→OFF split-terminator switch cgRNA (Mechanism 4B): the cgRNA:helper complex is active; hybridization of RNA trigger X to the cgRNA displaces the helper, inactivating the cgRNA. This mechanism offers the flexibility to rationally design the domains (as well as their complementary domains) "c" (linker), "d" (stem), and "e" (toehold) of the cgRNA. FIGS. 9D and 9E depict a second mechanism for an allosteric ON→OFF split-terminator switch cgRNA (Mechanism 4C): the cgRNA:helper complex is active; hybridization of RNA trigger X to the helper displaces the cgRNA, inactivating the cgRNA. This mechanism offers the flexibility to rationally design the terminator duplex (cgRNA domain "d" and RNA helper strand domains "d*") as well as toehold domain "e*" on the RNA helper strand), independent of the sequence of the target-binding region (domain "u").

Example—Logic, Function, and Mechanism for
Allosteric OFF→ON 5'-Inhibited Split-Terminator
Switch cgRNAs (Mechanism 5)

FIG. 25 depicts the logic, function, and mechanism for allosteric OFF→ON 5'-inhibited split-terminator switch cgRNAs. FIG. 25A depicts the conditional logic and function for an OFF→ON 5'-inhibited split-terminator switch cgRNA used in conjunction with different Cas protein effectors (for example, edit, silence, induce, bind): "if X then regulate Y" (if trigger X is detected, then edit, silence, induce, or bind target gene Y depending on the Cas effector). FIGS. 25B and 25C depict a mechanism for an allosteric OFF→ON 5'-inhibited split-terminator switch cgRNA: in some embodiments, the constitutively inactive cgRNA comprises a 5' fragment (cg5) and a 3' fragment (cg3):

1. such that cg5 and cg3 are inactive when not bound to each other,
2. such that in the absence of a cognate RNA trigger, cg5 and cg3 are configured to be inhibited from binding to each other,
3. and such that upon hybridization of the cognate RNA trigger to cg5, cg5 and cg3 hybridize to form a trigger:cg5:cg3 complex that activates the cgRNA, mediating the function of a Cas protein effector on a target gene.

This mechanism offers the flexibility to rationally design sequence domains (as well as their complementary domains) "a", "b", and "c", independent of the sequence of the target-binding region (domain "u").

Example—Logic, Function, and Mechanism for
Allosteric OFF→ON 3'-Inhibited Split-Terminator
Switch cgRNAs (Mechanism 6)

FIG. 26 depicts the logic, function, and mechanism for allosteric OFF→ON 3'-inhibited split-terminator switch cgRNAs. FIG. 26A depicts the conditional logic and function for an OFF→ON 3'-inhibited split-terminator switch cgRNA used in conjunction with different Cas protein effectors (for example, edit, silence, induce, bind): "if X then regulate Y" (if trigger X is detected, then edit, silence, induce, or bind target gene Y depending on the Cas effector). FIGS. 26B and 26C depict a mechanism for an allosteric OFF→ON 3'-inhibited split-terminator switch cgRNA: in some embodiments, the constitutively inactive cgRNA comprises a 5' fragment (cg5) and a 3' fragment (cg3):

1. such that cg5 and cg3 are inactive when not bound to each other, 2. such that in the absence of a cognate RNA trigger, cg5 and cg3 are configured to be inhibited from binding to each other,
3. and such that upon hybridization of the cognate RNA trigger to cg3, cg5 and cg3 hybridize to form a trigger: cg5:cg3 complex that activates the cgRNA, mediating the function of a Cas protein effector on a target gene.

This mechanism offers the flexibility to rationally design sequence domains (as well as their complementary domains) "a", "b", "c", and "d", independent of the sequence of the target-binding region (domain "u").

Example—Logic, Function, and Mechanism for Allosteric OFF→ON 5'- and 3'-Inhibited Split-Terminator Switch cgRNAs (Mechanism 7)

FIG. 27 depicts the logic, function, and mechanism for allosteric OFF→ON 5'- and 3'-inhibited split-terminator switch cgRNAs (Mechanism 7). FIG. 27A depicts the conditional logic and function for an OFF→ON 5'- and 3'-inhibited split-terminator switch cgRNA (Mechanism 7) used in conjunction with different Cas protein effectors (for example, edit, silence, induce, bind): "if X then regulate Y" (if trigger X is detected, then edit, silence, induce, or bind target gene Y depending on the Cas effector). FIGS. 27B and 27C depict a mechanism for an allosteric OFF→ON 5'- and 3'-inhibited split-terminator switch cgRNA (Mechanism 7): in some embodiments, the constitutively inactive cgRNA comprises a 5' fragment (cg5) and a 3' fragment (cg3):

1. such that cg5 and cg3 are inactive when not bound to each other,
2. such that in the absence of a cognate RNA trigger, cg5 and cg3 are configured to be inhibited from binding to each other,
3. and such that upon hybridization of the cognate RNA trigger to cg5, cg5 and cg3 hybridize to form a trigger: cg5:cg3 complex that activates the cgRNA, mediating the function of a Cas protein effector on a target gene.

In some embodiments, cg3 comprises a trigger mimic region with the same sequence as the cg5-binding region of the cognate RNA trigger, such that upon activation of the cgRNA by the cognate RNA trigger, the trigger mimic region is exposed and capable of serving as the cognate RNA trigger for a new copy of the cgRNA comprising a new copy of the 5' fragment cg5 and a new copy of the 3' fragment cg3. This mechanism offers the flexibility to rationally design sequence domains (as well as their complementary domains) "a", "b", "c", and "d", independent of the sequence of the target-binding region (domain "u").

Example—Logic, Function, and Mechanism for Allosteric OFF→ON 5'- and 3'-Inhibited Split-Terminator Switch cgRNAs (Mechanism 8)

Figure 28:
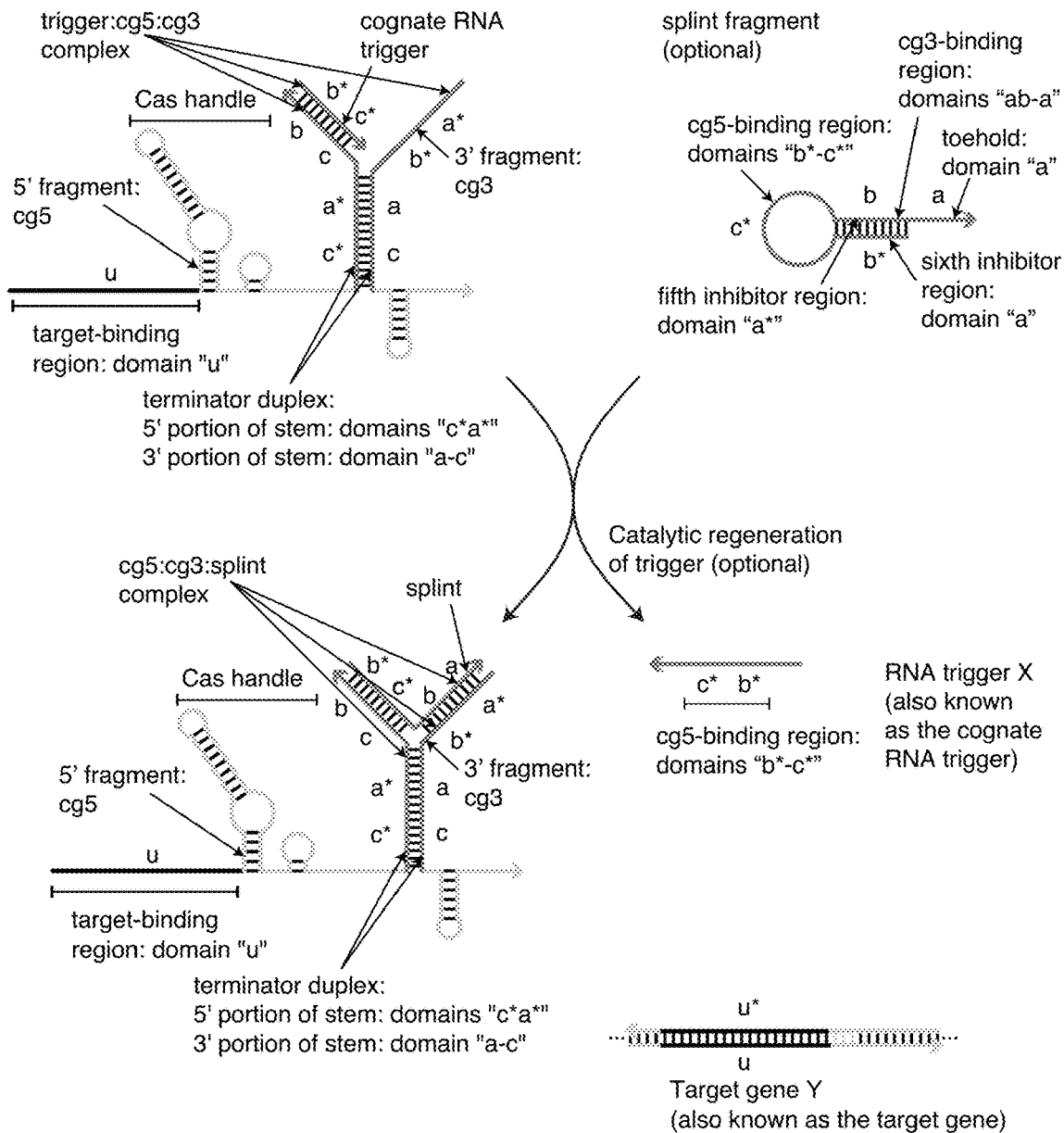

FIG. 28 depicts the logic, function, and mechanism for allosteric OFF→ON 5'- and 3'-inhibited split-terminator switch cgRNAs (Mechanism 8). FIG. 28A depicts the conditional logic and function for an OFF→ON 5'- and 3'-inhibited split-terminator switch cgRNA (Mechanism 8) used in conjunction with different Cas protein effectors (for example, edit, silence, induce, bind): "if X then regulate Y" (if trigger X is detected, then edit, silence, induce, or bind target gene Y depending on the Cas effector). FIGS. 28B, 28C, and 28D depict a mechanism for an allosteric OFF→ON 5'- and 3'-inhibited split-terminator switch cgRNA (Mechanism 8): in some embodiments, the constitutively inactive cgRNA comprises a 5' fragment (cg5) and a 3' fragment (cg3):

1. such that cg5 and cg3 are inactive when not bound to each other,
2. such that in the absence of a cognate RNA trigger, cg5 and cg3 are configured to be inhibited from binding to each other,
   and such that upon hybridization of the cognate RNA trigger to cg5, cg5 and cg3 hybridize to form a trigger:cg5:cg3 complex that activates the cgRNA, mediating the function of a Cas protein effector on a target gene.

In some embodiments, the cgRNA additionally comprises a splint fragment such that in the absence of the cognate RNA trigger the splint fragment is configured to be inhibited from binding cg5 and cg3, and such that upon activation of the cgRNA by the cognate RNA trigger, cg3 hybridizes to the split fragment which then hybridizes to cg5, displacing the trigger from cg5 to catalytically regenerate the trigger which can then serve as the cognate RNA trigger for a new copy of the cgRNA comprising a new copy of the 5' fragment cg5, a new copy of the 3' fragment cg3, and a new copy of the splint fragment. This mechanism offers the flexibility to rationally design sequence domains (as well as their complementary domains) "a", "b", and "c", independent of the sequence of the target-binding region (domain "u").

Example—Logic, Function, and Mechanism for Allosteric OFF→ON 5'- and 3'-Inhibited Split-Terminator Switch cgRNAs (Mechanism 9)

Figure 29:
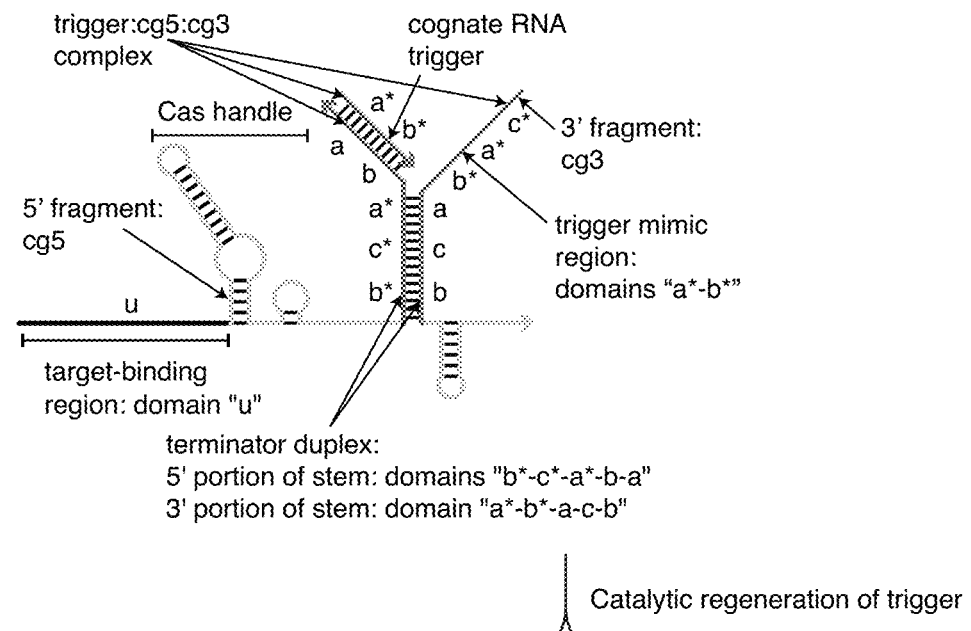
Figure 29:
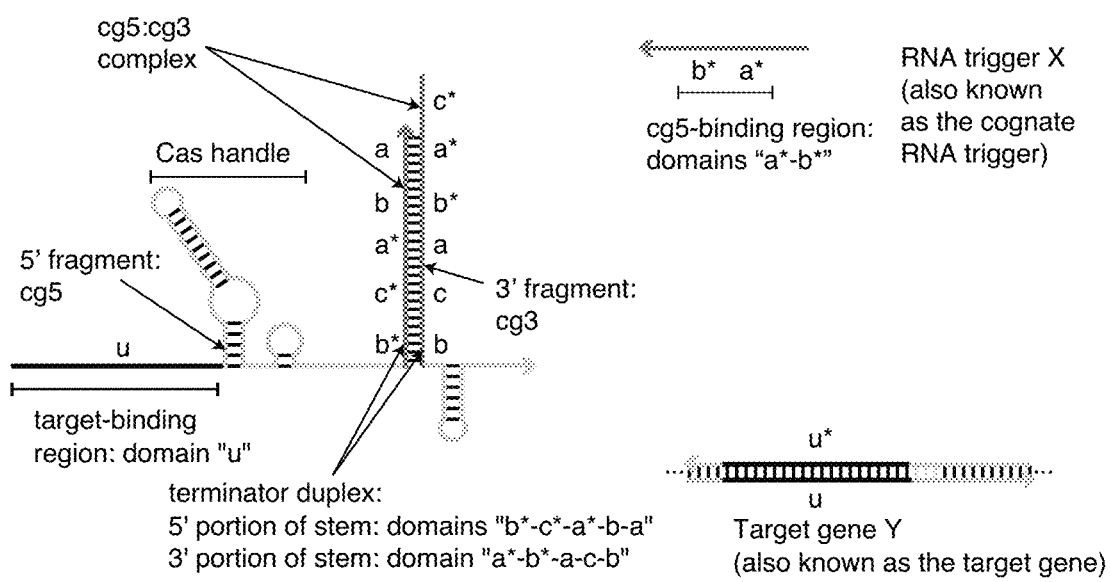

FIG. 29 depicts the logic, function, and mechanism for allosteric OFF→ON 5'- and 3'-inhibited split-terminator switch cgRNAs (Mechanism 9). FIG. 29A depicts the conditional logic and function for an OFF→ON 5'- and 3'-inhibited split-terminator switch cgRNA (Mechanism 9) used in conjunction with different Cas protein effectors (for example, edit, silence, induce, bind): "if X then regulate Y" (if trigger X is detected, then edit, silence, induce, or bind target gene Y depending on the Cas effector). FIGS. 29B, 29C, and 29D depict a mechanism for an allosteric OFF→ON 5'- and 3'-inhibited split-terminator switch cgRNA (Mechanism 9): in some embodiments, the constitutively inactive cgRNA comprises a 5' fragment (cg5) and a 3' fragment (cg3):

1. such that cg5 and cg3 are inactive when not bound to each other,
2. such that in the absence of a cognate RNA trigger, cg5 and cg3 are configured to be inhibited from binding to each other,
   and such that upon hybridization of the cognate RNA trigger to cg5, cg5 and cg3 are hybridize to form a trigger:cg5:cg3 complex that activates the cgRNA, mediating the function of a Cas protein effector on a target gene.

In some embodiments, cg3 additionally comprises a trigger mimic region such that upon activation of the cgRNA by the cognate RNA trigger, the trigger mimic region hybridizes to cg5 to displace the trigger, catalytically regenerating the trigger which can then serve as the cognate RNA trigger for a new copy of the cgRNA comprising a new copy of the 5' fragment cg5 and a new copy of the 3' fragment cg3. This mechanism offers the flexibility to rationally design sequence domains (as well as their complementary domains)

"a", "b", and "c", independent of the sequence of the target-binding region (domain "u").

Example—Depictions of Interactions Between Allosteric cgRNAs, RNA Triggers, and Cas9 or dCas9

FIG. 10 depicts interactions between allosteric cgRNAs, RNA triggers, and Cas9, dCas9 or Cas. FIG. 10A depicts interactions for an allosteric ON→OFF terminator switch cgRNA. In the ON state, the terminator switch cgRNA is constitutively active, directing the function of protein effector Cas9, dCas9, or Cas to a target gene Y in the absence of trigger. The extended loop and modified sequence domains in the terminator region are intended not to interfere with the activity of the cgRNA:Cas complex. In the OFF state, in the presence of RNA trigger X, hybridization of the trigger forms a structure incompatible with cgRNA mediation of Cas9, dCas9, and/or Cas function. FIG. 10B depicts interactions for an allosteric ON→OFF splinted switch cgRNA. In the ON state, the splinted switch cgRNA is constitutively active, directing the function of protein effector Cas9, dCas9, or Cas to a target gene Y in the absence of trigger. The extended loops in the Cas9 handle and terminator region are intended not to interfere with the activity of the cgRNA:Cas complex. In the OFF state, in the presence of RNA trigger X, hybridization of the trigger forms a splint that is structurally incompatible with cgRNA mediation of Cas9, dCas9, and/or Cas function. FIG. 10C depicts interactions for an allosteric OFF→ON split-terminator switch cgRNA. In the OFF state, the split-terminator switch cgRNA is constitutively inactive. In the absence of RNA trigger X, the cgRNA is incapable of directing the function of the protein effector Cas9, dCas9, and/or Cas. In the ON state, the complex of cgRNA and trigger X mediates the function of the protein effector Cas9, dCas9, or Cas on the target gene Y. The modified sequence domains in the terminator duplex do not to interfere with the activity of the cgRNA:trigger:Cas complex.

Example—Demonstration of Allosteric ON→OFF Terminator Switch cgRNAs in Bacteria

FIG. 11 demonstrates allosteric ON→OFF terminator switch cgRNAs performing conditional logic in *E. coli*. FIG. 11A depicts the mechanism for an allosteric ON→OFF terminator switch cgRNA: the constitutively active cgRNA is inactivated by hybridization of RNA trigger X. Rational sequence design of cgRNA terminator region (domains "d-e-f" comprising 6 nt linker, 4 nt stem, 30 nt loop) and complementary trigger region (domains "f*-e*-d*"). FIG. 11B depicts the conditional logic for an ON→OFF terminator switch cgRNA used in conjunction with silencing dCas9: "if not X then not Y" (if trigger X is not detected, then silence target gene Y). FIG. 11C demonstrates that expression of RNA trigger X (40 nt unstructured+synthetic terminator hairpin) toggles the cgRNA from ON→OFF, leading to an increase in fluorescence. Single-cell fluorescence intensities via flow cytometry. Induced expression (aTc) of silencing dCas9 and constitutive expression of mRFP target gene Y and either: standard gRNA (ideal ON state), cgRNA (ON state), cgRNA+RNA trigger X (OFF state; trigger expression is IPTG-induced), no-target gRNA that lacks target-binding region (ideal OFF state). Autofluorescence (AF): cells with no mRFP. FIGS. 11D and 11E demonstrate programmable conditional regulation using 3 orthogonal cgRNAs (A, B, C) and their corresponding cognate triggers ($X_A$, $X_B$, $X_C$). In FIG. 11D, raw fluorescence depicts ON→OFF conditional response to cognate trigger. Fold change=OFF/ON=[cognate trigger−AF]/[no trigger−AF]). In FIG. 11E, normalized fluorescence depicts orthogonality between non-cognate cgRNA/trigger pairs. Crosstalk=[non-cognate trigger−no trigger]/[cognate trigger−no trigger]). Bar graphs depict mean estimated standard error calculated based on the mean single-cell fluorescence over 20,000 cells for each of N=3 replicate wells (OFF:ON ratio and crosstalk calculated with uncertainty propagation). FIG. 11F depicts the sequences of cgRNAs A, B, C, and the sequences of triggers $X_A$, $X_B$, $X_C$. Nucleotides that are lower case italic are constrained by the target gene. Nucleotides shaded gray are constrained by dCas9. Nucleotides that are upper case italic are designed. Sequences are presented as DNA sequences; the corresponding RNA sequence is the same as the DNA sequence except that "U" replaces "T").

Figure 11A:
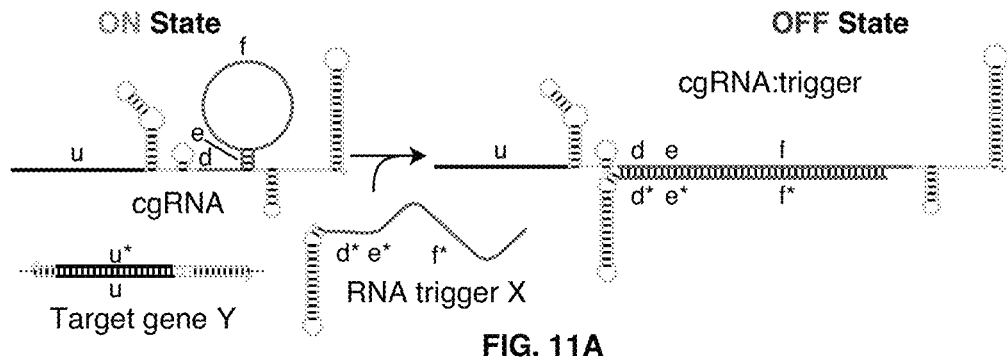
Figure 11B:
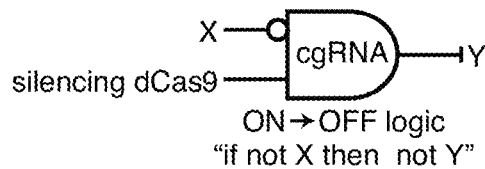
Figure 11C:
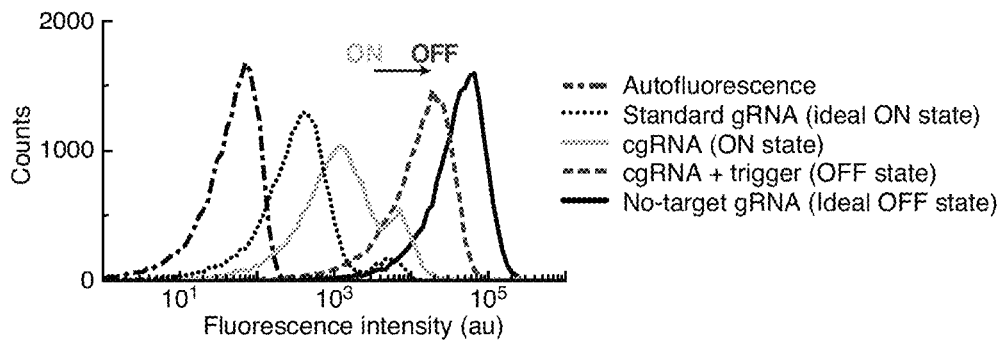
Figure 11D:
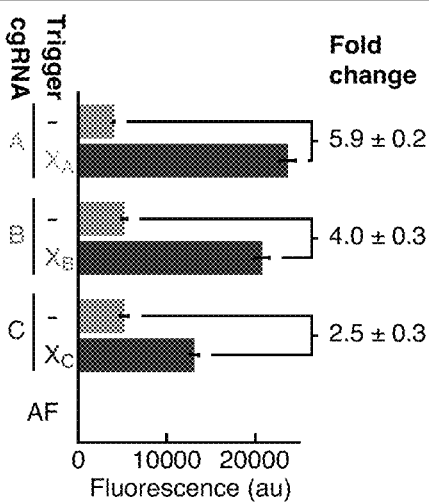
Figure 11E:
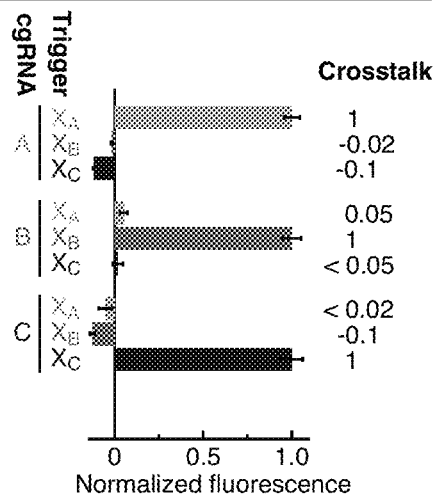

In *E. coli* expressing an allosteric ON→OFF terminator switch (FIG. 11A), silencing dCas9 and a fluorescent protein reporter (mRFP) as the target gene Y (conditional logic: "if not X then not Y'"; FIG. 11B), the cgRNA exhibits a strong conditional response to expression of RNA trigger X (FIG. 11C). FIG. 11D displays raw fluorescence data for a library of three orthogonal ON→OFF splinted switch cgRNAs with and without their cognate triggers. For this library of three cgRNA/trigger pairs, the median fold-change is approximately 4× for the ON→OFF conditional response to expression of the cognate trigger (FIG. 11D) and the median crosstalk between non-cognate/trigger pairs is approximately 2% (FIG. 11E).

Orthogonal cgRNA/trigger pairs were designed using software suite NUPACK®.[40,41] cgRNA/trigger plasmids were transformed into a modified *E. coli* MG1655 strain expressing genomically incorporated mRFP and sfGFP4.[5] Strains were grown overnight in EZ-RDM (Teknova), then diluted and grown to midlog phase (approximately 4 h). Cell density was normalized with fresh medium containing aTc for induction of silencing dCas9 expression and IPTG. Induced cells were grown for 12 h, with end-point fluorescence measured via flow cytometry.

Example—Demonstration of Allosteric ON→OFF Splinted Switch cgRNAs in Bacteria

FIG. 12 demonstrates allosteric ON→OFF splinted switch cgRNAs performing conditional logic in *E. coli*. FIG. 12A depicts the mechanism for an allosteric ON→OFF splinted switch cgRNA: the constitutively active cgRNA is inactivated by hybridization of RNA trigger X. Rational sequence design of the 35 nt Cas9 handle loop (domain "d") and an extended 35 nt terminator hairpin loop (domain "e"). FIG. 12B depicts the conditional logic for an ON→OFF splinted switch cgRNA used in conjunction with silencing dCas9: "if not X then not Y" (if trigger X is not detected, then silence target gene Y). FIG. 12C demonstrates that expression of RNA trigger X (70 nt unstructured+synthetic terminator hairpin) toggles the cgRNA from ON→OFF, leading to an increase in fluorescence. Single-cell fluorescence intensities via flow cytometry. Induced expression (aTc) of silencing dCas9 and constitutive expression of sfGFP target gene Y and either: standard gRNA (ideal ON state), cgRNA (ON state), cgRNA+RNA trigger X (OFF state), no-target gRNA that lacks target-binding region (ideal OFF state). Autofluorescence (AF): cells with no sfGFP. FIGS. 12D and 12E demonstrate programmable conditional regulation using 3 orthogonal cgRNAs (A, B, C) and their corresponding cognate triggers ($X_A$, $X_B$, $X_C$). In FIG. 12D, raw fluorescence depicts ON→OFF conditional response to cognate trigger. Fold change=OFF/ON=[cognate trigger−AF]/[no trigger−AF]). In FIG. 12E, normalized fluorescence depicts orthogonality between non-cognate cgRNA/trigger pairs. Crosstalk=[non-cognate trigger−no trigger]/[cognate trigger−no trigger]). Bar graphs depict mean±estimated standard error calculated based on the mean single-cell fluorescence over 20,000 cells for each of N=3 replicate wells (OFF:ON ratio and crosstalk calculated with uncertainty propagation). FIG. 12F depicts the sequences of cgRNAs A, B, C, and the sequences of triggers $X_A$, $X_B$, $X_C$. Nucleotides that are lower case italic are constrained by the target gene. Nucleotides shaded gray are constrained by dCas9. Nucleotides that are upper case italic are designed. Sequences are presented as DNA sequences; the corresponding RNA sequence is the same as the DNA sequence except that "U" replaces "T").

Figure 12A:
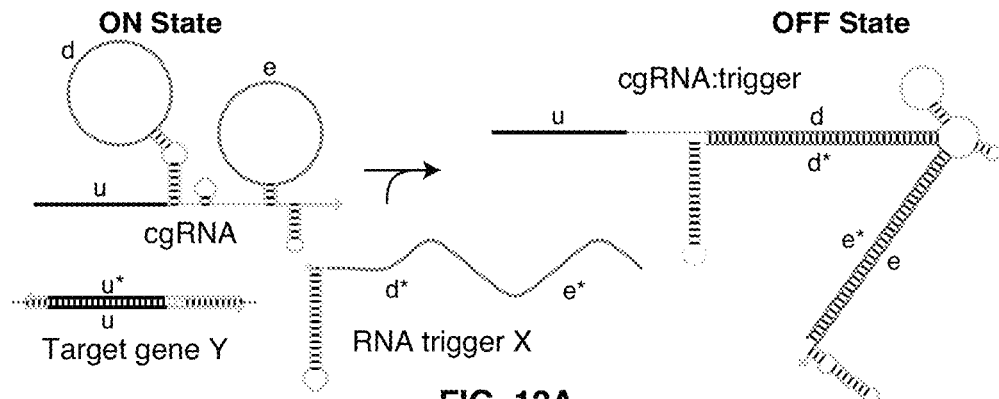
Figure 12B:
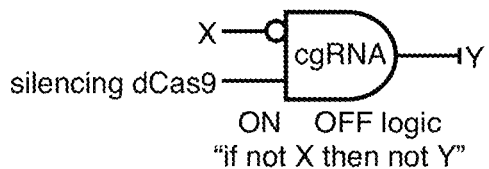
Figure 12C:
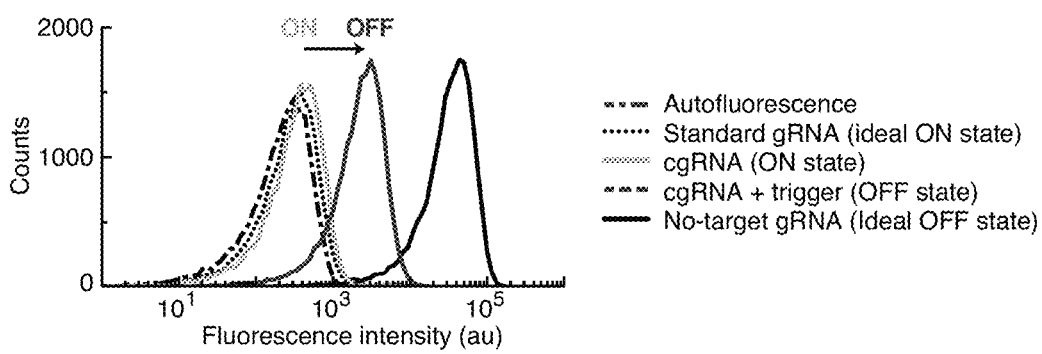
Figure 12D:
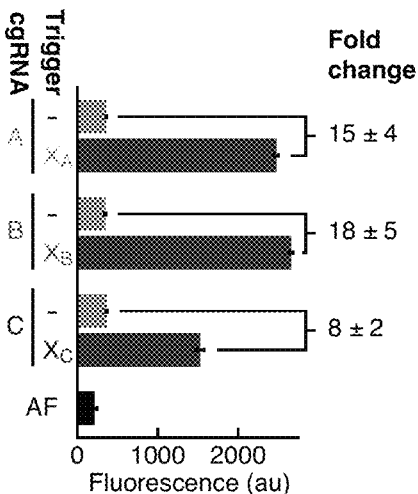
Figure 12E:
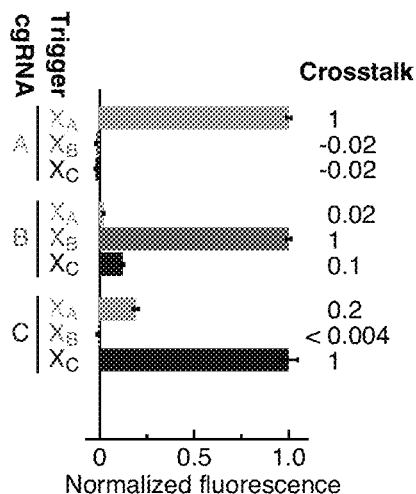

In *E. coli* expressing an allosteric ON→OFF splinted switch (FIG. 12A), silencing dCas9 and a fluorescent protein reporter (sfGFP) as the target gene Y (conditional logic: "if not X then not Y'"; FIG. 12B), the cgRNA exhibits a strong conditional response to expression of RNA trigger X (FIG. 12C). The ON state approaches the ideal ON state of a standard unconditional gRNA. FIG. 12D displays raw fluorescence data for a library of three orthogonal ON→OFF splinted switch cgRNAs with and without their cognate triggers. For this library of three cgRNA/trigger pairs, the median fold-change is approximately 15× for the ON→OFF conditional response to expression of the cognate trigger (FIG. 12D) and the median crosstalk between non-cognate/trigger pairs is approximately 2% (FIG. 12E).

Orthogonal cgRNA/trigger pairs were designed using software suite NUPACK®.[40,41] cgRNA/trigger plasmids were transformed into a modified *E. coli* MG1655 strain expressing genomically incorporated mRFP and sfGFP4.[5] Strains were grown overnight in EZ-RDM (Teknova), then diluted and grown to midlog phase (approximately 4 h). Cell density was normalized with fresh medium containing aTc for induction of silencing dCas9 expression. Induced cells were grown for 12 h, with end-point fluorescence measured via flow cytometry.

Example—Demonstration of Allosteric ON→OFF Terminator Switch cgRNAs in Human Cells FIG. 13 demonstrates allosteric ON→OFF terminator switch cgRNAs performing conditional logic in HEK 293T cells. FIG. 13A depicts the mechanism for an allosteric ON→OFF terminator switch cgRNA: the constitutively active cgRNA is inactivated by hybridization of RNA trigger X. Rational design of cgRNA terminator region (domains "d-e-f": 6 nt linker, 4 nt stem, 30 nt loop for FIGS. 13C-13H; 6 nt linker, 4 nt stem, 30 nt, 40 nt, 60 nt, 90 nt, or 140 nt loop for FIGS. 13I-13J) and complementary trigger region (domains "f*-e*-d*"). FIG. 13B depicts the conditional logic for an ON→OFF terminator switch cgRNA used in conjunction with inducing dCas9: "if not X then Y" (if trigger X is not detected, induce target gene Y). FIG. 13C demonstrates that expression of RNA trigger X (PEL+40 nt unstructured+hU6 terminator) toggles the cgRNA from ON→OFF, leading to a decrease in fluorescence. Single-cell fluorescence intensities via flow cytometry. Transfection of plasmids expressing inducing dCas9-VPR, Phi-YFP target gene Y, and either: standard gRNA+no-trigger control (ideal ON state), cgRNA+no-trigger control (ON state), cgRNA+ RNA trigger X (OFF state), no-target gRNA that lacks target-binding region+no-trigger control (ideal OFF state). The no-trigger control uses a random pool of triggers to provide a sequence-generic approximation of the metabolic load of trigger expression. FIGS. 13D-13G demonstrate programmable conditional regulation using a library of 4 orthogonal cgRNAs (Q, R, S, T) and their corresponding cognate triggers ($X_Q$, $X_R$, $X_S$, $X_T$). In FIG. 13D, raw fluorescence depicts ON→OFF conditional response to cognate trigger. In FIG. 13E, fold change=ON/OFF. In FIG. 13F, fractional dynamic range=(ON−OFF)/(ideal ON−ideal OFF). In FIG. 13G, crosstalk=(ON−OFF')/(ON−OFF) where OFF' corresponds to cgRNA+non-cognate trigger. Bar graphs depict mean±estimated standard error of the mean (with uncertainty propagation) calculated based on the mean single-cell fluorescence over 1545-3970 cells for each of N=3 replicate wells.

Figure 13A:
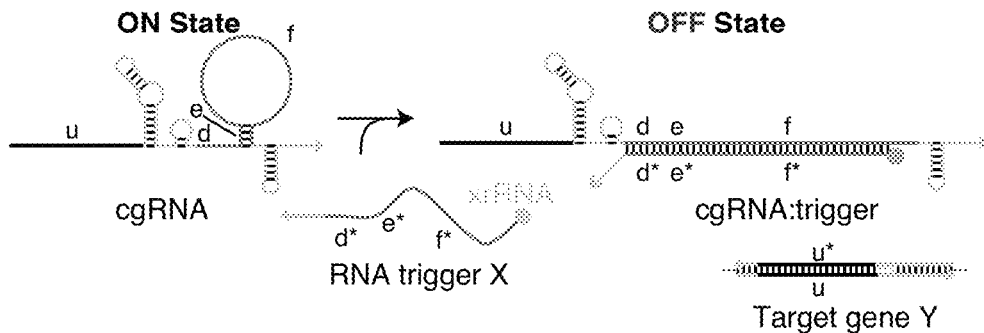
Figure 13B:
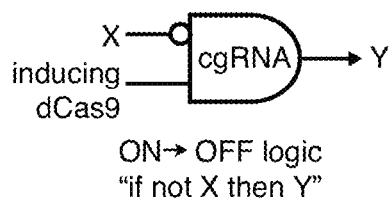
Figure 13C:
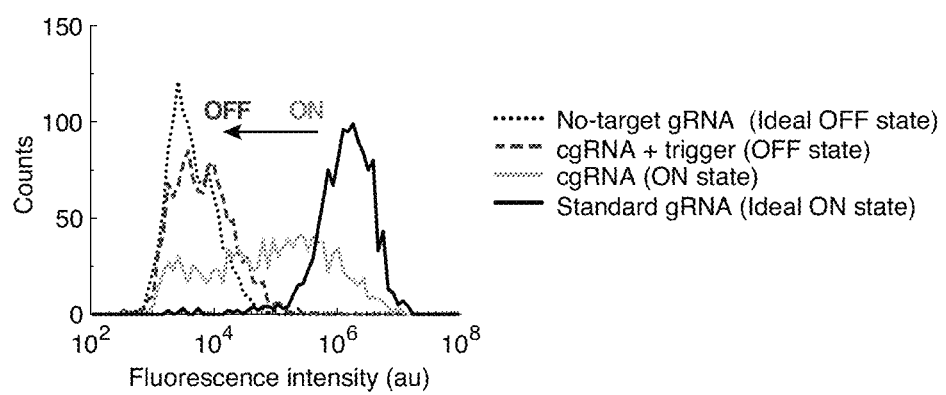
Figure 13D:
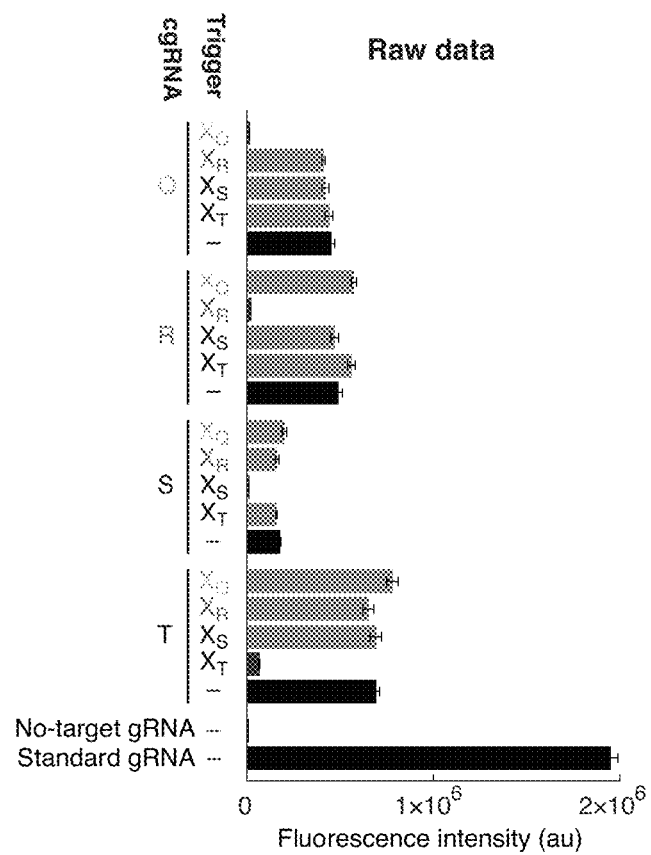
Figure 13E:
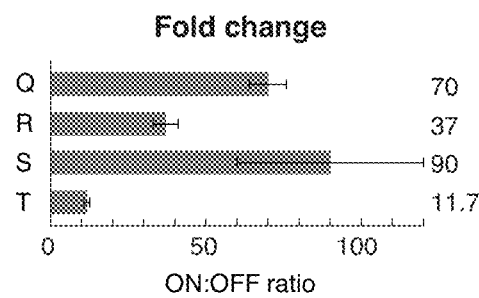
Figure 13F:
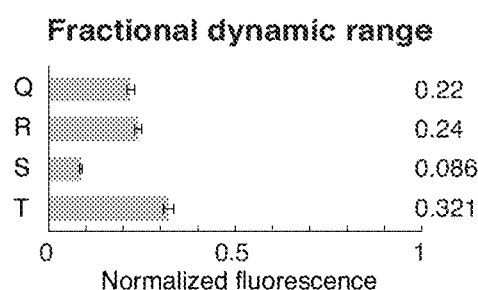
Figure 13G:
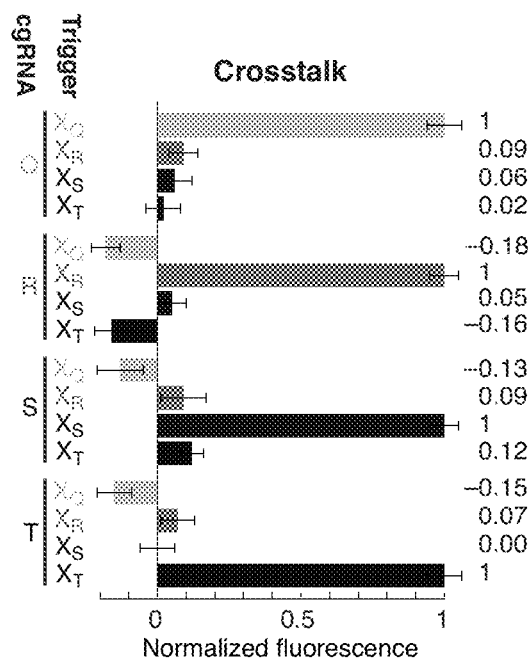
Figure 13I:
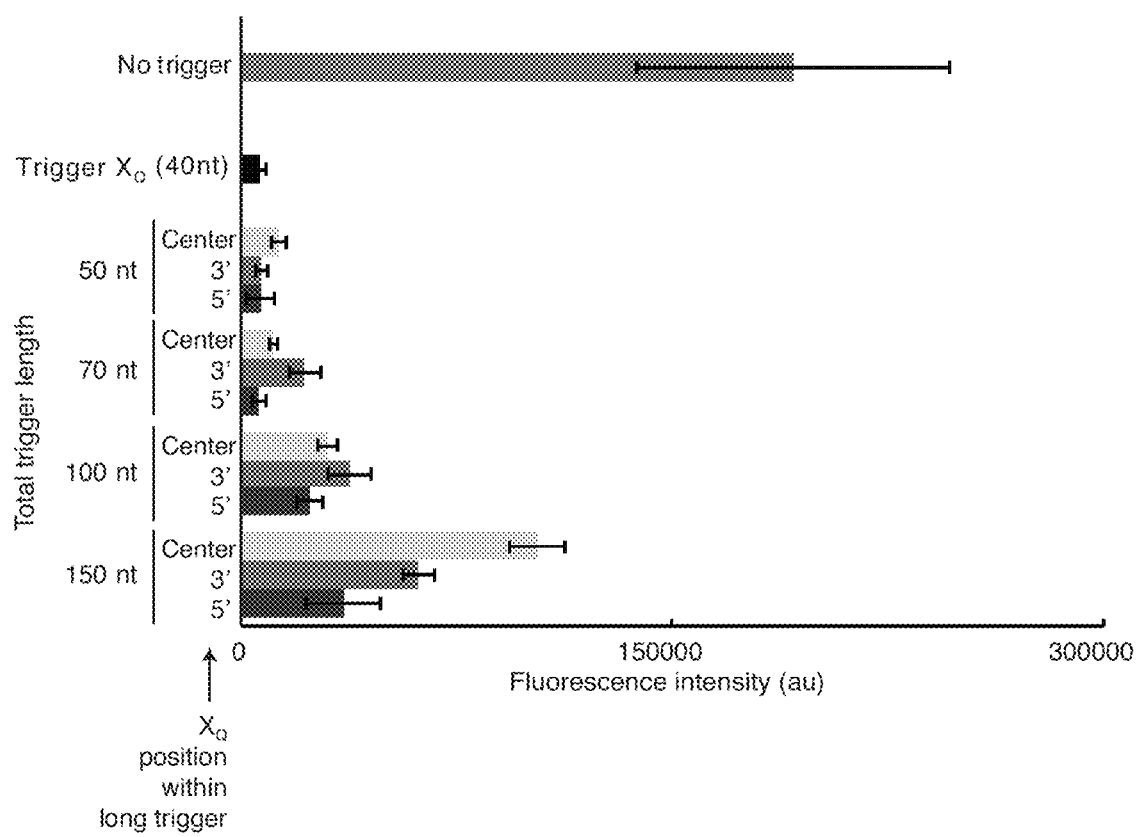

FIG. 13I demonstrates a conditional ON→OFF cgRNA response to RNA triggers of varying lengths. Expression of RNA trigger X (PEL+[40 nt, 50 nt, 70 nt, 100 nt, or 150 nt unstructured]+hU6 terminator) toggles the cgRNA Q from ON→OFF, leading to a decrease in fluorescence. For these studies, the 40 nt trigger sequence $X_Q$ is expressed at either the 5' end, 3'end, or in the middle of a 50 nt, 70 nt, 100 nt, or 150 nt sequence designed to have minimal structure. Bar graphs depict mean±estimated standard error of the mean (with uncertainty propagation) calculated based on the mean single-cell fluorescence over 1993-20393 cells for each of N=4 replicate wells.

FIG. 13H depicts the sequences of cgRNAs Q, R, S, T, and the sequences of triggers $X_Q$, $X_R$, $X_S$, $X_T$ for the studies of FIGS. 13C-13G; FIG. 13J depicts the sequences of the long triggers that incorporate $X_Q$ for the studies of FIG. 13I. Nucleotides that are lower case italic are constrained by the target binding site on the reporter plasmid. Nucleotides shaded gray are constrained by dCas9. Nucleotides that are upper case italic are designed. In FIG. 13I, underlined nucleotides depict the location of the $X_Q$ sequence within the context of the longer trigger sequence. The plain "C" nucleotide is a cloning artifact. Lower case plain nucleotides are constrained by the hU6 terminator sequence[46]. Bold nucleotides are a protective element (PEL) constrained by an xrRNA sequence derived from Dengue (Dengue 4, NC_002640.1)[47]. Sequences are presented as DNA sequences; the corresponding RNA sequence is the same as the DNA sequence except that "U" replaces "T").

In HEK 293T cells expressing an allosteric ON→OFF terminator switch cgRNA (FIG. 13A), inducing dCas9-VPR as the protein effector,[48] and a fluorescent protein reporter (Phi-YFP)[49,50] as the target gene Y (conditional logic: "if not X then Y"; FIG. 13B), the cgRNA exhibits a strong conditional response to expression of the RNA trigger X (FIG. 13C). The OFF state approaches the ideal OFF state of a no-target gRNA lacking the target-binding region. FIG. 13D displays raw fluorescence data for a library of four orthogonal ON→OFF terminator switch cgRNAs with each of four triggers. For each of four cgRNAs, the cognate trigger yields low fluorescence (OFF state) comparable to the ideal OFF state using a no-target gRNA lacking the target-binding region, while each of three non-cognate triggers yields high fluorescence (ON state) comparable to a no-trigger control. For this library of four cgRNA/trigger pairs, the median fold-change is approximately 50× for the ON→OFF conditional response to expression of the cognate trigger (FIG. 13E); the median fractional dynamic range is approximately 20% (FIG. 13F); the median crosstalk between non-cognate/trigger pairs is approximately 4%, and the median crosstalk modulus is approximately 9%.

To optimize fold-change, the goal is to maximize the ON→OFF or OFF→ON conditional response ratio with/without the cognate RNA trigger (higher is better). To optimize fractional dynamic range, the goal is to maximize the difference between conditional ON and OFF states as a fraction of the unconditional regulatory dynamic range of CRISPR/Cas using standard gRNAs (higher is better). To optimize crosstalk, the goal is to minimize sequence (and metabolic) interactions between cgRNAs and non-cognate triggers including the transcriptome (lower is better). The orthogonal cgRNA/trigger pairs were designed using software suite NUPACK®[40,41]. A cgRNA expression plasmid and a trigger expression plasmid were co-transfected with a plasmid expressing an inducing dCas9-VPR fusion[48] and a reporter plasmid containing a gRNA binding site upstream of a minimal CMV promoter for Phi-YFP expression.[51,52] The four plasmids were transiently transfected into HEK 293T cells with Lipofectamine 2000 and grown for 24 h, with end-point fluorescence measured via flow cytometry. Data analysis was performed on cells expressing high levels of both cgRNA and trigger fluorescent protein transfection controls.

Example—Demonstration of Allosteric OFF→ON Split-Terminator Switch cgRNAs in Human Cells FIG. 14 demonstrates allosteric OFF→ON split-terminator switch cgRNAs performing conditional logic in HEK 293T cells. FIG. 14A depicts the mechanism for an allosteric OFF→ON split-terminator switch cgRNA: the constitutively inactive cgRNA is activated by hybridization of RNA trigger X. Rational design of 4 bp terminator duplex (cgRNA domain "d" and trigger domain "d*"). FIG. 14B depicts the conditional logic for an OFF→ON split-terminator switch cgRNA used in conjunction with inducing dCas9: "if X then Y" (if trigger X is detected, induce target gene Y). FIG. 14C demonstrates that expression of RNA trigger X (4 nt+terminator hairpin) toggles the cgRNA from OFF→ON, leading to an increase in fluorescence. Single-cell fluorescence intensities via flow cytometry. Transfection of plasmids expressing inducing dCas9-VPR, Phi-YFP target gene Y, and either: no-target gRNA that lacks target-binding region+no-trigger control (ideal OFF state), cgRNA+no-trigger control (OFF state), cgRNA+RNA trigger X (ON state), standard gRNA+no-trigger control (ideal ON state). FIGS. 14D-14G demonstrate programmable conditional regulation using a library of 3 orthogonal cgRNAs (M,N,O) and their corresponding cognate triggers ($X_M$, $X_N$, $X_O$). In FIG. 14D, raw fluorescence depicts OFF→ON conditional response to cognate trigger. In FIG. 14E, fold change=ON/OFF. In FIG. 14F, fractional dynamic range= (ON−OFF)/(ideal ON−ideal OFF). In FIG. 14G, crosstalk= (ON'−OFF)/(ON−OFF) where ON' corresponds to cgRNA+non-cognate trigger. Bar graphs depict mean±estimated standard error of the mean (with uncertainty propagation) calculated based on the mean single-cell fluorescence over 1017-2394 cells for each of N=3 replicate wells. FIG. 14H depicts the sequences of cgRNAs M,N,O, and the sequences of triggers $X_M$, $X_N$, $X_O$. Nucleotides that are lower case italic are constrained by the target binding site on the reporter plasmid. Nucleotides shaded gray are constrained by dCas9. Nucleotides that are upper case italic are designed. The plain "C" nucleotide is a cloning artifact. Lower case plain nucleotides are constrained by the hU6 terminator sequence[46]. Sequences are presented as DNA sequences; the corresponding RNA sequence is the same as the DNA sequence except that "U" replaces "T"). The orthogonal cgRNA/trigger pairs were designed using software suite NUPACK®[40,41].

In HEK 293T cells expressing an allosteric OFF→ON split-terminator switch cgRNA (FIG. 14A), inducing dCas9-VPR as the protein effector,[48] and a fluorescent protein reporter (Phi-YFP)[49-50] as the target gene Y (conditional logic "if X then Y"; FIG. 14B), the cgRNA exhibits a strong conditional OFF→ON response to expression of the RNA trigger X (FIG. 14C). The OFF state approaches the ideal OFF state of a no-target gRNA lacking the target-binding region. FIG. 14D displays raw fluorescence data for a library of three orthogonal OFF→ON split-terminator switch cgRNAs with each of three triggers. The three cgRNAs have clean OFF states (low fluorescence) in the absence of trigger and strong ON states (high fluorescence) in response to expression of the cognate trigger. For this library of three cgRNA/trigger pairs, the median fold-change is approximately 150× for the conditional OFF→ON response to expression of the cognate trigger (FIG. 14E); the median fractional dynamic range is approximately 50% (FIG. 14F); the median crosstalk is approximately 4% (FIG. 14G).

To optimize fold-change, the goal is to maximize the ON→OFF or OFF→ON conditional response ratio with/without the cognate RNA trigger (higher is better). To optimize fractional dynamic range, the goal is to maximize the difference between conditional ON and OFF states as a fraction of the unconditional regulatory dynamic range of CRISPR/Cas using standard gRNAs (higher is better). To optimize crosstalk, the goal is to minimize sequence (and metabolic) interactions between cgRNAs and non-cognate triggers including the transcriptome (lower is better). The orthogonal cgRNA/trigger pairs were designed using software suite NUPACK®[40,41]. A cgRNA expression plasmid and a trigger expression plasmid were co-transfected with a plasmid expressing an inducing dCas9-VPR fusion[48] and a reporter plasmid containing a gRNA binding site upstream of a minimal CMV promoter for Phi-YFP expression.[51,52] The four plasmids were transiently transfected into HEK 293T cells with Lipofectamine 2000 and grown for 24 h, with end-point fluorescence measured via flow cytometry. Data analysis was performed on cells expressing high levels of both cgRNA and trigger fluorescent protein transfection controls.

Figure 14A:
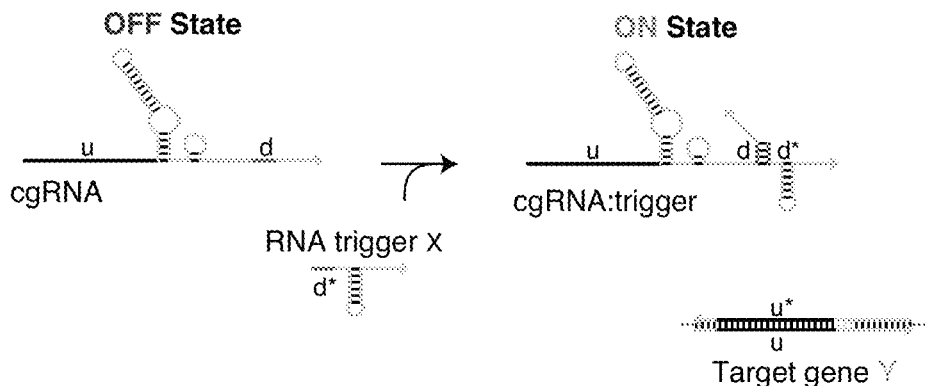
Figure 14B:
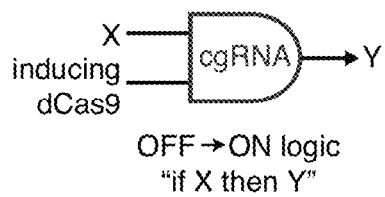
Figure 14C:
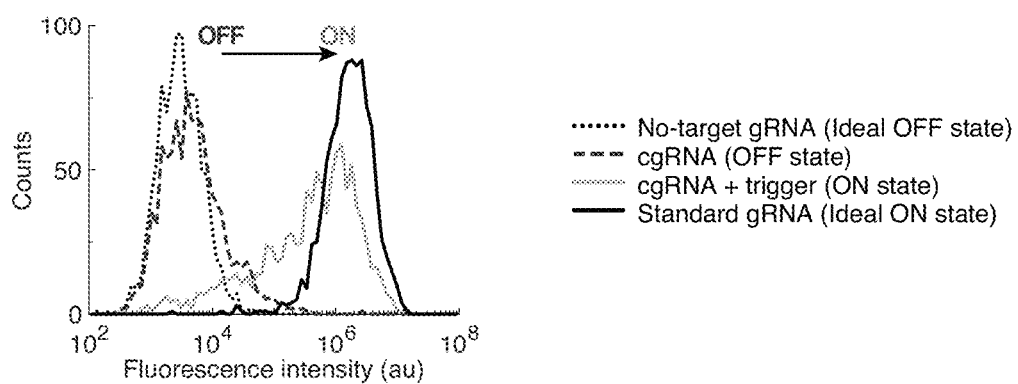
Figure 14D:
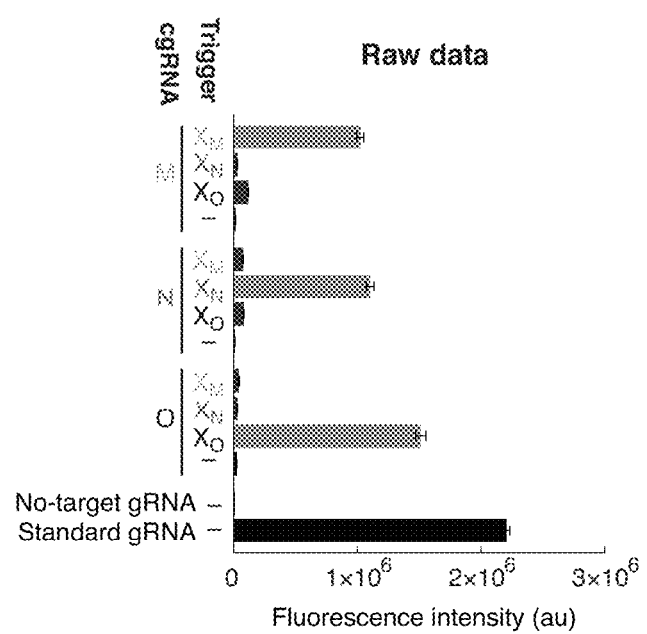
Figure 14E:
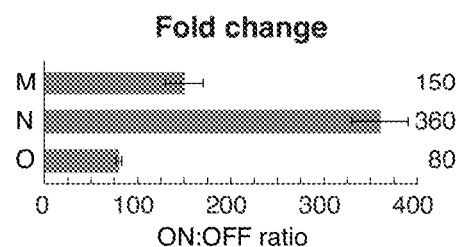
Figure 14F:
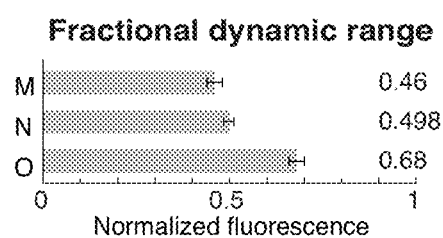
Figure 14G:
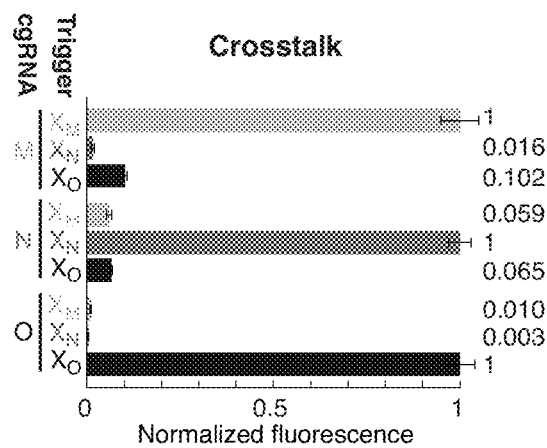

FIG. 14A-14H described above demonstrate split-terminator switch cgRNAs functioning in human cells using a 4 bp terminator duplex (formed via hybridization between domain "d" of the cgRNA and the reverse complementary domain "d*" in the trigger; see the mechanism schematic of FIG. 14A with domain lengths |d|=d*|=4 nt). FIG. 15A-15H demonstrate that mechanism functioning using a 10 bp terminator duplex (see the mechanism schematic of FIG. 15A with domain lengths |d|=d*|=10 nt).

Figure 15A:
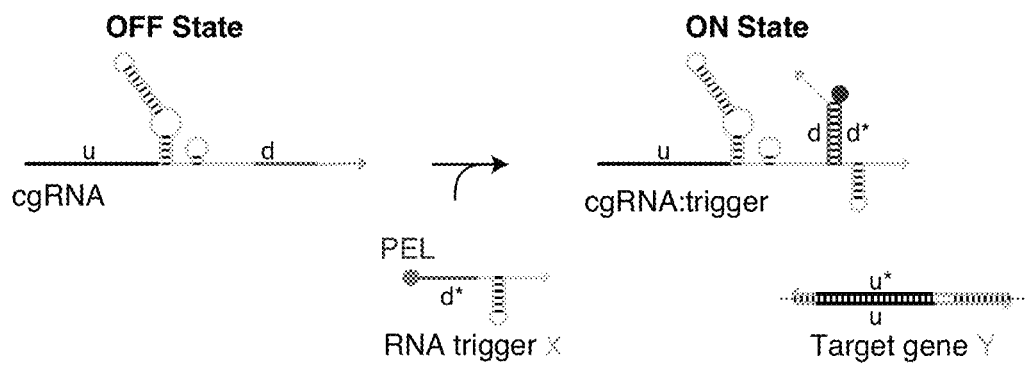
Figure 15B:
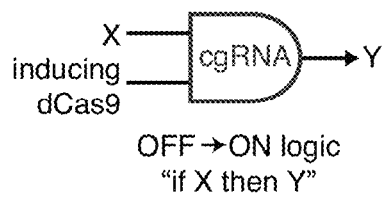
Figure 15C:
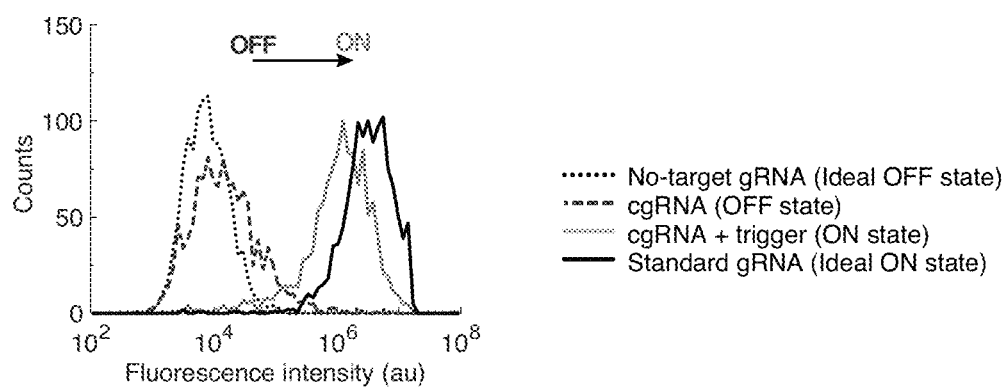
Figure 15D:
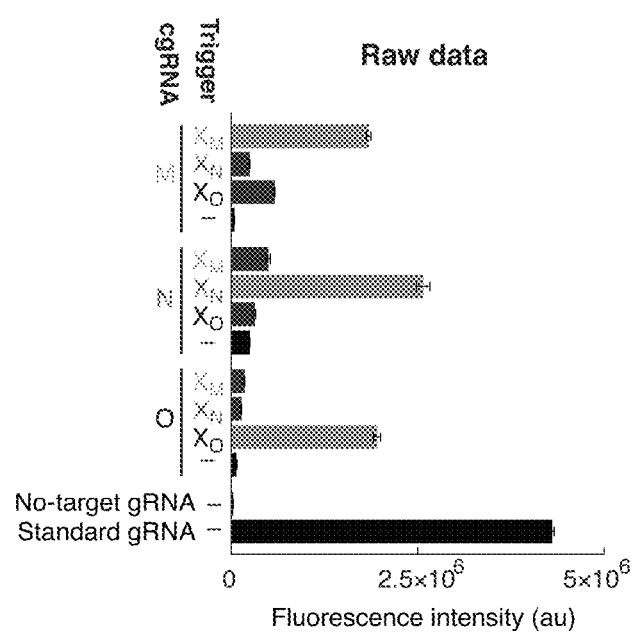
Figure 15E:
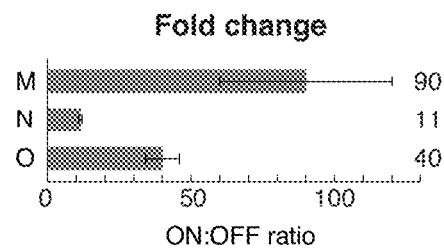
Figure 15F:
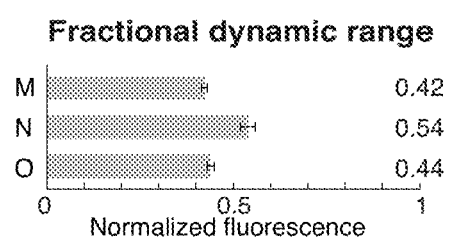
Figure 15G:
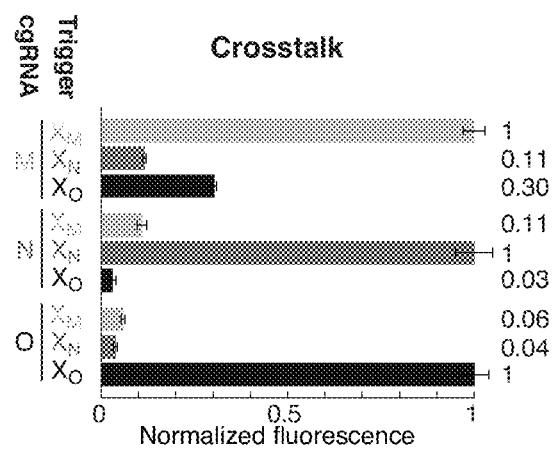

FIG. 15A depicts the mechanism for an allosteric OFF→ON split-terminator switch cgRNA: the constitutively inactive cgRNA is activated by hybridization of RNA trigger X. Rational design of 10 bp terminator duplex (cgRNA domain "d" and trigger domain "d*"). FIG. 15B depicts the conditional logic for an OFF→ON split-terminator switch cgRNA using in conjunction with inducing dCas9: "if X then Y" (if trigger X is detected, induce target gene Y). FIG. 15C demonstrates that expression of RNA trigger X (PEL+10 nt+terminator hairpin) toggles the cgRNA from OFF→ON, leading to an increase in fluorescence. Single-cell fluorescence intensities via flow cytometry. Transfection of plasmids expressing inducing dCas9-VPR, Phi-YFP target gene Y, and either: no-target gRNA that lacks target-binding region+no-trigger control (ideal OFF state), cgRNA+no-trigger control (OFF state), cgRNA+RNA trigger X (ON state), standard gRNA+no-trigger control (ideal ON state). FIGS. 15D-15G demonstrate programmable conditional regulation using a library of 3 orthogonal cgRNAs (M,N,O) and their corresponding cognate triggers ($X_M$, $X_N$, $X_O$). In FIG. 15D, raw fluorescence depicts OFF→ON conditional response to cognate trigger. In FIG. 15E, fold change=ON/OFF. In FIG. 15F, fractional dynamic range=(ON−OFF)/(ideal ON−ideal OFF). In FIG. 15G, crosstalk=(ON'−OFF)/(ON−OFF) where ON' corresponds to cgRNA+non-cognate trigger. Bar graphs depict mean±estimated standard error of the mean (with uncertainty propagation) calculated based on the mean single-cell fluorescence over 1244-2313 cells for each of N=3 replicate wells. FIG. 15H depicts the sequences of cgRNAs M,N,O, and the sequences of triggers $X_M$, $X_N$, $X_O$. Nucleotides that are lower case italic are constrained by the target binding site on the reporter plasmid. Nucleotides shaded gray are constrained by dCas9. Nucleotides that are upper case italic are designed. The plain "C" nucleotide is a cloning artifact. Lower case plain nucleotides are constrained by the hU6 terminator sequence[46]. Bold nucleotides are a protective element (PEL) constrained by an xrRNA sequence derived from Dengue (Dengue 4, NC_002640.1)[47]. Sequences are presented as DNA sequences; the corresponding RNA sequence is the same as the DNA sequence except that "U" replaces "T"). The orthogonal cgRNA/trigger pairs were designed using software suite NUPACK®[40,41]. A cgRNA expression plasmid and a trigger expression plasmid were co-transfected with a plasmid expressing an inducing dCas9-VPR fusion[48] and a reporter plasmid containing a gRNA binding site upstream of a minimal CMV promoter for Phi-YFP expression.[51,52] The four plasmids were transiently transfected into HEK 293T cells with Lipofectamine 2000 and grown for 24 h, with end-point fluorescence measured via flow cytometry. Data analysis was performed on cells expressing high levels of both cgRNA and trigger fluorescent protein transfection controls.

Figure 16A:
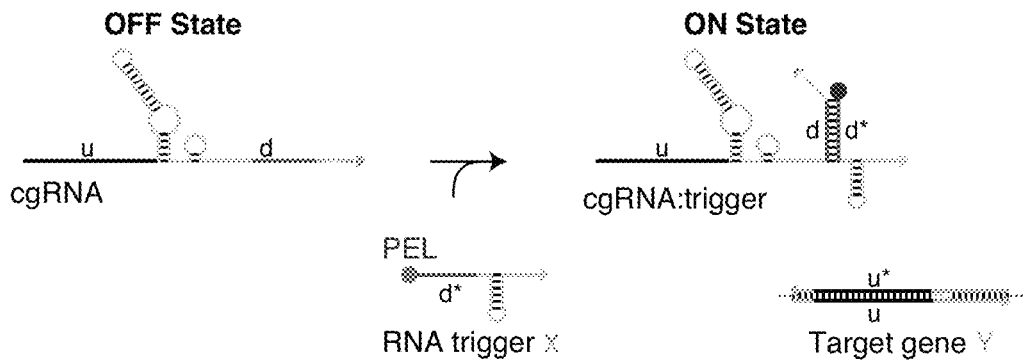
Figure 16B:
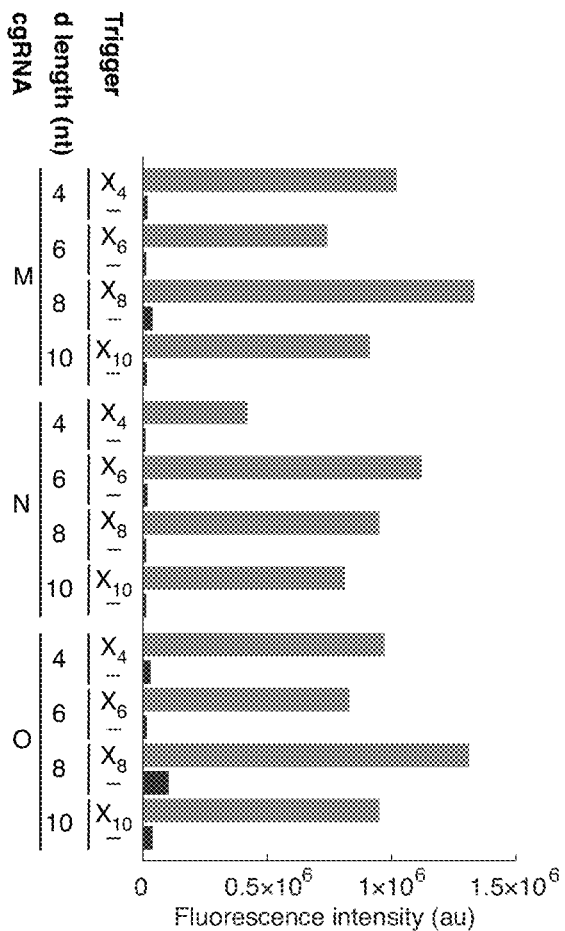
Figure 16C:
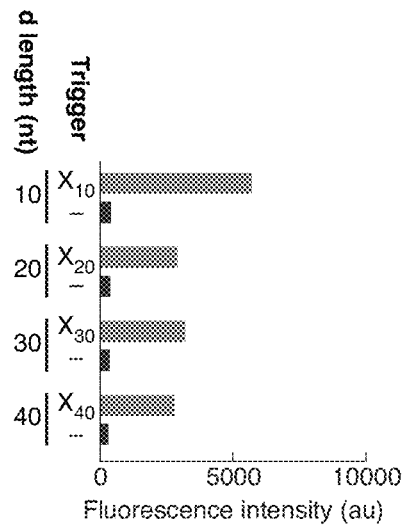

FIG. 16 demonstrates split-terminator switch cgRNAs functioning in HEK293T cells using terminator duplexes of different lengths ranging from |d|=40 nt to |d|=4 nt. FIG. 16A depicts the mechanism for an allosteric OFF→ON split-terminator switch cgRNA and trigger (depicted for a 10 bp terminator duplex with domain lengths |d|=d*|=10 nt). For terminator duplexes of length 4, 6, 8, or 10 bp (with domain length |d|=4, 6, 8, 10 nt), FIG. 16B demonstrates that expression of RNA trigger X (PEL+{4, 6, 8, 10} nt+terminator hairpin) toggles the cgRNA from OFF→ON in human cells, leading to an increase in fluorescence. For terminator duplexes of length 10, 20, 30, 40 bp (with domain length |d|=10, 20, 30, 40 nt), FIG. 16C demonstrates that expression of RNA trigger X (PEL+{10, 20, 30, 40} nt+terminator hairpin) toggles the cgRNA from OFF→ON in human cells, leading to an increase in fluorescence. Transfection of plasmids expressing inducing dCas9-VPR, Phi-YFP target gene Y, and either: cgRNA+no-trigger control (OFF state), cgRNA+RNA trigger X (ON state). For each set of conditions, 50,000 cells were collected from a single well, which was gated for live cells, single cells, and highly-transfected cells based on the cgRNA plasmid transfection control (miRFP670+), yielding approximately 2% of the cells. Bar graph depicts mean single-cell fluorescence over approximately 1000 cells for one well. FIG. 16D depicts the sequences of cgRNAs and triggers for the studies of FIG. 16B with terminator duplexes of 6, 8, or 10 bp (cgRNA and trigger sequences with 4 bp terminator duplexes are displayed in FIG. 14H). FIG. 16E depicts the sequences of cgRNAs and triggers for the studies of FIG. 16B with terminator duplexes of 10, 20, 30, or 40 bp. Nucleotides that are lower case italic are constrained by the target binding site on the reporter plasmid. Nucleotides shaded gray are constrained by dCas9. Nucleotides that are upper case italic are designed. The plain "C" nucleotide is a cloning artifact. Lower case plain nucleotides are constrained by the hU6 terminator sequence[46]. Bold nucleotides are a protective element (PEL) constrained by an xrRNA sequence derived from Dengue (Dengue 4, NC_002640.1)[47]. Sequences are presented as DNA sequences; the corresponding RNA sequence is the same as the DNA sequence except that "U" replaces "T").

Figure 17A:
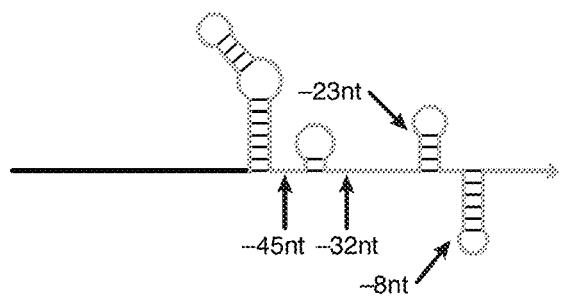
Figure 17B:
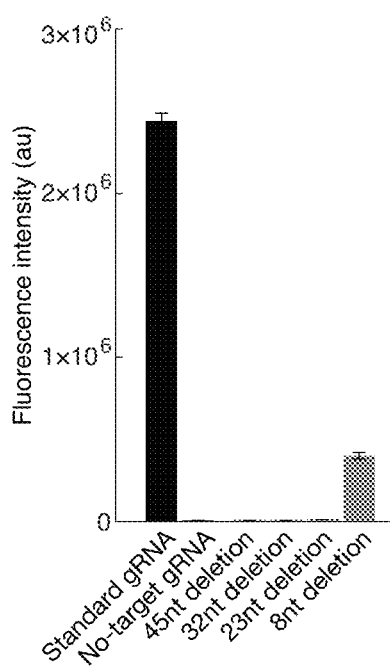
Figure 18A:
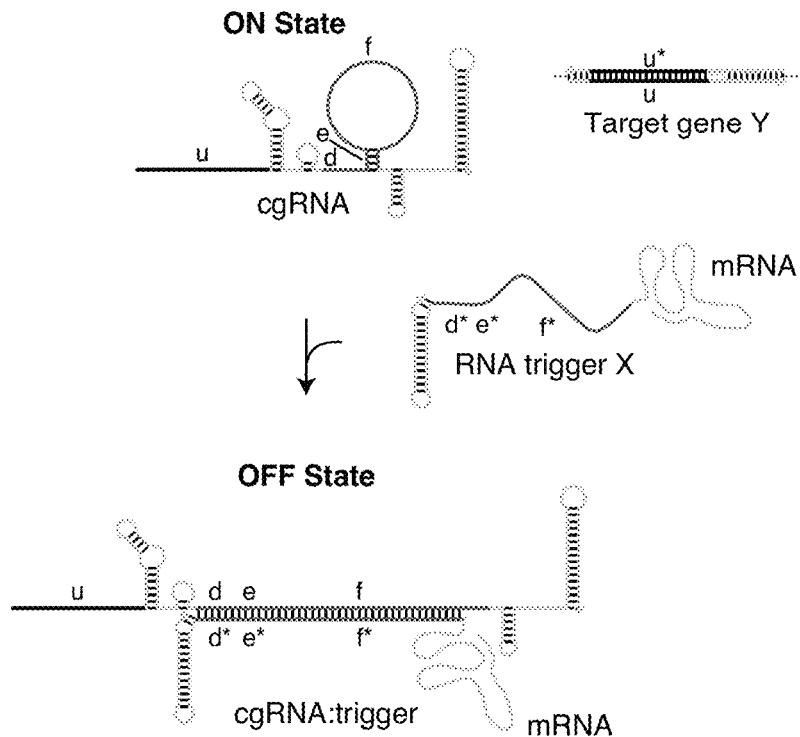
Figure 18B:
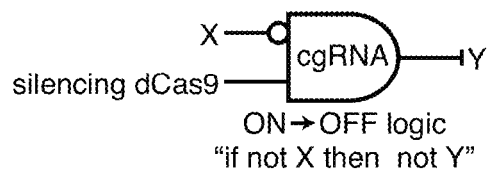
Figure 18C:
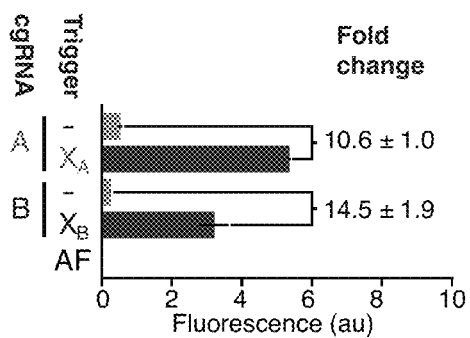
Figure 18D:
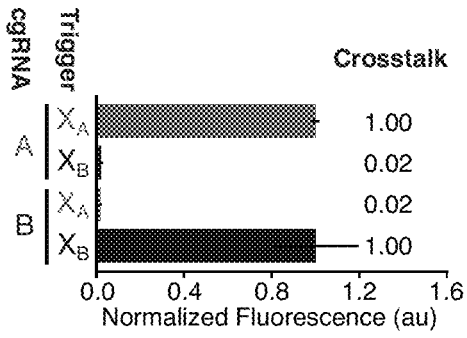

Example—Demonstration of Inactivation of a gRNA in Human Cells Via Truncation from the 3' End FIG. 17 demonstrates inactivation of a standard gRNA in BEK 293T cells by truncation of the gRNA from the 3' end, providing the basis for generating a clean OFF state for split-terminator switch cgRNAs. FIG. 17A depicts four truncation locations: 3' of the Cas9 handle (45 nt deletion), 3' of the nexus hairpin (32 nt deletion), in the loop of terminator hairpin 1 (23 nt deletion), and in the loop of terminator hairpin 2 (8 nt deletion). FIG. 18C demonstrates that all four truncation locations reduce the activity of the gRNA, with the 45 nt, 32 nt, and 23 nt truncations resulting in no detectable activity. Transfection of plasmids expressing inducing dCas9-VPR, Phi-YFP target gene Y, and either: standard gRNA+no-trigger control (ideal ON state), no-target gRNA that lacks target-binding region+no-trigger control (ideal OFF state), the 5' portion of a truncated gRNA+no-trigger control. Bar graphs depict mean±estimated standard error of the mean calculated based on the mean single-cell fluorescence over 2114-3085 cells for each of N=3 replicate wells. FIG. 17C depicts the sequences used in FIG. 17B. Nucleotides that are lower case italic are constrained by the target binding site on the reporter plasmid. Nucleotides shaded gray are constrained by dCas9. Lower case plain nucleotides are constrained by the hU6 terminator sequence[46]. Sequences are presented as DNA sequences; the corresponding RNA sequence is the same as the DNA sequence except that "U" replaces "T").

Figure 30A:
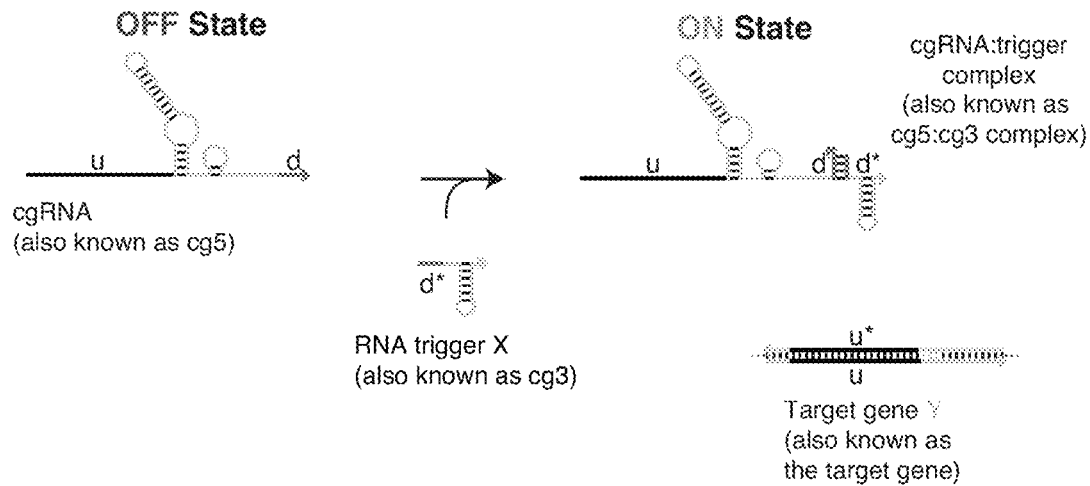
Figure 30B:
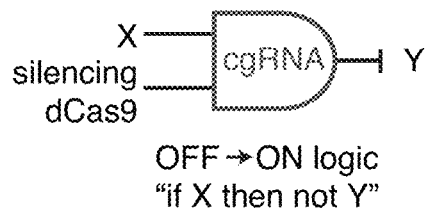
Figure 30C:
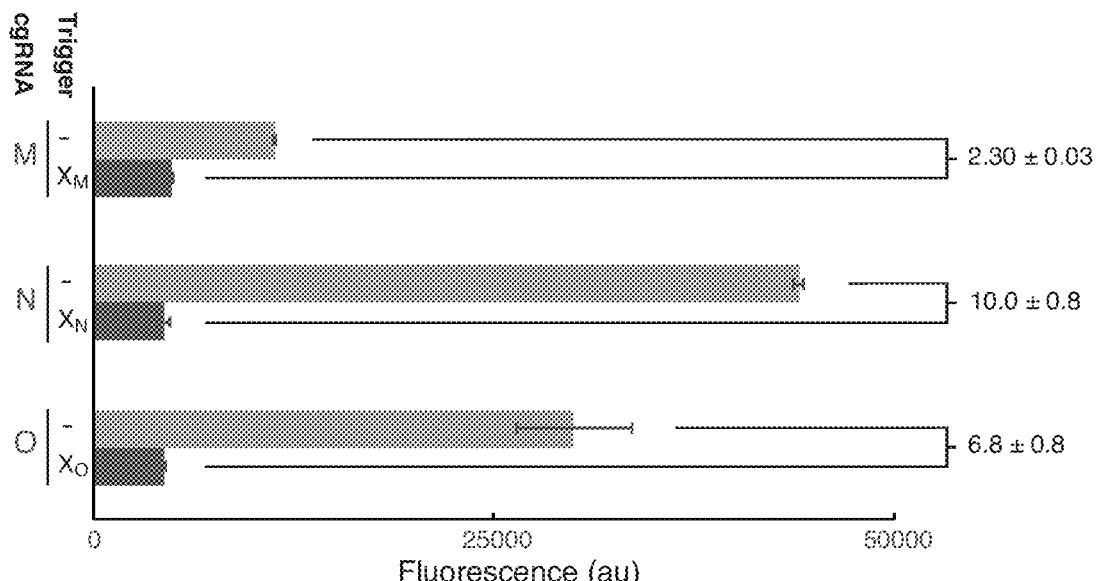

Example—Demonstration of Allosteric OFF→ON Split-Terminator Switch cgRNAs in Bacteria FIG. 30 demonstrates allosteric OFF→ON split-terminator switch cgRNAs performing conditional logic in E. coli. FIG. 30A depicts the mechanism for an allosteric OFF→ON split-terminator switch cgRNA: the constitutively inactive cgRNA is activated by hybridization of RNA trigger X. Rational design of 4 bp terminator duplex (cgRNA domain "d" and trigger domain "d*"). FIG. 30B depicts the conditional logic for an OFF→ON split-terminator switch cgRNA used in conjunction with silencing dCas9: "if X then not Y" (if trigger X is detected, then silence target gene Y). FIG. 30C demonstrates that expression of RNA trigger X (4 nt+terminator hairpin) toggles the activity of the cgRNA from OFF→ON (leading to a decrease in fluorescence) for each of three cgRNAs (M, N, O) with their corresponding cognate triggers ($X_M$, $X_N$, $X_O$). Induced expression (aTc) of silencing dCas9 and constitutive expression of sfGFP target gene Y and either: cgRNA (OFF state), cgRNA+RNA trigger X (ON state). In FIG. 30C, raw fluorescence depicts OFF→ON conditional response to cognate trigger. Fold change=OFF/ON=[no trigger]/[cognate trigger]. Bar graphs depict mean±estimated standard error calculated based on the mean single-cell fluorescence over 20,000 cells for each of N=2 replicate wells (OFF:ON ratio calculated with uncertainty propagation). FIG. 30D depicts the sequences of cgRNAs M, N, O, and the sequences of triggers $X_M$, $X_N$, $X_O$. Nucleotides that are lower case italic are constrained by the target gene. Nucleotides shaded gray are constrained by dCas9. Nucleotides that are upper case italic are designed. Sequences are presented as DNA sequences; the corresponding RNA sequence is the same as the DNA sequence except that "U" replaces "T").

In *E. coli* expressing an allosteric OFF→ON split terminator switch (FIG. 30A), silencing dCas9 and a fluorescent protein reporter (sfGFP) as the target gene Y (conditional logic: "if X then Y"; FIG. 30B), the cgRNA exhibits a strong conditional response to expression of RNA trigger X (FIG. 30C). FIG. 30C displays raw fluorescence data for a library of three orthogonal OFF→ON split terminator switch cgRNAs with and without their cognate triggers. For this library of three cgRNA/trigger pairs, the median fold-change is approximately 7× for the OFF→ON conditional response to expression of the cognate trigger (FIG. 30C).

cgRNA/trigger pairs were designed using software suite NUPACK®.[40,41] cgRNA/trigger plasmids were transformed into a modified *E. coli* MG1655 strain expressing genomically incorporated mRFP and sfGFP4.[5] Strains were grown overnight in EZ-RDM (Teknova), then diluted 500 fold with fresh medium containing aTc for induction of silencing dCas9 expression. Induced cells were grown for 12 h, with end-point fluorescence measured via flow cytometry.

Example—Demonstration of Allosteric ON→OFF Split-Terminator Switch cgRNAs in Human Cells FIG. 31 demonstrates allosteric ON→OFF split-terminator switch cgRNAs performing conditional logic in BEK 293T cells. FIG. 31A depicts the mechanism for an allosteric ON→OFF split-terminator switch cgRNAs (Mechanism 4B): the constitutively active cgRNA (comprising 5' fragment cg5 [also known as cgRNA] and 3' fragment cg3 [also known as helper]) is inactivated by hybridization of RNA trigger X (also known as the cognate RNA trigger) to cg5, displacing cg3 from cg5 to inactivate the cgRNA. FIG. 31B depicts the mechanism for an allosteric ON→OFF split-terminator switch cgRNAs (Mechanism 4C): the constitutively active cgRNA (comprising 5' fragment cg5 [also known as cgRNA] and 3' fragment cg3 [also known as helper]) is inactivated by hybridization of RNA trigger X (also known as the cognate RNA trigger) to cg3, displacing cg5 from cg3 to inactivate the cgRNA. Rational sequence design of domains "a", "b", "c", "a*", "b*", and "c*". FIG. 31C depicts the conditional logic for an ON→OFF split-terminator switch cgRNA used in conjunction with inducing dCas9: "if not X then Y" (if trigger X is not detected, induce target gene Y).

Figure 31A:
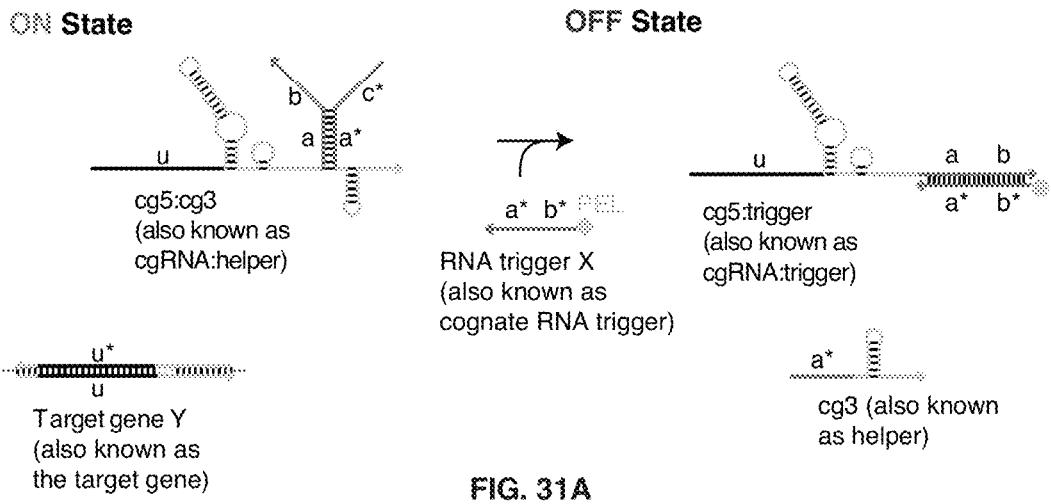
Figure 31B:
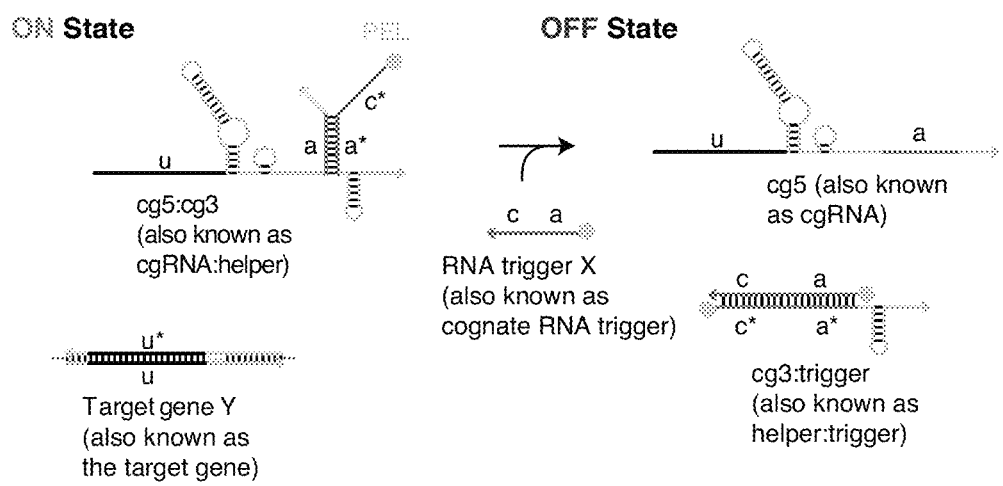
Figure 31C:
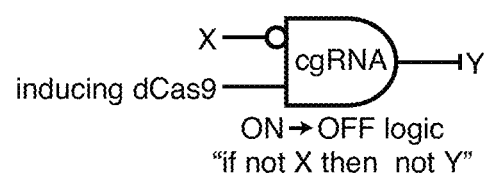
Figure 31D:
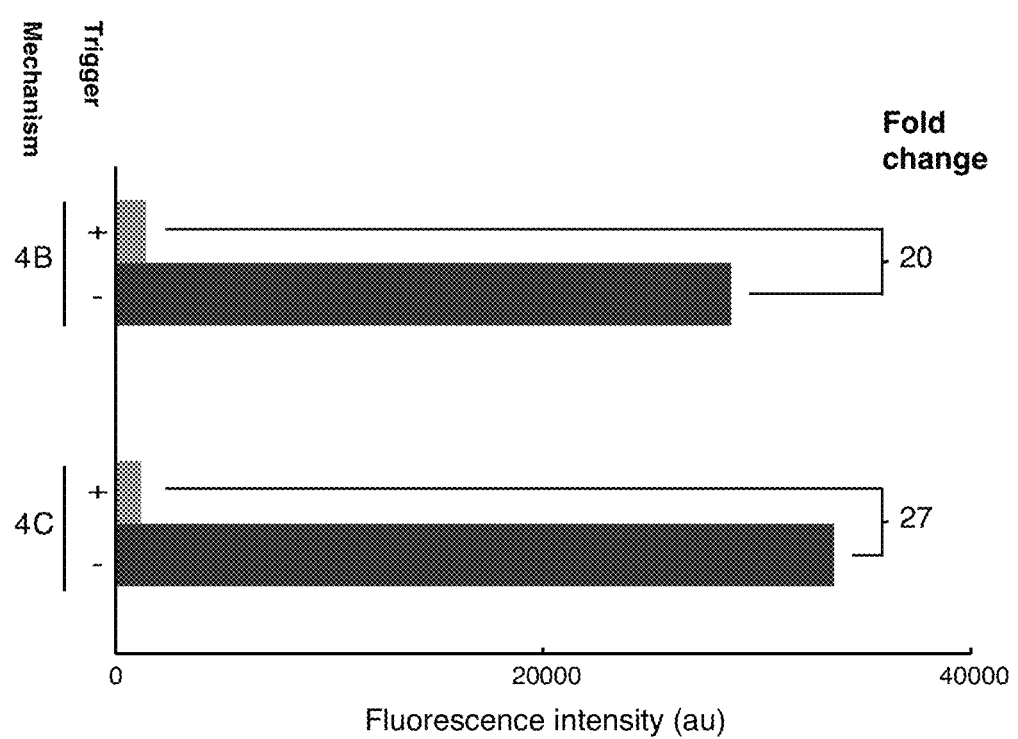
Figure 32A:
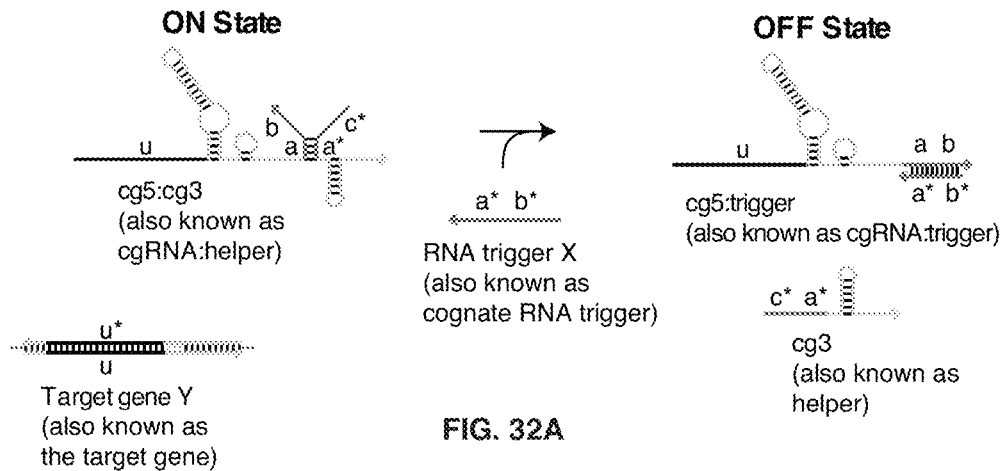
Figure 32B:
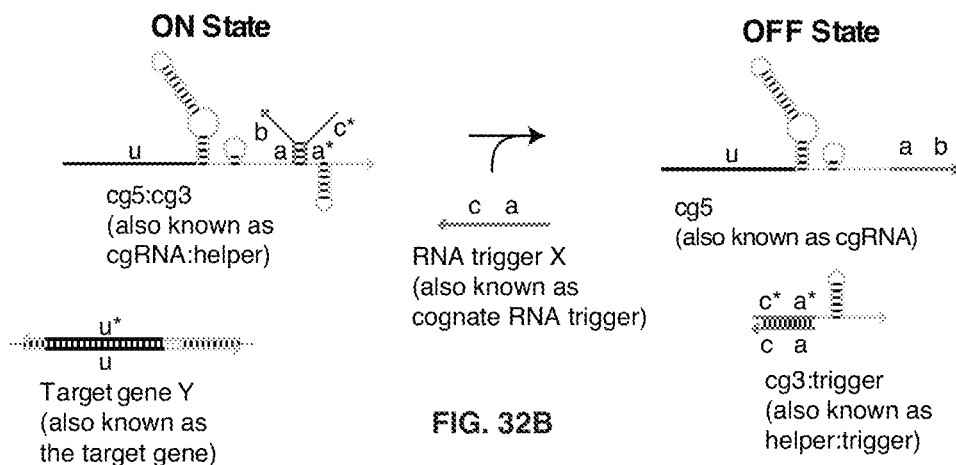
Figure 32C:
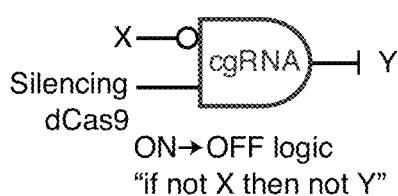
Figure 32D:
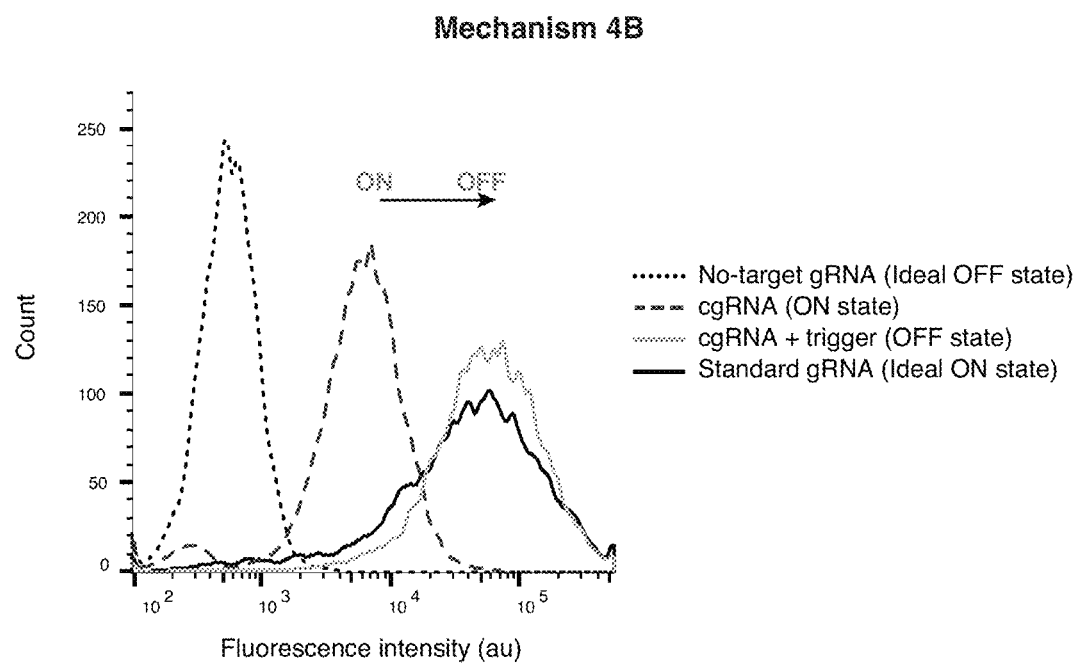
Figure 32E:
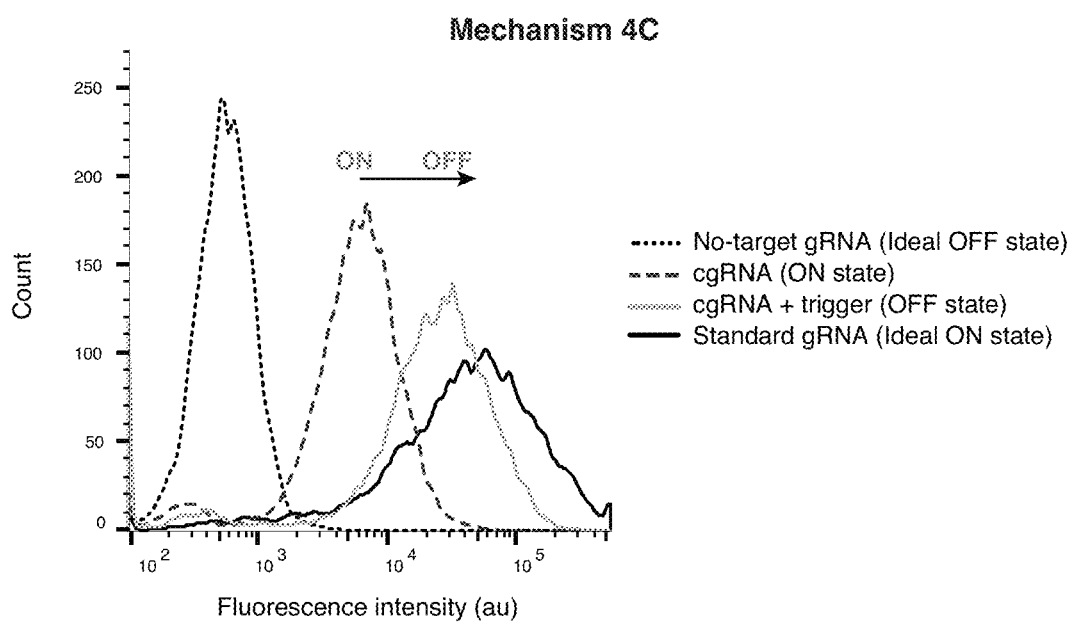

FIG. 31D demonstrates that expression of RNA trigger X (PEL+20 nt unstructured+hU6 terminator for Mechanism 4B; PEL+40 nt unstructured+hU6 terminator for Mechanism 4C) toggles the cgRNA from ON→OFF, leading to a decrease in fluorescence. Transfection of plasmids expressing inducing dCas9-VPR, Phi-YFP target gene Y, and either: cgRNA+no-trigger control (ON state), or cgRNA+RNA trigger X (OFF state). The no-trigger control uses a random pool of triggers to provide a sequence-generic approximation of the metabolic load of trigger expression. Background subtracted fluorescence by no-target gRNA that lacks target-binding region depicts ON→OFF conditional response to cognate trigger. Fold change=ON/OFF. Bar graphs depict the mean single-cell fluorescence over 1989-2305 cells for N=1 well. FIG. 31E depicts the sequences of cg5, cg3, and trigger for Mechanism 4B and 4C. Nucleotides that are lower case italic are constrained by the target binding site on the reporter plasmid. Nucleotides shaded gray are constrained by dCas9. Nucleotides that are upper case italic are designed. The plain "C" nucleotide is a cloning artifact. Lower case plain nucleotides are constrained by the hU6 terminator sequence[46]. Bold nucleotides are a protective element (PEL) constrained by an xrRNA sequence derived from Dengue (Dengue 4, NC_002640.1)[47]. Sequences are presented as DNA sequences; the corresponding RNA sequence is the same as the DNA sequence except that "U" replaces "T").

In HEK 293T cells expressing an allosteric ON→OFF split-terminator switch cgRNA (Mechanism 4B in FIG. 31A; Mechanism 4C in FIG. 31B), inducing dCas9-VPR as the protein effector,[48] and a fluorescent protein reporter (Phi-YFP)[49-50] as the target gene Y (conditional logic: "if not X then Y"; FIG. 31C), the cgRNA (comprising fragments cg5 and cg3) exhibits a strong conditional response to expression of the RNA trigger X (FIG. 31D).

To optimize fold-change, the goal is to maximize the ON→OFF or OFF→ON conditional response ratio with/without the cognate RNA trigger (higher is better). The cgRNA/trigger pairs were designed using software suite NUPACK®[40,41]. A cg5 and cg3 expression plasmid and a trigger expression plasmid were co-transfected with a plasmid expressing an inducing dCas9-VPR fusion[48] and a reporter plasmid containing a gRNA binding site upstream of a minimal CMV promoter for Phi-YFP expression.[51,52] The four plasmids were transiently transfected into HEK 293T cells with Lipofectamine 2000 and grown for 24 h, with end-point fluorescence measured via flow cytometry. Data analysis was performed on cells expressing high levels of both cgRNA and trigger fluorescent protein transfection controls.

Example—Demonstration of Allosteric ON 4 OFF Split-Terminator Switch cgRNAs in Bacteria FIG. 32 demonstrates allosteric ON→OFF split-terminator switch cgRNAs performing conditional logic in *E. coli*. FIG. 32A depicts the mechanism for an allosteric ON→OFF split-terminator switch cgRNAs (Mechanism 4B): the constitutively active cgRNA (comprising 5' fragment cg5 [also known as cgRNA] and 3' fragment cg3 [also known as helper]) is inactivated by hybridization of RNA trigger X (also known as the cognate RNA trigger) to cg5, displacing cg3 from cg5 to inactivate the cgRNA. FIG. 32B depicts the mechanism for an allosteric ON→OFF split-terminator switch cgRNAs (Mechanism 4C): the constitutively active cgRNA (comprising 5' fragment cg5 [also known as cgRNA] and 3' fragment cg3 [also known as helper]) is inactivated by hybridization of RNA trigger X (also known as the cognate RNA trigger) to cg3, displacing cg5 from cg3 to inactivate the cgRNA. FIG. 32C depicts the conditional logic for an ON→OFF split-terminator switch cgRNA used in conjunction with silencing dCas9: "if not X then not Y" (if trigger X is not detected, then silence target gene Y). FIGS. 32D (Mechanism 4B) and 32E (Mechanism 4C) demonstrate that expression of RNA trigger X (40 nt unstructured+synthetic terminator hairpin) toggles the cgRNA from ON→OFF, leading to an increase in single-cell fluorescence intensities via flow cytometry. Induced expression (aTc) of silencing dCas9 and constitutive expression of mRFP target gene Y and either: standard gRNA+no-trigger control (ideal ON state), cgRNA+no-trigger control (ON state), cgRNA+RNA trigger X (OFF state; trigger expression is Salicylate-induced), no-target gRNA that lacks target-binding region+no-trigger control (ideal OFF state). FIG. 32F depicts the sequences of cg5, cg3, trigger X (Mechanism 4B), trigger X (Mechanism 4C), and the no-trigger control. Nucleotides that are lower case italic are constrained by the target gene. Nucleotides shaded gray are constrained by dCas9. Nucleotides that are upper case italic are designed. Sequences are presented as DNA sequences; the corresponding RNA sequence is the same as the DNA sequence except that "U" replaces "T").

Orthogonal cgRNA/trigger pairs were designed using software suite NUPACK®.[40,41] cgRNA/trigger plasmids were transformed into *E. coli*.[5] Strains were grown overnight in EZ-RDM (Teknova), then diluted and seeded into the assay plate. Cells were grown in fresh medium containing aTc, IPTG, and Salicylate for induction of silencing dCas9 expression, cgRNA, and trigger RNA. Induced cells were grown for 12 h, with end-point fluorescence measured via flow cytometry.

Figure 33A:
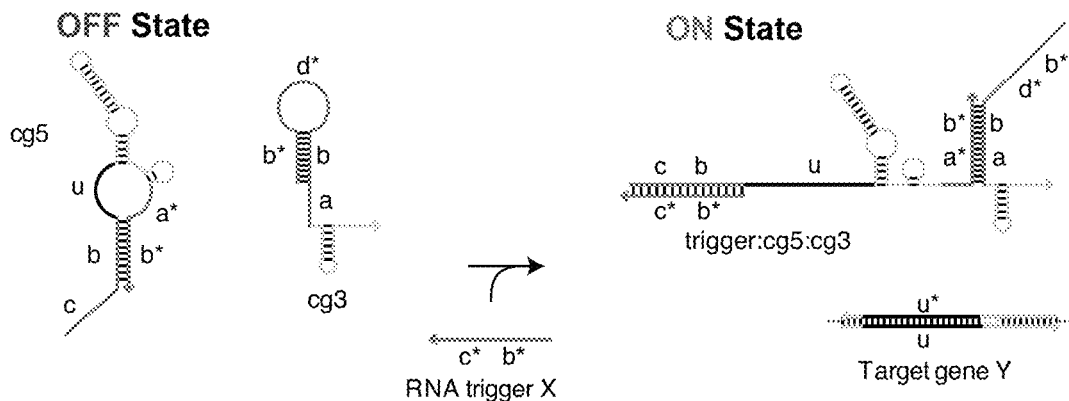
Figure 33B:
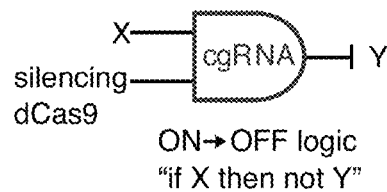
Figure 33C:
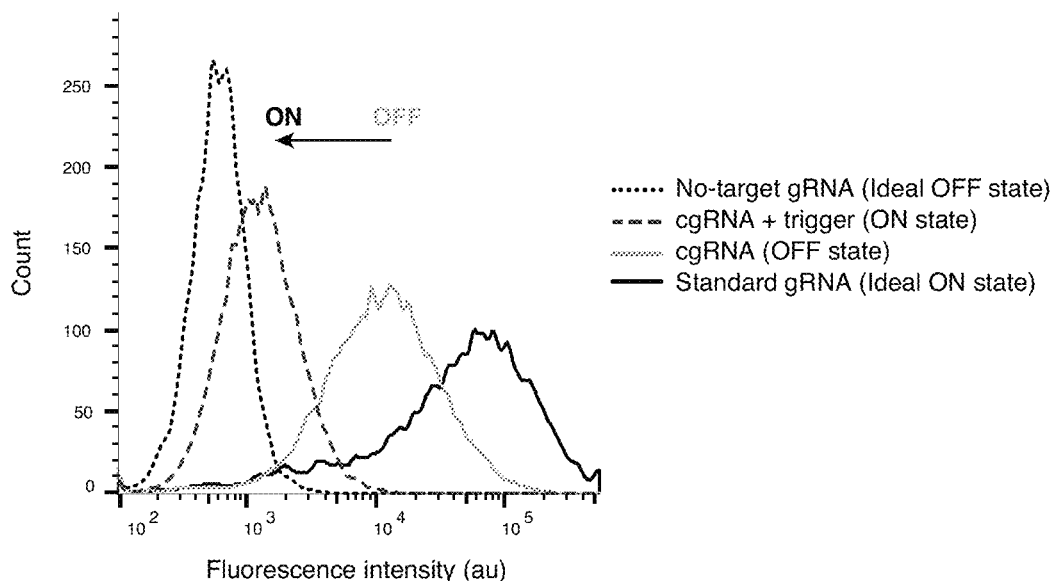

Example—Demonstration of Allosteric OFF→ON 5'- and 3'-Inhibited Split-Terminator Switch cgRNAs in Bacteria FIG. 33 demonstrates allosteric OFF→ON 5'- and 3'-inhibited split-terminator switch cgRNAs (Mechanism 7) performing conditional logic in *E. coli*. FIG. 33A depicts the mechanism for an allosteric OFF→ON 5'- and 3'-inhibited split-terminator switch cgRNA (Mechanism 7): the constitutively inactive cgRNA comprising 5' fragment cg5 and 3' fragment cg3 is activated by hybridization of RNA trigger X to cg5, allowing for cg5 to bind to cg3 and activate the cgRNA. FIG. 33B depicts the conditional logic for an OFF→ON 5'- and 3'-inhibited split-terminator switch cgRNA used in conjunction with silencing dCas9: "if X then not Y" (if trigger X is detected, then silence target gene Y). FIG. 33C demonstrates that expression of RNA trigger X (20 nt unstructured+synthetic terminator hairpin) toggles the cgRNA from OFF→ON, leading to a decrease in single-cell fluorescence intensities via flow cytometry. Induced expression (aTc) of silencing dCas9 and constitutive expression of mRFP target gene Y and either: standard gRNA+no-trigger control (ideal ON state), cgRNA+no-trigger control (ON state), cgRNA+RNA trigger X (OFF state; trigger expression is Salicylate-induced), no-target gRNA that lacks target-binding region+no-trigger control (ideal OFF state). FIG. 32F depicts the sequences of cg5, cg3, trigger X (Mechanism 4B), trigger X (Mechanism 4C), and the no-trigger control. Nucleotides that are lower case italic are constrained by the target gene. Nucleotides shaded gray are constrained by dCas9. Nucleotides that are upper case italic are designed. Sequences are presented as DNA sequences; the corresponding RNA sequence is the same as the DNA sequence except that "U" replaces "T").

Orthogonal cgRNA/trigger pairs were designed using software suite NUPACK®[40,41] cgRNA/trigger plasmids were transformed into *E. coli*.[5] Strains were grown overnight in EZ-RDM (Teknova), then diluted and seeded into the assay plate. Cells were grown in fresh medium containing aTc, IPTG, and Salicylate for induction of silencing dCas9 expression, cgRNA, and trigger RNA. Induced cells were grown for 12 h, with end-point fluorescence measured via flow cytometry.

Example—Demonstration of Allosteric cgRNAs Performing Conditional Logic in Response to mRNA Triggers FIG. 18 demonstrates allosteric cgRNAs performing conditional logic in response to detection of long RNA triggers in *E. coli*. FIG. 18A depicts the mechanism for an allosteric ON→OFF terminator switch cgRNA: the constitutively active cgRNA is inactivated by hybridization of RNA trigger X (which is a full-length mRNA trigger molecule containing subsequence "f*-e*-d*" that serves as the trigger domain). FIG. 18B depicts the conditional logic for an ON→OFF terminator switch cgRNA used in conjunction with silencing dCas9: "if not X then not Y" (if trigger X is not detected, then silence target gene Y). FIG. 18C demonstrates that expression of RNA trigger X (full-length mRNA) toggles the cgRNA from ON→OFF, leading to an increase in fluorescence. 18C and 18D demonstrate programmable conditional regulation using 2 orthogonal cgRNAs (A, B) and their corresponding cognate triggers (XA, XB). Induced expression (aTc) of silencing dCas9 and constitutive expression of mRFP target gene Y and either: cgRNA(ON state), cgRNA+RNA trigger X (OFF state; trigger expression is IPTG-induced). Autofluorescence (AF): cells with no mRFP. In FIG. 18C, raw fluorescence depicts ON→OFF conditional response to cognate trigger. Fold change=OFF/ON= [cognate trigger−AF]/[no trigger−AF]). In FIG. 18D, normalized fluorescence depicts orthogonality between non-cognate cgRNA/trigger pairs. Crosstalk=[non-cognate trigger−no trigger]/[cognate trigger−no trigger]). Bar graphs depict mean estimated standard error calculated based on the mean single-cell fluorescence over 20,000 cells for each of N=3 replicate wells (OFF:ON ratio and crosstalk calculated with uncertainty propagation). FIGS. 18E-18F depict the sequences of cgRNAs A, B and the sequences of mRNA trigger molecules XA, XB. Nucleotides that are lower case italic are constrained by the target gene. Nucleotides shaded gray are constrained by dCas9. Nucleotides in a cgRNA that are upper case bold are complementary to the trigger domain of the corresponding trigger molecule. Nucleotides in an mRNA trigger molecule are lower case except for the trigger domain which is upper case bold. Sequences are presented as DNA sequences; the corresponding RNA sequence is the same as the DNA sequence except that "U" replaces "T").

Example—Computational Sequence Design of Orthogonal cgRNA/Trigger Pairs

Figure 19A:
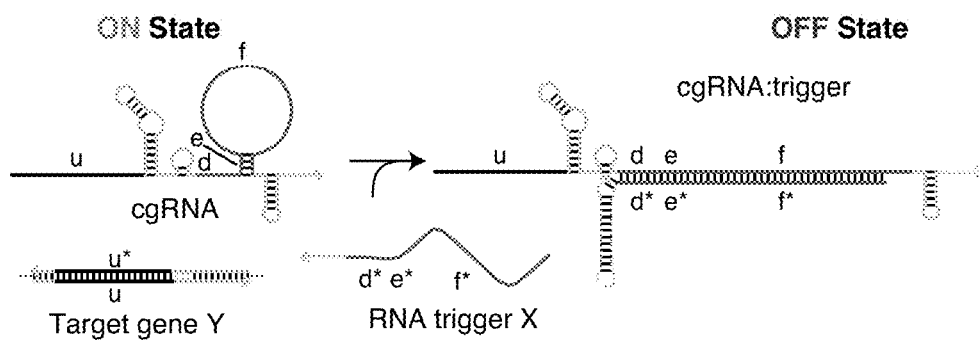
FIGS. 19A-19B depict the mechanism and target test tubes for computational sequence design of a library of orthogonal ON→OFF terminator switch cgRNAs/triggers.
Figure 19B:
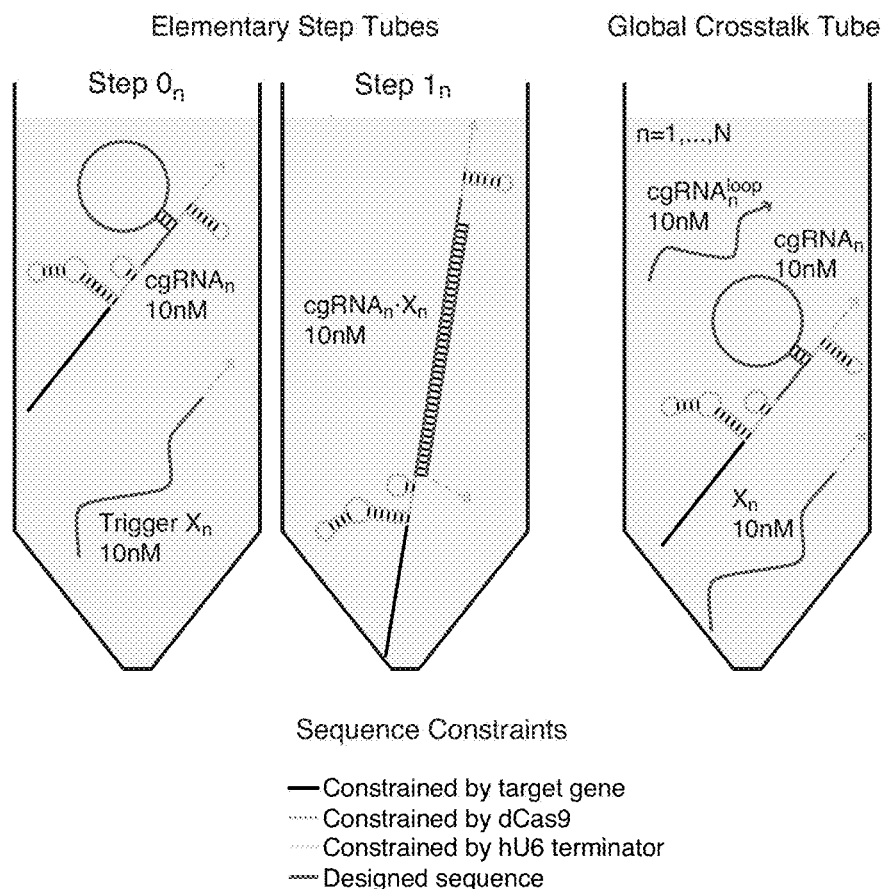
Figure 20A:
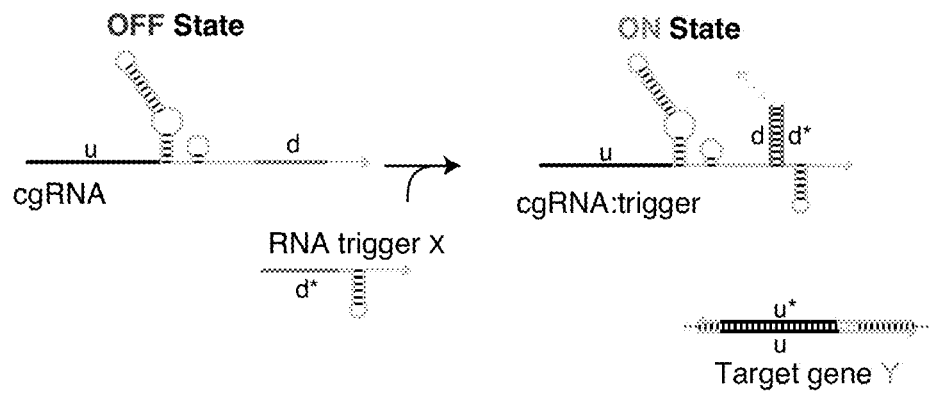
FIGS. 20A-20B depict the mechanism and target test tubes for computational sequence design of a library of orthogonal OFF→ON split-terminator switch cgRNAs/triggers.
Figure 20B:
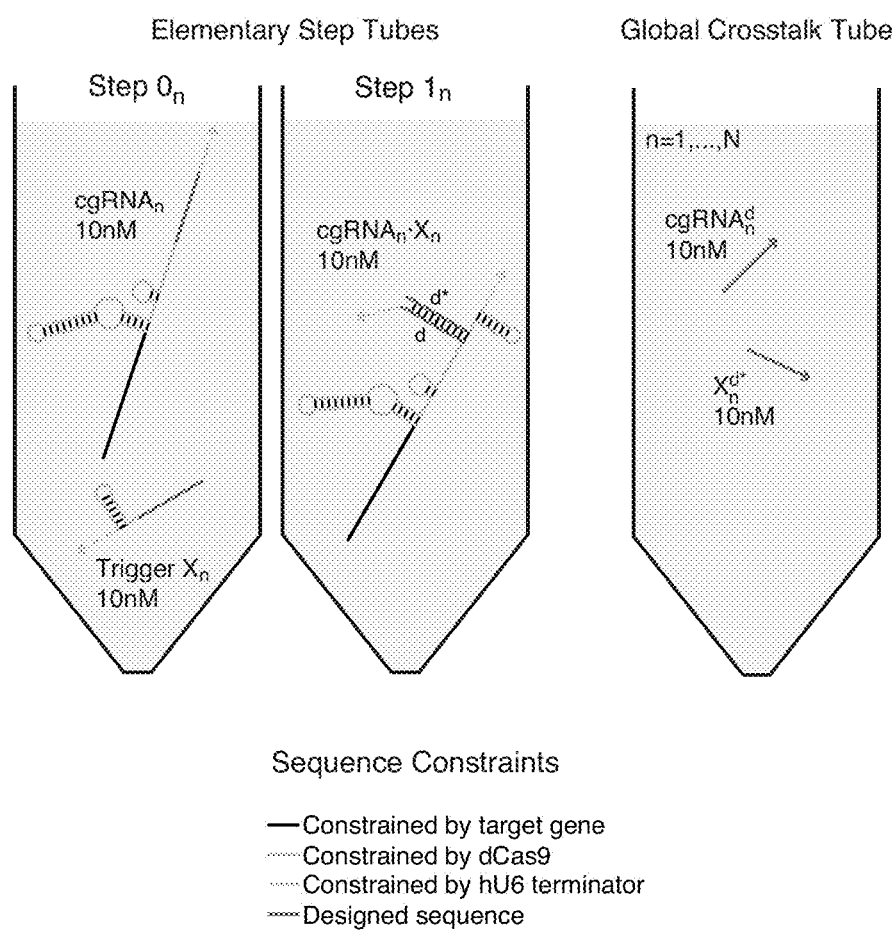

FIG. 19B displays target test tubes for the design of N orthogonal cgRNA/trigger pairs for the ON→OFF terminator switch mechanism (FIG. 19A). FIG. 20B displays target test tubes for the design of N orthogonal cgRNA/trigger pairs for the OFF→ON split-terminator switch mechanism (FIG. 20A). To design N orthogonal cgRNA/trigger pairs (systems), there are two elementary step tubes for each system (n=1, . . . , N): 1) A Reactants tube (Step 0n) containing cgRNAn and the corresponding trigger Xn; 2) A Products tube (Step 1n) containing the complex cgRNAn: Xn. Each target test tube contains a set of desired "on-target" complexes (each with the depicted target secondary structure and target concentration (10 nM in this example)) corresponding to the on-pathway hybridization products for a given step and a set of undesired "off-target" complexes (in this example, all complexes of up to 2 strands, each with a target concentration of 0 nM; not depicted) corresponding to on-pathway reactants and off-pathway hybridization crosstalk for a given step; these elementary step tubes are designed for full conversion of cognate reactants into cognate products and against local hybridization crosstalk between these same reactants. To design N orthogonal systems, there is a single global crosstalk tube containing a set of on-targets and off-targets for each system. The global crosstalk tube contains the depicted on-target complexes corresponding to reactive species generated during Steps 0 and 1 (each with the depicted target secondary structure and target concentration (10 nM in this example) as well as off-target complexes (for this example, all complexes of up to 2 strands, each with a target concentration of 0 nM; not depicted) corresponding to off-pathway interactions between these reactive species. Crucially, the global crosstalk tube ensemble omits the cognate products that the reactive species are intended to form (they appear as neither on-targets nor off-targets). Hence, all reactive species in the global crosstalk tube are forced to either perform no reaction (remaining as desired on-targets) or undergo a crosstalk reaction (forming undesired off-targets), providing the basis for minimization of global crosstalk during sequence optimization. To design a library of N orthogonal cgRNA/trigger pairs, all N cgRNAs have the same on-target structure, and all N triggers have the same on-target structure; within a library, the only difference between cgRNA/trigger pairs is the designed sequence; there are a total of 2N elementary step tubes plus 1 global crosstalk tube. For this example, sequence design was performed subject to complementarity constraints inherent to the reaction pathway (FIGS. 19A and 20A; domain "d" complementary to "d*", etc.), as well as to biological sequence constraints imposed by the the silencing target Y, the protein effector (dCas9), and the terminator; see the constraint shading in FIGS. 19B and 20B. The sequence was optimized by reducing the ensemble defect quantifying the average fraction of incorrectly paired nucleotides over the multi-tube ensemble.[41, 53, 54] Within the ensemble defect, defect weights were applied to prioritize design effort.[41] Optimization of the ensemble defect implemented both a positive design paradigm (explicitly designing for on-pathway elementary steps) and a negative-design paradigm (explicitly designing against off-pathway crosstalk).[41]

Example—Demonstration of Allosteric ON→OFF and OFF→ON cgRNAs Functioning in Multi-Cellular Organisms FIGS. 21 and 22 demonstrate allosteric cgRNAs functioning in developing chicken embryos.

FIG. 21 demonstrates an allosteric ON→OFF terminator switch cgRNA performing conditional logic in a chicken embryo (mechanism of FIG. 13A). FIG. 21A depicts the conditional logic for an ON→OFF terminator switch cgRNA used in conjunction with inducing dCas9: "if not X then Y" (if trigger X is not detected, induce target gene Y). For the experimental demonstration, five plasmids are electroporated into the left side and right side (independently for each side) of a developing chicken embryo (plasmids transfected into both sides: RFP transfection control, inducing dCas9, cgRNA, d2eGFP as the target gene Y; plasmid transfected into the left side only: non-cognate trigger X', plasmid transfected into the right side only: cognate trigger X). FIG. 21B displays RFP fluorescence for the transfection control on both sides of the embryo, demonstrating transfection into both sides of the embryo. FIG. 21C displays GFP fluorescence of the target gene Y, exhibiting high fluorescence on the left side of the embryo (ON state; non-cognate trigger) and low fluorescence on the right side of the embryo (OFF state; cognate trigger). The cognate trigger toggles the cgRNA from the ON state to the OFF state, leading to a large reduction in GFP fluorescence, corresponding to reduced expression of the target gene Y. FIG. 21D displays normalized fluorescence for representative regions in replicate embryos (one dot per embryo) for experiments with transfection of either: no trigger (ON state), non-cognate trigger (ON state), or cognate trigger (OFF state). Error bars represent standard error of the mean over replicate embryos. FIG. 21E depicts the sequences of cgRNAs, the cognate trigger X, and the non-cognate trigger X'. Nucleotides that are lower case italic are constrained by the target binding site on the reporter plasmid. Nucleotides shaded gray are constrained by dCas9. Nucleotides that are upper case italic are designed. The plain "C" nucleotide is a cloning artifact. Lower case plain nucleotides are constrained by the hU6 terminator sequence[46]. Bold nucleotides are a protective element (PEL) constrained by an xrRNA sequence derived from Dengue (Dengue 4, NC_002640.1)[47]. Sequences are presented as DNA sequences; the corresponding RNA sequence is the same as the DNA sequence except that "U" replaces "T").

Figure 21A:
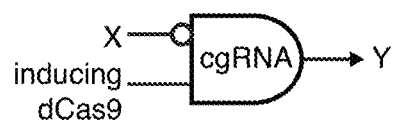
Figure 21B:
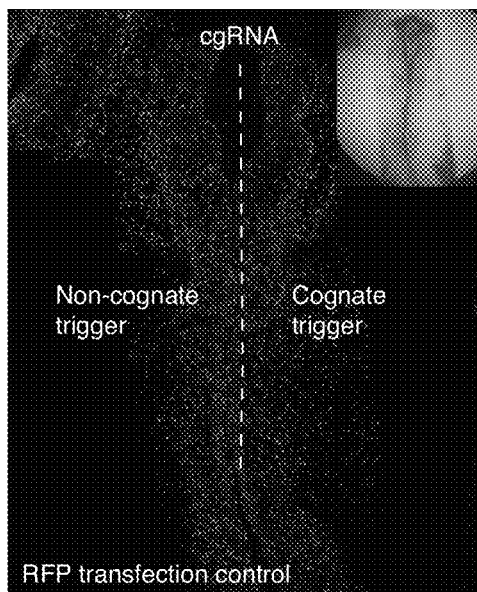
Figure 21C:
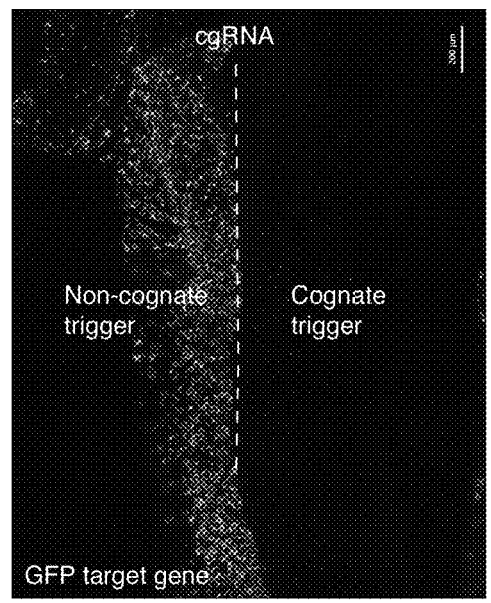
Figure 21D:
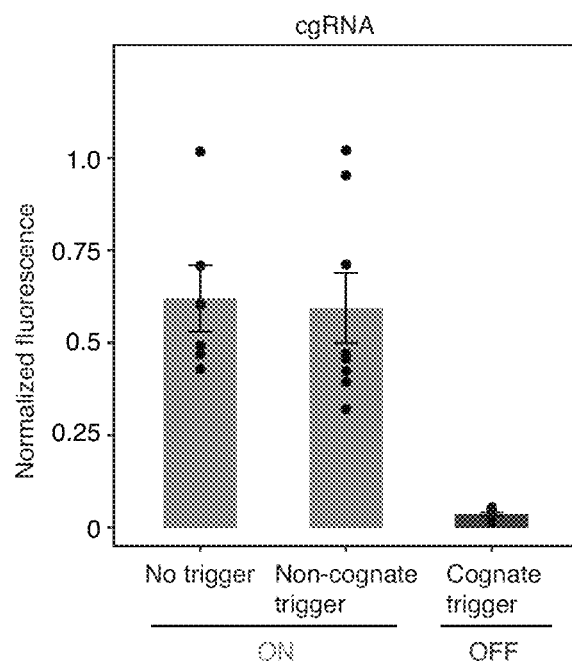
Figure 22A:
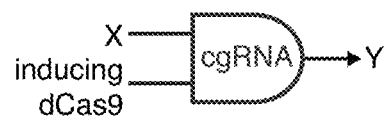
Figure 22B:
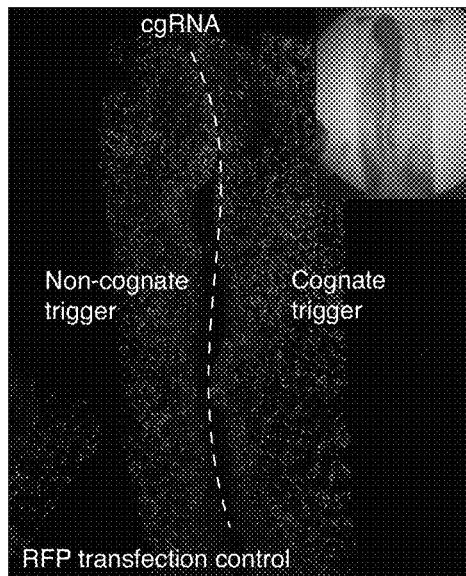
Figure 22C:
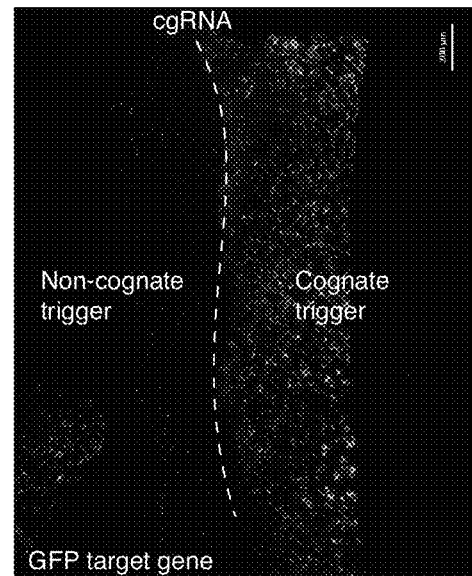
Figure 22D:
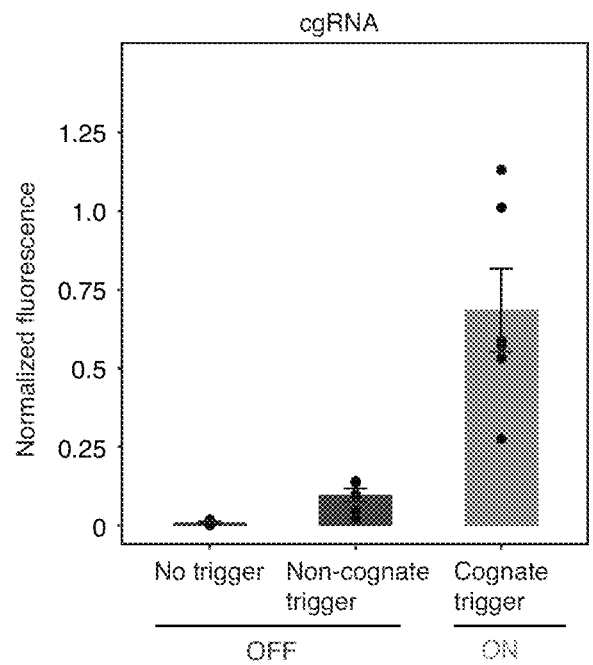

FIG. 22 demonstrates an allosteric OFF→ON split-terminator switch cgRNA performing conditional logic in a chicken embryo (mechanism of FIG. 15A). FIG. 22A depicts the conditional logic for an OFF→ON split-terminator switch cgRNA used in conjunction with inducing dCas9: "if X then Y" (if trigger X is detected, induce target gene Y). For the experimental demonstration, five plasmids are electroporated into the left side and right side (independently for each side) of a developing chicken embryo (plasmids transfected into both sides: RFP transfection control, inducing dCas9, cgRNA, d2eGFP as the target gene Y; plasmid transfected into the left side only: non-cognate trigger X', plasmid transfected into the right side only: cognate trigger X). FIG. 22B displays RFP fluorescence for the transfection control on both sides of the embryo, demonstrating transfection into both sides of the embryo. FIG. 22C displays GFP fluorescence of the target gene Y, exhibiting low fluorescence on the left side of the embryo (OFF state; non-cognate trigger) and high fluorescence on the right side of the embryo (ON state; cognate trigger). The cognate trigger toggles the cgRNA from the OFF to the ON state, leading to a large increase in GFP fluorescence, corresponding to increased expression of the target gene Y. FIG. 21D displays normalized fluorescence for representative regions in replicate embryos (one dot per embryo) for experiments with transfection of either: no trigger (OFF state), non-cognate trigger (OFF state), or cognate trigger (ON state). Error bars represent standard error of the mean over replicate embryos. FIG. 22E depicts the sequences of cgRNAs, the cognate trigger X, and the non-cognate trigger X'. Nucleotides that are lower case italic are constrained by the target binding site on the reporter plasmid. Nucleotides shaded gray are constrained by dCas9. Nucleotides that are upper case italic are designed. The plain "C" nucleotide is a cloning artifact. Lower case plain nucleotides are constrained by the hU6 terminator sequence[46]. Bold nucleotides are a protective element (PEL) constrained by an xrRNA sequence derived from Dengue (Dengue 4, NC_002640.1). 47 Sequences are presented as DNA sequences; the corresponding RNA sequence is the same as the DNA sequence except that "U" replaces "T").

REFERENCES (1) Cong, L.; Ran, F. A.; Cox, D.; Lin, S.; Barretto, R.; Habib, N.; Hsu, P. D.; Wu, X.; Jiang, W.; Marraffini, L. A.; Zhang, F. Multiplex Genome Engineering Using CRISPR/Cas Systems. *Science* 2013, 339 (6121), 819-823.

(2) Mali, P.; Yang, L.; Esvelt, K. M.; Aach, J.; Guell, M.; DiCarlo, J. E.; Norville, J. E.; Church, G. M. RNA-Guided Human Genome Engineering via Cas9. *Science* 2013, 339 (6121), 823.

(3) Zetsche, B.; Heidenreich, M.; Mohanraju, P.; Fedorova, I.; Kneppers, J.; DeGennaro, E. M.; Winblad, N.; Choudhury, S. R.; Abudayyeh, O. O.; Gootenberg, J. S.; Wu, W. Y.; Scott, D. A.; Severinov, K.; van der Oost, J.; Zhang, F. Multiplex Gene Editing by CRISPR-Cpf1 Using a Single CrRNA Array. *Nat Biotechnol* 2016, 35, 31-34.

(4) Knott, G. J.; Doudna, J. A. CRISPR-Cas Guides the Future of Genetic Engineering. *Science* 2018, 361 (6405), 866-869.

(5) Qi, L. S.; Larson, M. H.; Gilbert, L. A.; Doudna, J. A.; Weissman, J. S.; Arkin, A. P.; Lim, W. A. Repurposing CRISPR as an RNA-Guided Platform for Sequence-Specific Control of Gene Expression. *Cell* 2013, 152 (5), 1173-1183.

(6) Larson, M. H.; Gilbert, L. A.; Wang, X.; Lim, W. A.; Weissman, J. S.; Qi, L. S. CRISPR Interference (CRISPRi) for Sequence-Specific Control of Gene Expression. *Nat Protoc* 2013, 8, 2180-2196.

(7) Gilbert, L. A.; Larson, M. H.; Morsut, L.; Liu, Z.; Brar, G. A.; Torres, S. E.; Stern-Ginossar, N.; Brandman, O.; Whitehead, E. H.; Doudna, J. A.; Lim, W. A.; Weissman, J. S.; Qi, L. S. CRISPR-Mediated Modular RNA-Guided Regulation of Transcription in Eukaryotes. *Cell* 2013, 154 (2), 442-451.

(8) Anzalone, A. V.; Randolph, P. B.; Davis, J. R.; Sousa, A. A.; Koblan, L. W.; Levy, J. M.; Chen, P. J.; Wilson, C.; Newby, G. A.; Raguram, A.; Liu, D. R. Search-and-Replace Genome Editing without Double-Strand Breaks or Donor DNA. *Nature* 2019, 576 (7785), 149-157. https://doi.org/10.1038/s41586-019-1711-4.

(9) Liu, X. S.; Wu, H.; Krzisch, M.; Wu, X.; Graef, J.; Muffat, J.; Hnisz, D.; Li, C. H.; Yuan, B.; Xu, C.; Li, Y.; Vershkov, D.; Cacace, A.; Young, R. A.; Jaenisch, R. Rescue of Fragile X Syndrome Neurons by DNA Methylation Editing of the FMR1 Gene. *Cell* 2018, 172 (5), 979-992.e6.

(10) Myers, S. A.; Wright, J.; Peckner, R.; Kalish, B. T.; Zhang, F.; Carr, S. A. Discovery of Proteins Associated with a Predefined Genomic Locus via DCas9-APEX-Mediated Proximity Labeling. *Nat. Methods* 2018, 15 (6), 437-439.

(11) Morgan, S. L.; Mariano, N. C.; Bermudez, A.; Arruda, N. L.; Wu, F.; Luo, Y.; Shankar, G.; Jia, L.; Chen, H.; Hu, J.-F.; Hoffman, A. R.; Huang, C.-C.; Pitteri, S. J.; Wang, K. C. Manipulation of Nuclear Architecture through CRISPR-Mediated Chromosomal Looping. *Nat. Commun.* 2017, 8 (1), 15993.

(12) Ma, H.; Tu, L.-C.; Naseri, A.; Huisman, M.; Zhang, S.; Grunwald, D.; Pederson, T. Multiplexed Labeling of Genomic Loci with DCas9 and Engineered SgRNAs Using CRISPRainbow. *Nat. Biotechnol.* 2016, 34 (5), 528-530.

(13) Mückl, A.; Schwarz-Schilling, M.; Fischer, K.; Simmel, F. C. Filamentation and Restoration of Normal Growth in *Escherichia coli* Using a Combined CRISPRi SgRNA/Antisense RNA Approach. *PLoS One* 2018, 13 (9), e0198058.

(14) Aubrey, B. J.; Kelly, G. L.; Kueh, A. J.; Brennan, M. S.; O'Connor, L.; Milla, L.; Wilcox, S.; Tai, L.; Strasser, A.; Herold, M. J. An Inducible Lentiviral Guide RNA Platform Enables the Identification of Tumor-Essential Genes and Tumor-Promoting Mutations in Vivo. *Cell Rep.* 2015, 10 (8), 1422-1432.

(15) Bertero, A.; Pawlowski, M.; Ortmann, D.; Snijders, K.; Yiangou, L.; Cardoso de Brito, M.; Brown, S.; Bernard, W. G.; Cooper, J. D.; Giacomelli, E.; Gambardella, L.; Hannan, N. R. F.; Iyer, D.; Sampaziotis, F.; Serrano, F.; Zonneveld, M. C. F.; Sinha, S.; Kotter, M.; Vallier, L. Optimized Inducible ShRNA and CRISPR/Cas9 Platforms for in Vitro Studies of Human Development Using HPSCs. *Development* 2016, 143 (23), 4405.

(16) Chen, T.; Gao, D.; Zhang, R.; Zeng, G.; Yan, H.; Lim, E.; Liang, F. Chemically Controlled Epigenome Editing through an Inducible DCas9 System. *J. Am. Chem. Soc.* 2017, 139 (33), 11337-11340.

(17) Moroz-Omori, E. V.; Satyapertiwi, D.; Ramel, M.-C.; Hogset, H.; Sunyovszki, I. K.; Liu, Z.; Wojciechowski, J. P.; Zhang, Y.; Grigsby, C. L.; Brito, L.; Bugeon, L.; Dallman, M. J.; Stevens, M. M. Photoswitchable GRNAs for Spatiotemporally Controlled CRISPR-Cas-Based Genomic Regulation. *ACS Cent. Sci.* 2020, 6 (5), 695-703.

(18) Liu, Y.; Zou, R. S.; He, S.; Nihongaki, Y.; Li, X.; Razavi, S.; Wu, B.; Ha, T. Very Fast CRISPR on Demand. *Science* 2020, 368 (6496), 1265-1269.

(19) Jain, P. K.; Ramanan, V.; Schepers, A. G.; Dalvie, N. S.; Panda, A.; Fleming, H. E.; Bhatia, S. N. Development of Light-Activated CRISPR Using Guide RNAs with Photocleavable Protectors. *Angew. Chem. Int. Ed.* 2016, 55 (40), 12440-12444.

(20) Nihongaki, Y.; Otabe, T.; Sato, M. Emerging Approaches for Spatiotemporal Control of Targeted Genome with Inducible CRISPR-Cas9. *Anal Chem* 2018, 90 (1), 429-439.

(21) Shen, Z.; Zhang, X.; Chai, Y.; Zhu, Z.; Yi, P.; Feng, G.; Li, W.; Ou, G. Conditional Knockouts Generated by Engineered CRISPR-Cas9 Endonuclease Reveal the Roles of Coronin in *C. elegans* Neural Development. *Dev. Cell* 2014, 30 (5), 625-636.

(22) Ablain, J.; Durand, E. M.; Yang, S.; Zhou, Y.; Zon, L. I. A CRISPR/Cas9 Vector System for Tissue-Specific Gene Disruption in Zebrafish. *Dev. Cell* 2015, 32 (6), 756-764.

(23) Hirosawa, M.; Fujita, Y.; Parr, C. J. C.; Hayashi, K.; Kashida, S.; Hotta, A.; Woltjen, K.; Saito, H. Cell-Type-Specific Genome Editing with a MicroRNA-Responsive CRISPR-Cas9 Switch. *Nucleic Acids Res* 2017, 45 (13), e118.

(24) Briner, A. E.; Donohoue, P. D.; Gomaa, A. A.; Selle, K.; Slorach, E. M.; Nye, C. H.; Haurwitz, R. E.; Beisel, C. L.;

(24) May, A. P.; Barrangou, R. Guide RNA Functional Modules Direct Cas9 Activity and Orthogonality. *Mol Cell* 2014, 56 (2), 333-339.

(25) Nowak, C. M.; Lawson, S.; Zerez, M.; Bleris, L. Guide RNA Engineering for Versatile Cas9 Functionality. *Nucleic Acids Res* 2016, 44 (20), 9555-9564.

(26) Hanewich-Hollatz, M. H.; Chen, Z.; Hochrein, L. M.; Huang, J.; Pierce, N. A. Conditional Guide RNAs: Programmable Conditional Regulation of CRISPR/Cas Function in Bacterial and Mammalian Cells via Dynamic RNA Nanotechnology. *ACS Cent. Sci.* 2019, 5 (7), 1241-1249.

(27) Liu, Y.; Zhan, Y.; Chen, Z.; He, A.; Li, J.; Wu, H.; Liu, L.; Zhuang, C.; Lin, J.; Guo, X.; Zhang, Q.; Huang, W.; Cai, Z. Directing Cellular Information Flow via CRISPR Signal Conductors. *Nat Methods* 2016, 13, 938-944.

(28) Tang, W.; Hu, J. H.; Liu, D. R. Aptazyme-Embedded Guide RNAs Enable Ligand-Responsive Genome Editing and Transcriptional Activation. *Nat Commun* 2017, 8, 15939.

(29) Kundert, K.; Lucas, J. E.; Watters, K. E.; Fellmann, C.; Ng, A. H.; Heineike, B. M.; Fitzsimmons, C. M.; Oakes, B. L.; Qu, J.; Prasad, N.; Rosenberg, O. S.; Savage, D. F.; El-Samad, H.; Doudna, J. A.; Kortemme, T. Controlling CRISPR-Cas9 with Ligand-Activated and Ligand-Deactivated SgRNAs. *Nat Commun* 2019, 10 (1), 2127.

(30) Lee, Y. J.; Hoynes-O'Connor, A.; Leong, M. C.; Moon, T. S. Programmable Control of Bacterial Gene Expression with the Combined CRISPR and Antisense RNA System. *Nucleic Acids Res.* 2016, 44 (5), 2462-2473.

(31) Ferry, Q. R. V.; Lyutova, R.; Fulga, T. A. Rational Design of Inducible CRISPR Guide RNAs for de Novo Assembly of Transcriptional Programs. *Nat Commun* 2017, 8, 2109.

(32) Wang, X.-W.; Hu, L.-F.; Hao, J.; Liao, L.-Q.; Chiu, Y.-T.; Shi, M.; Wang, Y. A MicroRNA-Inducible CRISPR-Cas9 Platform Serves as a MicroRNA Sensor and Cell-Type-Specific Genome Regulation Tool. *Nat. Cell Biol.* 2019, 21 (4), 522-530.

(33) Siu, K.-H.; Chen, W. Riboregulated Toehold-Gated GRNA for Programmable CRISPR-Cas9 Function. *Nat. Chem. Biol.* 2019, 15 (3), 217-220.

(34) Oesinghaus, L.; Simmel, F. C. Switching the Activity of Cas12a Using Guide RNA Strand Displacement Circuits. *Nat. Commun.* 2019, 10 (1), 1-11.

(35) Chen, B.; Gilbert, L. A.; Cimini, B. A.; Schnitzbauer, J.; Zhang, W.; Li, G.-W.; Park, J.; Blackburn, E. H.; Weissman, J. S.; Qi, L. S.; Huang, B. Dynamic Imaging of Genomic Loci in Living Human Cells by an Optimized CRISPR/Cas System. *Cell* 2013, 155 (7), 1479-1491.

(36) Knight, S. C.; Tjian, R.; Doudna, J. A. Genomes in Focus: Development and Applications of CRISPR-Cas9 Imaging Technologies. *Angew Chem Int Ed* 2018, 57 (16), 4329-4337.

(37) Hilton, I. B.; D'Ippolito, A. M.; Vockley, C. M.; Thakore, P. I.; Crawford, G. E.; Reddy, T. E.; Gersbach, C. A. Epigenome Editing by a CRISPR-Cas9-Based Acetyltransferase Activates Genes from Promoters and Enhancers. *Nat Biotechnol* 2015, 33, 510.

(38) Gaudelli, N. M.; Komor, A. C.; Rees, H. A.; Packer, M. S.; Badran, A. H.; Bryson, D. I.; Liu, D. R. Programmable Base Editing of A$\cdot$T to G$\cdot$C in Genomic DNA without DNA Cleavage. *Nature* 2017, 551 (7681), 464-471.

(39) Hochrein, L. M.; Li, H.; Pierce, N. A. High-Performance Allosteric Conditional Guide RNAs for Mammalian Cell-Selective Regulation of CRISPR/Cas. *ACS Synth. Biol.* 2021, 10 (5), 964-971.

(40) Zadeh, J. N.; Steenberg, C. D.; Bois, J. S.; Wolfe, B. R.; Pierce, M. B.; Khan, A. R.; Dirks, R. M.; Pierce, N. A. NUPACK: Analysis and Design of Nucleic Acid Systems. *J. Comput. Chem.* 2011, 32 (1), 170-173.

(41) Wolfe, B. R.; Porubsky, N. J.; Zadeh, J. N.; Dirks, R. M.; Pierce, N. A. Constrained Multistate Sequence Design for Nucleic Acid Reaction Pathway Engineering. *J. Am. Chem. Soc.* 2017, 139 (8), 3134-3144.

(42) Wang, D.; Zhang, C.; Wang, B.; Li, B.; Wang, Q.; Liu, D.; Wang, H.; Zhou, Y.; Shi, L.; Lan, F.; Wang, Y. Optimized CRISPR Guide RNA Design for Two High-Fidelity Cas9 Variants by Deep *Learning. Nat Commun* 2019, 10 (1), 4284.

(43) Misteli, T.; Spector, D. L. Applications of the Green Fluorescent Protein in Cell Biology and Biotechnology. *Nat Biotech* 1997, 15 (10), 961-964.

(44) Tsien, R. Y. The Green Fluorescent Protein. *Annu Rev Biochem* 1998, 67 (1), 509-544.

(45) Zimmer, M. Green Fluorescent Protein (GFP): Applications, Structure, and Related Photophysical Behavior. *Chem Rev* 2002, 102 (3), 759-782.

(46) Gao, Z.; Herrera-Carrillo, E.; Berkhout, B. Delineation of the Exact Transcription Termination Signal for Type 3 Polymerase III. *Mol. Ther. Nucleic Acids* 2018, 10, 36-44.

(47) Kieft, J. S.; Rabe, J. L.; Chapman, E. G. New Hypotheses Derived from the Structure of a Flaviviral Xrn1-Resistant RNA: Conservation, Folding, and Host Adaptation. *RNA Biol* 2015, 12 (11), 1169-1177.

(48) Chavez, A.; Scheiman, J.; Vora, S.; Pruitt, B. W.; Tuttle, M.; Iyer, E. P. R.; Lin, S.; Kiani, S.; Guzman, C. D.; Wiegand, D. J.; Ter-Ovanesyan, D.; Braff, J. L.; Davidsohn, N.; Housden, B. E.; Perrimon, N.; Weiss, R.; Aach, J.; Collins, J. J.; Church, G. M. Highly Efficient Cas9-Mediated Transcriptional Programming. *Nat. Methods* 2015, 12 (4), 326-328.

(49) Mali, P.; Aach, J.; Stranges, P. B.; Esvelt, K. M.; Moosburner, M.; Kosuri, S.; Yang, L.; Church, G. M. CAS9 Transcriptional Activators for Target Specificity Screening and Paired Nickases for Cooperative Genome Engineering. *Nat. Biotechnol.* 2013, 31, 833-838.

(50) Nissim, L.; Perli, S. D.; Fridkin, A.; Perez-Pinera, P.; Lu, T. K. Multiplexed and Programmable Regulation of Gene Networks with an Integrated RNA and CRISPR/Cas Toolkit in Human Cells. *Mol. Cell* 2014, 54 (4), 698-710.

(51) Shagin, D. A.; Barsova, E. V.; Yanushevich, Y. G.; Fradkov, A. F.; Lukyanov, K. A.; Labas, Y. A.; Semenova, T. N.; Ugalde, J. A.; Meyers, A.; Nunez, J. M.; Widder, E. A.; Lukyanov, S. A.; Matz, M. V. GFP-like Proteins as Ubiquitous Metazoan Superfamily: Evolution of Functional Features and Structural Complexity. *Mol. Biol. Evol.* 2004, 21 (5), 841-850.

(52) Nissim, L.; Perli, S. D.; Fridkin, A.; Perez-Pinera, P.; Lu, T. K. Multiplexed and Programmable Regulation of Gene Networks with an Integrated RNA and CRISPR/Cas Toolkit in Human Cells. *Mol Cell* 2019, 54 (4), 698-710.

(53) Zadeh, J. N.; Wolfe, B. R.; Pierce, N. A. Nucleic Acid Sequence Design via Efficient Ensemble Defect Optimization. *J. Comput. Chem.* 2011, 32, 439-452.

(54) Wolfe, B. R.; Pierce, N. A. Sequence Design for a Test Tube of Interacting Nucleic Acid Strands. *ACS Synth. Biol.* 2015, 4 (10), 1086-1100.

What is claimed is:

1. An allosteric conditional guide RNA (cgRNA) comprising:
a 5' fragment (cg5) and a 3' fragment (cg3), wherein cg5 comprises a Cas handle, a target-binding region 5' of the Cas handle, and a cg3-binding region 3' of the Cas handle, wherein cg3 comprises a cg5-binding region, and wherein either cg5 or cg3 comprises a trigger-binding region:
  a. wherein the target-binding region is non-overlapping with the trigger-binding region and is configured not to bind to the trigger-binding region;
  b. wherein cg5 and cg3 are inactive when not bound to each other;
  c. wherein in the absence of a cognate RNA trigger, cg5 and cg3 are configured to be inhibited from binding to each other; and
  d. wherein upon hybridization of the cognate RNA trigger to either cg5 or cg3, cg5 and cg3 hybridize to form a trigger:cg5:cg3 complex that activates the cgRNA, thereby mediating the function of a Cas protein effector on a target gene that binds the target-binding region, wherein the Cas protein effector is configured to bind to the Cas handle that is 3' of the target-binding region.

2. The allosteric cgRNA of claim 1, wherein the cg5 comprises:
  a. the trigger-binding region, which comprises a first inhibitor region, and
  b. a second inhibitor region;
  wherein in the absence of the cognate RNA trigger, the first inhibitor region is configured to bind to the second inhibitor region, thereby inhibiting binding between cg5 and cg3.

3. The allosteric cgRNA of claim 2, wherein:
  a. the cognate RNA trigger comprises a cg5-binding region;
  b. the trigger-binding region further comprises a toehold of one or more unpaired nucleotides at one or both ends;
  c. the cg3-binding region of cg5 comprises a 5' portion of a stem of a terminator duplex; and
  d. the cg5-binding region of cg3 comprises a 3' portion of the stem of the terminator duplex;
  wherein upon hybridization of the cognate RNA trigger to cg5, cg5 hybridizes to cg3 to form the terminator duplex, thereby activating the cgRNA.

4. The allosteric cgRNA of claim 1, wherein cg3 comprises:
  a. the trigger-binding region, which comprises a first inhibitor region, and
  b. a second inhibitor region
  wherein in the absence of the cognate RNA trigger, the first inhibitor region is configured to bind the second inhibitor region, thereby inhibiting binding between cg5 and cg3.

5. The allosteric cgRNA of claim 4, wherein:
  a. the cognate RNA trigger comprises a cg3-binding region;
  b. the trigger-binding region further comprises a toehold of one or more unpaired nucleotides at one or both ends;
  c. the cg5-binding region of cg3 comprises a 3' portion of a stem of a terminator duplex; and
  d. the cg3-binding region of cg5 comprises a 5' portion of the stem of the terminator duplex;
  wherein upon hybridization of the cognate RNA trigger to cg3, cg3 hybridizes to cg5 to form the terminator duplex, thereby activating the cgRNA.

6. The allosteric cgRNA of claim 1, wherein cg5 comprises:
  a. the trigger-binding region, which comprises a first inhibitor region; and
  b. a second inhibitor region;
  and wherein cg3 further comprises:
  c. a third inhibitor region; and
  d. a fourth inhibitor region
  wherein in the absence of a cognate RNA trigger, the first inhibitor region is configured to bind the second inhibitor region and the third inhibitor region is configured to bind to the fourth inhibitor region, thereby inhibiting binding between cg5 and cg3.

7. The allosteric cgRNA of claim 6, wherein:
  a. the cognate RNA trigger comprises a cg5-binding region;
  b. the trigger-binding region of cg5 further comprises a toehold of one or more unpaired nucleotides at one or both ends;
  c. the cg3-binding region of cg5 comprises a 5' portion of a stem of a terminator duplex; and
  d. the cg5-binding region of cg3 comprises a 3' portion of the stem of the terminator duplex comprising a toehold of one or more unpaired nucleotides at one or both ends;
  wherein upon hybridization of the cognate RNA trigger to cg5, cg5 hybridizes to cg3 to form the terminator duplex, thereby activating the cgRNA.

8. The allosteric cgRNA of claim 6, wherein the trigger-binding region of cg5 is 5' of the target-binding region.

9. The allosteric cgRNA of claim 6, wherein cg3 comprises a trigger mimic region having a sequence identical to that of the cg5-binding region of the cognate RNA trigger, wherein upon activation of the cgRNA by the cognate RNA trigger, the trigger mimic region is exposed and capable of serving as the cognate RNA trigger for a new copy of the cgRNA comprising a new copy of the 5' fragment cg5 and a new copy of the 3' fragment cg3.

10. The allosteric cgRNA of claim 6, wherein the trigger-binding region of cg5 is 3' of the Cas handle.

11. The allosteric cgRNA of claim 6, wherein the cgRNA additionally comprises a splint as a third fragment wherein the splint comprises:
  a. a cg3-binding region comprising a fifth inhibitor region and further comprising a toehold of one or more unpaired nucleotides at one or both ends; and
  b. a cg5-binding region comprising a sixth inhibitor region;
  wherein in the absence of a cognate RNA trigger, the fifth inhibitor region is configured to bind the sixth inhibitor region, inhibiting binding of the splint to cg5 and cg3, and wherein upon activation of the cgRNA by the cognate RNA trigger, cg3 hybridizes to the cg3-binding region of the splint and the cg5-binding region of the splint hybridizes to cg5, displacing the trigger from cg5, and catalytically regenerating the trigger which then serves as the cognate RNA trigger for a new copy of the cgRNA comprising a new copy of the 5' fragment cg5 and a new copy of the 3' fragment cg3.

12. The allosteric cgRNA of claim 11, wherein the catalytically regenerated trigger serves as the cognate RNA trigger for a new copy of the cgRNA that further comprises a new copy of the splint fragment.

13. The allosteric cgRNA of claim 6, wherein cg3 comprises a trigger mimic region having a sequence identical to that of the cg5-binding region of the cognate RNA trigger, wherein upon activation of the cgRNA by the cognate RNA trigger, the trigger mimic region hybridizes to the trigger-binding region of cg5, displacing the trigger from cg5, and catalytically regenerating the trigger which can then serve as the cognate RNA trigger for a new copy of the cgRNA comprising a new copy of the 5' fragment cg5 and a new copy of the 3' fragment cg3.

14. The allosteric cgRNA of claim 1, wherein the trigger is, or is a subsequence of an mRNA, an rRNA, a lncRNA, a miRNA, or a tRNA.

15. The allosteric cgRNA of claim 1, wherein the cgRNA is expressed in a cell.

16. The allosteric cgRNA of claim 1, wherein the cgRNA is chemically synthesized.

17. The allosteric cgRNA of claim 1, wherein the cgRNA further comprises one or more additional regions at the 5' and/or the 3' end.

18. The allosteric cgRNA of claim 1, wherein the cgRNA and/or cognate RNA trigger comprises one or more chemical modifications that alter one or more of degradation properties, affinity, biological activity, and/or delivery properties of the cgRNA.

19. The allosteric cgRNA of claim 1, wherein the cgRNA and/or cognate RNA trigger comprises one or more chemical modifications selected from the group consisting of arabino nucleic acids (ANA), locked nucleic acids (LNA), peptide nucleic acids (PNA), phosphoroamidate DNA analogues, phosphorodiamidate morpholino oligomers (PMO), cyclohexene nucleic acids (CeNA), tricycloDNA (tcDNA), bridged nucleic acids (BNA), phosphorothioate modification, 2'-fluoro (2'-F) modification, 2'-fluoroarabino (2'-FANA) modification, 2'O-Methyl (2'O-Me) modification, and 2'O-(2-methoxyethyl) (2'O-MOE) modification.

20. The allosteric cgRNA of claim 1, wherein the cgRNA and/or cognate RNA trigger further comprises a protective element (PEL), wherein none, some, or all of the PEL sequence is derived from a component of a viral xrRNA sequence, and wherein the PEL reduces degradation of the cognate RNA trigger in a prokaryotic or eukaryotic cell.

21. The allosteric cgRNA of claim 1, wherein the cgRNA further comprises a protective element (PEL), wherein none, some, or all of the PEL sequence is derived from a component of a viral xrRNA, and wherein the PEL reduces degradation of the cgRNA in a prokaryotic or eukaryotic cell.

22. The allosteric cgRNA of claim 1, wherein the cgRNA works in conjunction with Cas to mediate cell-selective induction, silencing, editing, or binding of a target gene.

* * * * *